US009453241B2

(12) United States Patent
Pan

(10) Patent No.: US 9,453,241 B2
(45) Date of Patent: Sep. 27, 2016

(54) AAV-MEDIATED SUBCELLULAR TARGETING OF HETEROLOGOUS RHODOPSINS IN RETINAL GANGLION CELLS

(75) Inventor: Zhuo-Hua Pan, Troy, MI (US)

(73) Assignee: Wayne State University, Detroit, MI (US)

( * ) Notice: Subject to any disclaimer, the term of this patent is extended or adjusted under 35 U.S.C. 154(b) by 334 days.

(21) Appl. No.: 13/696,252

(22) PCT Filed: May 4, 2011

(86) PCT No.: PCT/US2011/035266
§ 371 (c)(1),
(2), (4) Date: Jun. 12, 2013

(87) PCT Pub. No.: WO2011/140279
PCT Pub. Date: Nov. 10, 2011

(65) Prior Publication Data
US 2013/0259833 A1    Oct. 3, 2013

Related U.S. Application Data

(60) Provisional application No. 61/331,125, filed on May 4, 2010.

(51) Int. Cl.
| | |
|---|---|
| *C12N 15/861* | (2006.01) |
| *C07K 14/705* | (2006.01) |
| *A61K 48/00* | (2006.01) |
| *C12N 15/85* | (2006.01) |
| *C07K 14/47* | (2006.01) |

(52) U.S. Cl.
CPC ......... *C12N 15/8616* (2013.01); *A61K 48/005* (2013.01); *C07K 14/4702* (2013.01); *C07K 14/705* (2013.01); *C07K 2319/01* (2013.01); *C12N 2750/14143* (2013.01)

(58) Field of Classification Search
CPC ............ A61K 48/005; C07K 14/4702; C07K 14/705; C07K 2319/01; C12N 15/8616; C12N 2750/14143; C12N 2799/025
USPC .................... 424/93.2; 435/320.1, 455, 456; 514/44 R
See application file for complete search history.

(56) References Cited

U.S. PATENT DOCUMENTS

| | | | |
|---|---|---|---|
| 4,498,919 A | 2/1985 | Mann | |
| 4,554,101 A | 11/1985 | Hopp | |
| 5,827,702 A | 10/1998 | Cuthbertson | |
| 6,610,287 B1 | 8/2003 | Breakefield et al. | |
| 7,144,733 B2 | 12/2006 | Miesenbook et al. | |
| 7,186,699 B2 | 3/2007 | Harding et al. | |
| 7,427,138 B2 | 9/2008 | Ellenbogen | |
| 7,824,869 B2 | 11/2010 | Hegemann et al. | |
| 8,470,790 B2 | 6/2013 | Pan et al. | |

| | | |
|---|---|---|
| 2004/0022766 A1 | 2/2004 | Acland et al. |
| 2005/0202398 A1 | 9/2005 | Hegemann et al. |
| 2005/0208022 A1 | 9/2005 | Masland |
| 2010/0015095 A1 | 1/2010 | Pan et al. |
| 2014/0121265 A1 | 5/2014 | Pan et al. |

FOREIGN PATENT DOCUMENTS

| | | |
|---|---|---|
| WO | WO 98/48027 | 10/1998 |
| WO | WO 0015822 | 3/2000 |
| WO | WO 0183692 | 11/2001 |
| WO | WO 2005/044096 | 5/2005 |
| WO | WO 2007/024391 A2 | 3/2007 |
| WO | WO 2007024391 A2 | 3/2007 |
| WO | WO2007024391 A2 * | 3/2007 |
| WO | WO 2007/131180 A2 | 11/2007 |
| WO | WO 2007131180 A2 * | 11/2007 |
| WO | WO 2011/140279 | 11/2011 |

OTHER PUBLICATIONS

Acland, GM et al., "Gene Therapyy Restores Vision in a Canine Model of Childhood Blindness," Nat. Genet. vol. 28, 2001, pp. 92-95—Abstract.
Ali et al., "Restoration of Photoreceptor Ultrastructure and Function in Retinal Degeneration Slow Mice by Gene Therapy," Nat. Genet. vol. 25, 2000, pp. 306-310—Abstract.
Banghart et al., "Light-activated ion channels for remote control of neuronal firing," Nat. Neurosci. vol. 7, 2004, pp. 1381-1386.
Baylor, D., "How Photons Start Vision," Proc. Natl. Acad. Sci. USA vol. 93, 1996, pp. 560-565.
Bennett, J et al., "Stable transgene expression in rod photoreceptors after recombinant adeno-associated virus-mediated gene transfer to monkey retina," Proc. Natl. Acad. Sci. USA vol. 96, 1999, pp. 9920-9925.
Bennett, J. et al., Adenovirus-mediated delivery of rhodopsin-promoted bcl-2 results in a delay in photoreceptor cell death in the rd/rd mouse, Gene Therapy vol. 5, 1998, pp. 1156-1164.
Bennett, J. et al., "Photoreceptor cell rescue in retinal degeneration (rd) mice by in vivo gene therapy," Nat. Med. vol. 2, 1996, pp. 649-654—Abstract.

*Primary Examiner* — Janet Epps-Smith
(74) *Attorney, Agent, or Firm* — Cooley LLP; Ivor R. Elrifi; Cynthia A. Kozakiewicz

(57) ABSTRACT

Microbial type rhodopsins, such as the light-gated cation-selective membrane channel, channel-rhodopsin-2 (Chop2/ChR2) or the ion pump halorhodopsin (HaloR) are expressed in retinal ganglion cells upon transduction using recombinant AAV vectors. Selective targeting of these transgenes for expression in discrete subcellular regions or sites is achieved by including a sorting motif in the vector that can target either the central area or surround (off-center) area of these cells. Nucleic acid molecules comprising nucleotide sequences encoding such rhodopsins and sorting motifs and their use in methods of differential expression of the transgene are disclosed. These compositions and methods provide significant improvements for restoring visual perception and various aspects of vision, particular in patients with retinal disease.

25 Claims, 1 Drawing Sheet

(56) References Cited

OTHER PUBLICATIONS

Berson. "Phototransduction in Ganglion-Cell Photoreceptors." Eur. J. Physiol. 454(2007):849-855.
Bi et al., "Ectopic expression of a microbial-type rhodopsin restores visual responses in mice with photoreceptor degeneration," Neuron Apr. 2006;50:23-33.
Borras. "Recent Developments in Ocular Gene Therapy." Exp. Eye Res. 76(2003):643-652—Abstract.
Casini et al. "Developmental Expression of Neurokinin-1 and Neurokinin-3 Receptors in the Rat Retina." J. Camp. Neural. 421 (2000):275-287—Abstract.
Chang, B. et al., "Retinal degeneration mutants in the mouse," Vision Res. vol. 42, 2002, pp. 517-525.
Communication Pursuant to Article 94(3) EPC issued by the European Patent Office for Application No. EP07797340.2, dated Sep. 25, 2014, 5 pages.
Flannery et al. "Looking Within for Vision." Neuron. 50.1 (2006):1-3.
Flannery JG et al., "Efficient photoreceptor-targeted gene expression in vivo by recombinant adeno-associated virus," Proc. Natl. Acad. Sci. USA vol. 94, 1997, pp. 6916-6921.
Greenberg KP et al., "In vivo Transgene Expression in ON-Type Retinal Ganglion Cells: Applications to Retinal Disease," ARVO Abstract 2007.
Hankins et al. "Melanopsin: An Exciting Photopigment." Trends Neurosci. 31.1 (2007):27-36—Abstract.
Hauswirth et al. "Ocular Gene Therapy: Quo Vadis?" Invest. Ophthal. Vis. Sci. 41.1 0(2000):2821-2826.
Hauswirth, WW, "The Consortium Project to Treat RPE65 Deficiency in Humans," Retina vol. 25, 2005, p. 60.
Haverkamp et al., "Immunocytochemical Description of Five Bipolar Cell Types of the Mouse Retina," J Comparative Neurol 2003;455:463-76).
Hossain et al. "Artificial Means for Restoring Vision." Brit. Med. J. 330(2005):30-33.
Humphries, P et al., "On the molecular genetics of retinitis pigmentosa," Science vol. 256, 1992, pp. 804-808—Abstract.
International Preliminary Report on Patentability and Written Opinion of the International Searching Authority for PCT/US2007/068263, dated Nov. 4, 2008, 6 pages.
International Search Report issued by the International Searching Authority for PCT/US2007/068263, dated May 15, 2008, 4 pages.
International Preliminary Report on Patentability and Written Opinion of the International Searching Authority for PCT/US2011/035266,dated Nov. 6, 2012, 5 pages.
International Search Report of the International Searching Authority for PCT/US2011/035266, dated Jul. 27, 2011, 4 pages.
Ishizuka et al., "Kinetic Evaluation of Photosensitivity in Genetically Engineered Neurons Expressing Green Algae Light-Gated Channels," Neurosci Res 2006 54:85-94, online Nov. 17, 2005.
Jacobson, S Protocol #0410-677, National Institutes of Health Recombinant DNA Advisory Committee (RAC) (2005), 47 pages.
Kay, MA et al., Viral Vectors for Gene Therapy: The Art of Turning Infectious Agents into Vehicles of Therapeutics, Nat. Med. vol. 7, 2001, pp. 33-40—Abstract.
Kumar-Singh, R et al., "Encapsidated adenovirus mini-chromosome-mediated delivery of genes to the retina: application to the rescue of photoreceptor degeneration." Hum. Mol. Genet. vol. 7, 1998, pp. 1893-1900.
Lanyi, JK, "Bacteriorhodopsin." Annu Rev Physiol. vol. 66, 2004, pp. 665-688—Abstract.
Lanyi, JK., "Halorhodopsin, a Light-Driven Electrogenic Chloride-Transport System," Physiol Rev. vol. 70, No. 2, 1990, pp. 319-330.
Lau, D. et al., "Retinal Degeneration is Slowed in Transgenic Rats by AAV-Mediated Delivery of FGF-2," Invest. Ophthalmol. Vis. Sci. vol. 41, 2000, pp. 3622-3633.
Lavail, MM et al., "Ribozyme rescue of photoreceptor cells in P23H transgenic rats: Long-term survival and late-stage therapy," Proc Natl Acad Sci USA vol. 97, 2000, pp. 11488-11493.

Lavail, MM et al., "Multiple growth factors, cytokines, and neurotrophins rescue photoreceptors from the damaging effects of constant light," Proc. Natl. Acad. Sci. USA vol. 89, 1992, pp. 11249-11253.
Lewin, AS et al., "Ribozyme Rescue of Photoreceptor Cells in a Transgenic Rat Model of Autosomal Dominant Retinitis Pigmentosa," Nat. Med. vol. 4, 1998, pp. 967-971.
Lin et al.,"Restoration of Visual Function in Retinal Degeneration Mice by Ectopic Expression of Melanopsin," PNAS 2008;1 05:16009-14.
McFarland et al. "Gene Therapy for Proliferative Ocular Diseases." Exp. Opin. Bioi. Ther. 4.7(2004):1 053-1058—Abstract.
Medeiros et al. "Preservation of Ganglion Cell Layer Neurons in Age-Related Macular Degeneration." Invest. Ophthal. Vis. Sci. 42.3(2001 ):795-803.
Melyan, Z. et al., "Addition of human melanopsin renders mammalian cells photoresponsive," Nature vol. 433, 2005, pp. 741-745.
Milam, AH et al., "Histopathology of the Human Retina in Retinitis Pigmentosa," Prog. Retin. Eye Res. vol. 17, 1998, pp. 175-205.
Nagel et al. "Channelrhodopsin-2, a Directly Light-Gated Cation-Selective Membrane Channel." PNAS. 1 00.24(2003):13940-13945—Abstract.
Nagel, G. et al., "Channelrhodopsin-1: A Light-Gated Proton Channel in Green Algae," Science vol. 296, 2002, pp. 2395-2398.
Nakajima, Y. et al., "Molecular Characterization of a Novel Retinal Metabotropic Glutamate Receptor mGluR6 with a High Agonist Selectivity for L-2-Amino-4-phosphonobutyrate," J Biol Chem vol. 268, 1993, pp. 11868-11873.
Oesterhelt, D et al., "Functions of a New Photoreceptor Membrane," Proc. Natl. Acad. Sci. USA vol. 70, 1973, pp. 2853-2857.
Oesterhelt, D., "The structure and mechanism of the family of retinal proteins from halophilic archaea," Curr. Opin. Struct. Biol. vol. 8, 1998, pp. 489-500.
Office Action issued by the United States Patent and Trademark Office for U.S. Appl. No. 12/299,574, dated Aug. 28, 2012, 15 pages.
Office Action issued by the United States Patent and Trademark Office for U.S. Appl. No. 12/299,574, dated Jan. 12, 2012, 10 pages.
Office Action issued by the United States Patent and Trademark Office for U.S. Appl. No. 13/899,198, dated Jul. 21, 2014, 20 pages.
Olshevskaya, EV et al., "The Y99C Mutation in Guanylyl Cyclase-Activating Protein 1 Increases Intracellular Ca2 and Causes Photoreceptor Degeneration in Transgenic Mice," J. Neurosci. vol. 24, 2004, pp. 6078-6085.
Pan et al., "Functional expression of a directly light-gated membrane channel in mammalian retinal neurons: A potential strategy for restoring light sensitivity to the retina after photoreceptor degeneration" Investigative Ophthalmology & Visual Science 46:E-Abstract 4631 (2005)—Abstract.
Panda, S. et al., "Illumination of the Melanopsin Signaling Pathway," Science vol. 307, 2005, pp. 600-604.
Qiu, X. et al,"Induction of photosensitivity by heterologous expression of melanopsin," Nature vol. 433, 2005, pp. 745-749.
Reutsky et al. "Patterned Optical Activation of Channelrhodopsin II Expressing Retinal Ganglion Cells." Proc. 3rd Int. IEEE EMBS COnt. Neural Engin. (2007):50-52.
Santos, AH et al., "Preservation of the Inner Retina in Retinitis Pigmentosa," Arch. Ophthalmol. vol. 115, 1997, pp. 511-515.
Sineshchekov, OA et al., "Two rhodopsins mediate phototaxis to low- and high-intensity light in Chlamydomonas reinhardtii," Proc. Natl. Acad. Sci. USA vol. 99, 2002, pp. 8689-8694.
Sung, CH et al., "Rhodopsin mutations in autosomal dominant retinitis pigmentosa," Proc. Natl. Acad. Sci. USA vol. 88, 1991, pp. 6481-6485.
Supplementary European Search Report issued by the European Patent Office for EP 07797340.2, dated Oct. 27, 2010, 7 pages.
Takahashi, M. et al., "Rescue from Photoreceptor Degeneration in the rd Mouse by Human Immunodeficiency Virus Vector-Mediated Gene Transfer," J Virol. vol. 73, 1999, pp. 7812-7816.
Tomita, H. et al., "Channelrhodopsins provide a breakthrough insight into strategies for curing blindness", *Journal of Genetics*,88:409-415 (2009).

(56) References Cited

OTHER PUBLICATIONS

Thyagarajan et al., "Visual Function in Mice with Photoreceptor Degeneration and Transgenic Expression of Channelrhodopsin 2 in Ganglion Cells," J Neurosci 201 0;30:8745-5.

Tomomura, M et al.,"Purification of Purkinje cells by fluorescence-activated cell sorting from transgenic mice that express green fluorescent protein," Eur. J. Neurosci. vol. 14, 2001, pp. 57-63.

Ueda et al., "The mGluR6 5' upstream transgene sequence directs a cell-specific and developmentally regulated expression in retinal cord and ON-type cone bipolar cells," J. Neuroscience 1997;17:3014-23.

Veraart et al., "Vision Rehabilitation in the case of Blindness," Expert Rev. Medical Devices 1(1):139-153 (2004)—Abstract.

Walther et al., "Viral Vectors for Gene Transfer a Review of Their Use in the Treatment of Human Diseases," Drugs vol. 60, 2000, pp. 249-271.

Wässle, H., "Parallel Processing in the Mammalian Retina," Nat. Rev. Neurosci. vol. 5, 2004, pp. 747-757.

Xue, et al, "Multiple-color optical activation, silencing, and desynchronization of neural activity, with single-spike temporal resolution," PLOS One 2007 LNKD-PUBMED:17375185, vol. 2, No. 3, 2007, p. e299.

Zemelman, BV et al., "Selective Photostimulation of Genetically ChARGed Neurons," Neuron vol. 33, 2002, pp. 15-22.

Zhang et al., "Multimodal fast optical interrogation of neural circuitry," Nature vol. 446, 2007, pp. 633-639.

Zrenner et al., "Will Retinal Implants Restore Vision?" Science 2002;295:1 022-5.

Tomita, H. et al. "Channelrhodopsins provide a breakthrough insight into strategies for curing blindness" Journal of Genetics 2009, vol. 88, pp. 409-415.

* cited by examiner

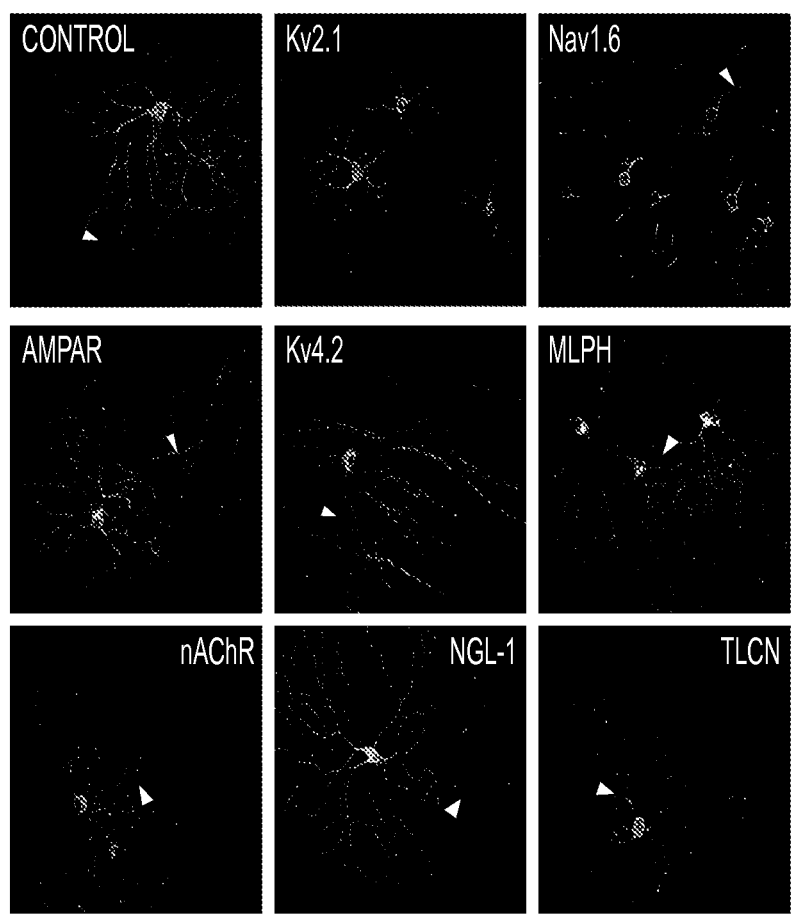

SEQUENCE LISTING

```
<160> NUMBER OF SEQ ID NOS: 47

<210> SEQ ID NO 1
<211> LENGTH: 195
<212> TYPE: DNA
<213> ORGANISM: Artificial Sequence
<220> FEATURE:
<223> OTHER INFORMATION: Kv2.1 Cytoplasmic C-terminus sorting motif

<400> SEQUENCE: 1
cagtctcagc ccatcctgaa cactaaggag atggcccctc agagtaaacc ccctgaggaa      60
ctggaaatga gctccatgcc atctccagtg gctcctctgc cagctaggac cgagggcgtg    120
attgacatga gaagcatgtc tagtatcgat agcttcattt cctgcgccac cgacttcccc    180
gaagctacaa ggttt                                                     195

<210> SEQ ID NO 2
<211> LENGTH: 65
<212> TYPE: PRT
<213> ORGANISM: Artificial Sequence
<220> FEATURE:
<223> OTHER INFORMATION: Kv2.1 Cytoplasmic C-terminus sorting motif

<400> SEQUENCE: 2

Gln Ser Gln Pro Ile Leu Asn Thr Lys Glu Met Ala Pro Gln Ser Lys
1               5                   10                  15

Pro Pro Glu Glu Leu Glu Met Ser Ser Met Pro Ser Pro Val Ala Pro
            20                  25                  30

Leu Pro Ala Arg Thr Glu Gly Val Ile Asp Met Arg Ser Met Ser Ser
        35                  40                  45

Ile Asp Ser Phe Ile Ser Cys Ala Thr Asp Phe Pro Glu Ala Thr Arg
    50                  55                  60

Phe
65

<210> SEQ ID NO 3
<211> LENGTH: 81
<212> TYPE: DNA
<213> ORGANISM: Artificial Sequence
<220> FEATURE:
<223> OTHER INFORMATION: Nav1.6 Ankyrin binding domain sorting motif
```

-continued

<400> SEQUENCE: 3

```
accgtgaggg tgcccatcgc cgtgggcgag agcgacttcg agaacctgaa caccgaggac    60
gtgagcagcg agagcgaccc c                                              81
```

<210> SEQ ID NO 4
<211> LENGTH: 27
<212> TYPE: PRT
<213> ORGANISM: Artificial Sequence
<220> FEATURE:
<223> OTHER INFORMATION: Nav1.6 Ankyrin binding domain sorting motif

<400> SEQUENCE: 4

```
Thr Val Arg Val Pro Ile Ala Val Gly Glu Ser Asp Phe Glu Asn Leu
1               5                   10                  15

Asn Thr Glu Asp Val Ser Ser Glu Ser Asp Pro
            20                  25
```

<210> SEQ ID NO 5
<211> LENGTH: 96
<212> TYPE: DNA
<213> ORGANISM: Artificial Sequence
<220> FEATURE:
<223> OTHER INFORMATION: NLG-1 Cytoplasmic C-terminal sorting motif

<400> SEQUENCE: 5

```
gtggtgctga ggactgcctg ccccctgac tacaccctgg ctatgaggag aagcccagac    60
gatgtgcccc tgatgacccc caacaccatc acaatg                             96
```

<210> SEQ ID NO 6
<211> LENGTH: 32
<212> TYPE: PRT
<213> ORGANISM: Artificial Sequence
<220> FEATURE:
<223> OTHER INFORMATION: NLG-1 Cytoplasmic C-terminal sorting motif

<400> SEQUENCE: 6

```
Val Val Leu Arg Thr Ala Cys Pro Pro Asp Tyr Thr Leu Ala Met Arg
1               5                   10                  15

Arg Ser Pro Asp Asp Val Pro Leu Met Thr Pro Asn Thr Ile Thr Met
            20                  25                  30
```

<210> SEQ ID NO 7
<211> LENGTH: 78
<212> TYPE: DNA
<213> ORGANISM: Artificial Sequence
<220> FEATURE:
<223> OTHER INFORMATION: MLPH Myosin binding domain sorting motif

<400> SEQUENCE: 7

```
agggaccagc tctgaacag caaaaagaaa aagaggctcc tgagcttcag ggacgtggac    60
ttcgaggagg acagcgac                                                 78
```

<210> SEQ ID NO 8
<211> LENGTH: 26
<212> TYPE: PRT
<213> ORGANISM: Artificial Sequence
<220> FEATURE:
<223> OTHER INFORMATION: MLPH Myosin binding domain sorting motif

<400> SEQUENCE: 8

```
Arg Asp Gln Pro Leu Asn Ser Lys Lys Lys Arg Leu Leu Ser Phe
1               5                   10                  15
```

Arg Asp Val Asp Phe Glu Glu Asp Ser Asp
            20                  25

<210> SEQ ID NO 9
<211> LENGTH: 141
<212> TYPE: DNA
<213> ORGANISM: Artificial Sequence
<220> FEATURE:
<223> OTHER INFORMATION: nAchR Tyrosine-Dileucine sorting motif

<400> SEQUENCE: 9
ggcgaggaca aggtgcggcc cgcctgtcag cacaagcctc ggcggtgcag cctggccagc      60
gtggagctga gcgccggcgc cggcccaccc accagcaacg gcaacctgct gtacatcggc     120
ttcagaggcc tggagggcat g                                               141

<210> SEQ ID NO 10
<211> LENGTH: 47
<212> TYPE: PRT
<213> ORGANISM: Artificial Sequence
<220> FEATURE:
<223> OTHER INFORMATION: nAchR Tyrosine-Dileucine sorting motif

<400> SEQUENCE: 10

Gly Glu Asp Lys Val Arg Pro Ala Cys Gln His Lys Pro Arg Arg Cys
1               5                   10                  15

Ala Leu Ala Ser Val Glu Leu Ser Ala Gly Ala Gly Pro Pro Thr Ser
            20                  25                  30

Asn Gly Asn Leu Leu Tyr Ile Gly Phe Arg Gly Leu Glu Gly Met
        35                  40                  45

<210> SEQ ID NO 11
<211> LENGTH: 48
<212> TYPE: DNA
<213> ORGANISM: Artificial Sequence
<220> FEATURE:
<223> OTHER INFORMATION: Kv4.2 Dileucine sorting motif

<400> SEQUENCE: 11
ttcgagcagc agcaccacca cctgctgcac tgcctggaga agaccacc                   48

<210> SEQ ID NO 12
<211> LENGTH: 16
<212> TYPE: PRT
<213> ORGANISM: Artificial Sequence
<220> FEATURE:
<223> OTHER INFORMATION: Kv4.2 Dileucine sorting motif

<400> SEQUENCE: 12

Phe Glu Gln Gln His His His Leu Leu His Cys Leu Glu Lys Thr Thr
1               5                   10                  15

<210> SEQ ID NO 13
<211> LENGTH: 192
<212> TYPE: DNA
<213> ORGANISM: Artificial Sequence
<220> FEATURE:
<223> OTHER INFORMATION: TLCN Phenylalanine-based sorting motif

<400> SEQUENCE: 13
cagagcacag cctgcaaaaa gggcgagtac aacgtgcagg aagctgagag ctctggcgaa      60
gccgtgtgtc tgaacggcgc cggaggcggt gccggcggag ctgccggcgc tgagggtggc     120
cctgaggccg ctggaggtgc cgctgagagc cccgctgagg gcgaagtctt tgccatccag     180

-continued

```
ctgacatctg ct                                                     192

<210> SEQ ID NO 14
<211> LENGTH: 64
<212> TYPE: PRT
<213> ORGANISM: Artificial Sequence
<220> FEATURE:
<223> OTHER INFORMATION: TLCN Phenylalanine-based sorting motif

<400> SEQUENCE: 14

Gln Ser Thr Ala Cys Lys Lys Gly Glu Tyr Asn Val Gln Glu Ala Glu
1               5                   10                  15

Ser Ser Gly Glu Ala Val Cys Leu Asn Gly Ala Gly Gly Gly Ala Gly
            20                  25                  30

Gly Ala Ala Gly Ala Glu Gly Gly Pro Glu Ala Ala Gly Gly Ala Ala
        35                  40                  45

Glu Ser Pro Ala Glu Gly Glu Val Phe Ala Ile Gln Leu Thr Ser Ala
    50                  55                  60

<210> SEQ ID NO 15
<211> LENGTH: 117
<212> TYPE: DNA
<213> ORGANISM: Artificial Sequence
<220> FEATURE:
<223> OTHER INFORMATION: AMPAR Cytoplasmic C-terminal sorting motif

<400> SEQUENCE: 15
gagttctgct acaagagcag gtccgaatct aagagaatga aaggcttttg tctgatcccc      60
cagcagagca tcaacgaggc cattcggacc agtacactgc ctcgcaatag cggagct       117

<210> SEQ ID NO 16
<211> LENGTH: 39
<212> TYPE: PRT
<213> ORGANISM: Artificial Sequence
<220> FEATURE:
<223> OTHER INFORMATION: AMPAR Cytoplasmic C-terminal sorting motif

<400> SEQUENCE: 16

Glu Phe Cys Tyr Lys Ser Arg Ser Glu Ser Lys Arg Met Lys Gly Phe
1               5                   10                  15

Cys Leu Ile Pro Gln Gln Ser Ile Asn Glu Ala Ile Arg Thr Ser Thr
            20                  25                  30

Leu Pro Arg Asn Ser Gly Ala
        35

<210> SEQ ID NO 17
<211> LENGTH: 141
<212> TYPE: DNA
<213> ORGANISM: Artificial Sequence
<220> FEATURE:
<223> OTHER INFORMATION: AAV2 5' ITR

<400> SEQUENCE: 17
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc t                                               141

<210> SEQ ID NO 18
<211> LENGTH: 141
<212> TYPE: DNA
<213> ORGANISM: Artificial Sequence
```

<220> FEATURE:
<223> OTHER INFORMATION: AAV2 3' ITR

<400> SEQUENCE: 18

```
aggaacccct agtgatggag ttggccactc cctctctgcg cgctcgctcg ctcactgagg    60
ccgggcgacc aaaggtcgcc cgacgcccgg gctttgcccg gcggcctca gtgagcgagc    120
gagcgcgcag ctgcctgcag g                                              141
```

<210> SEQ ID NO 19
<400> SEQUENCE: 19
000

<210> SEQ ID NO 20
<400> SEQUENCE: 20
000

<210> SEQ ID NO 21
<211> LENGTH: 945
<212> TYPE: DNA
<213> ORGANISM: Artificial Sequence
<220> FEATURE:
<223> OTHER INFORMATION: ChR2

<400> SEQUENCE: 21

```
atggattatg gaggcgccct gagtgccgtt gggcgcgagc tgctatttgt aacgaaccca    60
gtagtcgtca atggctctgt acttgtgcct gaggaccagt gttactgcgc gggctggatt    120
gagtcgcgtg gcacaaacgg tgcccaaacg cgtcgaacg tgctgcaatg gcttgctgct    180
ggcttctcca tcctactgct tatgttttac gcctaccaaa catggaagtc aacctgcggc    240
tgggaggaga tctatgtgtg cgctatcgag atggtcaagg tgattcttga gttcttcttc    300
gagtttaaga acccgtccat gctgtatcta gccacaggcc accgcgtcca gtggttgcgt    360
tacgccgagt ggcttctcac ctgcccggtc attctcattc acctgtcaaa cctgacgggc    420
ttgtccaacg actacagcag cgcgcactat ggtctgcttg tgtctgatat tggcacaatt    480
gtgtggggcg ccacttccgc tatgccacc ggatacgtca aggtcatctt cttctgcctg    540
ggtctgtgtt atggtgctaa cacgttcttt cacgctgcca aggcctacat cgagggttac    600
cataccgtgc cgaagggccg tgtcgccag gtggtgactg gcatggcttg gctcttcttc    660
gtatcatggg gtatgttccc catcctgttc atcctcggcc cgagggctt cggcgtcctg    720
agcgtgtacg gctccaccgt cggccacacc atcattgacc tgatgtcgaa gaactgctgg    780
ggtctgctcg gccactacct gcgcgtgctg atccacgagc atatcctcat ccacggcgac    840
attcgcaaga ccaccaaatt gaacattggt ggcactgaga ttgaggtcga cgcgtggtg    900
gaggacgagg ccgaggctgg cgcggtcaac aagggcaccg gcaag                    945
```

<210> SEQ ID NO 22
<400> SEQUENCE: 22
000

<210> SEQ ID NO 23
<211> LENGTH: 873
<212> TYPE: DNA
<213> ORGANISM: Artificial Sequence
<220> FEATURE:
<223> OTHER INFORMATION: HaloR

<400> SEQUENCE: 23

```
atgactgaga cattgccacc ggtaacggaa tcggctgttg cgctacaggc ggaggtgacc    60
cagagggagc tgttcgagtt cgttctcaac gaccccctcc tcgccagttc gctgtatatt   120
aatatcgcac tggcagggct gtcgatactg cttttcgtgt tcatgacgcg cggactcgac   180
gacccacggg cgaaactcat cgccgtttcg acgattttgg tgccggtggt ctctatcgcg   240
agctacaccg gccttgcatc ggggctcacc atcagcgtcc tcgagatgcc agccggccac   300
ttcgccgagg ggtcctcggt gatgctcggc ggcgaagagg tagacggcgt cgtgacgatg   360
tggggccgct atctgacgtg ggccctttcg acaccgatga tactgctggc gcttgggctg   420
cttgctggct ctaacgccac gaagctcttt accgccatca ccttcgacat cgcgatgtgt   480
gtcaccggcc tcgcagccgc gctgacgacc tcttcgcacc tgatgcggtg gttctggtac   540
gccatcagtt gtgcgtgttt cctcgtcgtc ctctacatcc tgctcgtcga gtgggcacag   600
gacgccaagg ctgccggtac tgcggatatg ttcaatacgc tgaagctgct gaccgttgtc   660
atgtggctcg gctaccccat cgtgtgggca ctcggcgttg agggcatcgc cgttcttccg   720
gtcggagtca cgtcgtgggg atacagcttc ctcgacatcg tcgcgaagta catcttcgcg   780
ttcctgctgc tcaactacct cacgtcgaac gagagcgtcg tctccggctc gatactcgac   840
gtgccgtccg cgtcgggcac tcccgctgac gac                                873
```

<210> SEQ ID NO 24
<400> SEQUENCE: 24

000

<210> SEQ ID NO 25
<211> LENGTH: 708
<212> TYPE: DNA
<213> ORGANISM: Artificial Sequence
<220> FEATURE:
<223> OTHER INFORMATION: GFP

<400> SEQUENCE: 25

```
aaaggagaag aactcttcac tggagttgtc ccaattcttg ttgaattaga tggtgatgtt    60
aacggccaca gttctctgt cagtggagag ggtgaaggtg atgcaacata cggaaaactt   120
accctgaagt tcatctgcac tactggcaaa ctgcctgttc catggccaac actagtcact   180
actctgtgct atggtgttca atgcttttca agatacccgg atcatatgaa acggcatgac   240
tttttcaaga gtgccatgcc cgaaggttat gtacaggaaa ggaccatctt cttcaaagat   300
gacggcaact acaagacacg tgctgaagtc aagtttgaag gtgataccct tgttaataga   360
atcgagttaa aggtattga cttcaaggaa gatggcaaca ttctgggaca caaattggaa   420
tacaactata actcacacaa tgtatacatc atggcagaca acaaaagaa tggaatcaaa   480
gtgaacttca gacccgcca acattgaa gatggaagcg ttcaactagc agaccattat   540
caacaaaata ctccaattgg cgatggccct gtccttttac cagacaacca ttacctgtcc   600
acacaatctg cccttttcgaa agatcccaac gaaaagagag accacatggt ccttcttgag   660
tttgtaacag ctgctgggat tacacatggc atggatgaac tgtacaac                708
```

<210> SEQ ID NO 26
<211> LENGTH: 972

<212> TYPE: DNA
<213> ORGANISM: Artificial Sequence
<220> FEATURE:
<223> OTHER INFORMATION: CAG promoter

<400> SEQUENCE: 26

```
ctagttatta atagtaatca attacggggt cattagttca tagcccatat atggagttcc      60
gcgttacata acttacggta aatggcccgc ctggctgacc gcccaacgac ccccgcccat     120
tgacgtcaat aatgacgtat gttcccatag taacgccaat agggactttc cattgacgtc    180
aatgggtgga gtatttacgg taaactgccc acttggcagt acatcaagtg tatcatatgc    240
caagtacgcc ccctattgac gtcaatgacg gtaaatggcc cgcctggcat tatgcccagt    300
acatgacctt atgggacttt cctacttggc agtacatcta cgtattagtc atcgctatta    360
ccatgcatgg tcgaggtgag ccccacgttc tgcttcactc tccccatctc ccccccctcc    420
ccacccccaa ttttgtattt atttattttt taattatttt gtgcagcgat ggggggcgggg   480
gggggggggg ggcgcgcgcc aggcggggcg gggcggggcg aggggcgggg cggggcgagg    540
cggagaggtg cggcggcagc caatcagagc ggcgcgctcc gaaagtttcc ttttatggcg    600
aggcggcggc ggcggcggcc ctataaaaag cgaagcgcgc ggcgggcggg agtcgctgcg    660
acgctgcctt cgccccgtgc cccgctccgc cgccgcctcg cgccgcccgc cccggctctg    720
actgaccgcg ttactcccac aggtgagcgg gcgggacggc ccttctcctc cgggctgtaa    780
ttagcgcttg gtttaatgac ggcttgtttc ttttctgtgg ctgcgtgaaa gccttgaggg    840
gctccgggag ggccctttgt gcgggggagg cggctcgggg ctgtccgcgg ggggacggct    900
gccttcgggg gggacgggc agggcgggt tcggcttctg cgtgtgaccg gcggctcta     960
gcagcctctg ct                                                        972
```

<210> SEQ ID NO 27
<211> LENGTH: 597
<212> TYPE: DNA
<213> ORGANISM: Artificial Sequence
<220> FEATURE:
<223> OTHER INFORMATION: Posttranscriptional regulatory element WPRE

<400> SEQUENCE: 27

```
gataatcaac ctctggatta caaaatttgt gaaagattga ctggtattct taactatgtt     60
gctccttta cgctatgtgg atacgctgct ttaatgcctt tgtatcatgc tattgcttcc    120
cgtatggctt tcattttctc ctccttgtat aaatcctggt tgctgtctct ttatgaggag    180
ttgtggcccg ttgtcaggca acgtggcgtg gtgtgcactg tgtttgctga cgcaaccccc    240
actggttggg gcattgccac cacctgtcag ctcctttccg ggactttcgc tttccccctc    300
cctattgcca cggcggaact catcgccgcc tgccttgccc gctgctggac aggggctcgg    360
ctgttgggca ctgacaattc cgtggtgttg tcggggaagc tgacgtcctt ccatggctg    420
ctcgcctgtg ttgccacctg gattctgcgc gggacgtcct tctgctacgt cccttcggcc    480
ctcaatccag cggaccttcc ttcccgcggc ctgctgccgg ctctgcggcc tcttccgcgt    540
cttcgccttc gccctcagac gagtcggatc tccctttggg ccgcctcccc gcctgat     597
```

<210> SEQ ID NO 28
<211> LENGTH: 479
<212> TYPE: DNA
<213> ORGANISM: Artificial Sequence
<220> FEATURE:
<223> OTHER INFORMATION: Polyadenylation sequence

<400> SEQUENCE: 28

```
acgggtggca tccctgtgac ccctccccag tgcctctcct ggccctggaa gttgccactc    60
cagtgcccac cagccttgtc ctaataaaat taagttgcat cattttgtct gactaggtgt   120
ccttctataa tattatgggg tggagggggg tggtatggag caaggggcaa gttgggaaga   180
caacctgtag ggcctgcggg gtctattggg aaccaagctg gagtgcagtg cacaatctt   240
ggctcactgc aatctccgcc tcctgggttc aagcgattct cctgcctcag cctcccgagt   300
tgttgggatt ccaggcatgc atgaccaggc tcagctaatt tttgtttttt tggtagagac   360
ggggtttcac catattggcc aggctggtct ccaactccta atctcaggtg atctacccac   420
cttggcctcc caaattgctg ggattacagg cgtgaaccac tgctcccttc cctgtcctt    479
```

<210> SEQ ID NO 29

<400> SEQUENCE: 29

000

<210> SEQ ID NO 30
<211> LENGTH: 4232
<212> TYPE: DNA
<213> ORGANISM: Artificial Sequence
<220> FEATURE:
<223> OTHER INFORMATION: 5'-ITR-CAG-ChR2-GFP-WPRE-bGHpolyA-ITR- 3'

<400> SEQUENCE: 30

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac taggggttcc tgcggccgca cgcgtgatat cctagttatt aatagtaatc   180
aattacgggg tcattagttc atagcccata tatggagttc cgcgttacat aacttacggt   240
aaatggcccg cctggctgac cgcccaacga ccccgccca ttgacgtcaa taatgacgta   300
tgttcccata gtaacgccaa tagggacttt ccattgacgt caatgggtgg agtatttacg   360
gtaaactgcc cacttggcag tacatcaagt gtatcatatg ccaagtacgc ccctattga    420
cgtcaatgac ggtaaatggc ccgcctggca ttatgcccag tacatgacct tatgggactt   480
tcctacttgg cagtacatct acgtattagt catcgctatt accatggtcatg gtcgaggtga   540
gccccacgtt ctgcttcact ctccccatct cccccccctc ccaccccca attttgtatt    600
tatttatttt ttaattattt tgtgcagcga tgggggcggg ggggggggg gggcgcgcgc    660
caggcggggc ggggcgggc gagggcgggg cggggcgag gcgagaggt gcggcggcag      720
ccaatcagag cggcgcgctc cgaaagtttc cttttatggc gaggcggcgg cggcggcggc   780
cctataaaaa gcgaagcgcg cggcgggcgg gagtcgctgc gacgctgcct tcgccccgtg   840
ccccgctccg ccgccgcctc gcgccgcccg cccggctct gactgaccgc gttactccca    900
caggtgagcg gcgggacgg cccttctcct ccgggctgta attagcgctt ggtttaatga    960
cggcttgttt cttttctgtg gctgcgtgaa agccttgagg ggctccggga gggccctttg   1020
tgcggggga gcggctcggg gctgtccgcg ggggacggc tgccttcggg gggacgggg      1080
cagggcgggg ttcggcttct ggcgtgtgac cggcggctct agcagcctct gctaaccatg   1140
ttcatgcctt cttctttttc ctacagctcc tgggcaacgt gctggttatt gtgctgtctc   1200
atcattttgg caaagaatta agcttgagct cgcgatccgc agccatggat tatgaggcg    1260
ccctgagtgc cgttgggcgc gagctgctat ttgtaacgaa cccagtagtc gtcaatggct   1320
```

```
ctgtacttgt gcctgaggac cagtgttact gcgcgggctg gattgagtcg cgtggcacaa    1380
acggtgccca acggcgtcg aacgtgctgc aatggcttgc tgctggcttc tccatcctac    1440
tgcttatgtt ttacgcctac caaacatgga agtcaacctg cggctgggag agatctatg    1500 tgtgcgctat cgagatggtc aaggtgattc ttgagttctt cttcgagttt aagaacccgt    1560
ccatgctgta tctagccaca ggccaccgcg tccagtggtt gcgttacgcc gagtggcttc    1620
tcacctgccc ggtcattctc attcacctgt caaacctgac gggcttgtcc aacgactaca    1680
gcaggcgcac tatgggtctg cttgtgtctg atattggcac aattgtgtgg ggcgccactt    1740
ccgctatggc caccggatac gtcaaggtca tcttcttctg cctgggtctg tgttatggtg    1800
ctaacacgtt ctttcacgct gccaaggcct acatcgaggg ttaccatacc gtgccgaagg    1860
gccggtgtcg ccaggtggtg actggcatgg cttggctctt cttcgtatca tggggtatgt    1920
tccccatcct gttcatcctc ggccccgagg gcttcggcgt cctgagcgtg tacggctcca    1980
ccgtcggcca caccatcatt gacctgatgt cgaagaactg ctggggtctg ctcggccact    2040
acctgcgcgt gctgatccac gagcatatcc tcatccacgg cgacattcgc aagaccacca    2100
aattgaacat tggtggcact gagattgagg tcgagacgct ggtggaggac gaggccgagg    2160
ctggcgcggt caacaagggc accggcaagg aattcggagg cggaggtgga gctagcaaag    2220
gagaagaact cttcactgga gttgtcccaa ttcttgttga attagatggt gatgttaacg    2280
gccacaagtt ctctgtcagt ggagagggtg aaggtgatgc aacatacgga aaacttaccc    2340
tgaagttcat ctgcactact ggcaaactgc ctgttccatg gccaacacta gtcactactc    2400
tgtgctatgg tgttcaatgc ttttcaagat acccggatca tatgaaacgg catgactttt    2460
tcaagagtgc catgcccgaa ggttatgtac aggaaaggac catcttcttc aaagatgacg    2520
gcaactacaa gacacgtgct gaagtcaagt ttgaaggtga tacccttgtt aatagaatcg    2580
agttaaaagg tattgacttc aaggaagatg gcaacattct gggacacaaa ttggaataca    2640
actataactc acacaatgta tacatcatgg cagacaaaca aaagaatgga atcaaagtga    2700
acttcaagac ccgccacaac attgaagatg gaagcgttca actagcagac cattatcaac    2760
aaaatactcc aattggcgat ggccctgtcc ttttaccaga caaccattac ctgtccacac    2820
aatctgccct ttcgaaagat cccaacgaaa agagagacca catggtcctt cttgagtttg    2880
taacagctgc tgggattaca catggcatgg atgaactgta caactaactc gagtctagac    2940
gtggtaccga taatcaacct ctggattaca aaatttgtga agattgact ggtattctta    3000 actatgttgc tcctttacg ctatgtggat acgctgcttt aatgcctttg tatcatgcta    3060
ttgcttcccg tatggctttc attttctcct ccttgtataa atcctggttg ctgtctcttt    3120
atgaggagtt gtggcccgtt gtcaggcaac gtggcgtggt gtgcactgtg tttgctgacg    3180
caacccccac tggttggggc attgccacca cctgtcagct cctttccggg actttcgctt    3240
tccccctccc tattgccacg gcggaactca tcgccgcctg ccttgcccgc tgctggacag    3300
gggctcggct gttgggcact gacaattccg tggtgttgtc ggggaagctg acgtccttc    3360 catggctgct cgcctgtgtt gccacctgga ttctgcgcgg acgtccttc tgctacgtcc    3420 cttcggccct caatccagcg gaccttcctt cccgcggcct gctgccggct ctgcggcctc    3480
ttccgcgtct tcgccttcgc cctcagacga gtcggatctc cctttgggcc gcctcccgc    3540 ctgatgcggg gatcctctag agtcgagaga tctacgggtg gcatccctgt gacccctccc    3600
cagtgcctct cctggccctg gaagttgcca ctccagtgcc caccagcctt gtcctaataa    3660
aattaagttg catcattttg tctgactagg tgtccttcta taatattatg gggtggaggg    3720
```

```
gggtggtatg gagcaagggg caagttggga agacaacctg tagggcctgc ggggtctatt      3780
gggaaccaag ctggagtgca gtggcacaat cttggctcac tgcaatctcc gcctcctggg      3840
ttcaagcgat tctcctgcct cagcctcccg agttgttggg attccaggca tgcatgacca      3900
ggctcagcta attttgtttt ttttggtaga cacggggttt caccatattg gccaggctgg      3960
tctccaactc ctaatctcag gtgatctacc caccttggcc tcccaaattg ctgggattac      4020
aggcgtgaac cactgctccc ttccctgtcc ttctgatttt gtaggtaacc acgtgcggac      4080
cgagcggccg caggaacccc tagtgatgga gttggccact ccctctctgc gcgctcgctc      4140
gctcactgag gccgggcgac caaaggtcgc ccgacgcccg ggctttgccc gggcggcctc      4200
agtgagcgag cgagcgcgca gctgcctgca gg                                    4232
```

<210> SEQ ID NO 31
<211> LENGTH: 3488
<212> TYPE: DNA
<213> ORGANISM: Artificial Sequence
<220> FEATURE:
<223> OTHER INFORMATION: 5'-ITR-CAG-ChR2-WPRE-bGHpolyA-ITR-3'

<400> SEQUENCE: 31

```
cctgcaggca gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac tagggttcc tgcggccgca cgcgtgatat cctagttatt aatagtaatc       180
aattacgggg tcattagttc atagcccata tatggagttc cgcgttacat aacttacggt       240
aaatggcccg cctggctgac cgcccaacga cccccgccca ttgacgtcaa taatgacgta       300
tgttcccata gtaacgccaa tagggacttt ccattgacgt caatgggtgg agtatttacg       360
gtaaactgcc cacttggcag tacatcaagt gtatcatatg ccaagtacgc cccctattga       420
cgtcaatgac ggtaaatggc ccgcctggca ttatgcccag tacatgacct tatgggactt       480
tcctacttgg cagtacatct acgtattagt catcgctatt accatgcatg gtcgaggtga       540
gccccacgtt ctgcttcact ctccccatct ccccccctc cccacccca atttgtatt         600 tatttatttt ttaattattt tgtgcagcga tggggcggg gggggggggg ggcgcgcgc         660 caggcgggc ggggcgggc gagggcggg gcggggcgag gcggagaggt gcggcggcag         720
ccaatcagag cggcgcgctc cgaaagtttc cttttatggc gaggcggcgg cggcggcggc      780
cctataaaaa gcgaagcgcg cggcgggcgg gagtcgctgc gacgctgcct tcgccccgtg      840
ccccgctccg ccgccgcctc gcgccgcccg ccccggctct gactgaccgc gttactccca      900
caggtgagcg gcgggacgg cccttctcct ccgggctgta attagcgctt ggtttaatga      960
cggcttgttt cttttctgtg gctgcgtgaa agccttgagg ggctccggga gggccctttg     1020 tgcggggga gcggctcggg gctgtccgcg ggggacggc tgccttcggg gggacgggg         1080 cagggcgggg ttcggcttct ggcgtgtgac cggcggctct agcagcctct gctaaccatg     1140
ttcatgcctt cttcttttc ctacagctcc tgggcaacgt gctggttatt gtgctgtctc     1200 atcatttgg caaagaatta agcttgagct cgcgatccgc agccatggat tatgaggcg      1260 ccctgagtgc cgttgggcgc gagctgctat ttgtaacgaa cccagtagtc gtcaatggct     1320
ctgtacttgt gcctgaggac cagtgttact gcgcgggctg gattgagtcg cgtggcacaa     1380
acggtgccca acggcgtcg aacgtgctgc aatggcttgc tgctggcttc tccatcctac     1440
tgcttatgtt ttacgcctac caaacatgga agtcaacctg cggctgggag gagatctatg     1500
```

```
tgtgcgctat cgagatggtc aaggtgattc ttgagttctt cttcgagttt aagaacccgt    1560
ccatgctgta tctagccaca ggccaccgcg tccagtggtt gcgttacgcc gagtggcttc    1620
tcacctgccc ggtcattctc attcacctgt caaacctgac gggcttgtcc aacgactaca    1680
gcaggcgcac tatgggtctg cttgtgtctg atattggcac aattgtgtgg ggcgccactt    1740
ccgctatggc caccggatac gtcaaggtca tcttcttctg cctgggtctg tgttatggtg    1800
ctaacacgtt cttttcacgct gccaaggcct acatcgaggg ttaccatacc gtgccgaagg    1860
gccggtgtcg ccaggtggtg actggcatgg cttggctctt cttcgtatca tggggtatgt    1920
tccccatcct gttcatcctc ggccccgagg gcttcggcgt cctgagcgtg tacggctcca    1980
ccgtcggcca caccatcatt gacctgatgt cgaagaactg ctggggtctg ctcggccact    2040
acctgcgcgt gctgatccac gagcatatcc tcatccacgg cgacattcgc aagaccacca    2100
aattgaacat tggtggcact gagattgagg tcgagacgct ggtggaggac gaggccgagg    2160
ctggcgcggt caacaagggc accggcaagg aattcggagg cggaggtgga gctagctaac    2220
tcgagtctag acgtggtacc ttgactggta ttcttaacta tgttgctcct tttacgctat    2280
gtggatacgc tgctttaatg ccttttgtatc atgctattgc ttcccgtatg gctttcattt    2340
tctcctcctt gtataaatcc tggttgctgt ctctttatga ggagttgtgg cccgttgtca    2400
ggcaacgtgg cgtggtgtgc actgtgtttg ctgacgcaac ccccactggt tggggcattg    2460
ccaccacctg tcagctcctt tccgggactt tcgctttccc cctccctatt gccacggcgg    2520
aactcatcgc cgcctgcctt gcccgctgct ggacaggggc tcggctgttg ggcactgaca    2580
attccgtggt gttgtcgggg aagctgacgt ccttttccatg gctgctcgcc tgtgttgcca    2640
cctggattct gcgcgggacg tccttctgct acgtcccttc ggccctcaat ccagcggacc    2700
ttccttcccg cggcctgctg ccggctctgc ggcctcttcc gcgtcttcgc cttcgccctc    2760
agacgagtcg gatctccctt gggccgcct ccccgcctga tgcgggatc ctctagagtc    2820 gagagatcta cgggtggcat ccctgtgacc cctccccagt gcctctcctg gccctggaag    2880
ttgccactcc agtgcccacc agccttgtcc taataaaatt aagttgcatc attttgtctg    2940
actaggtgtc cttctataat attatggggt ggaggggggt ggtatggagc aaggggcaag    3000
ttgggaagac aacctgtagg gcctgcgggg tctattggga accaagctgg agtgcagtgg    3060
cacaatcttg gctcactgca atctccgcct cctgggttca agcgattctc ctgcctcagc    3120
ctcccgagtt gttgggattc caggcatgca tgaccaggct cagctaattt tgttttttt    3180 ggtagagacg gggtttcacc atattggcca ggctggtctc caactcctaa tctcaggtga    3240
tctacccacc ttggcctccc aaattgctgg gattacaggc gtgaaccact gctcccttcc    3300
ctgtccttct gattttgtag gtaaccacgt gcggaccgag cggccgcagg aacccctagt    3360
gatggagttg gccactccct ctctgcgcgc tcgctcgctc actgaggccg ggcgaccaaa    3420
ggtcgcccga cgcccgggct ttgcccgggc ggcctcagtg agcgagcgag cgcgcagctg    3480
cctgcagg                                                            3488
```

<210> SEQ ID NO 32
<211> LENGTH: 4427
<212> TYPE: DNA
<213> ORGANISM: Artificial Sequence
<220> FEATURE:
<223> OTHER INFORMATION: 5'- ITR-CAG-ChR2-GFP-{Kv2.1 Motif}-WPRE-
      bGHpolyA-ITR- 3'

<400> SEQUENCE: 32

| | |
|---|---|
| cctgcaggca gctgcgcgct cgctcgctca ctgaggccgc ccgggcaaag cccgggcgtc | 60 |
| gggcgaccgg tggtcgcccg gcctcagtga gcgagcgagc gcgcagagag ggagtggcca | 120 |
| actccatcac taggggttcc tgcggccgca cgcgtgatat cctagttatt aatagtaatc | 180 |
| aattacgggt tcattagttc atagcccata tatggagttc cgcgttacat aacttacggt | 240 |
| aaatggcccg cctggctgac cgcccaacga ccccccgccca ttgacgtcaa taatgacgta | 300 |
| tgttcccata gtaacgccaa tagggacttt ccattgacgt caatgggtgg agtatttacg | 360 |
| gtaaactgcc cacttggcag tacatcaagt gtatcatatg ccaagtacgc cccctattga | 420 |
| cgtcaatgac ggtaaatggc ccgcctggca ttatgcccag tacatgacct tatgggactt | 480 |
| tcctacttgg cagtacatct acgtattagt catcgctatt accatgcatg gtcgaggtga | 540 |
| gccccacgtt ctgcttcact ctccccatct cccccccctc cccaccccca attttgtatt | 600 |
| tatttatttt ttaattattt tgtgcagcga tgggggcggg ggggggggggg gggcgcgcgc | 660 |
| caggcgggc ggggcgggc gaggggcggg gcggggcgag gcggagaggt gcggcggcag | 720 |
| ccaatcagag cggcgcgctc cgaaagtttc cttttatggc gaggcggcgg cggcggcggc | 780 |
| cctataaaaa gcgaagcgcg cggcgggcgg gagtcgctgc gacgctgcct tcgcccccgtg | 840 |
| ccccgctccg ccgccgcctc gcgccgcccg ccccggctct gactgaccgc gttactccca | 900 |
| caggtgagcg gcgggacgg cccttctcct ccgggctgta attagcgctt ggtttaatga | 960 |
| cggcttgttt cttttctgtg gctgcgtgaa agccttgagg ggctccggga gggcccttg | 1020 |
| tgcgggggga gcggctcggg gctgtccgcg gggggacggc tgccttcggg ggggacgggg | 1080 |
| cagggcgggg ttcggcttct ggcgtgtgac cggcggctct agcagcctct gctaaccatg | 1140 |
| ttcatgcctt cttctttttc ctacagctcc tgggcaacgt gctggttatt gtgctgtctc | 1200 |
| atcattttgg caaagaatta agcttgagct cgcgatccgc agccatggat tatggaggcg | 1260 |
| ccctgagtgc cgttgggcgc gagctgctat ttgtaacgaa cccagtagtc gtcaatggct | 1320 |
| ctgtacttgt gcctgaggac cagtgttact gcgcgggctg gattgagtcg cgtggcacaa | 1380 |
| acggtgccca aacggcgtcg aacgtgctgc aatggcttgc tgctggcttc tccatcctac | 1440 |
| tgcttatgtt ttacgcctac caaacatgga agtcaacctg cggctgggag gagatctatg | 1500 |
| tgtgcgctat cgagatggtc aaggtgattc ttgagttctt cttcgagttt aagaacccgt | 1560 |
| ccatgctgta tctagccaca ggccaccgcg tccagtggtt gcgttacgcc gagtggcttc | 1620 |
| tcacctgccc ggtcattctc attcacctgt caaacctgac gggcttgtcc aacgactaca | 1680 |
| gcaggcgcac tatgggtctg cttgtgtctg atattggcac aattgtgtgg ggcgccactt | 1740 |
| ccgctatggc caccggatac gtcaaggtca tcttcttctg cctgggtctg tgttatggtg | 1800 |
| ctaacacgtt ctttcacgct gccaaggcct acatcgaggg ttaccatacc gtgccgaagg | 1860 |
| gccggtgtcg ccaggtggtg actggcatgg cttggctctt cttcgtatca tggggtatgt | 1920 |
| tccccatcct gttcatcctc ggccccgagg gcttcggcgt cctgagcgtg tacggctcca | 1980 |
| ccgtcggcca caccatcatt gacctgatgt cgaagaactg ctgggtctg ctcggccact | 2040 |
| acctgcgcgt gctgatccac gagcatatcc tcatccacgg cgacattcgc aagaccacca | 2100 |
| aattgaacat tggtggcact gagattgagg tcgagacgct ggtggaggac gaggccgagg | 2160 |
| ctggcgcggt caacaagggc accggcaagg aattcggagg cggaggtgga gctagcaaag | 2220 |
| gagaagaact cttcactgga gttgtcccaa ttcttgttga attagatggt gatgttaacg | 2280 |
| gccacaagtt ctctgtcagt ggagagggtg aaggtgatgc aacatacgga aaacttaccc | 2340 |
| tgaagttcat ctgcactact ggcaaactgc ctgttccatg gccaacacta gtcactactc | 2400 |

```
tgtgctatgg tgttcaatgc ttttcaagat acccggatca tatgaaacgg catgactttt    2460
tcaagagtgc catgcccgaa ggttatgtac aggaaaggac catcttcttc aaagatgacg    2520
gcaactacaa gacacgtgct gaagtcaagt ttgaaggtga tacccttgtt aatagaatcg    2580
agttaaaagg tattgacttc aaggaagatg gcaacattct gggacacaaa ttggaataca    2640
actataactc acacaatgta tacatcatgg cagacaaaca aaagaatgga atcaaagtga    2700
acttcaagac ccgccacaac attgaagatg gaagcgttca actagcagac cattatcaac    2760
aaaatactcc aattggcgat ggccctgtcc ttttaccaga caaccattac ctgtccacac    2820
aatctgccct ttcgaaagat cccaacgaaa agagagacca catggtcctt cttgagtttg    2880
taacagctgc tgggattaca catggcatgg atgaactgta caaccagtct cagcccatcc    2940
tgaacactaa ggagatggcc cctcagagta accccctga ggaactggaa atgagctcca    3000
tgccatctcc agtggctcct ctgccagcta ggaccgaggg cgtgattgac atgagaagca    3060
tgtctagtat cgatagcttc atttcctgcg ccaccgactt ccccgaagct acaaggtttt    3120
aactcgagtc tagacgtggt accgataatc aacctctgga ttacaaaatt tgtgaaagat    3180
tgactggtat tcttaactat gttgctcctt ttacgctatg tggatacgct gctttaatgc    3240
ctttgtatca tgctattgct tcccgtatgg ctttcatttt ctcctccttg tataaatcct    3300
ggttgctgtc tctttatgag gagttgtggc ccgttgtcag gcaacgtggc gtggtgtgca    3360
ctgtgtttgc tgacgcaacc cccactggtt ggggcattgc caccacctgt cagctccttt    3420
ccgggacttt cgctttcccc ctccctattg ccacggcgga actcatcgcc gcctgccttg    3480
cccgctgctg gacaggggct cggctgttgg gcactgacaa ttccgtggtg ttgtcgggga    3540
agctgacgtc ctttccatgg ctgctcgcct gtgttgccac ctggattctg cgcgggacgt    3600
ccttctgcta cgtcccttcg gccctcaatc cagcggacct tccttcccgc ggcctgctgc    3660
cggctctgcg gcctcttccg cgtcttcgcc ttcgccctca gacgagtcgg atctcccttt    3720
gggccgcctc cccgcctgat gcggggatcc tctagagtcg agagatctac gggtggcatc    3780
cctgtgaccc ctccccagtg cctctcctgg cctggaagt tgccactcca gtgcccacca    3840
gccttgtcct aataaaatta agttgcatca ttttgtctga ctaggtgtcc ttctataata    3900
ttatggggtg gaggggggtg gtatggagca aggggcaagt tgggaagaca acctgtaggg    3960 cctgcgggt ctattgggaa ccaagctgga gtgcagtggc acaatcttgg ctcactgcaa    4020
tctccgcctc ctgggttcaa gcgattctcc tgcctcagcc tcccgagttg ttgggattcc    4080
aggcatgcat gaccaggctc agctaatttt tgtttttttg gtagagacgg ggtttcacca    4140
tattggccag gctggtctcc aactcctaat ctcaggtgat ctacccacct tggcctccca    4200
aattgctggg attacaggcg tgaaccactg ctcccttccc tgtccttctg attttgtagg    4260
taaccacgtg cggaccgagc ggccgcagga acccctagtg atggagttgg ccactccctc    4320
tctgcgcgct cgctcgctca ctgaggccgg gcgaccaaag gtcgcccgac gcccgggctt    4380
tgcccgggcg gcctcagtga gcgagcgagc gcgcagctgc ctgcagg                  4427
```

<210> SEQ ID NO 33
<211> LENGTH: 3719
<212> TYPE: DNA
<213> ORGANISM: Artificial Sequence
<220> FEATURE:
<223> OTHER INFORMATION: 5'-ITR-CAG-ChR2-{Kv2.1 Motif}-WPRE-
      bGHpolyA-ITR- 3'

<400> SEQUENCE: 33

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac taggggttcc tgcggccgca cgcgtgatat cctagttatt aatagtaatc   180
aattacgggg tcattagttc atagcccata tatggagttc cgcgttacat aacttacggt   240
aaatggcccg cctggctgac cgcccaacga ccccccgccca ttgacgtcaa taatgacgta   300
tgttcccata gtaacgccaa tagggacttt ccattgacgt caatgggtgg agtatttacg   360
gtaaactgcc cacttggcag tacatcaagt gtatcatatg ccaagtacgc ccctattga    420
cgtcaatgac ggtaaatggc ccgcctggca ttatgcccag tacatgacct tatgggactt   480
tcctacttgg cagtacatct acgtattagt catcgctatt accatgcatg gtcgaggtga   540
gccccacgtt ctgcttcact ctccccatct ccccccctc cccaccccca attttgtatt    600
tatttatttt ttaattattt tgtgcagcga tgggggcggg ggggggggg gggcgcgcgc    660
caggcgggc ggggcgggc gagggcggg gcggggcgag gcgagaggt gcggcggcag       720
ccaatcagag cggcgcgctc cgaaagtttc cttttatggc gaggcggcgg cggcggcggc   780
cctataaaaa gcgaagcgcg cggcgggcgg gagtcgctgc gacgctgcct cgccccgtg    840
ccccgctccg ccgccgcctc gcgccgcccg ccccggctct gactgaccgc gttactccca   900
caggtgagcg ggcgggacgg cccttctcct ccgggctgta attagcgctt ggtttaatga   960
cggcttgttt cttttctgtg gctgcgtgaa agccttgagg ggctccggga gggccctttg  1020
tgcggggga gcggctcggg gctgtccgcg ggggacggc tgccttcggg ggggacgggg    1080
cagggcgggg ttcggcttct ggcgtgtgac cggcggctct agcagcctct gctaaccatg  1140
ttcatgcctt cttcttttc ctacagctcc tgggcaacgt gctggttatt gtgctgtctc   1200
atcatttttgg caaagaatta agcttgagct cgcgatccgc agccatggat tatggaggcg  1260
ccctgagtgc cgttgggcgc gagctgctat ttgtaacgaa cccagtagtc gtcaatggct  1320
ctgtacttgt gcctgaggac cagtgttact gcgcgggctg gattgagtcg cgtggcacaa  1380
acggtgccca acggcgtcg aacgtgctgc aatggcttgc tgctggcttc tccatcctac   1440
tgcttatgtt ttacgcctac caaacatgga agtcaacctg cggctgggag gagatctatg  1500
tgtgcgctat cgagatggtc aaggtgattc ttgagttctt cttcgagttt aagaacccgt  1560
ccatgctgta tctagccaca ggccaccgcg tccagtggtt gcgttacgcc gagtggcttc  1620
tcacctgccc ggtcattctc attcacctgt caaacctgac gggcttgtcc aacgactaca  1680
gcaggcgcac tatgggtctg cttgtgtctg atattggcac aattgtgtgg ggcgccactt  1740
ccgctatggc caccggatac gtcaaggtca tcttcttctg cctgggtctg tgttatggtg  1800
ctaacacgtt ctttcacgct gccaaggcct acatcgaggg ttaccatacc gtgccgaagg  1860
gccggtgtcg ccaggtggtg actggcatgg cttggctctt cttcgtatca tggggtatgt  1920
tccccatcct gttcatcctc ggccccgagg gcttcggcgt cctgagcgtg tacggctcca  1980
ccgtcggcca caccatcatt gacctgatgt cgaagaactg ctgggtctg ctcggccact   2040
acctgcgcgt gctgatccac gagcatatcc tcatccacgg cgacattcgc aagaccacca   2100
aattgaacat tggtggcact gagattgagg tcgagacgct ggtggaggac gaggccgagg   2160
ctggcgcgt caacaagggc accggcaagg aattcggagg cggaggtgga gctagccagt   2220
ctcagcccat cctgaacact aaggagatgg ccccctcagag taaaccccct gaggaactgg   2280
aaatgagctc catgccatct ccagtggctc ctctgccagc taggaccgag ggcgtgattg    2340
```

| | |
|---|---|
| acatgagaag catgtctagt atcgatagct tcatttcctg cgccaccgac ttccccgaag | 2400 |
| ctacaaggtt ttaactcgag tctagacgtg gtaccgataa tcaacctctg gattacaaaa | 2460 |
| tttgtgaaag attgactggt attcttaact atgttgctcc ttttacgcta tgtggatacg | 2520 |
| ctgctttaat gcctttgtat catgctattg cttcccgtat ggctttcatt ttctcctcct | 2580 |
| tgtataaatc ctggttgctg tctctttatg aggagttgtg gcccgttgtc aggcaacgtg | 2640 |
| gcgtggtgtg cactgtgttt gctgacgcaa ccccccactgg ttggggcatt gccaccacct | 2700 |
| gtcagctcct ttccgggact ttcgctttcc ccctccctat tgccacggcg gaactcatcg | 2760 |
| ccgcctgcct tgcccgctgc tggacagggg ctcggctgtt gggcactgac aattccgtgg | 2820 |
| tgttgtcggg gaagctgacg tccttttccat ggctgctcgc ctgtgttgcc acctggattc | 2880 |
| tgcgcgggac gtccttctgc tacgtccctt cggccctcaa tccagcggac cttccttccc | 2940 |
| gcggcctgct gccggctctg cggcctcttc cgcgtcttcg ccttcgccct cagacgagtc | 3000 |
| ggatctccct ttgggccgcc tccccgcctg atgcggggat cctctagagt cgagagatct | 3060 |
| acgggtggca tccctgtgac ccctccccag tgcctctcct ggccctggaa gttgccactc | 3120 |
| cagtgcccac cagccttgtc ctaataaaat taagttgcat cattttgtct gactaggtgt | 3180 |
| ccttctataa tattatgggg tggaggggggg tggtatggag caaggggcaa gttgggaaga | 3240 |
| caacctgtag ggcctgcggg gtctattggg aaccaagctg gagtgcagtg gcacaatctt | 3300 |
| ggctcactgc aatctccgcc tcctgggttc aagcgattct cctgcctcag cctcccgagt | 3360 |
| tgttgggatt ccaggcatgc atgaccaggc tcagctaatt tttgtttttt tggtagagac | 3420 |
| ggggtttcac catattggcc aggctggtct ccaactccta atctcaggtg atctacccac | 3480 |
| cttggcctcc caaattgctg ggattacagg cgtgaaccac tgctcccttc cctgtccttc | 3540 |
| tgatttgta ggtaaccacg tgcggaccga gcggccgcag gaaccccttag tgatagagtt | 3600 |
| ggccactccc tctctgcgcg ctcgctcgct cactgaggcc gggcgaccaa aagtcgcccg | 3660 |
| acgcccgggc tttgcccggg cggcctcagt gagcgagcga gcgcgcagct gcctgcagg | 3719 |

<210> SEQ ID NO 34
<211> LENGTH: 4313
<212> TYPE: DNA
<213> ORGANISM: Artificial Sequence
<220> FEATURE:
<223> OTHER INFORMATION: 5' -ITR-CAG-ChR2-GFP-{Nav1.6 Motif}-WPRE-
bGHpolyA-ITR- 3'

<400> SEQUENCE: 34

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtgatat cctagttatt aatagtaatc | 180 |
| aattacgggg tcattagttc atagcccata tatggagttc cgcgttacat aacttacggt | 240 |
| aaatggcccg cctggctgac cgcccaacga ccccgccca ttgacgtcaa taatgacgta | 300 |
| tgttcccata gtaacgccaa tagggacttt ccattgacgt caatgggtgg agtatttacg | 360 |
| gtaaactgcc cacttggcag tacatcaagt gtatcatatg ccaagtacgc cccctattga | 420 |
| cgtcaatgac ggtaaatggc ccgcctggca ttatgcccag tacatgacct tatggactt | 480 |
| tcctacttgg cagtacatct acgtattagt catcgctatt accatgcatg gtcgaggtga | 540 |
| gccccacgtt ctgcttcact ctccccatct ccccccctc cccacccca attttgtatt | 600 |
| tatttatttt ttaattattt tgtgcagcga tggggcgggg gggggggggg gggcgcgcgc | 660 |

```
caggcggggc ggggcggggc gaggggcggg gcggggcgag gcggagaggt gcggcggcag    720
ccaatcagag cggcgcgctc cgaaagtttc cttttatggc gaggcggcgg cggcggcggc    780
cctataaaaa gcgaagcgcg cggcgggcgg gagtcgctgc gacgctgcct tcgcccgtg    840
ccccgctccg ccgccgcctc gcgccgcccg ccccggctct gactgaccgc gttactccca    900
caggtgagcg ggcgggacgg cccttctcct ccgggctgta attagcgctt ggtttaatga    960
cggcttgttt cttttctgtg gctgcgtgaa agccttgagg ggctccggga gggccctttg   1020
tgcgggggga gcggctcggg gctgtccgcg ggggacggc tgccttcggg ggggacgggg   1080
cagggcgggg ttcggcttct ggcgtgtgac cggcggctct agcagcctct gctaaccatg   1140
ttcatgcctt cttcttttc ctacagctcc tgggcaacgt gctggttatt gtgctgtctc    1200
atcattttgg caaagaatta agcttgagct cgcgatccgc agccatggat tatgaggcg    1260
ccctgagtgc cgttgggcgc gagctgctat ttgtaacgaa cccagtagtc gtcaatggct    1320
ctgtacttgt gcctgaggac cagtgttact gcgcgggctg gattgagtcg cgtggcacaa    1380
acggtgccca acggcgtcg aacgtgctgc aatggcttgc tgctggcttc tccatcctac    1440
tgcttatgtt ttacgcctac caaacatgga agtcaacctg cggctgggag gagatctatg    1500
tgtgcgctat cgagatggtc aaggtgattc ttgagttctt cttcgagttt aagaacccgt    1560
ccatgctgta tctagccaca ggccaccgcg tccagtggtt gcgttacgcc gagtggcttc    1620
tcacctgccc ggtcattctc attcacctgt caaacctgac gggcttgtcc aacgactaca    1680
gcaggcgcac tatgggtctg cttgtgtctg atattggcac aattgtgtgg ggcgccactt    1740
ccgctatggc caccggatac gtcaaggtca tcttcttctg cctgggtctg tgttatggtg    1800
ctaacacgtt ctttcacgct gccaaggcct acatcgaggg ttaccatacc gtgccgaagg    1860
gccggtgtcg ccaggtggtg actggcatgg cttggctctt cttcgtatca tggggtatgt    1920
tccccatcct gttcatcctc ggccccgagg gcttcggcgt cctgagcgtg tacggctcca    1980
ccgtcggcca caccatcatt gacctgatgt cgaagaactg ctggggtctg ctcggccact    2040
acctgcgcgt gctgatccac gagcatatcc tcatccacgg cgacattcgc aagaccacca    2100
aattgaacat tggtggcact gagattgagg tcgagacgct ggtggaggac gaggccgagg    2160
ctggcgcggt caacaagggc accggcaagg aattcggagg cggaggtgga gctagcaaag    2220
gagaagaact cttcactgga gttgtcccaa ttcttgttga attagatggt gatgttaacg    2280
gccacaagtt ctctgtcagt ggagagggtg aaggtgatgc aacatacgga aaacttaccc    2340
tgaagttcat ctgcactact ggcaaactgc ctgttccatg gccaacacta gtcactactc    2400
tgtgctatgg tgttcaatgc ttttcaagat acccggatca tatgaaacgg catgactttt    2460
tcaagagtgc catgcccgaa ggttatgtac aggaaaggac catcttcttc aaagatgacg    2520
gcaactacaa gacacgtgct gaagtcaagt ttgaaggtga taccttgtt aatagaatcg    2580
agttaaaagg tattgacttc aaggaagatg gcaacattct gggacacaaa ttggaataca    2640
actataactc acacaatgta tacatcatgg cagacaaaca aaagaatgga atcaaagtga    2700
acttcaagac ccgccacaac attgaagatg aagcgttca actagcagac cattatcaac    2760
aaaatactcc aattggcgat ggccctgtcc ttttaccaga caaccattac ctgtccacac    2820
aatctgccct ttcgaaagat cccaacgaaa agagagacca catggtcctt cttgagtttg    2880
taacagctgc tgggattaca catggcatgg atgaactgta caacaccgtg agggtgccca    2940
tcgccgtggg cgagagcgac ttcgagaacc tgaacaccga ggacgtgagc agcgagagcc    3000
accctaact cgagtctaga cgtggtaccg ataatcaacc tctggattac aaaatttgtg    3060
```

```
aaagattgac tggtattctt aactatgttg ctccttttac gctatgtgga tacgctgctt    3120
taatgccttt gtatcatgct attgcttccc gtatggcttt cattttctcc tccttgtata    3180
aatcctggtt gctgtctctt tatgaggagt tgtggcccgt tgtcaggcaa cgtggcgtgg    3240
tgtgcactgt gtttgctgac gcaaccccca ctggttgggg cattgccacc acctgtcagc    3300
tcctttccgg gactttcgct ttccccctcc ctattgccac ggcggaactc atcgccgcct    3360
gccttgcccg ctgctggaca ggggctcggc tgttgggcac tgacaattcc gtggtgttgt    3420
cggggaagct gacgtccttt ccatggctgc tcgcctgtgt tgccacctgg attctgcgcg    3480
ggacgtcctt ctgctacgtc ccttcggccc tcaatccagc ggaccttcct tcccgcggcc    3540
tgctgccggc tctgcggcct cttccgcgtc ttcgccttcg ccctcagacg agtcggatct    3600 cccttgggc cgcctcccg cctgatgcgg ggatcctcta gagtcgagag atctacgggt    3660
ggcatccctg tgacccctcc ccagtgcctc tcctggccct ggaagttgcc actccagtgc    3720
ccaccagcct tgtcctaata aaattaagtt gcatcatttt gtctgactag gtgtccttct    3780
ataatattat ggggtggagg ggggtggtat ggagcaaggg gcaagttggg aagacaacct    3840
gtagggcctg cggggtctat tgggaaccaa gctggagtgc agtggcacaa tcttggctca    3900
ctgcaatctc cgcctcctgg gttcaagcga ttctcctgcc tcagcctccc gagttgttgg    3960
gattccaggc atgcatgacc aggctcagct aattttgtt ttttttggtag agacggggtt    4020 tcaccatatt ggccaggctg gtctccaact cctaatctca ggtgatctac ccaccttggc    4080
ctcccaaatt gctgggatta caggcgtgaa ccactgctcc cttccctgtc cttctgattt    4140
tgtaggtaac cacgtgcgga ccgagcggcc gcaggaaccc ctagtgatgg agttggccac    4200
tccctctctg cgcgctcgct cgctcactga ggccgggcga ccaaaggtcg cccgacgccc    4260
gggctttgcc cggcggcct cagtgagcga gcagcgcgc agctgcctgc agg              4313
```

<210> SEQ ID NO 35
<211> LENGTH: 3605
<212> TYPE: DNA
<213> ORGANISM: Artificial Sequence
<220> FEATURE:
<223> OTHER INFORMATION: 5' -ITR-CAG-ChR2-{Nav1.6Motif}-WPRE-
      bGHpolyA-ITR- 3'

<400> SEQUENCE: 35

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggccgca cgcgtgatat cctagttatt aatagtaatc     180
aattacgggg tcattagttc atagcccata tatggagttc cgcgttacat aacttacggt     240
aaatggcccg cctggctgac cgcccaacga ccccgccca ttgacgtcaa taatgacgta     300
tgttcccata gtaacgccaa tagggacttt ccattgacgt caatgggtgg agtatttacg     360
gtaaactgcc cacttggcag tacatcaagt gtatcatatg ccaagtacgc cccctattga     420
cgtcaatgac ggtaaatggc ccgcctggca ttatgcccag tacatgacct tatgggactt     480
tcctacttgg cagtacatct acgtattagt catcgctatt accatgcatg gtcgaggtga     540
gccccacgtt ctgcttcact ctccccatct ccccccctc cccacccca attttgtatt     600 tatttatttt ttaattattt tgtgcagcga tgggggcggg ggggggggg gggcgcgcgc     660 caggcggggc gggcggggc gagggcgggg cggggcgag gcgagaggt gcggcggcag        720 ccaatcagag cggcgcgctc cgaaagtttc cttttatggc gaggcggcgg cggcggcggc      780
```

```
cctataaaaa gcgaagcgcg cggcgggcgg gagtcgctgc gacgctgcct tcgccccgtg    840
ccccgctccg ccgccgcctc gcgccgcccg ccccggctct gactgaccgc gttactccca    900
caggtgagcg ggcgggacgg cccttctcct ccgggctgta attagcgctt ggtttaatga    960
cggcttgttt cttttctgtg gctgcgtgaa agccttgagg ggctccggga gggccctttg   1020
tgcgggggga gcggctcggg gctgtccgcg gggggacggc tgccttcggg ggggacgggg   1080
cagggcgggg ttcggcttct ggcgtgtgac cggcggctct agcagcctct gctaaccatg   1140
ttcatgcctt cttcttttc ctacagctcc tgggcaacgt gctggttatt gtgctgtctc   1200
atcattttgg caaagaatta agcttgagct cgcgatccgc agccatggat tatggaggcg   1260
ccctgagtgc cgttgggcgc gagctgctat ttgtaacgaa cccagtagtc gtcaatggct   1320
ctgtacttgt gcctgaggac cagtgttact gcgcgggctg gattgagtcg cgtggcacaa   1380
acggtgccca acggcgtcg aacgtgctgc aatggcttgc tgctggcttc tccatcctac   1440
tgcttatgtt ttacgcctac caaacatgga agtcaacctg cggctgggag agatctatg    1500 tgtgcgctat cgagatggtc aaggtgattc ttgagttctt cttcgagttt aagaacccgt   1560
ccatgctgta tctagccaca ggccaccgcg tccagtggtt gcgttacgcc gagtggcttc   1620
tcacctgccc ggtcattctc attcacctgt caaacctgac gggcttgtcc aacgactaca   1680
gcaggcgcac tatgggtctg cttgtgtctg atattggcac aattgtgtgg ggcgccactt   1740
ccgctatggc caccggatac gtcaaggtca tcttcttctg cctgggtctg tgttatggtg   1800
ctaacacgtt ctttcacgct gccaaggcct acatcgaggg ttaccatacc gtgccgaagg   1860
gccggtgtcg ccaggtggtg actggcatgg cttggctctt cttcgtatca tggggtatgt   1920
tccccatcct gttcatcctc ggccccgagg gcttcggcgt cctgagcgtg tacggctcca   1980
ccgtcggcca caccatcatt gacctgatgt cgaagaactg ctggggtctg ctcggccact   2040
acctgcgcgt gctgatccac gagcatatcc tcatccacgg cgacattcgc aagaccacca   2100
aattgaacat tggtggcact gagattgagg tcgagacgct ggtggaggac gaggccgagg   2160
ctggcgcggt caacaagggc accggcaagg aattcggagg cggaggtgga gctagcaccg   2220
tgagggtgcc catcgccgtg ggcgagagcg acttcgagaa cctgaacacc gaggacgtga   2280
gcagcgagag cgaccccctaa ctcgagtcta gacgtggtac cgataatcaa cctctggatt   2340
acaaaatttg tgaaagattg actggtattc ttaactatgt tgctcctttt acgctatgtg   2400
gatacgctgc tttaatgcct ttgtatcatg ctattgcttc ccgtatggct ttcattttct   2460
cctccttgta taaatcctgg ttgctgtctc tttatgagga gttgtggccc gttgtcaggc   2520
aacgtggcgt ggtgtgcact gtgtttgctg acgcaacccc cactggttgg ggcattgcca   2580
ccacctgtca gctcctttcc gggactttcg ctttccccct ccctattgcc acggcggaac   2640
tcatcgccgc ctgccttgcc cgctgctgga caggggctcg gctgttgggc actgacaatt   2700
ccgtggtgtt gtcggggaag ctgacgtcct ttccatggct gctcgcctgt gttgccacct   2760
ggattctgcg cgggacgtcc ttctgctacg tcccttcggc cctcaatcca gcggaccttc   2820
cttcccgcgg cctgctgccg gctctgcggc ctcttccgcg tcttcgcctt cgccctcaga   2880
cgagtcggat ctccctttgg gccgcctccc cgcctgatgc ggggatcctc tagagtcgag   2940
agatctacgg gtggcatccc tgtgacccct ccccagtgcc tctcctggcc ctggaagttg   3000
ccactccagt gcccaccagc cttgtcctaa taaaattaag ttgcatcatt ttgtctgact   3060
aggtgtcctt ctataatatt atgggtggga ggggggtggt atggagcaag gggcaagttg   3120
```

-continued

```
ggaagacaac ctgtagggcc tgcggggtct attgggaacc aagctggagt gcagtggcac    3180
aatcttggct cactgcaatc tccgcctcct gggttcaagc gattctcctg cctcagcctc    3240
ccgagttgtt gggattccag gcatgcatga ccaggctcag ctaattttg ttttttttggt    3300 agagacgggg tttcaccata ttggccaggc tggtctccaa ctcctaatct caggtgatct    3360
acccaccttg gcctcccaaa ttgctgggat tacaggcgtg aaccactgct cccttccctg    3420
tccttctgat tttgtaggta accacgtgcg gaccgagcgg ccgcaggaac ccctagtgat    3480
ggagttggcc actccctctc tgcgcgctcg ctcgctcact gaggccgggc gaccaaaggt    3540
cgcccgacgc ccgggctttg cccggcggc ctcagtgagc gagcgagcgc gcagctgcct    3600
gcagg                                                               3605
```

<210> SEQ ID NO 36
<211> LENGTH: 4328
<212> TYPE: DNA
<213> ORGANISM: Artificial Sequence
<220> FEATURE:
<223> OTHER INFORMATION: 5'- ITR-CAG-ChR2-GFP-{NLG1 Motif}-WPRE-bGHpolyA-ITR- 3'

<400> SEQUENCE: 36

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtgatat cctagttatt aatagtaatc    180
aattacgggg tcattagttc atagcccata tatggagttc cgcgttacat aacttacggt    240
aaatggcccg cctggctgac cgcccaacga cccccgccca ttgacgtcaa taatgacgta    300
tgttcccata gtaacgccaa tagggacttt ccattgacgt caatgggtgg agtatttacg    360
gtaaactgcc cacttggcag tacatcaagt gtatcatatg ccaagtacgc ccctattga    420 cgtcaatgac ggtaaatggc ccgcctggca ttatgcccag tacatgacct tatgggactt    480
tcctacttgg cagtacatct acgtattagt catcgctatt accatgcatg gtcgaggtga    540
gccccacgtt ctgcttcact ctccccatct ccccccctc cccaccccca attttgtatt    600
tatttatttt ttaattattt tgtgcagcga tgggggcggg ggggggggg gggcgcgcgc    660 caggcgggc gggcgggc gaggggcggg gcggggcgag gcggagaggt gcggcggcag    720
ccaatcagag cggcgcgctc cgaaagtttc ctttatggc gaggcggcgg cggcggcggc    780
cctataaaaa gcgaagcgcg cggcgggcgg gagtcgctgc gacgctgcct tcgccccgtg    840
ccccgctccg ccgccgcctc gcgccgcccg cccggctct gactgaccgc gttactccca    900
caggtgagcg ggcgggacgg cccttctcct ccgggctgta attagcgctt ggtttaatga    960
cggcttgttt cttttctgtg gctgcgtgaa agccttgagg ggctccggga gggccctttg   1020
tgcgggggga gcggctcggg gctgtccgcg ggggacggc tgccttcggg gggacgggg    1080 cagggcgggg ttcggcttct ggcgtgtgac cggcggctct agcagcctct gctaaccatg   1140
ttcatgcctt cttctttttc ctacagctcc tgggcaacgt gctggttatt gtgctgtctc   1200
atcattttgg caaagaatta agcttgagct cgcgatccgc agccatggat tatgggaggcg  1260 ccctgagtgc cgttgggcgc gagctgctat ttgtaacgaa cccagtagtc gtcaatggct   1320
ctgtacttgt gcctgaggac cagtgttact gcgcgggctg gattgagtcg cgtggcacaa   1380
acggtgccca acggcgtcg aacgtgctgc aatggcttgc tgctggcttc tccatcctac    1440
tgcttatgtt ttacgcctac caaacatgga agtcaacctg cggctgggag gagatctatg   1500
```

```
tgtgcgctat cgagatggtc aaggtgattc ttgagttctt cttcgagttt aagaacccgt   1560
ccatgctgta tctagccaca ggccaccgcg tccagtggtt gcgttacgcc gagtggcttc   1620
tcacctgccc ggtcattctc attcacctgt caaacctgac gggcttgtcc aacgactaca   1680
gcaggcgcac tatgggtctg cttgtgtctg atattggcac aattgtgtgg ggcgccactt   1740
ccgctatggc caccggatac gtcaaggtca tcttcttctg cctgggtctg tgttatggtg   1800
ctaacacgtt cttgcacgct gccaaggcct acatcgaggg ttaccatacc gtgccgaagg   1860
gccggtgtcg ccaggtggtg actggcatgg cttggctctt cttcgtatca tggggtatgt   1920
tccccatcct gttcatcctc ggccccgagg gcttcggcgt cctgagcgtg tacggctcca   1980
ccgtcggcca caccatcatt gacctgatgt cgaagaactg ctggggtctg ctcggccact   2040
acctgcgcgt gctgatccac gagcatatcc tcatccacgg cgacattcgc aagaccacca   2100
aattgaacat tggtggcact gagattgagg tcgagacgct ggtggaggac gaggccgagg   2160
ctggcgcggt caacaagggc accggcaagg aattcggagg cggaggtgga gctagcaaag   2220
gagaagaact cttcactgga gttgtcccaa ttcttgttga attagatggt gatgttaacg   2280
gccacaagtt ctctgtcagt ggagagggtg aaggtgatgc aacatacgga aaacttaccc   2340
tgaagttcat ctgcactact ggcaaactgc ctgttccatg gccaacacta gtcactactc   2400
tgtgctatgg tgttcaatgc ttttcaagat acccggatca tatgaaacgg catgactttt   2460
tcaagagtgc catgcccgaa ggttatgtac aggaaaggac catcttcttc aaagatgacg   2520
gcaactacaa gacacgtgct gaagtcaagt ttgaaggtga taccttgtt aatagaatcg   2580
agttaaaagg tattgacttc aaggaagatg gcaacattct gggacacaaa ttggaataca   2640
actataactc acacaatgta tacatcatgg cagacaaaca aaagaatgga atcaaagtga   2700
acttcaagac ccgccacaac attgaagatg gaagcgttca actagcagac cattatcaac   2760
aaaatactcc aattggcgat ggccctgtcc ttttaccaga caaccattac ctgtccacac   2820
aatctgccct ttcgaaagat cccaacgaaa agagagacca catggtcctt cttgagtttg   2880
taacagctgc tgggattaca catggcatgg atgaactgta caacgtggtt cttcggaccg   2940
cctgtccccc agattacaca ctagctatga ggaggtcacc tgatgatgtt cccttaatga   3000
cacccaacac cattacaatg taactcgagt ctagacgtgg taccgataat caacctctgg   3060
attacaaaat ttgtgaaaga ttgactggta ttcttaacta tgttgctcct tttacgctat   3120
gtggatacgc tgctttaatg ccttttgtatc atgctattgc ttcccgtatg gctttcattt   3180
tctcctcctt gtataaatcc tggttgctgt ctctttatga ggagttgtgg cccgttgtca   3240
ggcaacgtgg cgtggtgtgc actgtgtttg ctgacgcaac ccccactggt tggggcattg   3300
ccaccacctg tcagctcctt tccgggactt tcgctttccc cctccctatt gccacggcgg   3360
aactcatcgc cgcctgcctt gcccgctgct ggacaggggc tcggctgttg ggcactgaca   3420
attccgtggt gttgtcgggg aagctgacgt cctttccatg gctgctcgcc tgtgttgcca   3480
cctggattct gcgcgggacg tccttctgct acgtcccttc ggccctcaat ccagcggacc   3540
ttccttcccg cggcctgctg ccggctctgc ggcctcttcc gcgtcttcgc cttcgccctc   3600
agacgagtcg gatctccctt tgggccgcct ccccgcctga tgcgggatc ctctagagtc   3660
gagagatcta cgggtggcat ccctgtgacc cctccccagt gcctctcctg gccctggaag   3720
ttgccactcc agtgcccacc agccttgtcc taataaaatt aagttgcatc attttgtctg   3780
actaggtgtc cttctataat attatggggt ggagggggg ggtatggagc aaggggcaag   3840
ttgggaagac aacctgtagg gcctgcgggg tctattggga accaagctgg agtgcagtgg   3900
```

```
cacaatcttg gctcactgca atctccgcct cctgggttca agcgattctc ctgcctcagc    3960
ctcccgagtt gttgggattc caggcatgca tgaccaggct cagctaattt ttgttttttt    4020
ggtagagacg gggtttcacc atattggcca ggctggtctc caactcctaa tctcaggtga    4080
tctacccacc ttggcctccc aaattgctgg gattacaggc gtgaaccact gctcccttcc    4140
ctgtccttct gattttgtag gtaaccacgt gcggaccgag cggccgcagg aaccccctagt   4200 gatagagttg gccactccct ctctgcgcgc tcgctcgctc actgaggccg gcgaccaaa    4260 ggtcgcccga cgcccgggct tgcccgggc ggcctcagtg agcgagcgag cgcgcagctg    4320
cctgcagg                                                            4328

<210> SEQ ID NO 37
<211> LENGTH: 3620
<212> TYPE: DNA
<213> ORGANISM: Artificial Sequence
<220> FEATURE:
<223> OTHER INFORMATION: 5'- ITR-CAG-ChR2-{NLG-1Motif}-WPRE-
      bGHpolyA-ITR- 3'

<400> SEQUENCE: 37
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtgatat cctagttatt aatagtaatc    180
aattacgggg tcattagttc atagcccata tatggagttc cgcgttacat aacttacggt    240
aaatggcccg cctggctgac cgcccaacga cccccgccca ttgacgtcaa taatgacgta    300
tgttcccata gtaacgccaa tagggacttt ccattgacgt caatgggtgg agtatttacg    360
gtaaactgcc cacttggcag tacatcaagt gtatcatatg ccaagtacgc ccctattga    420 cgtcaatgac ggtaaatggc ccgcctggca ttatgcccag tacatgacct tatgggactt    480
tcctacttgg cagtacatct acgtattagt catcgctatt accatgcatg gtcgaggtga    540
gccccacgtt ctgcttcact ctccccatct ccccccctc cccaccccca attttgtatt    600
tatttatttt ttaattattt tgtgcagcga tggggggcggg gggggggggg gggcgcgcgc    660
caggcggggc ggggcggggc gaggggcggg gcggggcgag gcggagaggt gcggcggcag    720
ccaatcagag cggcgcgctc cgaaagtttc cttttatggc gaggcggcgg cggcggcggc    780
cctataaaaa gcgaagcgcg cggcgggcgg gagtcgctgc gacgctgcct tcgccccgtg    840
ccccgctccg ccgccgcctc gcgccgcccg cccggctct gactgaccgc gttactccca    900
caggtgagcg gcgggacgg ccccttctcct ccgggctgta attagcgctt ggtttaatga    960
cggcttgttt cttttctgtg gctgcgtgaa agccttgagg ggctccggga gggccctttg   1020
tgcgggggga gcggctcggg gctgtccgcg ggggacggc tgccttcggg ggggacgggg    1080
cagggcgggg ttcggcttct ggcgtgtgac cggcggctct agcagcctct gctaaccatg    1140
ttcatgcctt cttctttttc ctacagctcc tgggcaacgt gctggttatt gtgctgtctc    1200
atcattttgg caaagaatta agcttgagct cgcgatccgc agccatggat tatggaggcg    1260
ccctgagtgc cgttgggcgc gagctgctat ttgtaacgaa cccagtagtc gtcaatggct    1320
ctgtacttgt gcctgaggac cagtgttact gcgcgggctg gattgagtcg cgtggcacaa    1380
acggtgccca acggcgtcg aacgtgctgc aatggcttgc tgctggcttc tccatcctac    1440
tgcttatgtt ttacgcctac caaacatgga agtcaacctg cggctgggag gagatctatg    1500
tgtgcgctat cgagatggtc aaggtgattc ttgagttctt cttcgagttt aagaacccgt    1560
```

```
ccatgctgta tctagccaca ggccaccgcg tccagtggtt gcgttacgcc gagtggcttc    1620
tcacctgccc ggtcattctc attcacctgt caaacctgac gggcttgtcc aacgactaca    1680
gcaggcgcac tatgggtctg cttgtgtctg atattggcac aattgtgtgg ggcgccactt    1740
ccgctatggc caccggatac gtcaaggtca tcttcttctg cctgggtctg tgttatggtg    1800
ctaacacgtt cttttcacgct gccaaggcct acatcgaggg ttaccatacc gtgccgaagg    1860
gccggtgtcg ccaggtggtg actggcatgg cttggctctt cttcgtatca tggggtatgt    1920
tccccatcct gttcatcctc ggccccgagg gcttcggcgt cctgagcgtg tacggctcca    1980
ccgtcggcca ccatcatt gacctgatgt cgaagaactg ctggggtctg ctcggccact      2040
acctgcgcgt gctgatccac gagcatatcc tcatccacgg cgacattcgc aagaccacca    2100
aattgaacat tggtggcact gagattgagg tcgagacgct ggtggaggac gaggccgagg    2160
ctggcgcggt caacaagggc accggcaagg aattcggagg cggaggtgga gctagcgtgg    2220
ttcttcggac cgcctgtccc ccagattaca cactagctat gaggaggtca cctgatgatg    2280
ttcccttaat gacacccaac accattacaa tgtaactcga gtctagacgt ggtaccgata    2340
atcaacctct ggattacaaa atttgtgaaa gattgactgg tattcttaac tatgttgctc    2400
cttttacgct atgtggatac gctgctttaa tgcctttgta tcatgctatt gcttcccgta    2460
tggctttcat tttctcctcc ttgtataaat cctggttgct gtctctttat gaggagttgt    2520
ggcccgttgt caggcaacgt ggcgtggtgt gcactgtgtt tgctgacgca acccccactg    2580 gttgggcat tgccaccacc tgtcagctcc tttccgggac tttcgctttc ccctcccta     2640 ttgccacggc ggaactcatc gccgcctgcc ttgcccgctg ctggacaggg gctcggctgt    2700
tgggcactga caattccgtg gtgttgtcgg ggaagctgac gtccttttcca tggctgctcg    2760 cctgtgttgc cacctggatt ctgcgcggga cgtccttctg ctacgtccct tcggccctca    2820
atccagcgga ccttccttcc cgcggcctgc tgccggctct gcggcctctt ccgcgtcttc    2880
gccttcgccc tcagacgagt cggatctccc tttgggccgc ctccccgcct gatgcgggga    2940
tcctctagag tcgagagatc tacggtggc atccctgtga ccctcccca gtgcctctcc      3000 tggccctgga agttgccact ccagtgccca ccagccttgt cctaataaaa ttaagttgca    3060 tcatttttgtc tgactaggtg tccttctata atattatggg gtggagggg gtggtatgga    3120 gcaaggggca agttgggaag acaacctgta gggcctgcgg ggtctattgg gaaccaagct    3180
ggagtgcagt ggcacaatct tggctcactg caatctccgc ctcctgggtt caagcgattc    3240
tcctgcctca gcctcccgag ttgttgggat tccaggcatg catgaccagg ctcagctaat    3300
ttttgttttt ttggtagaga cggggtttca ccatattggc caggctggtc tccaactcct    3360
aatctcaggt gatctacca ccttggcctc ccaaattgct gggattacag gcgtgaacca     3420
ctgctccctt ccctgtcctt ctgattttgt aggtaaccac gtgcggaccg agcggccgca    3480 ggaacccta gtgatggagt tggccactcc ctctctgcgc gctcgctcgc tcactgaggc     3540
cgggcgacca aggtcgcccc gacgcccggg ctttgcccgg gcggcctcag tgagcgagcg    3600
agcgcgcagc tgcctgcagg                                                3620
```

<210> SEQ ID NO 38
<211> LENGTH: 4310
<212> TYPE: DNA
<213> ORGANISM: Artificial Sequence
<220> FEATURE:
<223> OTHER INFORMATION: 5'- ITR-CAG-ChR2-GFP-{MLPH Motif}-WPRE-
      bGHpolyA-ITR- 3'

<400> SEQUENCE: 38

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggccgca cgcgtgatat cctagttatt aatagtaatc    180
aattacgggg tcattagttc atagcccata tatggagttc cgcgttacat aacttacggt     240
aaatggcccg cctggctgac cgcccaacga cccccgccca ttgacgtcaa taatgacgta     300
tgttcccata gtaacgccaa tagggacttt ccattgacgt caatgggtgg agtatttacg     360
gtaaactgcc cacttggcag tacatcaagt gtatcatatg ccaagtacgc cccctattga     420
cgtcaatgac ggtaaatggc ccgcctggca ttatgcccag tacatgacct tatgggactt     480
tcctacttgg cagtacatct acgtattagt catcgctatt accatgcatg gtcgaggtga     540
gccccacgtt ctgcttcact ctccccatct cccccccctc cccacccccca attttgtatt    600
tatttatttt ttaattattt tgtgcagcga tgggggcggg gggggggggg gggcgcgcgc     660
caggcgggc ggggcgggc gagggcggg gcggggcgag gcggagaggt gcggcggcag       720
ccaatcagag cggcgcgctc cgaaagtttc cttttatggc gaggcggcgg cggcggcggc    780
cctataaaaa gcgaagcgcg cggcgggcgg gagtcgctgc gacgctgcct tcgccccgtg    840
ccccgctccg ccgccgcctc gcgccgcccg ccccggctct gactgaccgc gttactccca    900
caggtgagcg ggcgggacgg cccttctcct ccgggctgta attagcgctt ggtttaatga     960
cggcttgttt ctttttctgtg gctgcgtgaa agccttgagg ggctccggga gggccctttg  1020
tgcggggga gcggctcggg gctgtccgcg gggggacggc tgccttcggg ggggacgggg   1080
cagggcgggg ttcggcttct ggcgtgtgac cggcggctct agcagcctct gctaaccatg   1140
ttcatgcctt cttctttttc ctacagctcc tgggcaacgt gctggttatt gtgctgtctc   1200
atcattttgg caaagaatta agcttgagct cgcgatccgc agccatggat tatggaggcg   1260
ccctgagtgc cgttgggcgc gagctgctat ttgtaacgaa cccagtagtc gtcaatggct   1320
ctgtacttgt gcctgaggac cagtgttact gcgcgggctg gattgagtcg cgtggcacaa   1380
acggtgccca acggcgtcg aacgtgctgc aatggcttgc tgctggcttc tccatcctac    1440
tgcttatgtt ttacgcctac caaacatgga agtcaacctg cggctgggag gagatctatg   1500
tgtgcgctat cgagatggtc aaggtgattc ttgagttctt cttcgagttt aagaacccgt   1560
ccatgctgta tctagccaca ggccaccgcg tccagtggtt gcgttacgcc gagtggcttc   1620
tcacctgccc ggtcattctc attcacctgt caaacctgac gggcttgtcc aacgactaca   1680
gcaggcgcac tatgggtctg cttgtgtctg atattggcac aattgtgtgg ggcgccactt    1740
ccgctatggc caccggatac gtcaaggtca tcttcttctg cctgggtctg tgttatggtg   1800
ctaacacgtt cttcacgct gccaaggcct acatcgaggg ttaccatacc gtgccgaagg    1860
gccggtgtcg ccaggtggtg actggcatgg cttggctctt cttcgtatca tgggtatgt   1920
tccccatcct gttcatcctc ggccccgagg gcttcggcgt cctgagcgtg tacggctcca  1980
ccgtcggcca caccatcatt gacctgatgt cgaagaactg ctgggtctg ctcggccact    2040
acctgcgcgt gctgatccac gagcatatcc tcatccacgg cgacattcgc aagaccacca    2100
aattgaacat tggtggcact gagattgagg tcgagacgct ggtggaggac gaggccgagg   2160
ctggcgcggt caacaagggc accggcaagg aattcgagg cggaggtgga gctagcaaag    2220
gagaagaact cttcactgga gttgtcccaa ttcttgttga attagatggt gatgttaacg    2280
```

| | | |
|---|---|---|
| gccacaagtt ctctgtcagt ggagagggtg aaggtgatgc aacatacgga aaacttaccc | 2340 | |
| tgaagttcat ctgcactact ggcaaactgc ctgttccatg ccaacacta gtcactactc | 2400 | |
| tgtgctatgg tgttcaatgc ttttcaagat acccggatca tatgaaacgg catgactttt | 2460 | |
| tcaagagtgc catgcccgaa ggttatgtac aggaaaggac catcttcttc aaagatgacg | 2520 | |
| gcaactacaa gacacgtgct gaagtcaagt ttgaaggtga tacccttgtt aatagaatcg | 2580 | |
| agttaaaagg tattgacttc aaggaagatg gcaacattct gggacacaaa ttggaataca | 2640 | |
| actataactc acacaatgta tacatcatgg cagacaaaca aaagaatgga atcaaagtga | 2700 | |
| acttcaagac ccgccacaac attgaagatg gaagcgttca actagcagac cattatcaac | 2760 | |
| aaaatactcc aattggcgat ggccctgtcc ttttaccaga caaccattac ctgtccacac | 2820 | |
| aatctgccct ttcgaaagat cccaacgaaa agagagacca catggtcctt cttgagtttg | 2880 | |
| taacagctgc tgggattaca catggcatgg atgaactgta acagggac cagcctctga | 2940 | |
| acagcaaaaa gaaaagagg ctcctgagct caggagcgt ggacttcgag gaggacagcg | 3000 | |
| actaactcga gtctagacgt ggtaccgata atcaacctct ggattacaaa atttgtgaaa | 3060 | |
| gattgactgg tattcttaac tatgttgctc cttttacgct atgtggatac gctgctttaa | 3120 | |
| tgcctttgta tcatgctatt gcttcccgta tggctttcat tttctcctcc ttgtataaat | 3180 | |
| cctggttgct gtctctttat gaggagttgt ggcccgttgt caggcaacgt ggcgtggtgt | 3240 | |
| gcactgtgtt tgctgacgca acccccactg gttgggcat gccaccacc tgtcagctcc | 3300 | |
| tttccgggac tttcgctttc cccctcccta ttgccacggc ggaactcatc gccgcctgcc | 3360 | |
| ttgcccgctg ctggacaggg gctcggctgt tgggcactga caattccgtg tgttgtcgg | 3420 | |
| ggaagctgac gtccttcca tggctgctcg cctgtgttgc cacctggatt ctgcgcggga | 3480 | |
| cgtccttctg ctacgtccct tcggccctca atccagcgga ccttccttcc cgcggcctgc | 3540 | |
| tgccggctct gcggcctctt ccgcgtcttc gccttcgccc tcagacgagt cggatctccc | 3600 | |
| tttgggccgc ctccccgcct gatgcgggga tcctctagag tcgagagatc tacgggtggc | 3660 | |
| atccctgtga cccctcccca gtgcctctcc tggccctgga agttgccact ccagtgccca | 3720 | |
| ccagccttgt cctaataaaa ttaagttgca tcattttgtc tgactaggtg tccttctata | 3780 | |
| atattatggg gtggagggg gtggtatgga gcaaggggca agttgggaag acaacctgta | 3840 | |
| gggcctgcgg ggtctattgg gaaccaagct ggagtgcagt ggcacaatct tggctcactg | 3900 | |
| caatctccgc ctcctgggtt caagcgattc tcctgcctca gcctcccgag ttgttgggat | 3960 | |
| tccaggcatg catgaccagg ctcagctaat ttttgttttt ttggtagaga cggggtttca | 4020 | |
| ccatattggc caggctggtc tccaactcct aatctcaggt gatctaccca ccttggcctc | 4080 | |
| ccaaattgct gggattacag gcgtgaacca ctgctccctt ccctgtcctt ctgattttgt | 4140 | |
| aggtaaccac gtgcggaccg agcggccgca ggaaccccta gtgatggagt tggccactcc | 4200 | |
| ctctctgcgc gctcgctcgc tcactgaggc cgggcgacca aggtcgccc gacgcccggg | 4260 | |
| ctttgcccgg gcggcctcag tgagcgagcg agcgcgcagc tgcctgcagg | 4310 | |

<210> SEQ ID NO 39
<211> LENGTH: 3602
<212> TYPE: DNA
<213> ORGANISM: Artificial Sequence
<220> FEATURE:
<223> OTHER INFORMATION: 5'- ITR-CAG-ChR2-{MLPH-Motif}-WPRE-bGHpolyA-ITR- 3'

<400> SEQUENCE: 39

| | |
|---|---|
| cctgcaggca gctgcgcgct cgctcgctca ctgaggccgc ccgggcaaag cccgggcgtc | 60 |
| gggcgacctt tggtcgcccg gccgcagtga gcgagcgagc gcgcagagag ggagtggcca | 120 |
| actccatcac taggggttcc tgcggccgca cgcgtgatat cctagttatt aatagtaatc | 180 |
| aattacgggg tcattagttc atagcccata tatggagttc cgcgttacat aacttacggt | 240 |
| aaatggcccg cctggctgac cgcccaacga ccccgccca ttgacgtcaa taatgacgta | 300 |
| tgttcccata gtaacgccaa tagggacttt ccattgacgt caatgggtgg agtatttacg | 360 |
| gtaaactgcc cacttggcag tacatcaagt gtatcatatg ccaagtacgc cccctattga | 420 |
| cgtcaatgac ggtaaatggc ccgcctggca ttatgcccag tacatgacct tatgggactt | 480 |
| tcctacttgg cagtacatct acgtattagt catcgctatt accatgcatg gtcgaggtga | 540 |
| gccccacgtt ctgcttcact ctccccatct cccccccctc cccaccccca attttgtatt | 600 |
| tatttatttt ttaattattt tgtgcagcga tgggggcggg ggggggggg gggcgcgcgc | 660 |
| caggcgggc ggggcgggc gaggggcggg gcggggcgag gcggagaggt gcggcggcag | 720 |
| ccaatcagag cggcgcgctc cgaaagtttc cttttatggc gaggcggcgg cggcggcggc | 780 |
| cctataaaaa gcgaagcgcg cggcgggcgg gagtcgctgc gacgctgcct tcgcccgtg | 840 |
| ccccgctccg ccgccgcctc gcgccgcccg ccccggctct gactgaccgc gttactccca | 900 |
| caggtgagcg ggcgggacgg cccttctcct ccgggctgta attagcgctt ggtttaatga | 960 |
| cggcttgttt cttttctgtg gctgcgtgaa agccttgagg ggctccggga gggccctttg | 1020 |
| tgcgggggga gcggctcggg gctgtccgcg ggggggacggc tgccttcggg ggggacgggg | 1080 |
| cagggcgggg ttcggcttct ggcgtgtgac cggcggctct agcagcctct gctaaccatg | 1140 |
| ttcatgcctt cttctttttc ctacagctcc tgggcaacgt gctggttatt gtgctgtctc | 1200 |
| atcattttgg caaagaatta agcttgagct cgcgatccgc agccatggat tatggaggcg | 1260 |
| ccctgagtgc cgttgggcgc gagctgctat ttgtaacgaa cccagtagtc gtcaatggct | 1320 |
| ctgtacttgt gcctgaggac cagtgttact gcgcgggctg gattgagtcg cgtggcacaa | 1380 |
| acggtgccca acggcgtcg aacgtgctgc aatggcttgc tgctggcttc tccatcctac | 1440 |
| tgcttatgtt ttacgcctac caaacatgga agtcaacctg cggctgggag gagatctatg | 1500 |
| tgtgcgctat cgagatggtc aaggtgattc ttgagttctt cttcgagttt aagaacccgt | 1560 |
| ccatgctgta tctagccaca ggccaccgcg tccagtggtt gcgttacgcc gagtggcttc | 1620 |
| tcacctgccc ggtcattctc attcacctgt caaacctgac gggcttgtcc aacgactaca | 1680 |
| gcaggcgcac tatgggtctg cttgtgtctg atattggcac aattgtgtgg ggcgccactt | 1740 |
| ccgctatggc caccggatac gtcaaggtca tcttcttctg cctgggtctg tgttatggtg | 1800 |
| ctaacacgtt ctttcacgct gccaaggcct acatcgaggg ttaccatacc gtgccgaagg | 1860 |
| gccggtgtcg ccaggtggtg actggcatgg cttggctctt cttcgtatca tggggtatgt | 1920 |
| tccccatcct gttcatcctc ggccccgagg gcttcggcgt cctgagcgtg tacggctcca | 1980 |
| ccgtcggcca caccatcatt gacctgatgt cgaagaactg ctgggtctg ctcggccact | 2040 |
| acctgcgcgt gctgatccac gagcatatcc tcatccacgg cgacattcgc aagaccacca | 2100 |
| aattgaacat tggtggcact gagattgagg tcgagacgct ggtggaggac gaggccgagg | 2160 |
| ctggcgcggt caacaagggc accggcaagg aattcggagg cggaggtgga gctagcaggg | 2220 |
| accagcctct gaacagcaaa agaaaaaaga ggctcctgag cttcagggac gtggacttcg | 2280 |
| aggaggacag cgactaactc gagtctagac gtggtaccga taatcaacct ctggattaca | 2340 |
| aaatttgtga agattgact ggtattctta actatgttgc tccttttacg ctatgtggat | 2400 |

-continued

```
acgctgcttt aatgcctttg tatcatgcta ttgcttccg tatggcttc attttctcct    2460 ccttgtataa atcctggttg ctgtctcttt atgaggagtt gtggcccgtt gtcaggcaac    2520
gtggcgtggt gtgcactgtg tttgctgacg caacccccac tggttggggc attgccacca    2580
cctgtcagct cctttccggg actttcgctt tccccctccc tattgccacg gcggaactca    2640
tcgccgcctg ccttgcccgc tgctggacag gggctcggct gttgggcact gacaattccg    2700
tggtgttgtc ggggaagctg acgtcctttc catggctgct cgcctgtgtt gccacctgga    2760
ttctgcgcgg gacgtccttc tgctacgtcc cttcggccct caatccagcg gaccttcctt    2820
cccgcggcct gctgccggct ctgcggcctc ttccgcgtct tcgccttcgc cctcagacga    2880
gtcggatctc cctttgggcc gcctcccgc ctgatgcggg gatcctctag agtcgagaga    2940
tctacgggtg gcatcctgt gaccctccc cagtgcctct cctggccctg aagttgcca     3000 ctccagtgcc caccagcctt gtcctaataa aattaagttg catcattttg tctgactagg    3060
tgtccttcta taatattatg gggtggaggg ggtggtatg gagcaaggg caagttggga      3120 agacaacctg tagggcctgc ggggtctatt gggaaccaag ctggagtgca gtggcacaat    3180
cttggctcac tgcaatctcc gcctcctggg ttcaagcgat tctcctgcct cagcctcccg    3240
agttgttggg attccaggca tgcatgacca ggctcagcta attttgttt ttttggtaga    3300 gacgggtttt caccatattg gccaggctgg tctccaactc ctaatctcag gtgatctacc   3360
caccttggcc tcccaaattg ctgggattac aggcgtgaac cactgctccc ttccctgtcc    3420 ttctgattt gtaggtaacc acgtgcggac cgagcggccg caggaacccc tagtgatgga    3480
gttggccact ccctctctgc gcgctcgctc gctcactgag gccgggcgac caaaggtcgc    3540
ccgacgcccg ggctttgccc gggcggcctc agtgagcgag cgagcgcgca gctgcctgca    3600
gg                                                                  3602
```

<210> SEQ ID NO 40
<211> LENGTH: 4361
<212> TYPE: DNA
<213> ORGANISM: Artificial Sequence
<220> FEATURE:
<223> OTHER INFORMATION: 5'- ITR-CAG-HaloR-GFP-{Kv2.1 Motif}-WPRE-
    bGHpolyA-ITR- 3'

<400> SEQUENCE: 40

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtgatat cctagttatt aatagtaatc    180
aattacgggg tcattagttc atagcccata tatggagttc cgcgttacat aacttacggt    240
aaatggcccg cctggctgac cgcccaacga cccccgccca ttgacgtcaa taatgacgta    300
tgttcccata gtaacgccaa tagggacttt ccattgacgt caatgggtgg agtatttacg    360
gtaaactgcc cacttggcag tacatcaagt gtatcatatg ccaagtacgc ccctattga     420 cgtcaatgac ggtaaatggc ccgcctggca ttatgcccag tacatgacct tatgggactt    480
tcctacttgg cagtacatct acgtattagt catcgctatt accatgcatg gtcgaggtga    540
gccccacgtt ctgcttcact ctccccatct cccccctc ccaccccca attttgtatt       600 tatttatttt ttaattattt tgtgcagcga tgggggcggg ggggggggg gggcgcgcgc      660 caggcggggc ggggcgggc gagggcggg gcggggcgag gcgagaggt gcggcggcag       720 ccaatcagag cggcgcgctc cgaaagtttc cttttatggc gaggcggcgg cggcggcggc    780
```

```
cctataaaaa gcgaagcgcg cggcgggcgg gagtcgctgc gacgctgcct tcgccccgtg    840
ccccgctccg ccgccgcctc gcgccgcccg ccccggctct gactgaccgc gttactccca    900
caggtgagcg ggcgggacgg cccttctcct ccgggctgta attagcgctt ggtttaatga    960
cggcttgttt cttttctgtg gctgcgtgaa agccttgagg ggctccggga gggccctttg   1020
tgcgggggga gcggctcggg gctgtccgcg gggggacggc tgccttcggg ggggacgggg   1080
cagggcgggg ttcggcttct ggcgtgtgac cggcggctct agcagcctct gctaaccatg   1140
ttcatgcctt cttcttttc ctacagctcc tgggcaacgt gctggttatt gtgctgtctc   1200
atcattttgg caaagaatta agcttgagct cgcgatccgc agccatgact gagacattgc   1260
caccggtaac ggaatcggct gttgcgctac aggcggaggt gacccagagg gagctgttcg   1320
agttcgttct caacgacccc ctcctcgcca gttcgctgta tattaatatc gcactggcag   1380
ggctgtcgat actgcttttc gtgttcatga cgcgcggact cgacgaccca cgggcgaaac   1440
tcatcgccgt ttcgacgatt ttggtgccgg tggtctctat cgcgagctac accggccttg   1500
catcggggct caccatcagc gtcctcgaga tgccagccgg ccacttcgcc gagggtcct   1560
cggtgatgct cggcggcgaa gaggtagacg gcgtcgtgac gatgtggggc cgctatctga   1620
cgtgggccct ttcgacaccg atgatactgc tggcgcttgg gctgcttgct ggctctaacg   1680
ccacgaagct ctttaccgcc atcaccttcg acatcgcgat gtgtcacc ggcctcgcag    1740
ccgcgctgac gacctcttcg cacctgatgc ggtggttctg gtacgccatc agttgtgcgt   1800
gtttcctcgt cgtcctctac atcctgctcg tcgagtgggc acaggacgcc aaggctgccg   1860
gtactgcgga tatgttcaat acgctgaagc tgctgaccgt tgtcatgtgg ctcggctacc   1920
ccatcgtgtg ggcactcggc gttgagggca tcgccgttct tccggtcgga gtcacgtcgt   1980
ggggatacag cttcctcgac atcgtcgcga agtacatctt cgcgttcctg ctgctcaact   2040
acctcacgtc gaacgagagc gtcgtctccg gctcgatact cgacgtgccg tccgcgtcgg   2100
gcactcccgc tgacgacgaa ttcggaggcg gaggtggagc tagcaaagga gaagaactct   2160
tcactggagt tggagttgtc ccaattcttg ttgaattaga tggtgatgtt aacggccaca   2220
agttctctgt cagtggagag ggtgaaggtg atgcaacata cggaaaactt accctgaagt   2280
tcatctgcac tactggcaaa ctgcctgttc catggccaac actagtcact actctgtgct   2340
atggtgttca atgcttttca agatacccgg atcatatgaa acggcatgac ttttcaaga   2400
gtgccatgcc cgaaggttat gtacaggaaa ggaccatctt cttcaaagat gacggcaact   2460
acaagacacg tgctgaagtc aagtttgaag gtgataccct tgttaataga atcgagttaa   2520
aaggtattga cttcaaggaa gatggcaaca ttctgggaca caaattggaa tacaactata   2580
actcacacaa tgtatacatc atggcagaca acaaaagaa tggaatcaaa gtgaacttca   2640
agacccgcca caacattgaa gatggaagcg ttcaactagc agaccattat caacaaaata   2700
ctccaattgg cgatggccct gtccttttac cagacaacca ttacctgtcc acacaatctg   2760
cccttcgaa agatcccaac gaaaagagag accacatggt ccttcttgag tttgtaacag   2820
ctgctgggat tacacatggc atggatgaac tgtacaacca gtctcagccc atcctgaaca   2880
ctaaggagat ggcccctcag agtaaacccc ctgaggaact ggaaatgagc tccatgccat   2940
ctccagtggc tcctctgcca gctaggaccg agggcgtgat tgacatgaga agcatgtcta   3000
gtatcgatag cttcatttcc tgcgccaccg acttccccga agctacaagg ttttaactcg   3060
agtctagacg tggtaccgat aatcaacctc tggattacaa aatttgtgaa agattgactg   3120
```

-continued

```
gtattcttaa ctatgttgct cctttacgc tatgtggata cgctgcttta atgcctttgt   3180
atcatgctat tgcttcccgt atggctttca ttttctcctc cttgtataaa tcctggttgc   3240
tgtctcttta tgaggagttg tggcccgttg tcaggcaacg tggcgtggtg tgcactgtgt   3300
ttgctgacgc aaccccact ggttggggca ttgccaccac ctgtcagctc ctttccggga   3360
ctttcgcttt ccccctccct attgccacgg cggaactcat cgccgcctgc cttgcccgct   3420
gctggacagg ggctcggctg ttgggcactg acaattccgt ggtgttgtcg gggaagctga   3480
cgtcctttcc atggctgctc gcctgtgttg ccacctggat tctgcgcggg acgtccttct   3540
gctacgtccc ttcggccctc aatccagcgg accttccttc ccgcggcctg ctgccggctc   3600
tgcggcctct tccgcgtctt cgccttcgcc ctcagacgag tcggatctcc ctttgggccg   3660
cctccccgcc tgatgcgggg atcctctaga gtcgagagat ctacgggtgg catccctgtg   3720
acccctcccc agtgcctctc ctggccctgg aagttgccac tccagtgccc accagccttg   3780
tcctaataaa attaagttgc atcattttgt ctgactaggt gtccttctat aatattatgg   3840
ggtggagggg ggtggtatgg agcaaggggc aagttgggaa gacaacctgt agggcctgcg   3900
gggtctattg ggaaccaagc tggagtgcag tggcacaatc ttggctcact gcaatctccg   3960
cctcctgggt tcaagcgatt ctcctgcctc agcctcccga gttgttggga ttccaggcat   4020
gcatgaccag gctcagctaa ttttgtttt tttggtagag acggggtttc accatattgg   4080
ccaggctggt ctccaactcc taatctcagg tgatctaccc accttggcct ccaaattgc    4140
tgggattaca ggcgtgaacc actgctccct tccctgtcct tctgattttg taggtaacca   4200
cgtgcggacc gagcggccgc aggaacccct agtgatggag ttggccactc cctctctgcg   4260
cgctcgctcg ctcactgagg ccgggcgacc aaaggtcgcc cgacgcccgg gctttgcccg   4320
ggcggcctca gtgagcgagc gagcgcgcag ctgcctgcag g                       4361
```

<210> SEQ ID NO 41
<211> LENGTH: 3647
<212> TYPE: DNA
<213> ORGANISM: Artificial Sequence
<220> FEATURE:
<223> OTHER INFORMATION: 5' -ITR-CAG-HaloR-{Kv2.1 Motif}-WPRE-
      bGHpolyA-ITR- 3'

<400> SEQUENCE: 41

```
cctgcaggca gctgcgcgct cgctcgctca ctgaggccgc cgggcaaag cccgggcgtc     60
gggcgacctt tggtcgcccg gcctcagtga gcgagcgagc gcgcagagag ggagtggcca   120
actccatcac taggggttcc tgcggccgca cgcgtgatat cctagttatt aatagtaatc   180
aattacgggg tcattagttc atagcccata tatggagttc cgcgttacat aacttacggt   240
aaatggcccg cctggctgac cgcccaacga ccccccgccca ttgacgtcaa taatgacgta   300
tgttcccata gtaacgccaa tagggactt ccattgacgt caatgggtgg agtatttacg   360
gtaaactgcc cacttggcag tacatcaagt gtatcatatg ccaagtacgc ccctattga   420
cgtcaatgac ggtaaatggc ccgcctggca ttatgcccag tacatgacct tatgggactt   480
tcctacttgg cagtacatct acgtattagt catcgctatt accatgcatg gtcgaggtga   540
gccccacgtt ctgcttcact ctccccatct ccccccctc ccaccccca attttgtatt   600
tatttatttt ttaattattt tgtgcagcga tgggggcggg gggggggggg gggcgcgcgc   660
caggcggggc gggcggggc gaggggcggg cggggcgag gcgagaggt gcggcggcag   720
ccaatcagag cggcgcgctc cgaaagtttc cttttatggc gaggcggcgg cggcggcggc   780
```

```
cctataaaaa gcgaagcgcg cggcgggcgg gagtcgctgc gacgctgcct tcgcccgtg       840 ccccgctccg ccgccgcctc gcgccgcccg ccccggctct gactgaccgc gttactccca      900
caggtgagcg gcgggacggg cccttctcct ccgggctgta attagcgctt ggtttaatga      960
cggcttgttt cttttctgtg gctgcgtgaa agccttgagg ggctccggga gggccctttg     1020 tgcggggga gcggctcggg gctgtccgcg gggggacggc tgccttcggg ggggacgggg      1080
cagggcgggg ttcggcttct ggcgtgtgac cggcggctct agcagcctct gctaaccatg     1140
ttcatgcctt cttctttttc ctacagctcc tgggcaacgt gctggttatt gtgctgtctc     1200
atcattttgg caaagaatta agcttgagct cgcgatccgc agccatgact gagacattgc     1260
caccggtaac ggaatcggct gttgcgctac aggcggaggt gacccagagg gagctgttcg     1320
agttcgttct caacgacccc ctcctcgcca gttcgctgta tattaatatc gcactggcag     1380
ggctgtcgat actgcttttc gtgttcatga cgcgcggact cgacgaccca cgggcgaaac     1440
tcatcgccgt ttcgacgatt ttggtgccgg tggtctctat cgcgagctac accggccttg     1500
catcggggct caccatcagc gtcctcgaga tgccagccgg ccacttcgcc gaggggtcct     1560
cggtgatgct cggcggcgaa gaggtagacg gcgtcgtgac gatgtggggc cgctatctga     1620
cgtgggccct ttcgacaccg atgatactgc tggcgcttgg gctgcttgct ggctctaacg     1680
ccacgaagct cttaccgcc atcaccttcg acatcgcgat gtgtgtcacc ggcctcgcag     1740
ccgcgctgac gacctcttcg cacctgatgc ggtggtctg gtacgccatc agttgtgcgt     1800
gtttcctcgt cgtcctctac atcctgctcg tcgagtgggc acaggacgcc aaggctgccg     1860
gtactgcgga tatgttcaat acgctgaagc tgctgaccgt tgtcatgtgg ctcggctacc     1920
ccatcgtgtg ggcactcggc gttgagggca tcgccgttct tccggtcgga gtcacgtcgt     1980
ggggatacag cttcctcgac atcgtcgcga agtacatctt cgcgttcctg ctgctcaact     2040
acctcacgtc gaacgagagc gtcgtctccg gctcgatact cgacgtgccg tccgcgtcgg     2100
gcactcccgc tgacgacgaa ttcggaggcg gaggtggagc tagccagtct cagcccatcc     2160
tgaacactaa ggagatggcc cctcagagta aaccccctga ggaactggaa atgagctcca     2220
tgccatctcc agtggctcct ctgccagcta ggaccgaggg cgtgattgac atgagaagca     2280
tgtctagtat cgatagcttc atttcctgcg ccaccgactt ccccgaagct acaaggtttt     2340
aactcgagtc tagacgtggt accgataatc aacctctgga ttacaaaatt tgtgaaagat     2400
tgactggtat tcttaactat gttgctcctt ttacgctatg tggatacgct gctttaatgc     2460
ctttgtatca tgctattgct tcccgtatgg ctttcatttt ctcctccttg tataaatcct     2520
ggttgctgtc tctttatgag gagttgtggc ccgttgtcag gcaacgtggc gtggtgtgca     2580
ctgtgtttgc tgacgcaacc cccactggtt ggggcattgc caccacctgt cagctccttt     2640
ccgggacttt cgctttcccc ctccctattg ccacggcgga actcatcgcc gcctgccttg     2700
cccgctgctg acaggggct cggctgttgg gcactgacaa ttccgtggtg ttgtcgggga     2760
agctgacgtc ctttccatgg ctgctcgcct gtgttgccac ctggattctg cgcgggacgt     2820
ccttctgcta cgtcccttcg ccctcaatc cagcggacct tccttcccgc ggcctgctgc      2880
cggctctgcg gcctcttccg cgtcttgcc ttcgccctca gacgagtcgg atctcccttt     2940
gggccgcctc cccgcctgat gcggggatcc tctagagtcg agagatctac gggtggcatc     3000
cctgtgaccc ctccccagtg cctctcctgg ccctggaagt tgccactcca gtgcccacca     3060
gccttgtcct aataaaatta agttgcatca ttttgtctga ctaggtgtcc ttctataata     3120
ttatggggtg gagggggggtg gtatggagca agggcaagt tgggaagaca acctgtaggg     3180
```

```
cctgcggggt ctattgggaa ccaagctgga gtgcagtggc acaatcttgg ctcactgcaa    3240
tctccgcctc ctgggttcaa gcgattctcc tgcctcagcc tcccgagttg ttgggattcc    3300
aggcatgcat gaccaggctc agctaatttt tgttttttg gtagagacgg ggtttcacca     3360
tattggccag gctggtctcc aactcctaat ctcaggtgat ctacccacct ggcctccca     3420 aattgctggg attacaggcg tgaaccactg ctcccttccc tgtccttctg attttgtagg    3480
taaccacgtg cggaccgagc ggccgcagga accctagtg atggagttgg ccactccctc     3540
tctgcgcgct cgctcgctca ctgaggccgg gcgaccaaag gtcgcccgac gcccgggctt    3600
tgcccgggcg gcctcagtga gcgagcgagc gcgcagctgc ctgcagg                  3647

<210> SEQ ID NO 42
<211> LENGTH: 4247
<212> TYPE: DNA
<213> ORGANISM: Artificial Sequence
<220> FEATURE:
<223> OTHER INFORMATION: 5' -ITR-CAG-HaloR-GFP-{Nav1.6 Motif}-WPRE-
      bGHpolyA-ITR- 3'

<400> SEQUENCE: 42
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca    120
actccatcac taggggttcc tgcggccgca cgcgtgatat cctagttatt aatagtaatc    180
aattacgggg tcattagttc atagcccata tatggagttc cgcgttacat aacttacggt    240
aaatggcccg cctggctgac cgcccaacga ccccgcccca ttgacgtcaa taatgacgta    300
tgttcccata gtaacgccaa tagggacttt ccattgacgt caatgggtgg agtatttacg    360
gtaaactgcc cacttggcag tacatcaagt gtatcatatg ccaagtacgc cccctattga    420
cgtcaatgac ggtaaatggc ccgcctggca ttatgcccag tacatgacct tatgggactt    480
tcctacttgg cagtacatct acgtattagt catcgctatt accatgcatg gtcgaggtga    540
gccccacgtt ctgcttcact ctccccatct ccccccctc cccacccca attttgtatt      600 tatttatttt ttaattattt tgtgcagcga tggggcggg gggggggggg gggcgcgcgc     660
caggcggggc ggggcggggc gaggggcggg gcggggcgag gcggagaggt gcggcggcag    720
ccaatcagag cggcgcgctc cgaaagtttc cttttatggc gaggcggcgg cggcggcggc    780
cctataaaaa gcgaagcgcg cggcgggcgg gagtcgctgc gacgctgcct tcgccccgtg    840
ccccgctccg ccgccgcctc gcgccgcccg ccccggctct gactgaccgc gttactccca    900
caggtgagcg ggcgggacgg cccttctcct ccgggctgta attagcgctt ggtttaatga    960
cggcttgttt ctttttctgtg gctgcgtgaa agccttgagg ggctccggga gggccctttg   1020
tgcgggggga gcggctcggg gctgtccgcg gggggacggc tgccttcggg ggggacgggg   1080
cagggcgggg ttcggcttct ggcgtgtgac cggcggctct agcagcctct gctaaccatg    1140
ttcatgcctt cttctttttc ctacagctcc tgggcaacgt gctggttatt gtgctgtctc    1200
atcattttgg caaagaatta agcttgagct cgcgatccgc agccatgact gagacattgc    1260
caccggtaac ggaatcggct gttgcgctac aggcggaggt gacccagagg gagctgttcg    1320
agttcgttct caacgacccc ctcctcgcca gttcgctgta tattaatatc gcactggcag    1380
ggctgtcgat actgctttc gtgttcatga cgcgcggact cgacgaccca cgggcgaaac    1440
tcatcgccgt ttcgacgatt ttggtgccgg tggtctctat cgcgagctac accgccttg    1500 catcggggct caccatcagc gtcctcgaga tgccagccgg ccacttcgcc gagggtcct   1560
```

```
cggtgatgct cggcggcgaa gaggtagacg gcgtcgtgac gatgtggggc cgctatctga      1620
cgtgggccct ttcgacaccg atgatactgc tggcgcttgg gctgcttgct ggctctaacg      1680
ccacgaagct ctttaccgcc atcaccttcg acatcgcgat gtgtgtcacc ggcctcgcag      1740
ccgcgctgac gacctcttcg cacctgatgc ggtggttctg gtacgccatc agttgtgcgt      1800
gtttcctcgt cgtcctctac atcctgctcg tcgagtgggc acaggacgcc aaggctgccg      1860
gtactgcgga tatgttcaat acgctgaagc tgctgaccgt tgtcatgtgg ctcggctacc      1920
ccatcgtgtg ggcactcggc gttgagggca tcgccgttct tccggtcgga gtcacgtcgt      1980
ggggatacag cttcctcgac atcgtcgcga agtacatctt cgcgttcctg ctgctcaact      2040
acctcacgtc gaacgagagc gtcgtctccg gctcgatact cgacgtgccg tccgcgtcgg      2100
gcactcccgc tgacgacgaa ttcggaggcg gaggtggagc tagcaaagga gaagaactct      2160
tcactggagt tggagttgtc ccaattcttg ttgaattaga tggtgatgtt aacggccaca      2220
agttctctgt cagtggagag ggtgaaggtg atgcaacata cggaaaactt accctgaagt      2280
tcatctgcac tactggcaaa ctgcctgttc catggccaac actagtcact actctgtgct      2340
atggtgttca atgcttttca agatacccgg atcatatgaa acggcatgac ttttttcaaga     2400
```

```
gtgccatgcc cgaaggttat gtacaggaaa ggaccatctt cttcaaagat gacggcaact      2460
acaagacacg tgctgaagtc aagtttgaag gtgataccct tgttaataga atcgagttaa      2520
aaggtattga cttcaaggaa gatggcaaca ttctgggaca caaattggaa tacaactata      2580
actcacacaa tgtatacatc atggcagaca aacaaaagaa tggaatcaaa gtgaacttca      2640
agacccgcca acattgaa gatggaagcg ttcaactagc agaccattat caacaaaata      2700
```

```
ctccaattgg cgatggccct gtccttttac cagacaacca ttacctgtcc acacaatctg      2760
ccctttcgaa agatcccaac gaaaagagag accacatggt ccttcttgag tttgtaacag      2820
ctgctgggat tacacatggc atggatgaac tgtacaacac cgtgagggtg cccatcgccg      2880
tgggcgagag cgacttcgag aacctgaaca ccgaggacgt gagcagcgag agcgaccct       2940 aactcgagtc tagacgtggt accgataatc aacctctgga ttacaaaatt tgtgaaagat      3000
tgactggtat tcttaactat gttgctcctt ttacgctatg tggatacgct gctttaatgc      3060
ctttgtatca tgctattgct tcccgtatgg ctttcatttt ctcctccttg tataaatcct      3120
ggttgctgtc tctttatgag gagttgtggc ccgttgtcag caacgtggc gtggtgtgca       3180 ctgtgtttgc tgacgcaacc cccactggtt ggggcattgc caccacctgt cagctccttt      3240
ccgggacttt cgctttcccc ctccctattg ccacggcgga actcatcgcc gcctgccttg      3300
cccgctgctg gacaggggct cggctgttgg gcactgacaa ttccgtggtg ttgtcgggga      3360
agctgacgtc ctttccatgg ctgctcgcct gtgttgccac ctggattctg cgcgggacgt      3420
ccttctgcta cgtcccttcg gcccctcaatc cagcggacct tccttcccgc ggcctgctgc      3480
cggctctgcg gcctcttccg cgtcttcgcc ttcgccctca gacgagtcgg atctcccttt      3540
gggccgcctc cccgcctgat gcggggatcc tctagagtcg agagatctac gggtggcatc      3600
cctgtgaccc ctccccagtg cctctcctgg ccctggaagt tgccactcca gtgcccacca      3660
gccttgtcct aataaaatta agttgcatca ttttgtctga ctaggtgtcc ttctataata      3720
ttatggggtg gagggggggtg gtatggagca aggggcaagt tgggaagaca acctgtaggg      3780
cctgcggggt ctattgggaa ccaagctgga gtgcagtggc acaatcttgg ctcactgcaa      3840
tctccgcctc ctgggttcaa gcgattctcc tgcctcagcc tcccgagttg ttgggattcc      3900
```

```
aggcatgcat gaccaggctc agctaatttt tgttttttg gtagagacgg ggtttcacca    3960
tattggccag gctggtctcc aactcctaat ctcaggtgat ctacccacct tggcctccca    4020
aattgctggg attacaggcg tgaaccactg ctcccttccc tgtccttctg attttgtagg    4080
taaccacgtg cggaccgagc ggccgcagga accccctagtg atggagttgg ccactcccctc   4140 tctgcgcgct cgctcgctca ctgaggccgg gcgaccaaag gtcgcccgac gcccgggctt    4200
tgcccgggcg ccgcagtga gcgagcgagc gcgcagctgc ctgcagg                   4247
```

<210> SEQ ID NO 43
<211> LENGTH: 3533
<212> TYPE: DNA
<213> ORGANISM: Artificial Sequence
<220> FEATURE:
<223> OTHER INFORMATION: 5'- ITR-CAG-HaloR-{Nav1.6 Motif}-WPRE-
     bGHpolyA-ITR- 3'

<400> SEQUENCE: 43

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca    120
actccatcac tagggttcc tgcggccgca cgcgtgatat cctagttatt aatagtaatc    180
aattacgggg tcattagttc atagcccata tatggagttc cgcgttacat aacttacggt    240
aaatggcccg cctggctgac cgcccaacga ccccgccca ttgacgtcaa taatgacgta    300
tgttcccata gtaacgccaa tagggacttt ccattgacgt caatgggtgg agtatttacg    360
gtaaactgcc cacttggcag tacatcaagt gtatcatatg ccaagtacgc ccctattga    420 cgtcaatgac ggtaaatggc ccgcctggca ttatgcccag tacatgacct tatgggactt    480
tcctacttgg cagtacatct acgtattagt catcgctatt accatgcatg gtcgaggtga    540
gccccacgtt ctgcttcact ctccccatct cccccccctc ccacccccca atttgtatt    600 tatttatttt ttaattatt tgtgcagcga tggggcggg gggggggggg gggcgcgcgc    660 caggcgggc ggggcggggc gaggggcggg gcggggcgag gcggagaggt gcggcggcag    720
ccaatcagag cggcgcgctc cgaaagttc cttttatggc gaggcggcgg cggcggcggc    780
cctataaaaa gcgaagcgcg cggcgggcgg gagtcgctgc gacgctgcct tcgccccgtg    840
ccccgctccg ccgccgcctc gcgccgcccg cccggctct gactgaccgc gttactccca    900
caggtgagcg ggcgggacgg ccccttctcct ccgggctgta attagcgctt ggtttaatga    960
cggcttgttt cttttctgtg gctgcgtgaa agccttgagg ggctccggga gggccctttg   1020
tgcgggggga gcggctcggg gctgtccgcg ggggacggc tgccttcggg ggggacgggg   1080
cagggcgggg ttcggcttct ggcgtgtgac cggcggctct agcagcctct gctaaccatg   1140
ttcatgcctt cttctttttc ctacagctcc tgggcaacgt gctggttatt gtgctgtctc   1200 atcatttgg caaagaatta agcttgagct cgcgatccgc agccatgact gagacattgc   1260
caccggtaac ggaatcggct gttgcgctac aggcggaggt gacccagagg gagctgttcg   1320
agttcgttct caacgacccc ctcctcgcca gttcgctgta tattaatatc gcactggcag   1380
ggctgtcgat actgcttttc gtgttcatga cgcgcggact cgacgaccca cgggcgaaac   1440
tcatcgccgt ttcgacgatt ttggtgccgg tggtctctat cgcgagctac accgccttg   1500 catcggggct caccatcagc gtcctcgaga tgccagccgg ccacttcgcc gaggggtcct   1560
cggtgatgct cggcggcgaa gaggtagacg cgtcgtgac gatgtgggc cgctatctga   1620 cgtgggcct ttcgacaccg atgatactgc tggcgcttgg gctgcttgct ggctctaacg   1680
```

```
ccacgaagct ctttaccgcc atcaccttcg acatcgcgat gtgtgtcacc ggcctcgcag    1740
ccgcgctgac gacctcttcg cacctgatgc ggtggttctg gtacgccatc agttgtgcgt    1800
gtttcctcgt cgtcctctac atcctgctcg tcgagtgggc acaggacgcc aaggctgccg    1860
gtactgcgga tatgttcaat acgctgaagc tgctgaccgt tgtcatgtgg ctcggctacc    1920
ccatcgtgtg ggcactcggc gttgagggca tcgccgttct tccggtcgga gtcacgtcgt    1980
ggggatacag cttcctcgac atcgtcgcga agtacatctt cgcgttcctg ctgctcaact    2040
acctcacgtc gaacgagagc gtcgtctccg gctcgatact cgacgtgccg tccgcgtcgg    2100
gcactcccgc tgacgacgaa ttcgaggcg gaggtggagc tagcaccgtg agggtgccca    2160
tcgccgtggg cgagagcgac ttcgagaacc tgaacaccga ggacgtgagc agcgagagcg    2220 accctaact cgagtctaga cgtggtaccg ataatcaacc tctggattac aaaatttgtg    2280
aaagattgac tggtattctt aactatgttg ctccttttac gctatgtgga tacgctgctt    2340
taatgccttt gtatcatgct attgcttccc gtatggcttt cattttctcc tccttgtata    2400
aatcctggtt gctgtctctt tatgaggagt tgtggcccgt tgtcaggcaa cgtggcgtgg    2460
tgtgcactgt gtttgctgac gcaaccccca ctggttgggg cattgccacc acctgtcagc    2520
tcctttccgg gactttcgct ttcccctccc ctattgccac ggcggaactc atcgccgcct    2580
gccttgcccg ctgctggaca ggggctcggc tgttgggcac tgacaattcc gtggtgttgt    2640
cggggaagct gacgtccttt ccatggctgc tcgcctgtgt tgccacctgg attctgcgcg    2700
ggacgtcctt ctgctacgtc ccttcggccc tcaatccagc ggaccttcct tcccgcggcc    2760
tgctgccggc tctgcggcct cttccgcgtc ttcgccttcg ccctcagacg agtcggatct    2820
ccctttgggc cgcctccccg cctgatgcgg ggatcctcta gagtcgagag atctacgggt    2880
ggcatccctg tgacccctcc ccagtgcctc tcctggccct ggaagttgcc actccagtgc    2940
ccaccagcct tgtcctaata aaattaagtt gcatcatttt gtctgactag gtgtccttct    3000
ataatattat ggggtggagg ggggtggtat ggagcaaggg gcaagttggg aagacaacct    3060
gtagggcctg cggggtctat tgggaaccaa gctggagtgc agtggcacaa tcttggctca    3120
ctgcaatctc cgcctcctgg gttcaagcga ttctcctgcc tcagcctccc gagttgttgg    3180
gattccaggc atgcatgacc aggctcagct aattttgtt tttttggtag agacggggtt    3240
tcaccatatt ggccaggctg gtctccaact cctaatctca ggtgatctac ccaccttggc    3300
ctcccaaatt gctgggatta caggcgtgaa ccactgctcc cttccctgtc cttctgattt    3360
tgtaggtaac cacgtgcgga ccgagcggcc gcaggaaccc ctagtgatgg agttggccac    3420
tccctctctg cgcgctcgct cgctcactga ggccgggcga ccaaaggtcg cccgacgccc    3480
gggctttgcc cgggcggcct cagtgagcga gcgagcgcgc agctgcctgc agg          3533
```

<210> SEQ ID NO 44
<211> LENGTH: 4262
<212> TYPE: DNA
<213> ORGANISM: Artificial Sequence
<220> FEATURE:
<223> OTHER INFORMATION: 5'-ITR-CAG-HaloR-GFP-{NLG-1 Motif}-WPRE-
      bGHpolyA-ITR- 3'

<400> SEQUENCE: 44

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca    120
actccatcac taggggttcc tgcggccgca cgcgtgatat cctagttatt aatagtaatc    180
```

| | |
|---|---|
| aattacgggg tcattagttc atagcccata tatggagttc cgcgttacat aacttacggt | 240 |
| aaatggcccg cctggctgac cgcccaacga cccccgccca ttgacgtcaa taatgacgta | 300 |
| tgttcccata gtaacgccaa tagggacttt ccattgacgt caatgggtgg agtatttacg | 360 |
| gtaaactgcc cacttggcag tacatcaagt gtatcatatg ccaagtacgc ccctattga | 420 |
| cgtcaatgac ggtaaatggc ccgcctggca ttatgcccag tacatgacct tatgggactt | 480 |
| tcctacttgg cagtacatct acgtattagt catcgctatt accatgcatg gtcgaggtga | 540 |
| gccccacgtt ctgcttcact ctccccatct cccccccctc ccacccccca attttgtatt | 600 |
| tatttatttt ttaattattt tgtgcagcga tggggggggg gggggggggg gggcgcgcgc | 660 |
| caggcgggc gggggcgggc gagggcggg gcggggcgag gcggagaggt gcggcggcag | 720 |
| ccaatcagag cggcgcgctc cgaaagtttc cttttatggc gaggcggcgg cggcggcggc | 780 |
| cctataaaaa gcgaagcgcg cggcgggcgg gagtcgctgc gacgctgcct tcgccccgtg | 840 |
| ccccgctccg ccgccgcctc gcgccgcccg cccccggctct gactgaccgc gttactccca | 900 |
| caggtgagcg ggcgggacgg cccttctcct ccgggctgta attagcgctt ggtttaatga | 960 |
| cggcttgttt cttttctgtg gctgcgtgaa agccttgagg ggctccggga gggccctttg | 1020 |
| tgcgggggga gcggctcggg gctgtccgcg ggggacggc tgccttcggg ggggacgggg | 1080 |
| cagggcgggg ttcggcttct ggcgtgtgac cggcggctct agcagcctct gctaaccatg | 1140 |
| ttcatgcctt cttctttttc ctacagctcc tgggcaacgt gctggttatt gtgctgtctc | 1200 |
| atcattttgg caaagaatta agcttgagct cgcgatccgc agccatgact gagacattgc | 1260 |
| caccggtaac ggaatcggct gttgcgctac aggcggaggt gacccagagg gagctgttcg | 1320 |
| agttcgttct caacgacccc ctcctcgcca gttcgctgta tattaatatc gcactggcag | 1380 |
| ggctgtcgat actgcttttc gtgttcatga gcgcggact cgacgaccca cgggcgaaac | 1440 |
| tcatcgccgt ttcgacgatt ttggtgccgg tggtctctat cgcgagctac accggccttg | 1500 |
| catcggggct caccatcagc gtcctcgaga tgccagccgg ccacttcgcc gaggggtcct | 1560 |
| cggtgatgct cggcggcgaa gaggtagacg gcgtcgtgac gatgtggggc cgctatctga | 1620 |
| cgtgggccct ttcgacaccg atgatactgc tggcgcttgg gctgcttgct ggctctaacg | 1680 |
| ccacgaagct cttaccgcc atcaccttcg acatcgcgat gtgtgtcacc ggcctcgcag | 1740 |
| ccgcgctgac gacctcttcg cacctgatgc ggtggttctg gtacgccatc agttgtgcgt | 1800 |
| gtttcctcgt cgtcctctac atcctgctcg tcgagtgggc acaggacgcc aaggctgccg | 1860 |
| gtactgcgga tatgttcaat acgctgaagc tgctgaccgt tgtcatgtgg ctcggctacc | 1920 |
| ccatcgtgtg ggcactcggc gttgagggca tcgccgttct tccggtcgga gtcacgtcgt | 1980 |
| ggggatacag cttcctcgac atcgtcgcga agtacatctt cgcgttcctg ctgctcaact | 2040 |
| acctcacgtc gaacgagagc gtcgtctccg gctcgatact cgacgtgccg tccgcgtcgg | 2100 |
| gcactcccgc tgacgacgaa ttcggaggcg gaggtggagc tagcaaagga gaagaactct | 2160 |
| tcactggagt tggagttgtc ccaattcttg ttgaattaga tggtgatgtt aacggccaca | 2220 |
| agttctctgt cagtggagag ggtgaaggtg atgcaacata cggaaaactt accctgaagt | 2280 |
| tcatctgcac tactggcaaa ctgcctgttc catggccaac actagtcact actctgtgct | 2340 |
| atggtgttca atgcttttca agatacccgg atcatatgaa acggcatgac ttttcaaga | 2400 |
| gtgccatgcc cgaaggttat gtacaggaaa ggaccatctt cttcaaagat gacggcaact | 2460 |
| acaagacacg tgctgaagtc aagtttgaag gtgatacct tgttaataga atcgagttaa | 2520 |
| aaggtattga cttcaaggaa gatggcaaca ttctgggaca caaattggaa tacaactata | 2580 |

-continued

```
actcacacaa tgtatacatc atggcagaca aacaaaagaa tggaatcaaa gtgaacttca    2640
agacccgcca caacattgaa gatggaagcg ttcaactagc agaccattat caacaaaata    2700
ctccaattgg cgatggccct gtccttttac cagacaacca ttacctgtcc acacaatctg    2760 cccttttcgaa agatcccaac gaaaagagag accacatggt ccttcttgag tttgtaacag    2820
ctgctgggat tacacatggc atggatgaac tgtacaacgt ggttcttcgg accgcctgtc    2880
ccccagatta cacactagct atgaggaggt cacctgatga tgttccctta atgacaccca    2940
acaccattac aatgtaactc gagtctagac gtggtaccga taatcaacct ctggattaca    3000
aaatttgtga agattgact ggtattctta actatgttgc tccttttacg ctatgtggat    3060
acgctgcttt aatgcctttg tatcatgcta ttgcttcccg tatggctttc attttctcct    3120
ccttgtataa atcctggttg ctgtctcttt atgaggagtt gtggcccgtt gtcaggcaac    3180
gtggcgtggt gtgcactgtg tttgctgacg caaccccac tggttgggggc attgccacca    3240 cctgtcagct cctttccggg actttcgctt tcccctccc tattgccacg gcggaactca    3300
tcgccgcctg ccttgcccgc tgctggacag gggctcggct gttgggcact gacaattccg    3360
tggtgttgtc ggggaagctg acgtccttc catggctgct cgcctgtgtt gccacctgga    3420
ttctgcgcgg gacgtccttc tgctacgtcc cttcggccct caatccagcg gaccttcctt    3480
cccgcggcct gctgccggct ctgcggcctc ttccgcgtct tcgccttcgc cctcagacga    3540
gtcggatctc cctttgggcc gcctcccgc ctgatgcggg gatcctctag agtcgagaga    3600
tctacgggtg gcatccctgt gacccctccc cagtgcctct cctggccctg gaagttgcca    3660
ctccagtgcc caccagcctt gtcctaataa aattaagttg catcattttg tctgactagg    3720
tgtccttcta taatattatg gggtggaggg ggtggtatg gagcaagggg caagttggga    3780
agacaacctg tagggcctgc ggggtctatt gggaaccaag ctggagtgca gtggcacaat    3840
cttggctcac tgcaatctcc gcctcctggg ttcaagcgat tctcctgcct cagcctcccg    3900
agttgttggg attccaggca tgcatgacca ggctcagcta attttttgtt ttttggtaga    3960
gacggggttt caccatattg gccaggctgg tctccaactc ctaatctcag gtgatctacc    4020 cacccttggcc tcccaaattg ctgggattac aggcgtgaac cactgctccc ttccctgtcc    4080
ttctgatttt gtaggtaacc acgtgcggac cgagcggccg caggaaccc tagtgatgga    4140 gttggccact ccctctctgc gcgctcgctc gctcactgag gccgggcgac caaaggtcgc    4200
ccgacgcccg ggctttgccc gggcggcctc agtgagcgag cgagcgcgca gctgcctgca    4260
gg                                                                    4262
```

<210> SEQ ID NO 45
<211> LENGTH: 3626
<212> TYPE: DNA
<213> ORGANISM: Artificial Sequence
<220> FEATURE:
<223> OTHER INFORMATION: 5'-ITR-CAG-HaloR-{NLG-1 Motif}-WPRE-
    bGHpolyA-ITR- 3'

<400> SEQUENCE: 45

```
cctgcaggca gctgcgcgct cgctcgctca ctgaggccgc cgggcaaag cccgggcgtc      60 gggcgacctt tggtcgcccg gcctcagtga gcgagcgagc gcgcagagag ggagtggcca    120
actccatcac tagggggttcc tgcggccgca cgcgtgatat cctagttatt aatagtaatc    180
aattacgggg tcattagttc atagcccata tatggagttc cgcgttacat aacttacggt    240
aaatggcccg cctggctgac cgcccaacga cccccgccca ttgacgtcaa taatgacgta    300
```

```
tgttcccata gtaacgccaa tagggacttt ccattgacgt caatgggtgg agtatttacg     360
gtaaactgcc cacttggcag tacatcaagt gtatcatatg ccaagtacgc ccctattga     420 cgtcaatgac ggtaaatggc ccgcctggca ttatgcccag tacatgacct tatgggactt     480
tcctacttgg cagtacatct acgtattagt catcgctatt accatgcatg gtcgaggtga     540
gccccacgtt ctgcttcact ctccccatct ccccccctc ccacccca attttgtatt        600 tatttatttt ttaattattt tgtgcagcga tgggggcggg gggggggggg gggcgcgcgc     660
caggcggggc ggggcggggc gagggcggg gcggggcgag gcggagaggt gcggcggcag      720
ccaatcagag cggcgcgctc cgaaagtttc cttttatggc gaggcggcgg cggcggcggc     780
cctataaaaa gcgaagcgcg cggcgggcgg gagtcgctgc gacgctgcct tcgccccgtg     840
ccccgctccg ccgccgcctc gcgccgcccg ccccggctct gactgaccgc gttactccca     900
caggtgagcg ggcgggacgg cccttctcct ccgggctgta attagcgctt ggtttaatga     960
cggcttgttt cttttctgtg gctgcgtgaa agccttgagg ggctccggga gggccctttg    1020 tgcggggga gcggctcggg gctgtccgcg ggggacggc tgccttcggg ggggacgggg      1080
cagggcgggg ttcggcttct ggcgtgtgac cggcggctct agcagcctct gctaaccatg    1140
ttcatgcctt cttctttttc ctacagctcc tgggcaacgt gctggttatt gtgctgtctc    1200
atcattttgg caaagaatta agcttgagct cgcgatccgc agccatgact gagacattgc    1260
caccggtaac ggaatcggct gttgcgctac aggcggaggt gacccagagg gagctgttcg    1320
agttcgttct caacgacccc ctcctcgcca gttcgctgta tattaatatc gcactggcag    1380
ggctgtcgat actgcttttc gtgttcatga cgcgcggact cgacgaccca cgggcgaaac    1440
tcatcgccgt ttcgacgatt ttggtgccgg tggtctctat cgcgagctac accggccttg    1500
catcggggct caccatcagc gtcctcgaga tgccagccgg ccacttcgcc gaggggtcct    1560
cggtgatgct cggcggcgaa gaggtagacg gcgtcgtgac gatgtggggc cgctatctga    1620
cgtgggccct ttcgacaccg atgatactgc tggcgcttgg gctgcttgct ggctctaacg    1680
ccacgaagct cttttaccgcc atcaccttcg acatcgcgat gtgtgtcacc ggcctcgcag    1740
ccgcgctgac gacctcttcg cacctgatgc ggtggttctg gtacgccatc agttgtgcgt    1800
gtttcctcgt cgtcctctac atcctgctcg tcgagtgggc acaggacgcc aaggctgccg    1860
gtactgcgga tatgttcaat acgctgaagc tgctgaccgt tgtcatgtgg ctcggctacc    1920
ccatcgtgtg ggcactcggc gttgagggca tcgccgttct tccggtcgga gtcacgtcgt    1980
ggggatacag cttcctcgac atcgtcgcga agtacatctt cgcgttcctg ctgctcaact    2040
acctcacgtc gaacgagagc gtcgtctccg gctcgatact cgacgtgccg tccgcgtcgg    2100
gcactcccgc tgacgacgaa ttcggaggcg gaggtggagc tagcgtggtt cttcggaccg    2160
cctgtccccc aaaaaagagg ctcctgagct tcagggacgt ggacttcgag gaggacagcg    2220
attacacact agctatgagg aggtcacctg atgatgttcc cttaatgaca cccaacacca    2280
ttacaatgta actcgagtct agacgtggta ccgataatca acctctggat tacaaaattt    2340
gtgaaagatt gactggtatt cttaactatg ttgctccttt tacgctatgt ggatacgctg    2400
ctttaatgcc tttgtatcat gctattgctt cccgtatggc tttcatttc tcctccttgt     2460 ataaatcctg gttgctgtct ctttatgagg agttgtggcc cgttgtcagg caacgtggcg    2520
tggtgtgcac tgtgtttgct gacgcaaccc ccactggttg ggcattgcc accacctgtc     2580 agctcctttc cgggactttc gctttccccc tccctattgc cacggcggaa ctcatcgccg    2640
```

```
cctgccttgc cgctgctgg acaggggctc ggctgttggg cactgacaat tccgtggtgt    2700
tgtcggggaa gctgacgtcc tttccatggc tgctcgcctg tgttgccacc tggattctgc    2760
gcgggacgtc cttctgctac gtcccttcgg ccctcaatcc agcggacctt ccttcccgcg    2820
gcctgctgcc ggctctgcgg cctcttccgc gtcttcgcct tcgccctcag acagtcgga    2880 tctcccttg ggccgcctcc ccgcctgatg cggggatcct ctagagtcga gagatctacg    2940
ggtggcatcc ctgtgacccc tccccagtgc ctctcctggc cctggaagtt gccactccag    3000
tgcccaccag ccttgtccta ataaaattaa gttgcatcat tttgtctgac taggtgtcct    3060
tctataatat tatggggtgg aggggggtgg tatggagcaa ggggcaagtt gggaagacaa    3120
cctgtagggc ctgcgggtc tattgggaac caagctggag tgcagtggca caatcttggc    3180
tcactgcaat ctccgcctcc tgggttcaag cgattctcct gcctcagcct ccgagttgt    3240 tgggattcca ggcatgcatg accaggctca gctaattttt gttttttgg tagagacggg    3300 gtttcaccat attggccagg ctggtctcca actcctaatc tcaggtgatc tacccacctt    3360
ggcctcccaa attgctggga ttacaggcgt gaaccactgc tcccttccct gtccttctga    3420
ttttgtaggt aaccacgtgc ggaccgagcg ccgcagggt aaccacgtgc ggaccgagcg    3480
gccgcaggaa cccctagtga tggagttggc cactccctct ctgcgcgctc gctcgctcac    3540
tgaggccggg cgaccaaagg tcgcccgacg cccgggcttt gcccgggcgg cctcagtgag    3600
cgagcgagcg cgcagctgcc tgcagg                                        3626
```

<210> SEQ ID NO 46
<211> LENGTH: 4244
<212> TYPE: DNA
<213> ORGANISM: Artificial Sequence
<220> FEATURE:
<223> OTHER INFORMATION: 5' -ITR-CAG-HaloR-GFP-{MLPH Motif}-WPRE-
    bGHpolyA-ITR- 3'

<400> SEQUENCE: 46

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgatat cctagttatt aatagtaatc     180
aattacgggg tcattagttc atagcccata tatggagttc cgcgttacat aacttacggt     240
aaatggcccg cctggctgac cgcccaacga ccccccgccca ttgacgtcaa taatgacgta     300
tgttcccata gtaacgccaa tagggacttt ccattgacgt caatgggtgg agtatttacg     360
gtaaactgcc cacttggcag tacatcaagt gtatcatatg ccaagtacgc cccctattga     420
cgtcaatgac ggtaaatggc ccgcctggca ttatgcccag tacatgacct tatgggactt     480
tcctacttgg cagtacatct acgtattagt catcgctatt accatgcatg gtcgaggtga     540
gccccacgtt ctgcttcact ctccccatct ccccccctc cccaccccca tttttgtatt     600
tatttatttt ttaattattt tgtgcagcga tgggggcggg gggggggggg gggcgcgcgc     660
caggcggggc ggggcggggc gaggggcggg gcggggcgag gcggagaggt gcggcggcag     720
ccaatcagag cggcgcgctc cgaaagtttc cttttatggc gaggcggcgg cggcggcggc     780
cctataaaaa gcgaagcgcg cggcgggcgg gagtcgctgc gacgctgcct tcgccccgtg     840
ccccgctccg ccgccgcctc gcgccgcccg ccccggctct gactgaccgc gttactccca     900
caggtgagcg gcgggacgg cccttctcct ccgggctgta attagcgctt ggtttaatga     960
cggcttgttt cttttctgtg gctgcgtgaa agccttgagg ggctccggga gggccctttg    1020
```

```
tgcgggggga gcggctcggg gctgtccgcg gggggacggc tgccttcggg ggggacgggg    1080
cagggcgggg ttcggcttct ggcgtgtgac cggcggctct agcagcctct gctaaccatg    1140
ttcatgcctt cttctttttc ctacagctcc tgggcaacgt gctggttatt gtgctgtctc    1200
atcattttgg caaagaatta agcttgagct cgcgatccgc agccatgact gagacattgc    1260
caccggtaac ggaatcggct gttgcgctac aggcggaggt gacccagagg gagctgttcg    1320
agttcgttct caacgacccc ctcctcgcca gttcgctgta tattaatatc gcactggcag    1380
ggctgtcgat actgcttttc gtgttcatga cgcgcggact cgacgaccca cgggcgaaac    1440
tcatcgccgt ttcgacgatt ttggtgccgt tggtctctat cgcgagctac accggccttg    1500
catcggggct caccatcagc gtcctcgaga tgccagccgg ccacttcgcc gaggggtcct    1560
cggtgatgct cggcggcgaa gaggtagacg cgtcgtgac gatgtggggc cgctatctga    1620
cgtgggccct ttcgacaccg atgatactgc tggcgcttgg gctgcttgct ggctctaacg    1680
ccacgaagct cttaccgcc atcaccttcg acatcgcgat gtgtgtcacc ggcctcgcag    1740
ccgcgctgac gacctcttcg cacctgatgc ggtggttctg gtacgccatc agttgtgcgt    1800
gtttcctcgt cgtcctctac atcctgctcg tcgagtgggc acaggacgcc aaggctgccg    1860
gtactgcgga tatgttcaat acgctgaagc tgctgaccgt tgtcatgtgg ctcggctacc    1920
ccatcgtgtg ggcactcggc gttgagggca tcgccgttct tccggtcgga gtcacgtcgt    1980
ggggatacag cttcctcgac atcgtcgcga agtacatctt cgcgttcctg ctgctcaact    2040
acctcacgtc gaacgagagc gtcgtctccg gctcgatact cgacgtgccg tccgcgtcgg    2100
gcactcccgc tgacgacgaa ttcggaggcg gaggtggagc tagcaaagga gaagaactct    2160
tcactggagt tggagttgtc ccaattcttg ttgaattaga tggtgatgtt aacggccaca    2220
agttctctgt cagtggagag ggtgaaggtg atgcaacata cggaaaactt accctgaagt    2280
tcatctgcac tactggcaaa ctgcctgttc catggccaac actagtcact actctgtgct    2340
atggtgttca atgcttttca agataccegg atcatatgaa acggcatgac ttttcaaga    2400 gtgccatgcc cgaaggttat gtacaggaaa ggaccatctt cttcaaagat gacggcaact    2460
acaagacacg tgctgaagtc aagtttgaag gtgataccct tgttaataga atcgagttaa    2520
aaggtattga cttcaaggaa gatggcaaca ttctgggaca caaattggaa tacaactata    2580
actcacacaa tgtatacatc atggcagaca acaaaagaa tggaatcaaa gtgaacttca    2640
agacccgcca caacattgaa gatggaagcg ttcaactagc agaccattat caacaaaata    2700
ctccaattgg cgatggccct gtccttttac cagacaacca ttacctgtcc acacaatctg    2760
ccctttcgaa agatcccaac gaaaagagag accacatggt ccttcttgag tttgtaacag    2820
ctgctgggat tacacatggc atggatgaac tgtacaacag gaccagcct ctgaacagca    2880 aaaagaaaaa gaggctcctg agcttcaggg acgtggactt cgaggaggac agcgactaac    2940
tcgagtctag acgtggtacc gataatcaac ctctggatta caaaatttgt gaaagattga    3000
ctggtattct taactatgtt gctccttta cgctatgtgg atacgctgct ttaatgcctt    3060
tgtatcatgc tattgcttcc cgtatggctt tcattttctc ctccttgtat aaatcctggt    3120
tgctgtctct ttatgaggag ttgtggcccg ttgtcaggca acgtggcgtg gtgtgcactg    3180
tgtttgctga cgcaacccc actggttggg gcattgccac cacctgtcag ctcctttccg    3240
ggactttcgc tttccccctc cctattgcca cggcggaact catcgccgcc tgccttgccc    3300
gctgctggac aggggctcgg ctgttgggca ctgacaattc cgtggtgttg tcggggaagc    3360
tgacgtcctt tccatggctg ctcgcctgtg ttgccacctg gattctgcgc gggacgtcct    3420
```

```
tctgctacgt cccttcggcc ctcaatccag cggaccttcc ttcccgcggc ctgctgccgg    3480
ctctgcggcc tcttccgcgt cttcgccttc gccctcagac gagtcggatc tccctttggg    3540
ccgcctcccc gcctgatgcg gggatcctct agagtcgaga gatctacggg tggcatccct    3600
gtgacccctc cccagtgcct ctcctggccc tggaagttgc cactccagtg cccaccagcc    3660
ttgtcctaat aaaattaagt tgcatcattt tgtctgacta ggtgtccttc tataatatta    3720
tggggtggag gggggtggta tggagcaagg ggcaagttgg gaagacaacc tgtagggcct    3780
gcggggtcta ttgggaacca agctggagtg cagtggcaca atcttggctc actgcaatct    3840
ccgcctcctg ggttcaagcg attctcctgc ctcagcctcc cgagttgttg ggattccagg    3900
catgcatgac caggctcagc taatttttgt ttttttggta gagacggggt ttcaccatat    3960
tggccaggct ggtctccaac tcctaatctc aggtgatcta cccaccttgg cctcccaaat    4020
tgctgggatt acaggcgtga accactgctc ccttccctgt ccttctgatt ttgtaggtaa    4080
ccacgtgcgg accgagcggc cgcaggaacc cctagtgatg gagttggcca ctccctctct    4140
gcgcgctcgc tcgctcactg aggccgggcg accaaaggtc gcccgacgcc cgggctttgc    4200
ccgggcggcc tcagtgagcg agcgagcgcg cagctgcctg cagg                      4244
```

<210> SEQ ID NO 47
<211> LENGTH: 3530
<212> TYPE: DNA
<213> ORGANISM: Artificial Sequence
<220> FEATURE:
<223> OTHER INFORMATION: 5' -ITR-CAG-HaloR-{MLPH Motif}-WPRE-
       bGHpolyA-ITR- 3'

<400> SEQUENCE: 47

```
cctgcaggca gctgcgcgct cgctcgctca ctgaggccgc cgggcaaag cccgggcgtc      60 gggcgacctt tggtcgcccg gcctcagtga gcgagcgagc gcgcagagag ggagtggcca    120
actccatcac taggggttcc tgcggccgca cgcgtgatat cctagttatt aatagtaatc    180
aattacgggg tcattagttc atagcccata tatggagttc cgcgttacat aacttacggt    240
aaatggcccg cctggctgac cgcccaacga ccccgcccca ttgacgtcaa taatgacgta    300
tgttcccata gtaacgccaa tagggacttt ccattgacgt caatgggtgg agtatttacg    360
gtaaactgcc cacttggcag tacatcaagt gtatcatatg ccaagtacgc cccctattga    420
cgtcaatgac ggtaaatggc ccgcctggca ttatgcccag tacatgacct tatgggactt    480
tcctacttgg cagtacatct acgtattagt catcgctatt accatgcatg gtcgaggtga    540
gccccacgtt ctgcttcact ctccccatct cccccccctc cccaccccca attttgtatt    600
tatttatttt ttaattattt tgtgcagcga tgggggcggg ggggggggg gggcgcgcgc      660 caggcggggc gggcggggc gagggcggg gcggggcgag gcggagaggt gcggcggcag      720
ccaatcagag cggcgcgctc cgaaagtttc cttttatggc gaggcggcgg cggcggcggc    780
cctataaaaa gcgaagcgcg cggcgggcgg gagtcgctgc gacgctgcct tcgccccgtg    840
ccccgctccg ccgccgcctc gcgccgcccg ccccggctct gactgaccgc gttactccca    900
caggtgagcg gcgggacgg cccttctcct ccggctgta attagcgctt ggtttaatga      960
cggcttgttt cttttctgtg gctgcgtgaa agccttgagg ggctccggga gggccctttg    1020 tgcggggga gcggctcggg gctgtccgcg ggggacggc tgccttcggg ggacgggg       1080 cagggcgggg ttcggcttct ggcgtgtgac cggcggctct agcagcctct gctaaccatg    1140
ttcatgcctt cttctttttc ctacagctcc tgggcaacgt gctggttatt gtgctgtctc    1200
```

```
atcattttgg caaagaatta agcttgagct cgcgatccgc agccatgact gagacattgc    1260
caccggtaac ggaatcggct gttgcgctac aggcggaggt gacccagagg gagctgttcg    1320
agttcgttct caacgacccc ctcctcgcca gttcgctgta tattaatatc gcactggcag    1380
ggctgtcgat actgcttttc gtgttcatga cgcgcggact cgacgaccca cgggcgaaac    1440
tcatcgccgt ttcgacgatt ttggtgccgg tggtctctat cgcgagctac accggccttg    1500
catcggggct caccatcagc gtcctcgaga tgccagccgg ccacttcgcc gaggggtcct    1560
cggtgatgct cggcggcgaa gaggtagacg gcgtcgtgac gatgtggggc cgctatctga    1620
cgtgggccct ttcgacaccg atgatactgc tggcgcttgg gctgcttgct ggctctaacg    1680
ccacgaagct ctttaccgcc atcaccttcg acatcgcgat gtgtgtcacc ggcctcgcag    1740
ccgcgctgac gacctcttcg cacctgatgc ggtggttctg gtacgccatc agttgtgcgt    1800
gtttcctcgt cgtcctctac atcctgctcg tcgagtgggc acaggacgcc aaggctgccg    1860
gtactgcgga tatgttcaat acgctgaagc tgctgaccgt tgtcatgtgg ctcggctacc    1920
ccatcgtgtg ggcactcggc gttgagggca tcgccgttct tccggtcgga gtcacgtcgt    1980
ggggatacag cttcctcgac atcgtcgcga agtacatctt cgcgttcctg ctgctcaact    2040
acctcacgtc gaacgagagc gtcgtctccg gctcgatact cgacgtgccg tccgcgtcgg    2100
gcactcccgc tgacgacgaa ttcggaggcg gaggtggagc tagcagggac cagcctctga    2160
acagcaaaaa gaaaagagg ctcctgagct tcagggacgt ggacttcgag gaggacagcg    2220
actaactcga gtctagacgt ggtaccgata atcaacctct ggattacaaa atttgtgaaa    2280
gattgactgg tattcttaac tatgttgctc cttttacgct atgtggatac gctgctttaa    2340
tgcctttgta tcatgctatt gcttcccgta tggctttcat tttctcctcc ttgtataaat    2400
cctggttgct gtctctttat gaggagttgt ggcccgttgt caggcaacgt ggcgtggtgt    2460
gcactgtgtt tgctgacgca accccactg gttgggcat tgccaccacc tgtcagctcc    2520
tttccgggac tttcgctttc cccctcccta ttgccacggc ggaactcatc gccgcctgcc    2580
ttgcccgctg ctggacaggg gctcggctgt tgggcactga caattccgtg gtgttgtcgg    2640
ggaagctgac gtccttttcca tggctgctcg cctgtgttgc cacctggatt ctgcgcggga    2700
cgtccttctg ctacgtccct tcggccctca atccagcgga ccttccttcc gcggcctgc    2760 tgccggctct gcggcctctt ccgcgtcttc gccttcgccc tcagacgagt cggatctccc    2820
tttgggccgc ctccccgcct gatgcgggga tcctctagag tcgagagatc tacgggtggc    2880
atccctgtga ccccctcccca gtgcctctcc tggccctgga agttgccact ccagtgccca    2940
ccagccttgt cctaataaaa ttaagttgca tcattttgtc tgactaggtg tccttctata    3000
atattatggg gtggaggggg gtggtatgga caagggca agttgggaag acaacctgta    3060
gggcctgcgg ggtctattgg gaaccaagct ggagtgcagt ggcacaatct ggctcactg    3120 caatctccgc ctcctgggtt caagcgattc tcctgcctca gcctcccgag ttgtgggat    3180 tccaggcatg catgaccagg ctcagctaat ttttgttttt ttggtagaga cggggtttca    3240
ccatattggc caggctggtc tccaactcct aatctcaggt gatctaccca ccttggcctc    3300
ccaaattgct gggattacag gcgtgaacca ctgctccctt ccctgtcctt ctgattttgt    3360
aggtaaccac gtgcggaccg agcggccgca ggaaccccta gtgatggagt tggccactcc    3420
ctctctgcgc gctcgctcgc tcactgaggc cgggcgacca aggtcgccc gacgcccggg    3480 ctttgcccgg gcggcctcag tgagcgagcg agcgcgcagc tgcctgcagg    3530
```

AAV-MEDIATED SUBCELLULAR TARGETING OF HETEROLOGOUS RHODOPSINS IN RETINAL GANGLION CELLS

RELATED APPLICATIONS

This application is a U.S. National Stage Application, filed under 35 U.S.C. §371, of International Patent Application No.: PCT/US2011/035266, filed May 4, 2011, which claims the benefit of U.S. Provisional Patent Application No. 61/331,125, filed May 4, 2010. The contents of each of which are incorporated herein by reference in their entireties.

STATEMENT OF RIGHTS TO INVENTIONS MADE UNDER FEDERALLY SPONSORED RESEARCH

This invention was funded in part by grants (R01EY017130, P30EY040689) from the National Eye Institute of the National Institutes of Health, which provides to the United States government certain rights in this invention.

SEQUENCE LISTING

The instant application contains a Sequence Listing which has been submitted electronically as a text file, created on May 1, 2015, named RTRO-702N01US_Sequence Listing_ST25.txt, and 108 kilobytes in size. The sequence listing is hereby incorporated by reference.

BACKGROUND OF THE INVENTION

1. Field of the Invention

The present invention in the field of molecular biology and medicine relates to the targeting of microbial-type rhodopsins, such as the light-gated cation-selective membrane channel, channelrhodopsin-2 (Chop2 or ChR2) or the ion pump halorhodopsin (HaloR) in retinal ganglion cells as a basis for restoring visual perception and various aspects of vision.

2. Description of the Background Art

Vision normally begins when rods and cones (photoreceptors) convert light signals to electrical signals that are then relayed through second- and third-order retinal neurons and the optic nerve to the lateral *geniculate* nucleus and, then to the visual cortex where visual images are formed (Baylor, D, 1996, *Proc. Natl. Acad. Sci. USA* 93:560-565; Wässle, H, 2004, *Nat. Rev. Neurosci.* 5:747-57). The severe loss of photoreceptor cells can be caused by congenital retinal degenerative diseases, such as retinitis pigmentosa (RP) (Sung, C H et al., 1991, *Proc. Natl. Acad. Sci. USA* 88:6481-85; Humphries, P et al., 1992, *Science* 256:804-8; Welcher, R G et al., in: S J Ryan, Ed, *Retina*, Mosby, St. Louis (1994), pp. 335-466), and can result in complete blindness. Age-related macular degeneration (AMD) also results from degeneration and death of photoreceptor cells, which can cause severe visual impairment within the centrally located best visual area of the visual field.

As rods and cones are lost in humans as well as rodents and other animals, little or no signal is sent to the brain. There are currently no effective treatments or cures for inherited retinal degenerations that cause partial or total blindness.

Approaches to treatment of retinal degeneration include (1) preservation of remaining photoreceptors in patients with retinal degenerative disease, and (2) replacement of photoreceptors lost to retinal degeneration. For the first approach, neuroprotection with neurotrophic factors (LaVail, M M et al., 1992, *Proc. Natl. Acad. Sci. USA* 89:11249-53) and virus-vector-based delivery of wild-type genes for recessive null mutations (Acland, G M et al., 2001, *Nat. Genet.* 28:92-95) have come the furthest—to the point of clinical trials (Hauswirth, W W, 2005, Retina 25, S60; Jacobson, S, Protocol #0410-677, for adeno-associated viral (AAV)-mediated gene replacement therapy in Leber's Congenital Amaurosis (LCA), a specific form of retinal degeneration. This approach is not applicable in patients in advanced stages of retinal degeneration where photoreceptor cells must be replaced. One replacement approach involves transplantation of normal tissue or cells to the diseased retina. Another involves electrical-stimulation of remaining light-insensitive neurons via retinal implants in lieu of the lost cells (prosthetic substitution). Both methods face many obstacles. Hence, there is a continuing need for vision-restoring therapies for inherited blinding disease.

Histological studies in animal models of photoreceptor degeneration and in postmortem human eyes from patients with almost complete photoreceptor loss due to RP showed preservation of a significant number of inner retinal neurons, making retinal gene therapy a possible therapeutic option (e.g., U.S. Pat. No. 5,827,702; WO 00/15822 (2000) and WO 98/48097 (1998)).

Retinal gene transfer of a reporter gene, green fluorescent protein (GFP), using a recombinant AAV (rAAV) was demonstrated in normal primates (Bennett, J et al. 1999 *Proc. Natl. Acad. Sci. USA* 96, 9920-25). However, the restoration of vision in a blinding disease of animals, particularly in humans and other mammals, caused by genetic defects in retinal pigment epithelium (RPE) and/or photoreceptor cells has not been achieved. Bennett and colleagues have described rescue of photoreceptors by gene therapy in a mutant RPE65 gene model of rapid degeneration of photoreceptors and replacement therapy with the normal gene to replace/supplant the mutant gene. (US Pat Publ 2004/0022766, Acland et al.). This therapy showed some success in a naturally-occurring dog model of human LCA—the RPE65 mutant dog.

Heterologous expression of *Drosophila* rhodopsin (Zemelman, B V et al., 2002, *Neuron* 33:15-22) and melanopsin, the putative photopigment of the intrinsic photosensitive retinal ganglion cells ("RGC") has been reported (Melyan, Z. et al., 2005, *Nature* 433:741-5; Panda, S. et al., 2005, *Science* 307:600-604; Qiu, X. et al., 2005, *Nature* 433:745-9). These photopigments, however, are coupled to membrane channels via a G protein signaling cascade and use cis-isoforms of retinaldehyde as their chromophore. Expression of multiple genes would be required to render photosensitivity and their light response kinetics is rather slow.

The present inventor's work, including the present invention, utilizes microbial-type rhodopsins that are similar to bacteriorhodopsin (Oesterhelt, D et al., 1973, *Proc. Natl. Acad. Sci. USA* 70:2853-7), whose conformation change is caused by reversible photoisomerization of their chromophore group, all-trans retinaldehyde, and is directly coupled to ion movement through the membrane (Oesterhelt, D., 1998, *Curr. Opin. Struct. Biol.* 8:489-500). Two microbial-type opsins, channelopsin-1 and -2 (Chop1 and Chop2), have been cloned from *Chlamydomonas reinhardtii* (Nagel, G. et al., 2002, *Science* 296:2395-8; Sineshchekov, O A et al., 2002, *Proc. Natl. Acad. Sci. USA* 99:8689-94;

Nagel, G. et al., 2003, *Proc. Natl. Acad. Sci. USA* 100, 13940-45) and shown to form directly light-gated membrane channels when expressed in *Xenopus laevis* oocytes or HEK293 cells in the presence of all-trans retinal. Chop2, a seven transmembrane domain protein, becomes photo-switchable when bound to the chromophore all-trans retinal. Chop2 is particularly attractive because its functional light-sensitive channel, channelrhodopsin-2 (Chop2 retinalidene abbreviated ChR2) with the attached chromophore is permeable to physiological cations. Unlike animal rhodopsins, which only bind the 11-cis conformation, Chop2/ChR2 binds all-trans retinal isomers, obviating the need for all-trans to 13-cis isomerization supplied by the vertebrate visual cycle.

However, the long-term compatibility of expressing ChR2 in native neurons in vivo in general and the properties of ChR2-mediated light responses in retinal neurons in particular remained unknown until the work of the present inventor and colleagues. Indeed their work (and that of others) represent the pioneering demonstration of the (a) feasibility of restoring light sensitivity to a degenerate retina, (b) transmission of light-driven information to higher visual centers, and mediation of visually guided behaviors through such prosthetic interventions. This work proved that the insertion of such "optical neuromodulators" or "light sensors" as ChR2 into normally photo-insensitive retinal neurons is a promising approach for restoring sight to profoundly blind individuals. These strategies included the delivery of the directly photosensitive cation channel ChR2 and the photosensitive chloride pump halorhodopsin (abbreviated herein "HaloR" and elsewhere "NpHR" or "eNpHR" because of its origin from *Natronobacterium pharaonis* (Lanyi, J K et al. *J. Biol. Chem.* 265:1253-1260 (1990). Such work has been reported by the present inventor's group (Bi, A. et al., *Neuron* 50:23-33 (2006), Ivanova, E et al., *Mol Vis.* 15:1680-9 (2009), Zhang, Y. et al., *J. Neurosci.* 29:9186-96 (2009), primarily with ChR2. Others have delivered and expressed ChR2 (Lagali et al., *Nat. Neurosci.* 11:667-675 (2008); NpHR by (Busskamp V. et al., *Science* 329, 413-417 (2010); synthetically engineered potassium (SPARK) and glutamate (LiGluR) channels (Greenberg, K P et al., *Invest. Ophthalmol. Vis. Sci.* 47, 4750 (2006; abstract); Kolstad et al., *Invest. Ophthalmol. Vis. Sci* 49:3897 (2009; Abstract) and the G protein-coupled receptor melanopsin (Lin, B. et al., *Proc. Natl. Acad. Sci. USA* 105:16009-16014 (2008)) in normally nonphotosensitive bipolar, amacrine, and ganglion cells or nonfunctional photoreceptors.

The present inventor and colleagues (Bi, A. et al., *Neuron* 50:23-33 (2006); WO2007/131180) disclosed adeno-associated virus (AAV2)-mediated expression of exogenously delivered light-gated membrane cation channel, ChR2, or light-driven chloride ion pump, HaloR, in inner retinal neurons and demonstrated that expression of ChR2 in surviving inner retinal neurons of a mouse with photoreceptor degeneration can restore the ability of the retina to encode light signals and transmit the light signals to the visual cortex.

The present inventor and colleagues (Zhang, Y. et al., *J Neurosci.* 29:9186-96 (2009 Jul. 22) reported that the expression HaloR can effectively restore OFF responses in inner retinal neurons of mice with retinal degeneration. HaloR-expressing RGCs respond to light with rapid hypopolarization and suppression of spike activity. After termination of the light stimulus, their membrane potential exhibited a rapid rebound overshoot with robust sustained or transient spike firing. Coexpression of ChR2/HaloR in RGCs produced ON, OFF, and even ON-OFF responses, depending on the wavelength of the light stimulus. Suggesting that the expression of multiple microbial rhodopsins such as ChR2 and HaloR is a possible strategy to restore both ON and OFF light responses in the retina after the death of rod and cone photoreceptors.

The present invention is a refinement and significant step forward of the inventor's prior work, being directed to differential, subcellular "site-selective expression" of these light-sensor-encoding nucleic acids by adding sorting or targeting motifs to the vectors that confer such selectivity. This adds to the "spatial resolution" of vision restoration achieved in this manner in those suffering vision loss or blindness caused, for example, by any of a number of retinal degenerative diseases. The present inventor's approach does not require, introducing exogenous cells and tissues or physical devices, thus avoiding obstacles encountered by existing approaches, though the combined use of the present approach with visual prostheses or devices is also envisioned.

SUMMARY OF THE INVENTION

The present inventor has discovered that differentially targeted expression of ChR2 and HaloR to different subcellular regions in RGCs recreates the antagonistic center-surround receptive field in these cells that further permits improvement of the visual spatial processing for restored vision. The primary spatial distinction of expression is in center vs. peripheral regions of the cells. Peripheral is also referred to in the art as the "surround" or as "off center," terms that are well understood.

RGCs are rendered light sensitive by expression of ChR2 and/or HaloR selectively in somatodendritic region while being kept to a minimum in the axonal region. This enables maintenance of visual spatial processing. This is based on the discovery that a number of "sorting motifs" also referred to here as "targeting motifs, "sorting sequences" or "targeting sequences" present in a vector that comprises the light sensor encoding nucleic acid. Such a motif mediates site- or region-selective expression of the ChR2 or HaloR in subcellular regions of a retinal neuron, preferably an RGC. This targeting serves as a basis for enhanced spatial control and specificity, and results in transmission of appropriate signals, providing better contrast, which more closely resembling signals from a healthy, intact retina, to higher centers of the visual cortex to compensate for damage and degeneration in retinal photoreceptors.

The present invention is directed to a nucleic acid molecule encoding a rhodopsin for differential expression in subcellular regions of a retinal neuron, preferably an RGC, which molecule comprises:

(a) a first nucleotide sequence encoding a light-gated channel rhodopsin or a light-driven ion pump rhodopsin;
(b) linked in frame to (a), a second nucleotide sequence encoding a peptide or polypeptide sorting motif;
(c) operatively linked to (a) and (b), a promoter sequence, and optionally, transcriptional regulatory sequences; and
(d) a polyadenylation sequence preferably from bovine growth hormone (bGHpolyA).

Preferably the nucleic promoter and regulator sequence comprise a cytomegalovirus enhancer/chicken β-actin promoter (CAG), preferably SEQ ID NO:26, and woodchuck hepatitis virus posttranscriptional regulatory element (WPRE), preferably SEQ ID NO:27, and (d) is preferably SEQ ID NO:28.

The nucleic acid molecule may further comprise, linked in frame with (a) and (b), a third nucleotide sequence encoding a reporter polypeptide, preferably GFP; a preferred sequence is SEQ ID NO:25.

In the above nucleic acid molecule, the light-gated channel rhodopsin is preferably ChR2, such as SEQ ID:22, or a biologically active fragment, most preferably SEQ ID NO: 22. The light driven ion pump rhodopsin is preferably HaloR, most preferably SEQ ID NO:24.

In one embodiment of the above nucleic acid molecule, the sorting motif is one that targets the center of the neuron's receptive field, for example, to one or more of the following subcellular regions: the soma, the proximal dendritic region, or the axon initial segment. Preferred sorting motif-encoding sequences are a nucleotide sequence encoding (a) voltage-gated potassium channel 2.1 (Kv2.1), which is or comprises SEQ ID NO:1; or (b) the ankyrin binding domain of voltage-gated sodium channel 1.6 (Nav1.6), which is or comprises SEQ ID NO:3. The encoded amino acid sequence of the motif is preferably (a) the sequence of Kv2.1, which is or comprises SEQ ID NO:2; or (b) the sequence of the ankyrin-binding domain of Nav1.6, which is or comprises SEQ ID NO:4.

In another preferred embodiment of the above nucleic acid molecule, the motif is one that targets the rhodopsin (±the reporter gene) to the surround or off-center part of the neuron's receptive field, for example, to the somatodendritic region of the neurons. Preferred sorting motif-encoding sequences are a nucleotide sequence encoding (a) the cytoplasmic C-terminal segment of neuroligin-1 (NLG-1), which is or comprises SEQ ID NO:5; or (b) the myosin binding domain of melanophilin (MLPH), which is or comprises SEQ ID NO:7. The encoded amino acid sequence of the motif is preferably (a) the sequence of the cytoplasmic C-terminal segment of NLG-1 which is or comprises, SEQ ID NO:6; or (b) the sequence of the myosin-binding domain of MLPH, which is or comprises SEQ ID NO:8.

Also provided is a recombinant adeno-associated virus expression vector, preferably an AAV2 vector, comprising any of the above nucleic acid molecules. In the vector, the sequence of the nucleic acid molecule is flanked at its 5' end by a 5' inverted terminal repeat (ITR) and at its 3' end by a 3' ITR of the AAV, preferably AAV2. The sequence of these ITR is preferably SEQ ID NO:17 and SEQ ID NO:18, respectively.

As above, in one embodiment of the expression vector, the sorting motif is one that targets the center of the neuron's receptive field. A preferred nucleotide sequence encoding the motif is (a) the sequence encoding Kv2.1, which is or comprises SEQ ID NO:1; or (b) the sequence encoding the ankyrin binding domain of Nav1.6, which is or comprises SEQ ID NO:3. Preferably, in the expression vector, the amino acid sequence of the encoded motif is (a) the acid sequence of Kv2.1, which is or comprises SEQ ID NO:3; or (b) the sequence of the ankyrin binding domain of Nav1.6, which is or comprises SEQ ID NO:4.

In another embodiment of the expression vector, the sorting motif is one that targets the surround or off-center of the neuron's receptive field. Here, the motif is selected from the group consisting of nucleotide sequence encoding (a) the cytoplasmic C-terminal segment of NLG-1, which is or comprises SEQ ID NO:5; or (b) myosin binding domain of MLPH, which is or comprises SEQ ID NO:7. Preferably, in the expression vector, the amino acid sequence of the encoded motif is (a) the sequence of the cytoplasmic C-terminal segment NLG-1, which is or comprises SEQ ID NO:6; or (b) the sequence of the myosin-binding domain of MLPH, which is or comprises SEQ ID NO:8.

The above expression vector can have one of the following schematic structures:

(a)  5'-ITR-CAG-ChR2-GFP-{Motif}-WPRE-bGHpolyA-ITR-3'

(b)  5'-ITR-CAG-ChR2-{Motif}-WPRE-bGHpolyA-ITR-3'

(c)  5'-ITR-CAG-HaloR-GFP-{Motif}-WPRE-bGHpolyA-ITR-3'

(d)  5'-ITR-CAG-HaloR-{Motif}-WPRE-bGHpolyA-ITR-3' wherein {Motif} is nucleotide sequence encoding the sorting motif, and wherein, any two or more of ChR2, GFP and Motif or HaloR, GFP and Motif, are linked in-frame.

In the foregoing, vector, the Motif is preferably selected from the group consisting of (i) the nucleotide sequence encoding Kv2.1, which is or comprises SEQ ID NO:1; or (ii) the nucleotide sequence encoding the ankyrin binding domain of Nav1.6, which is or comprises SEQ ID NO:3

(iii) the nucleotide sequence encoding cytoplasmic C-terminal segment of NLG-1, which is or comprises SEQ ID NO:5; or (iv) the nucleotide sequence encoding myosin binding domain of MLPH, which is or comprises SEQ ID NO:7.

A preferred expression vector for targeting ChR2 to the center of the neuron's receptive field has the schematic structure and nucleotide sequence selected from the following group

```
                                      SEQ ID NO: 32
(a) 5'-ITR-CAG-ChR2-GFP-{Kv2.1 Motif)-WPRE-
    bGHpolyA-ITR-3',;

SEQ ID NO: 33
(b) 5'-ITR-CAG-ChR2-{Kv2.1 Motif)-WPRE-bGHpolyA-
    ITR-3',;

SEQ ID NO: 34
(c) 5'-ITR-CAG-ChR2-GFP-{Nav2.6 Motif)-WPRE-
    bGHpolyA-ITR-3',
    and;

SEQ ID NO: 35
(d) 5'-ITR-CAG-ChR2-{Nav2.6 Motif)-WPRE-bGHpolyA-
    ITR-3',.
```

A preferred expression vector for targeting ChR2 to the surround or off-center of the neuron's receptive field has the schematic structure and nucleotide sequence selected from the following group

```
                                      SEQ ID NO: 36
(a)  5'-ITR-CAG-ChR2-GFP-{NLG-1 Motif)-WPRE-
     bGHpolyA-ITR-3',;

SEQ ID NO: 37
(b)  5'-ITR-CAG-ChR2-{NLG-1 Motif)-WPRE-bGHpolyA-
     ITR-3',;
```

-continued (c) 5'-ITR-CAG-ChR2-GFP-{MLPH Motif}-WPRE-bGHpolyA-ITR-3', and;  SEQ ID NO: 38

(d) 5'-ITR-CAG-ChR2-{MLPH Motif}-WPRE-bGHpolyA-ITR-3',.  SEQ ID NO: 39

A preferred expression vector targeting HaloR to the center of the neuron's receptive field has the schematic structure and nucleotide sequence selected from the following group:

(a) 5'-ITR-CAG-HaloR-GFP-{Kv2.1 Motif}-WPRE-bGHpolyA-ITR-3',;  SEQ ID NO: 40

(b) 5'-ITR-CAG-HaloR-{Kv2.1 Motif}-WPRE-bGHpolyA-ITR-3',;  SEQ ID NO: 41

(c) 5'-ITR-CAG-HaloR-{Nav2.6 Motif}-WPRE-bGHpolyA-ITR-3', and;  SEQ ID NO: 42

(d) 5'-ITR-CAG-HaloR-GFP-{Nav2.6 Motif}-WPRE-bGHpolyA-ITR-3',;  SEQ ID NO: 43

A preferred expression vector for targeting HaloR to the surround or off-center of the neuron's receptive field has the schematic structure and nucleotide sequence selected from the following group (a) 5'-ITR-CAG-HaloR-GFP-{NLG-1 Motif}-WPRE-bGHpolyA-ITR-3',;  SEQ ID NO: 44

(b) 5'-ITR-CAG-HaloR-{NLG-1 Motif}-WPRE-bGHpolyA-ITR-3',;  SEQ ID NO: 45

(c) 5'-ITR-CAG-HaloR-GFP-{MLPH Motif}-WPRE-bGHpolyA-ITR-3', and;  SEQ ID NO: 46

(c) 5'-ITR-CAG-HaloR-{MLPH Motif}-WPRE-bGHpolyA-ITR-3',.  SEQ ID NO: 47

Preferably the above expression vector further comprises AAV vector backbone nucleotide sequence SEQ ID NO:29 linked to the 3' end of the AAV 3'ITR sequence.

The present invention is directed to a method of restoring light sensitivity to a retina, comprising:
(a) delivering to retinal neuron, preferably an RGC, a nucleic acid expression vector that encodes
(i) a light-gated channel rhodopsin or a light-driven ion pump rhodopsin;
(ii) a sorting motif that targets (i) to be expressed in selected subcellular regions of the neurons;
(iii) optionally, a reporter polypeptide; and
(iv) operatively linked to (i), (ii) and (iii) a promoter sequence, and optionally, transcriptional regulatory sequences; and
(b) expressing the vector in the neurons,
wherein the expression of the sorting motif with the rhodopsin results in selected expression of the rhodopsin and, when present, the reporter polypeptide, in subcellular regions of the RGC for which the motifs are selective, thereby restoring the light sensitivity.

Also provided is a method of selectively expressing a light-gated channel rhodopsin or a light-driven ion pump rhodopsin in a desired subcellular site or sites of a retinal neuron, preferably an RGC, comprising
a) delivering to the RGC a nucleic acid molecule or expression vector that encodes
(i) a light-gated channel rhodopsin, preferably ChR2, or a light-driven ion pump rhodopsin, preferably HaloR;
(ii) a sorting motif that targets the rhodopsin to be expressed in the desired site or sites;
(iii) operatively linked to (i) and (ii) a promoter sequence, and optionally, transcriptional regulatory sequences; and
(b) expressing the vector in the desired sites of the RGC.

In one embodiment of the method, the desired subcellular site is soma, proximal dendritic region, or axon initial segment, where preferably the motif is one that targets the rhodopsin to the center of the RGCs receptive field.

In another embodiment of the method, the desired subcellular site is the somatodendritic region, where preferably the motif is one that targets the surround or off-center of the RGCs receptive field.

In all the above methods, the nucleic acid molecule comprises any of the molecules above and the vector is the any of expression vectors above.

BRIEF DESCRIPTION OF THE DRAWINGS

FIG. 1 is a group of photomicrographs comparing fluorescence intensity (originally green, converted to white, on black background) from green fluorescent protein (GFP) encoded in frame with ChR2 with or without (control) a sorting motif. The sorting motifs tested, as indicated in abbreviated form in the panels (described in more detail elsewhere in this document), were: Kv2.1, Nav1.6, AMPAR, Kv4.2, MLPH, nAchR, NGL-1 AND TLCN. The arrowheads in each panel point to the axon of the ChR2-GFP expressing RGCs. The results appear in tabular form in Table 2, below.

DESCRIPTION OF THE PREFERRED EMBODIMENTS

The present inventors discovered that certain protein sorting motifs used in AAV-mediated transduction direct targeted expression of Chop2 or HaloR or, for visualization, a test reporter gene (Green fluorescent protein, GFP) to RGCs results in differential expression of the targeted reporter gene in different compartments or subcellular sites of the RGCs.

The present Examples show differential expression of ubiquitously expressing light sensitive channels, namely ChR2 driven by the CAG promoter and under the influence of various targeting motifs in distinct subcellular regions or sites of retinal ganglion cells.

However, targeting of depolarizing membrane channels, such as ChR2, to the ON-type retinal neurons might result in better useful vision.

In addition, expression of light sensors in more distal retinal neurons, such as bipolar cells, would utilize the remaining signal processing functions of the degenerate retina.

By expressing a depolarizing light sensor, such as ChR2, in ON type retinal neurons (ON type ganglion cells and/or ON type bipolar cells) and expressing a hypopolarizing light sensor, such as HaloR (a chloride pump) (Han, X et al., 2007, *PLoS ONE*, March 21; 2:e299; Zhang, F et al., 2007; *Nature* 446:633-9; present inventors' results) in OFF type retinal neurons (OFF type ganglion cells and/or OFF type bipolar cells) could create ON and OFF pathways in photoreceptor degenerated retinas.

According to the present invention, the followings approaches used to restore the light sensitivity of inner retinal neurons are enhanced by the use, disclosed herein, of peptide/polypeptide sorting motifs expressed using recombinant vectors in selected subcellular sites/regions of retinal neurons, particularly RGC.

(1) Ubiquitously expressing light sensitive channels, such as ChR2, are employed to produced membrane depolarization in all types of ganglion cells (both ON and OFF ganglion cells), or all types of bipolar cells (rod bipolar cells, and ON and OFF cone bipolar cells). The AAV vector with CAG promoter has already partially achieved this approach in rodent retinas, as exemplified herein.

(2) A depolarizing light sensor, such as ChR2, is targeted to ON type retinal neurons such as ON type ganglion cells or ON type bipolar cells. Fragments of a human gap junctional protein (connexin-36) promoter were found to target GFP in ON-type retinal ganglion cells by using AAV-2 virus vector (Greenberg K P et al., 2007, *ARVO abstract*, 2007). A readily packable shorter version of mGluR6 promoter of (<2.5 kb) would allow targeting of ChR2 to ON type bipolar cells (both rod bipolar cells and ON type cone bipolar cells).

(3) Cell specific promoters are used to target the specific types of retinal neurons. A promoter that could target rod bipolar cells is Pcp2 (L7) promoter (Tomomura, M et al., 2001, *Eur J Neurosci.* 14:57-63). The length of the active promoter is preferably less than 2.5 Kb so it can be packaged into the AAV viral cassette.

(4) A depolarizing light sensor, such as ChR2, is targeted to ON type ganglion cells or ON type cone bipolar cells and a hypopolarizing light sensor, such as halorhodopsin, to OFF type ganglion cells or OFF type cone bipolar cells to create ON and OFF pathways. As described above, an adequately short (packable) version of mGluR6 promoter (<2.5 kb) would allow targeting of ChR2 to ON type bipolar cells. The Neurokinin-3 (NK-3) promoter would be used to target halorhodopsin to OFF cone bipolar cells (Haverkamp, S et al., 2002, *J Compar. Neurol.* 455:463-76.

(5) A depolarizing light sensor, such as ChR2, is targeted to rod bipolar cells and their target AII amacrine cells, an ON type retinal cell (which communicate with ON and OFF cone bipolar cells).

Sorting Motifs

Table 1 describes the sorting peptide/polypeptide motifs examined by the present inventors presenting both the nucleotide and amino acid sequences, and a conclusion about their effects on sorting or targeting of the linked encoded proteins to different subcellular sites.

TABLE 1

Description of Sorting Motifs.

| Name | Source Protein (ref) | Sorting Motif | Subcellular Targeted Site (Receptive Field) |
|------|---------------------|---------------|---------------------------------------------|
| Kv2.1 | Voltage-gated potassium channel 2.1[1] | Cytoplasmic C-terminus | Proximal dendrites, soma (center) |
|  | aa sequence: (SEQ ID NO: 2) QSQPILNTKEMAPQSKPPEELEMSSM PSPVAPLPARTEGVIDMRSMSSIDSF ISCATDFPEATRF (65) | nt sequence: (SEQ ID NO: 1) CAG TCT CAG CCC ATC CTG AAC ACT AAG GAG ATG GCC CCT CAG AGT AAA CCC CCT GAG GAA CTG GAA ATG AGC TCC ATG CCA TCT CCA GTG GCT CCT CTG CCA GCT AGG ACC GAG GGC GTG ATT GAC ATG AGA GAC ATG TCT AGT ATC GAT AGC TTC ATT TCC TGC GCC ACC GAC TTC CCC GAA GCT ACA AGG TTT | |
| Nav1.6 | Voltage-gated sodium channel 1.6[2,3] | Ankyrin binding domain | Axon initial segment, soma (center) |
|  | aa sequence: (SEQ ID NO: 4) TVRVPIAVGE SDFENLNTED VSSESDP (27) | nt sequence: (SEQ ID NO: 3) ACC GTG AGG GTG CCC ATC GCC GTG GGC GAG AGC GAC TTC GAG AAC CTG AAC ACC GAG GAC GTG AGC AGC GAG AGC GAC CCC | |
| NLG-1 | Neuroligin-1[4] | Cytoplasmic C-terminal | Somatodendrtic (surround = off center) |
|  | aa sequence: (SEQ ID NO: 6) VVLRTACPPDYTLAMRRSPDDVPLMT PNTITM (31) | nt sequence: (SEQ ID NO: 5) GTG GTG CTG AGG ACT GCC TGC CCC CCT GAC TAC ACC CTG GCT ATG AGG AGA AGC CCA GAC GAT GTG CCC CTG ATG ACC CCC AAC ACC ATC ACA ATG | |
| MLPH | Melanophilin[5] | Myosin binding domain | Somatodendritic (surround = off center) |
|  | aa sequence: (SEQ ID NO: 8) RDQPLNSKKKKRLLSFRDVDFEEDSD (26) | nt sequence: (SEQ ID NO: 7) AGG GAC CAG CCT CTG AAC AGC AAA AAG AAA AAG AGG CTC CTG AGC TTC AGG GAC GTG GAC TTC GAG GAG GAC AGC GAC | |
| nAchR | Nicotinic acetylcholine receptor α7 subunit[6] | Tyrosine-Dileucine | Somatodendritic (surround = off center) |
|  | aa sequence: (SEQ ID NO: 10) GEDKVRPACQHKPRRCALASVELSAG AGPPTSNGNLLYIGFRGLEGM (47) | nt sequence: (SEQ ID NO: 9) GGC GAG GAC AAG GTG CGG CCC GCC TGT CAG CAC AAG CCT CGG CGG TGC AGC CTG GCC AGC GTG GAG CTG AGC GCC GGC GCC GGC CCA CCC ACC AGC AAC GGC AAC CTG CTG TAC ATC GGC TTC AGA GGC CTG GAG GGC ATG | |

TABLE 1-continued

Description of Sorting Motifs.

| Name | Source Protein (ref) | Sorting Motif | Subcellular Targeted Site (Receptive Field) |
|------|----------------------|---------------|---------------------------------------------|
| Kv4.2 | Voltage-gated potassium channel 4.2[7]<br>aa sequence: (SEQ ID NO: 12)<br>FEQQHHHLLH CLEKTT (16) | Dileucine<br>nt sequence: (SEQ ID NO: 11)<br>TTC GAG CAG CAG CAC CAC CAC CTG CTG CAC TGC CTG GAG AAG ACC ACC | Somatodendritic<br>(surround = off center) |
| TLCN | Telencephalin[8]<br>aa sequence: (SEQ ID NO: 14)<br>QSTACKKGEYNVQEAESSGEAVCLNG AGGGAGGAAGAEGGPEAAGGAAESPA EGEVFAIQLTSA (65) | Phenylalanine-based<br>Nucleotide sequence: (SEQ ID NO: 13)<br>CAG AGC ACA GCC TGC AAA AAG GGC GAG TAC AAC GTG CAG GAA GCT GAG AGC TCT GGC GAA GCC GTG TGT CTG AAC GGC GCC GGA GGC GGT GCC GGC GGA GCT GCC GGC GCT GAG GGT GGC CCT GAG GGC GCT GGA GGT GCC GCT GAG AGC CCC GCT GAG GGC GAA GTC TTT GCC ATC CAG CTG ACA TCT GCT | Somatodendritic<br>(surround = off-center) |
| AMPAR | AMPA receptor GluR1 subunit[9]<br>aa sequence: (SEQ ID NO: 16)<br>EFCYKSRSESKRMKGFCLIPQQSINE AIRTSTLPRNSGA (39) | Cytoplasmic C-terminal<br>Nucleotide sequence: (SEQ ID NO: 15)<br>GAG TTC TGC TAC AAG AGC AGG TCC GAA TCT AAG AGA ATG AAA GGC TTT TGT CTG ATC CCC CAG CAG AGC ATC AAC GAG GCC ATT CGG ACC AGT ACA CTG CCT CGC AAT AGC GGA GCT | Somatodendritic<br>(surround = off-center) |

(Legend to Table 1)
Name: Each sorting motif was named based on the "source protein" from which it was derived.
Motif: the functional name or location of each motif.
Subcellular targeted site: the reported site of preferential subcellular targeting.
Receptive Field: the central vs. surround (off-center or peripheral) region of the cell
Superscripted numbers refer to the following references:
[1]Lim ST, et al. . Neuron. 25: 385-97 (2000).
[2]Garrido, J. et al. Science 300: 2091 (2003).
[3]Bioko, T. et al., J. Neurosci. 232306-2313 (2003).
[4]Rosales, C. et al. Eur. J. Neurosci. 22, 2381-2386 (2005).
[5]Lewis, T. et al. Nat. Neurosci. 12, 568-576 (2009).
[6]Xu, J. et al. J. Neurosci. 26: 9780-9793 (2006).
[7]Rivera, J. et al. Nat. Neurosci. 6: 243-250 (2003).
[8]Mitsui, S. et al., J. Neurosci. 25: 1122-1131 (2005).
[9]Dotti, F. et al., J. Neurosci. 20: 1-5 (2000).
Name: Each sorting motif was named based on the protein from which it was derived.

The functional consequence of expressing ubiquitously expressing light sensitive channels, namely ChR2, in RGC by CAG promoter, coupled with the targeting to selected subcellular sites suggest that this will contribute to restoring useful vision. However, targeting of depolarizing membrane channels, such as ChR2, to ON-type retinal neurons might result in better useful vision. By expressing a depolarizing light sensor, such as ChR2, in the desired subcellular regions of ON type retinal neurons (ON type RGC and/or ON type bipolar cells) and expressing a hypopolarizing light sensor, such as HaloR in selected subcellular sites of OFF type retinal neurons (OFF type RGC and/or OFF type bipolar cells) could create even more useful ON and OFF pathways in photoreceptor degenerated retinas that is possible without the selective targeting mediated by the sorting motifs described here. A preferred embodiment would be:

(1) By employing a "center-targeting" motif, such as Kv2.1 or Nav1.6, target ChR2 to the center receptive field of ON RGC, while targeting HaloR to the surround (=off-center) of such cells using motifs such as NLG-1 or MLPH. Activation by light of such cells would result in depolarization (stimulation) of the center and hypopolarization (inhibition) of the surround.

(2) By employing a "center-targeting" motif, such as Kv2.1 or Nav1.6, target HaloR to the center receptive field of OFF RGC, while targeting ChR2 to the surround of such cells using motifs such as NLG-1 or MLPH. Activation by light of such cells would result in inhibition of the center and stimulation of the surround.

Such combined treatment would enhance not only signal transmission but contrast and hence visual resolution in such molecularly enhanced or modified cells. This more closely resembles the physiological effects of signals transmitted to these cells by retinal photoreceptors in a normal vision state. Such specificity and selectivity would be aided by the use of ON cell-specific promoters and OFF cell-specific promoters compared to the ubiquitous promoters exemplified here. Once such promoters are identified, they would be inserted into the various vectors described here in place of CAG. Use of the present composition and methods Vectors According to the various embodiments of the present invention, a variety of known nucleic acid vectors may be used in these methods, e.g., recombinant viruses, such as recombinant adeno-associated virus (rAAV), recombinant adenoviruses, recombinant retroviruses, recombinant poxviruses, and other known viruses in the art, as well as plasmids, cosmids and phages, etc. Many publications well-known in the art discuss the use of a variety of such vectors for delivery of genes. See, e.g., Ausubel et al., *Current Protocols in Molecular Biology*, John Wiley & Sons, New York, latest edition; Kay, M A. et al., 2001, *Nat. Med.,* 7:33-40; and Walther W et al., 2000, *Drugs* 60:249-71). Methods for assembly of the recombinant vectors are well-known. See, for example, WO00/15822 and other references cited therein, all of which are incorporated by reference.

There are advantages and disadvantages to the various viral vector systems. The limits of how much DNA can be packaged is one determinant in choosing which system to employ. rAAV tend to be limited to about 4.5 kb of DNA, whereas lentivirus (e.g., retrovirus) system can accommodate 4-5 kb.

AAV Vectors

Adeno-associated viruses are small, single-stranded DNA viruses which require a helper virus for efficient replication (Berns, K I, *Parvoviridae: the viruses and their replication*, p. 1007-1041 (vol. 2), in Fields, B N et al., *Fundamental Virology*, 3rd Ed., (Lippincott-Raven Publishers, Philadelphia (1995)). The 4.7 kb genome of AAV has two inverted terminal repeats (ITR) and two open reading frames (ORFs) which encode the Rep proteins and Cap proteins, respectively. The Rep reading frame encodes four proteins of molecular weights 78, 68, 52 and 40 kDa. These proteins primarily function in regulating AAV replication and rescue and integration of the AAV into the host cell chromosomes. The Cap reading frame encodes three structural proteins of molecular weights 85 (VP1), 72 (VP2) and 61 (VP3) kDa which form the virion capsid (Berns, supra). VP3 comprises >80% of total AAV virion proteins.

Flanking the rep and cap ORFs at the 5' and 3' ends are 145 bp ITRs, the first 125 bps of which can form Y- or T-shaped duplex structures. The two ITRs are the only cis elements essential for AAV replication, rescue, packaging and integration of the genome. Two conformations of AAV ITRs called "flip" and "flop" exist (Snyder, R O et al., 1993, *J Virol.*, 67:6096-6104; Berns, K I, 1990 *Microbiol Rev*, 54:316-29). The entire rep and cap domains can be excised and replaced with a transgene such as a reporter or therapeutic transgene (Carter, B J, in *Handbook of Parvoviruses*, P. Tijsser, ed., CRC Press, pp. 155-68 (1990)).

AAVs have been found in many animal species, including primates, canine, fowl and human (Murphy, F A et al., *The Classification and Nomenclature of Viruses: Sixth Rept of the Int'l Comm on Taxonomy of Viruses, Arch Virol*, Springer-Verlag, 1995). Six primate serotypes are known (AAV1, AAV2, AAV3, AAV4, AAV5 and AAV6) (and more are known that infect other classes of mammals).

The AAV ITR sequences and other AAV sequences employed in generating the minigenes, vectors, and capsids, and other constructs used in the present invention may be obtained from a variety of sources. For example, the sequences may be provided by any of the above 6 AAV serotypes or other AAV serotypes or other densoviruses, including both presently known human AAV and yet to yet-to-be-identified serotypes. Similarly, AAVs known to infect other animal species may be the source of ITRs used in the present molecules and constructs. Capsids from a variety of serotypes of AAV may be combined in various mixtures with the other vector components (e.g., WO01/83692 (Hildiger et al.; U.S. Pat. No. 7,056,502; US Pat Pub. 2003/0013189 (Wilson et al). Indeed there are advantages to various virion types related to their vulnerability to pre-existing immunity in humans, the efficiency of transduction, and/or duration of expression. Thus it may be preferable to use pseudotyped, rAAV virions wherein the rAAV2 ITRs described herein are combined with AAV5 capsid proteins. Such constructs may be advantageous because humans are less likely to have been pre-exposed to AAV5 vs. AAV2, and therefore are less likely to have immunological memory (e.g., circulating antibodies or capsid-specific T lymphocytes). For other descriptions of the use of various of these rAAV virions, see, for example, WO2005/021768 (Tak et al.); Adriaansen, J et al., *Ann Rheum Dis* 2005, 64:1677-1684; US Pat. Pub. 2004-072351 (Womer et al.); U.S Pat. Pub. 2005/0255089 (Chiorini et al.), Adriaansen, J et al., *Ann Rheum Dis* 2005, 64:1677-1684, all of these references concerning rAAV are incorporated by reference in their entirety. In general, while rAAV vectors have been exemplified herein, the present invention includes AAV2 ITR's combined with capsid proteins of any of 6 known primate AAV serotypes. It is also known in the art that certain mutations in capsid proteins can enhance transfection efficiency, and it would within the ordinary skill of the art to test and select appropriate mutations for use in the present invention. Many of these viral strains or serotypes are available from the American Type Culture Collection (ATCC), Manassas, Va., or are available from a variety of other sources (academic or commercial).

It may be desirable to synthesize sequences used in preparing the vectors and viruses of the invention using known techniques, based on published AAV sequences, e.g., available from a variety of databases. The source of the sequences utilized to prepare the present constructs is not considered to be limiting. Similarly, the selection of the AAV serotype and species (of origin) is within the skill of the art and is not considered limiting.

The rAAV Minigene or Cassette

As used herein, the rAAV construct (e.g., a minigene or cassette) is packaged into a rAAV virion. At minimum, the rAAV minigene is formed by AAV ITRs and a heterologous nucleic acid molecule for delivery to a host cell. Most suitably, the minigene comprises ITRs, most preferably AAV2 ITRs, located 5' and 3' to the heterologous sequence (rhodopsin protein and targeting sequence) being expressed. Vectors comprising 5' ITR and 3' ITR sequences arranged in tandem, e.g., 5' to 3' or a head-to-tail, or in another configuration may also be useful. Other embodiments include a minigene with multiple copies of the ITRs, or one in which 5' ITRs (or conversely, 3' ITRs) are located both 5' and 3' to the heterologous sequence. The ITRs sequences may be located immediately upstream and/or downstream of the heterologous sequence; intervening sequences may be present. As noted, the preferred ITRs are from AAV2, but they may also originate from AAV5 or from any other AAV serotype. Moreover, the present construct or minigene may include 5' ITRs from one serotype and 3' ITRs from another.

The AAV sequences used are preferably the 140145 by cis-acting 5' and 3' ITR sequences (e.g., Carter, B J, supra). Preferably, the entire ITR sequence is used, although minor modifications are permissible. The most ITR's used in the present examples are

5' ITR:

(SEQ ID NO: 17)

```
cctgcaggca gctgcgcgct cgctcgctca ctgaggccgc ccgggcaaag cccgggcgtc
gggcgacctt tggtcgcccg gcctcagtga gcgagcgagc gcgcagagag ggagtggcca
actccatcac taggggttcc t                                        141
```

```
-continued
3' ITR:
                                                             (SEQ ID NO: 18)
aggaacccct agtgatggag ttggccactc cctctctgcg cgctcgctcg ctcactgagg
ccgggcgacc aaaggtcgcc cgacgcccgg gctttgcccg ggcggcctca gtgagcgagc
gagcgcgcag ctgcctgcag g                                          141
```

Methods for modifying these ITR sequences are well-known (e.g., Sambrook, J. et al., *Molecular Cloning: A Laboratory Manual*, 3$^{rd}$ Edition, Cold Spring Harbor Press, Cold Spring Harbor, N.Y., 2001; Brent, R et al., eds., *Current Protocols in Molecular Biology*, John Wiley & Sons, Inc., 2003; Ausubel, F M et al., eds., *Short Protocols in Molecular Biology*, 5$^{th}$ edition, Current Protocols, 2002; Carter et al., supra; and Fisher, K et al., 1996 *J Virol.* 70:520-32). It is conventional to engineer the rAAV virus using known methods (e.g., Bennett, J et al. 1999, supra).

An example of such a molecule employed in the present invention is a "cis-acting" plasmid containing the heterologous sequence, preferably the ChR2 (any of SEQ ID NO:30-39) or HaloR sequence (any of SEQ ID NO:40-47, with or without an in-frame GFP sequence, with an in-frame sorting motif, promoter/regulatory sequences, all flanked by the 5' and 3' AAV ITR sequences.

The heterologous sequence encodes a protein or polypeptide which is desired to be delivered to and expressed in a cell and a targeting motif that differentially targets the polypeptide to particular subcellular regions of the cell, preferably an RGC.

The Transgene(s) being Targeted and Expressed

In a most preferred embodiment, the heterologous sequence is a nucleic acid molecule that functions as a transgene. The term "transgene" as used herein refers to a nucleic acid sequence heterologous to the AAV sequence, and encoding a desired product, preferably ChR2 or HaloR plus the sorting motif, and the regulatory sequences which direct or modulate transcription and/or translation of this nucleic acid in a host cell, enabling expression in such cells of the encoded product. Preferred polypeptide products are those that can be delivered to the eye, particularly to retinal neurons, most preferably to RGC.

The transgene/targeting sequence is delivered and differentially expressed in selected subcellular sites as directed by the sorting motif, in order to treat or otherwise improve the vision status of a subject with an ocular disorder. The targeted ocular cells are preferably retinal neurons, namely, bipolar cells and most preferably, RGC.

Based on the studies reported in WO2007/131180, the brightness of the light needed to stimulate evoked potential in transduced mouse retinas, indicates that a channel opsin with increased light sensitivity may be more desirable. This can be achieved by selection of a suitable naturally occurring opsin, for example other microbial-type rhodopsins, or by modifying the light sensitivity of ChR2 as well as its other properties, such as ion selectivity and spectral sensitivity, to produce diversified light-sensitive channels to better fit the need for vision restoration.

Different transgenes may be used to encode separate subunits of a protein being delivered, or to encode different polypeptides the co-expression of which is desired. If a single transgene includes DNA encoding each of several subunits, the DNA encoding each subunit may be separated by an internal ribozyme entry site (IRES), which is preferred for short subunit-encoding DNA sequences (e.g., total DNA, including IRES is <5 kB). Other methods which do not employ an IRES may be used for co-expression, e.g., the use of a second internal promoter, an alternative splice signal, a co- or post-translational proteolytic cleavage strategy, etc., all of which are known in the art.

The coding sequence or non-coding sequence of the present nucleic acids, including all domains to be expressed preferably are codon-optimized for the species in which they are to be expressed, particularly mammals and humans. Such codon-optimization is routine in the art.

While a preferred transgene encodes a full length polypeptide, preferably ChR2, the present invention is also directed to vectors that encode a biologically active fragment of ChR2 (nucleotides: SEQ ID NO:19; amino acids: SEQ ID NO:20) or a (preferably conservative) amino acid substitution variant or mutant of ChR2, or a full length HaloR (nucleotide SEQ ID NO:23; amino acid SEQ ID NO:24) or a biologically active fragment, variant, mutant, or fusion/chimeric nucleic acid encoding a fusion protein. A preferred point mutation named CatCh (calcium translocating channelrhodopsin (mutation at L132C) mediates an accelerated response time and a voltage response that is ~70-fold more light sensitive than that of wild-type ChR2; these properties stem from enhanced Ca2+ permeability. (Kleinlogel, S et al., *Nature Neuroscience* 14:513-518 (2011)). Such variants, mutants and fragments of any other polypeptide of the invention to be expressed in retinal neurons are within the scope of this invention. When a fragment or variant of the full length and native coding sequence is expressed by the targets cells being transformed and is able to endow such cells with light sensitivity that is functionally equivalent to that of the full length or substantially full length polypeptide having a native, rather than variant, amino acid sequence. A biologically active fragment or variant is a "functional equivalent"—a term that is well understood in the art and is further defined in detail herein. The requisite biological activity of the encoded fragment or variant, using any method disclosed herein or known in the art to establish activity of a channel opsin, has the following activity relative to the wild-type native polypeptide: about 50%, about 55%, about 60%, about 65%, about 70%, about 75%, about 80%, about 85%, about 90%, about 95%, about 99%, and any range derivable therein, such as, for example, from about 70% to about 80%, and more preferably from about 81% to about 90%; or even more preferably, from about 91% to about 99%.

It should be appreciated that any variations in the coding sequences of the present nucleic acids and vectors that, as a result of the degeneracy of the genetic code, express a polypeptide of the same sequence, are included within the scope of this invention.

The amino acid sequence identity of the encoded polypeptide variants of the present invention are determined using standard methods, typically based on certain mathematical algorithms. In a preferred embodiment, the percent identity between two amino acid sequences is determined using the Needleman and Wunsch (*J. Mol. Biol.* 48:444-453 (1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Meyers and Miller (CABIOS, 4:11-17 (1989)) which has been incorporated into the ALIGN program (version 2.0), using a PAM120 weight residue table, a gap length penalty of 12 and a gap penalty of 4. The nucleotide and amino acid sequences of the present invention can further be used as a "query sequence" to perform a search against public databases, for example, to identify other family members or related sequences. Such searches can be performed using the NBLAST and XBLAST programs (Altschul et al. (1990) *J. Mol. Biol.* 215:403-10). BLAST nucleotide searches can be performed with the NBLAST program, score=100, wordlength=12 to obtain nucleotide sequences homologous to, e.g., DAN encoding Chop2 of *C. reinhardtii*. BLAST protein searches can be performed with the XBLAST program, score=50, wordlength=3 to obtain amino acid sequences homologous to the appropriate reference protein such as Chop2. To obtain gapped alignments for comparison purposes, Gapped BLAST can be utilized (Altschul et al. (1997) *Nucleic Acids Res.* 25:3389-3402). When utilizing BLAST and Gapped BLAST programs, the default parameters of the respective programs (e.g. XBLAST and NBLAST) can be used. See World Wide Web URL ncbi.nlm.nih.gov.

The preferred amino acid sequence variant has the following degrees of sequence identity with the native, full length channel opsin polypeptide, preferably Chop2 from *C. reinhardtii* (SEQ ID NO:_) or with a fragment thereof (e.g., SEQ ID NO:_): about 50%, about 55%, about 60%, about 65%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, from about 70% to about 80%, and more preferably from about 81% to about 90%; or even more preferably, from about 91% to about 99% identity. A preferred biologically active fragment comprises or consists of SEQ ID NO:3, which corresponds to residues 1-315 of the full length SEQ ID NO:6, or comprises or consists of SEQ ID NO:8.

Any of a number of known recombinant methods are used to produce a DNA molecule encoding the fragment or variant. For production of a variant, it is routine to introduce mutations into the coding sequence to generate desired amino acid sequence variants of the invention. Site-directed mutagenesis is a well-known technique for which protocols and reagents are commercially available (e.g., Zoller, M J et al., 1982, *Nucl Acids Res* 10:6487-6500; Adelman, J P et al., 1983, *DNA* 2:183-93). These mutations include simple deletions or insertions, systematic deletions, insertions or substitutions of clusters of bases or substitutions of single bases.

In terms of functional equivalents, it is well understood by those skilled in the art that, inherent in the definition of a "biologically functional equivalent" protein, polypeptide, gene or nucleic acid, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted.

In particular, the shorter the length of the polypeptide, the fewer amino acids changes should be made. Longer fragments may have an intermediate number of changes. The full length polypeptide protein will have the most tolerance for a larger number of changes. It is also well understood that where certain residues are shown to be particularly important to the biological or structural properties of a polypeptide residues in a binding regions or an active site, such residues may not generally be exchanged. In this manner, functional equivalents are defined herein as those poly peptides which maintain a substantial amount of their native biological activity.

For a detailed description of protein chemistry and structure, see Schulz, G E et al., *Principles of Protein Structure*, Springer-Verlag, New York, 1978, and Creighton, T. E., *Proteins: Structure and Molecular Properties*, W.H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups:

| | | |
|---|---|---|
| 1 | Small aliphatic, nonpolar or slightly polar residues | Ala, Ser, Thr (Pro, Gly); |
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

The hydropathy index of amino acids may also be considered in selecting variants. Each amino acid has been assigned a hydropathy index on the basis of their hydrophobicity and charge characteristics, these are: Ile (+4.5); Val (+4.2); Leu (+3.8); Phe (+2.8); Cys (+2.5); Met (+1.9); Ala (+1.8); Glycine (−0.4); Thr (−0.7); Ser (−0.8); Trp (−0.9); Tyr (−1.3); Pro (−1.6); His (−12); Glu (−3.5); Gln (−3.5); Asp (−3.5); Asn (−3.5); Lys (−3.9); and Arg (−4.5). The importance of the hydropathy index in conferring interactive biological function on a proteinaceous molecule is generally understood in the art (Kyte and Doolittle, 1982, *J. Mol. Biol.* 157:105-32). It is known that certain amino acids may be substituted for other amino acids having a similar hydropathy index or score and still retain a similar biological activity. In making changes based upon the hydropathy index, the substitution of amino acids whose hydropathy indices are within ±2 is preferred, those which are within ±1 are particularly preferred, and those within ±0.5 are even more particularly preferred. It is also understood in the art that the substitution of like amino acids can be made effectively on the basis of hydrophilicity, particularly where the biological functional equivalent polypeptide thereby created is intended for use in certain of the present embodiments. U.S. Pat. No. 4,554,101, discloses that the greatest local average hydrophilicity of a proteinaceous molecule, as governed by the hydrophilicity of its adjacent amino acids, correlates with a biological property of the molecule. See U.S. Pat. No. 4,554,101 for a hydrophilicity values. In making changes based upon similar hydrophilicity values, the substitution of amino acids whose hydrophilicity values are within ±2 is preferred, those which are within ±1 are particularly preferred, and those within ±0.5 are even more particularly preferred.

Vector Components and their Sequences.

Promoters/Regulatory Sequences

The expression vector of the present invention includes appropriate sequences operably linked to the coding sequence(s) or ORF(s) to promote its expression in a targeted host cell. "Operably linked" sequences include both expression control sequences such as. promoters that are contiguous with the coding sequences and expression control sequences that act in trans or distally to control the expression of the polypeptide product.

Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., Kozak consensus sequence); sequences that enhance nucleic acid or protein stability; and when desired, sequences that enhance protein processing and/or secretion. Many varied expression control sequences, including native and non-native, constitutive, inducible and/or tissue-specific, are known in the art and may be utilized herein, depending upon the type of expression desired.

Expression control sequences for eukaryotic cells typically include a promoter, an enhancer, such as one derived from an immunoglobulin gene, SV40, CMV, etc., and a polyadenylation sequence which may include splice donor and acceptor sites. The polyadenylation (polyA) sequence generally is inserted 3' to the coding sequence and 5' to the 3' ITR sequence. The polyA from bovine growth hormone (bGH) is a suitable sequence and is abbreviated "bGH-polyA" (SEQ ID NO:28).

The regulatory sequences useful herein may also contain an intron, such as one located between the promoter/enhancer sequence and the coding sequence. One useful intron sequence is derived from SV40, and is referred to as the SV40 T intron sequence. Another includes the woodchuck hepatitis virus post-transcriptional element. (See, for example, Wang L and Verma, I, 1999, *Proc Nat'l Acad Sci USA*, 96:3906-10).

An IRES sequence, or other suitable system as discussed above, may be used to produce more than one polypeptide from a single transcript. An exemplary IRES is the poliovirus IRES which supports transgene expression in photoreceptors, RPE and ganglion cells. Preferably, the IRES is located 3' to the coding sequence in the present vector, preferably an rAAV vector.

The promoter may be selected from a number of constitutive or inducible promoters that can drive expression of the selected transgene in an ocular setting, preferably in retinal neurons. A preferred promoter is "cell-specific", meaning that it is selected to direct expression of the selected transgene in a particular ocular cell type, such as photoreceptor cells.

A preferred constitutive promoters include the exemplified hybrid cytomegalovirus (CMV) immediate early enhancer/chicken β-actin promoter-exon 1-intron 1 element (together abbreviated as "CAG" SEQ ID NO:26, herein) used along with woodchuck hepatitis virus posttranscriptional regulatory element (abbreviated herein as "WPRE"; SEQ ID NO:27 herein). However, for human safety, other posttranscriptional regulatory elements known in the art can readily be substituted for WPRE.

Other useful promoters include RSV LTR promoter/enhancer, the SV40 promoter, the CMV promoter, the dihydrofolate reductase (DHFR) promoter, and the phosphoglycerol kinase (PGK) promoter. Additional useful promoters are disclosed in W. W. Hauswirth et al., 1998, WO98/48027 and A. M. Timmers et al., 2000, WO00/15822. Promoters that were found to drive RPE cell-specific gene expression in vivo include (1) a 528-bp promoter region (bases 1-528 of a murine 11-cis retinol dehydrogenase (RDH) gene (Driessen, C A et al., 1995, *Invest. Ophthalmol. Vis. Sci.* 36:1988-96; Simon, A. et al., 1995, *J. Biol. Chem* 270:1107-12, 1995; Simon, A. et al., 1996, *Genomics* 36:424-3) Genbank Accession Number X97752); (2) a 2274-bp promoter region) from a human cellular retinaldehyde-binding protein (CRALBP) gene (Intres, R et al., 1994, *J. Biol. Chem.* 269:25411-18; Kennedy, B N et al., 1998, *J. Biol. Chem.* 273:5591-8, 1998), Genbank Accession Number L34219); and (3) a 1485-bp promoter region from human RPE65 (Nicoletti, A et al., 1998, *Invest. Ophthalmol. Vis. Sci.* 39, 637-44, Genbank Accession Number U20510). These three promoters in WO00/15822 promoted RPE-cell-specific expression of GFP. It is envisioned that minor sequence variations in the various promoters and promoter regions discussed herein—whether additions, deletions or mutations, whether naturally occurring or introduced in vitro, will not affect their ability to drive expression in the cellular targets of the coding sequences of the present invention. Furthermore, the use of other promoters, even if not yet discovered, that are characterized by abundant and/or specific expression in retinal cells, particularly in bipolar or ganglion cells, is specifically included within the scope of this invention.

Another useful promoter is from a mGluR6 promoter-region of the Grm6 gene (GenBank accession number BC041684), a gene that controls expression of metabotropic glutamate receptor 6 ((Ueda Y et al., 1997, *J Neurosc.* 17:3014-23). The genomic sequence is shown in GenBank accession number—AL627215. A preferred example of this promoter region sequence from the above GenBank record consists of 11023 nucleotides. The original Umeda et al., study employed a 10 kb promoter, but the actual length of the promoter and the sequence that comprises control elements of Grm6 can be adjusted by increasing or decreasing the fragment length. It is a matter of routine testing to select and verify the action of the optimally sized fragment from the Grm6 gene that drives transgenic expression of a selected coding sequence, preferably ChR2 or HaloR, in the desired target cells, preferably in bipolar cells which are rich in glutamate receptors, particularly the "on" type bipolar cells, which are the most bipolar cells in the retina (Nakajima, Y., et al., 1993, *J Biol Chem* 268:11868-73). Use of such a large promoter is not compatible with the packaging capabilities of rAAV virions, so would require a different delivery vector system known in the art, or identification of a shorter sequence (<2.5 kb) that could be packaged in an rAAV vector of the present invention.

Another promoter is the Pcp2 (L7) promoter (Tomomura, M et al., 2001, *Eur J Neurosci.* 14:57-63). Again, the length of the active promoter is preferably less than 2.5 Kb so it can be packaged into the rAAV viral cassette.

The neurokinin-3 (NK-3) promoter could be used to target HalorR to OFF cells (Haverkamp, S et al., 2002, *J Comparative Neurology*, 455:463-76.

An inducible promoter is used to control the amount and timing of production of the transgene product in an ocular cell. Such promoters can be useful if the gene product has some undesired, e.g., toxic, effects in the cell if it accumulates excessively. Inducible promoters include those known in the art, such as the Zn-inducible sheep metallothionine (MT) promoter, the dexamethasone (Dex)-inducible mouse mammary tumor virus (MMTV) promoter; the T7 promoter; the ecdysone insect promoter; the tetracycline-repressible system; the tetracycline-inducible system; the RU486-inducible system; and the rapamycin-inducible system. Any inducible promoter the action of which is tightly regulated and is specific for the particular target ocular cell type, may be used. Other useful types of inducible promoters are ones regulated by a specific physiological state, e.g., temperature, acute phase, a cell's replicating or differentiation state.

Selection of the various vector and regulatory elements for use herein are conventional, well-described, and readily available. See, e.g., Sambrook et al., supra; and Ausubel et al., supra. It will be readily appreciated that not all vectors and expression control sequences will function equally well to express the present transgenes Chop2 or HaloR. Clearly, the skilled artisan may apply routine selection among the known expression control sequences without departing from the scope of this invention and based upon general knowledge as well as the guidance provided herein. One skilled in the art can select one or more expression control sequences, operably link them to the coding sequence being expressed to make a minigene, insert the minigene or vector into an AAV vector, preferably rAAV2, and cause packaging of the vector into infectious particles or virions following one of the known packaging methods for rAAV.

Production of the rAAV

The rAAV2 used in the present invention may be constructed and produced using the materials and methods described herein and those well-known in the art. The methods that are preferred for producing any construct of this invention are conventional and include genetic engineering, recombinant engineering, and synthetic techniques, such as those set forth in reference cited above.

Briefly, to package an rAAV construct into an rAAV virion, a sequences necessary to express AAV rep and AAV cap or functional fragments thereof as well as helper genes essential for AAV production must be present in the host cells. See, for example U.S. Pat. Pub. 2007/0015238, which describes production of pseudotyped rAAV virion vectors encoding AAV Rep and Cap proteins of different serotypes and AdV transcription products that provide helper functions. For example, AAV rep and cap sequences may be introduced into the host cell in any known manner including, without limitation, transfection, electroporation, liposome delivery, membrane fusion, biolistic deliver of DNA-coated pellets, viral infection and protoplast fusion. Devices specifically adapted for delivering DNA to specific regions within and around the eye for the purpose of gene therapy have been described (for example, U.S. Pat. Pub. 2005/0277868, incorporated by reference) are used within the scope of this invention. Such devices utilize electroporation and electromigration, providing, e.g., two electrodes on a flexible support that can be placed behind the retina. A third electrode is part of a hollow support, which can also be used to inject the molecule to the desired area. The electrodes can be positioned around the eye, including behind the retina or within the vitreous.

These sequences may exist stably in the cell as an episome or be stably integrated into the cell's genome. They may also be expressed more transiently in the host cell. As an example, a useful nucleic acid molecule comprises, from 5' to 3', a promoter, an optional spacer between the promoter and the start site of the rep sequence, an AAV rep sequence, and an AAV cap sequence.

The rep and cap sequences, along with their expression control sequences, are preferably provided in a single vector, though they may be provided separately in individual vectors. The promoter may be any suitable constitutive, inducible or native promoter. The delivery molecule that provides the Rep and Cap proteins may be in any form, preferably a plasmid which may contain other non-viral sequences, such as those to be employed as markers. This molecule typically excludes the AAV ITRs and packaging sequences. To avoid the occurrence of homologous recombination, other viral sequences, particularly adenoviral sequences, are avoided. This plasmid is preferably one that is stably expressed.

Conventional genetic engineering or recombinant DNA techniques described in the cited references are used. The rAAV may be produced using a triple transfection method with either the calcium phosphate (Clontech) or Effectene™ reagent (Qiagen) according to manufacturer's instructions. See, also, Herzog et al., Nat. Med. 5:56-63 (1999).

The rAAV virions are produced by culturing host cells comprising a rAAV as described in Bi et al., supra, and WO2007/131180, which includes a rAAV construct to be packaged into a rAAV virion, an AAV rep sequence and an AAV cap sequence, all under control of regulatory sequences directing expression.

Suitable viral helper genes, such as adenovirus E2A, E4Orf6 and VA, may be added to the culture preferably on separate plasmids. Thereafter, the rAAV virion which directs expression of the transgene is isolated in the absence of contaminating helper virus or wild type AAV.

It is conventional to assess whether a particular expression control sequence is suitable for a given transgene, and choose the one most appropriate for expressing the transgene. For example, a target cell may be infected in vitro, and the number of copies of the transgene in the cell monitored by Southern blots or quantitative PCR. The level of RNA expression may be monitored by Northern blots quantitative RT-PCR. The level of protein expression may be monitored by Western blot, immunohistochemistry, immunoassay including enzyme immunoassay (EIA) such as enzyme-linked immunosorbent assays (ELISA), radioimmunoassays (RIA) or by other methods. Specific embodiments are described below.

Preferred Vectors of the Invention

This section lists a number of vectors useful in the present invention that comprise the following nucleotide sequences encoding (a) Light Sensor: ChR2 coding sequence (preferably SEQ ID NO:21) or HaloR coding sequence (SEQ ID NO:23)
(b) Optionally, a reporter "gene" preferably GFP (SEQ ID NO:25)
(c) 5' and 3' ITRs from AAV2, SEQ ID NO:17 and 18, respectively.
(d) CAG Promoter/Regulatory sequence (SEQ ID NO:26)
(e) Posttranscriptional Regulatory element WPRE (SEQ ID NO:27)
(f) Polyadenylation sequence (SEQ ID NO:28)

In addition to the foregoing, the vector preferably contains
(g) the rAAV2 backbone sequences (SEQ ID NO:29) located 3' from the 3' ITR.

These vectors, their "schematic representation" several linear vector diagrams and annotated sequences are shown below. The following annotation is used in all the sequences:
ITR's: *lowercase,bold,italic,underscore*
CAG: UPPERCASE (underscore)

Chop2/ChR2 (used interchangeably here): *UPPERCASE, ITALIC*
GFP: UPPERCASE (nonbold, non-italic)
Sorting Motif: UPPERCASE, (double underscore)
WPRE: UPPERCASE (underscore)
bGHpolyA: *UPPERCASE*, (italic)
intervening vector nucleotides/cloning carryover: lower case (not italic)

(1) Two examples of vectors that do not have the Sorting Motif present but are "poised" for insertion of the motif (with the insertion point shown in the sequence)

(A) ITR — CAG — Chop2 — GFP — WPRE — bGH polyA — ITR
Motif Insertion Site

SEQ ID NO: 30
ITR–CAG–ChR2–GFP–{insertion site for Sorting Motif}–WPRE–bGHpolyA–ITR'

←start AAV2 ITR
*cctgcaggca gctgcgcgct cgctcgctca ctgaggccgc ccgggcaaag cccgggcgtc*

*gggcgaccttt tggtcgcccg gcctcagtga gcgagcgagc gcgcagagag ggagtggcca*

*actccatcac tagggg ttcc t*gcggccgca cgcgtgatat cCTAGTTATT AATAGTAATC
               end AAV2 ITR→↑                     ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GGCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGGA GCGGCTCGGG GCTGTCCGCG GGGGACGGC TGCCTTCGGG GGGGACGGGG end CAG pomoter/enhancer→↓
CAGGGCGGGG TTCGGCTTCT GGCGTGTGAC CGGCGGCTCT AGCAGCCTCT GCTAaccatg ttcatgcctt cttcttttc ctacagctcc tgggcaacgt gctggttatt gtgctgtctc
                                               ↓←start ChR2
atcattttgg caaagaatta agcttgagct cgcgatccgc agcc *ATG GAT TAT GGA*

*GGC GCC CTG AGT GCC GTT GGG CGC GAG CTG CTA TTT GTA ACG AAC CCA*

*GTA GTC GTC AAT GGC TCT GTA CTT GTG CCT GAG GAC CAG TGT TAC TGC*

*GCG GGC TGG ATT GAG TCG CGT GGC ACA AAC GGT GCC CAA ACG GCG TCG*

*AAC GTG CTG CAA TGG CTT GCT GCT GGC TTC TCC ATC CTA CTG CTT ATG*

*TTT TAC GCC TAC CAA ACA TGG AAG TCA ACC TGC GGC TGG GAG GAG ATC*

*TAT GTG TGC GCT ATC GAG ATG GTC AAG GTG ATT CTT GAG TTC TTC TTC*

*GAG TTT AAG AAC CCG TCC ATG CTG TAT CTA GCC ACA GGC CAC CGC GTC*

CAG TGG TTG CGT TAC GCC GAG TGG CTT CTC ACC TGC CCG GTC ATT CTC

ATT CAC CTG TCA AAC CTG ACG GGC TTG TCC AAC GAC TAC AGC AGG CGC

ACT ATG GGT CTG CTT GTG TCT GAT ATT GGC ACA ATT GTG TGG GGC GCC

ACT TCC GCT ATG GCC ACC GGA TAC GTC AAG GTC ATC TTC TTC TGC CTG

GGT CTG TGT TAT GGT GCT AAC ACG TTC TTT CAC GCT GCC AAG GCC TAC

ATC GAG GGT TAC CAT ACC GTG CCG AAG GGC CGG TGT CGC CAG GTG GTG

ACT GGC ATG GCT TGG CTC TTC TTC GTA TCA TGG GGT ATG TTC CCC ATC

CTG TTC ATC CTC GGC CCC GAG GGC TTC GGC GTC CTG AGC GTG TAC GGC

TCC ACC GTC GGC CAC ACC ATC ATT GAC CTG ATG TCG AAG AAC TGC TGG

GGT CTG CTC GGC CAC TAC CTG CGC GTG CTG ATC CAC GAG CAT ATC CTC

ATC CAC GGC GAC ATT CGC AAG ACC ACC AAA TTG AAC ATT GGT GGC ACT

GAG ATT GAG GTC GAG ACG CTG GTG GAG GAC GAG GCC GAG GCT GGC GCG

GTC AAC AAG GGC ACC GGC AAG gaattcggag gcggaggtgg agctagc
                end ChR2→↑

↓←start GFP
AAA GGA GAA GAA CTC TTC ACT GGA GTT GTC CCA ATT CTT GTT GAA TTA

GAT GGT GAT GTT AAC GGC CAC AAG TTC TCT GTC AGT GGA GAG GGT GAA

GGT GAT GCA ACA TAC GGA AAA CTT ACC CTG AAG TTC ATC TGC ACT ACT

GGC AAA CTG CCT GTT CCA TGG CCA ACA CTA GTC ACT ACT CTG TGC TAT

GGT GTT CAA TGC TTT TCA AGA TAC CCG GAT CAT ATG AAA CGG CAT GAC

TTT TTC AAG AGT GCC ATG CCC GAA GGT TAT GTA CAG GAA AGG ACC ATC

TTC TTC AAA GAT GAC GGC AAC TAC AAG ACA CGT GCT GAA GTC AAG TTT

GAA GGT GAT ACC CTT GTT AAT AGA ATC GAG TTA AAA GGT ATT GAC TTC

AAG GAA GAT GGC AAC ATT CTG GGA CAC AAA TTG GAA TAC AAC TAT AAC

TCA CAC AAT GTA TAC ATC ATG GCA GAC AAA CAA AAG AAT GGA ATC AAA

GTG AAC TTC AAG ACC CGC CAC AAC ATT GAA GAT GGA AGC GTT CAA CTA

GCA GAC CAT TAT CAA CAA AAT ACT CCA ATT GGC GAT GGC CCT GTC CTT

TTA CCA GAC AAC CAT TAC CTG TCC ACA CAA TCT GCC CTT TCG AAA GAT

CCC AAC GAA AAG AGA GAC CAC ATG GTC CTT CTT GAG TTT GTA ACA GCT end GFP→↓
GCT GGG ATT ACA CAT GGC ATG GAT AGG CTG TAC AAC ( )
            Motif-coding sequence inserted here↑

↓←start WPRE
taactcgagt ctagacgtgg tacc<u>GATAAT CAACCTCTGG ATTACAAAAT TTGTGAAAGA</u>

<u>TTGACTGGTA TTCTTAACTA TGTTGCTCCT TTTACGCTAT GTGGATACGC TGCTTTAATG</u>

<u>CCTTTGTATC ATGCTATTGC TTCCCGTATG GCTTTCATTT TCTCCTCCTT GTATAAATCC</u>

<u>TGGTTGCTGT CTCTTTATGA GGAGTTGTGG CCCGTTGTCA GGCAACGTGG CGTGGTGTGC</u>

```
ACTGTGTTTG CTGACGCAAC CCCCACTGGT TGGGGCATTG CCACCACCTG TCAGCTCCTT

TCCGGGACTT TCGCTTTCCC CCTCCCTATT GCCACGGCGG AACTCATCGC CGCCTGCCTT

GCCCGCTGCT GGACAGGGGC TCGGCTGTTG GGCACTGACA ATTCCGTGGT GTTGTCGGGG

AAGCTGACGT CCTTTCCATG GCTGCTCGCC TGTGTTGCCA CCTGGATTCT GCGCGGGACG

TCCTTCTGCT ACGTCCCTTC GGCCCTCAAT CCAGCGGACC TTCCTTCCCG CGGCCTGCTG

CCGGCTCTGC GGCCTCTTCC GCGTCTTCGC CTTCGCCCTC AGACGAGTCG GATCTCCCTT

TGGGCCGCCT CCCCGCCTGA Tgcggggatc tctagagtc gagagatctA CGGGTGGCAT
                      end WPRE→↑                    ↑←start bGH-polyA

CCCTGTGACC CCTCCCCAGT GCCTCTCCTG GCCCTGGAAG TTGCCACTCC AGTGCCCACC

AGCCTTGTCC TAATAAAATT AAGTTGCATC ATTTTGTCTG ACTAGGTGTC CTTCTATAAT

ATTATGGGGT GGAGGGGGGT GGTATGGAGC AAGGGGCAAG TTGGGAAGAC AACCTGTAGG

GCCTGCGGGG TCTATTGGGA ACCAAGCTGG AGTGCAGTGG CACAATCTTG GCTCACTGCA

ATCTCCGCCT CCTGGGTTCA AGCGATTCTC CTGCCTCAGC CTCCCGAGTT GTTGGGATTC

CAGGCATGCA TGACCAGGCT CAGCTAATTT TTGTTTTTTT GGTAGAGACG GGGTTTCACC

ATATTGGCCA GGCTGGTCTC CAACTCCTAA TCTCAGGTGA TCTACCCACC TTGGCCTCCC

AAATTGCTGG GATTACAGGC GTGAACCACT GCTCCCTTCC CTGTCCTTct gattttgtag
                                                     end bGH-polyA→↑

↓←start AAV2 ITR
gtaaccacgt gcggaccgag cggccgcagg aaccctagt gatggagttg gccactccct ctctgcgcgc tcgctcgctc actgaggccg ggcgaccaaa ggtcgcccga cgcccgggct ttgcccgggc ggcctcagtg agcgagcgag cgcgcagctg cctgcagg
                                              end AAV2 ITR→↑

(B) SEQ ID NO: 31 (Same as above but without GFP)
ITR—CAG—ChR2—(insertion site for Sorting Motif)—WPRE—bGHpolyA—ITR'

←start AAV2 ITR
cctgcaggca gctgcgcgct cgctcgctca ctgaggccgc ccgggcaaag cccgggcgtc gggcgacctt tggtcgcccg gcctcagtga gcgagcgagc gcgcagagag ggagtggcca actccatcac tagggggttcc tgcggccgca cgcgtgatat cCTAGTTATT AATAGTAATC
                      end AAV2 ITR→↑                 ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC
```

-continued

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GGCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGGA GCGGCTCGGG GCTGTCCGCG GGGGACGGC TGCCTTCGGG GGGGACGGGG end CAG pomoter/enhancer→↓
CAGGGCGGGG TTCGGCTTCT GGCGTGTGAC CGGCGGCTCT AGCAGCCTCT GCTAaccatg ttcatgcctt cttctttttc ctacagctcc tgggcaacgt gctggttatt gtgctgtctc ↓←start ChR2
atcattttgg caaagaatta agcttgagct cgcgatccgc agcc ATG GAT TAT GGA

GGC GCC CTG AGT GCC GTT GGG CGC GAG CTG CTA TTT GTA ACG AAC CCA

GTA GTC GTC AAT GGC TCT GTA CTT GTG CCT GAG GAC CAG TGT TAC TGC

GCG GGC TGG ATT GAG TCG CGT GGC ACA AAC GGT GCC CAA ACG GCG TCG

AAC GTG CTG CAA TGG CTT GCT GCT GGC TTC TCC ATC CTA CTG CTT ATG

TTT TAC GCC TAC CAA ACA TGG AAG TCA ACC TGC GGC TGG GAG GAG ATC

TAT GTG TGC GCT ATC GAG ATG GTC AAG GTG ATT CTT GAG TTC TTC TTC

GAG TTT AAG AAC CCG TCC ATG CTG TAT CTA GCC ACA GGC CAC CGC GTC

CAG TGG TTG CGT TAC GCC GAG TGG CTT CTC ACC TGC CCG GTC ATT CTC

ATT CAC CTG TCA AAC CTG ACG GGC TTG TCC AAC GAC TAC AGC AGG CGC

ACT ATG GGT CTG CTT GTG TCT GAT ATT GGC ACA ATT GTG TGG GGC GCC

ACT TCC GCT ATG GCC ACC GGA TAC GTC AAG GTC ATC TTC TTC TGC CTG

GGT CTG TGT TAT GGT GCT AAC ACG TTC TTT CAC GCT GCC AAG GCC TAC

ATC GAG GGT TAC CAT ACC GTG CCG AAG GGC CGG TGT CGC CAG GTG GTG

ACT GGC ATG GCT TGG CTC TTC TTC GTA TCA TGG GGT ATG TTC CCC ATC

CTG TTC ATC CTC GGC CCC GAG GGC TTC GGC GTC CTG AGC GTG TAC GGC

TCC ACC GTC GGC CAC ACC ATC ATT GAC CTG ATG TCG AAG AAC TGC TGG

GGT CTG CTC GGC CAC TAC CTG CGC GTG CTG ATC CAC GAG CAT ATC CTC

ATC CAC GGC GAC ATT CGC AAG ACC ACC AAA TTG AAC ATT GGT GGC ACT

GAG ATT GAG GTC GAG ACG CTG GTG GAG GAC GAG GCC GAG GCT GGC GCG

GTC AAC AAG GGC ACC GGC AAG gaattcggag gcggaggtgg agctagc
                     end ChR2→↑

{ } taactcgagt ctagacgtgg tacc TTGACTGGTA TTCTTAACTA TGTTGCTCCT
↑←Motif-coding sequence     ↑←start WPRE
inserted here

TTTACGCTAT GTGGATACGC TGCTTTAATG CCTTTGTATC ATGCTATTGC TTCCCGTATG

GCTTTCATTT TCTCCTCCTT GTATAAATCC TGGTTGCTGT CTCTTTATGA GGAGTTGTGG

CCCGTTGTCA GGCAACGTGG CGTGGTGTGC ACTGTGTTTG CTGACGCAAC CCCCACTGGT

TGGGGCATTG CCACCACCTG TCAGCTCCTT TCCGGGACTT TCGCTTTCCC CCTCCCTATT

```
GCCACGGCGG AACTCATCGC CGCCTGCCTT GCCCGCTGCT GGACAGGGGC TCGGCTGTTG

GGCACTGACA ATTCCGTGGT GTTGTCGGGG AAGCTGACGT CCTTTCCATG GCTGCTCGCC

TGTGTTGCCA CCTGGATTCT GCGCGGGACG TCCTTCTGCT ACGTCCCTTC GGCCCTCAAT

CCAGCGGACC TTCCTTCCCG CGGCCTGCTG CCGGCTCTGC GGCCTCTTCC GCGTCTTCGC

CTTCGCCCTC AGACGAGTCG GATCTCCCTT TGGGCCGCCT CCCCGCCTGA Tgcggggatc
                                                    end WPRE→↑ ctctagagtc gagagatctA CGGGTGGCAT CCCTGTGACC CCTCCCCAGT GCCTCTCCTG
                    ↑←start bGH-polyA

GCCCTGGAAG TTGCCACTCC AGTGCCCACC AGCCTTGTCC TAATAAAATT AAGTTGCATC

ATTTTGTCTG ACTAGGTGTC CTTCTATAAT ATTATGGGGT GGAGGGGGGT GGTATGGAGC

AAGGGGCAAG TTGGGAAGAC AACCTGTAGG GCCTGCGGGG TCTATTGGGA ACCAAGCTGG

AGTGCAGTGG CACAATCTTG GCTCACTGCA ATCTCCGCCT CCTGGGTTCA AGCGATTCTC

CTGCCTCAGC CTCCCGAGTT GTTGGGATTC CAGGCATGCA TGACCAGGCT CAGCTAATTT

TTGTTTTTTT GGTAGAGACG GGGTTTCACC ATATTGGCCA GGCTGGTCTC CAACTCCTAA

TCTCAGGTGA TCTACCCACC TTGGCCTCCC AAATTGCTGG GATTACAGGC GTGAACCACT

GCTCCCTTCC CTGTCCTTct gattttgtag gtaaccacgt gcggaccgag cggccgcagg
   end bGH-polyA→↑                                   start AAV2 ITR→↑ aaccccctagt gatggagttg gccactccct ctctgcgcgc tcgctcgctc actgaggccg ggcgaccaaa ggtcgcccga cgcccgggct ttgcccgggc ggcctcagtg agcgagcgag cgcgcagctg cctgcagg
   end AAV2 ITR→↑
```

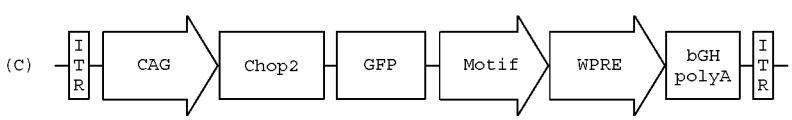

SEQ ID NO: 32  5'-ITR—CAG—ChR2—GFP—(Kv2.1 Motif)—WPRE—bGHpolyA—ITR-3

```
←start AAV2 ITR
cctgcaggca gctgcgcgct cgctcgctca ctgaggccgc ccgggcaaag cccgggcgtc gggcgaccgg tggtcgcccg gcctcagtga gcgagcgagc gcgcagagag ggagtggcca actccatcac taggggttcc tgcggccgca cgcgtgatat cCTAGTTATT AATAGTAATC
         end AAV2 ITR→↑                        ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC
```

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GGCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGGA GCGGCTCGGG GCTGTCCGCG GGGGACGGC TGCCTTCGGG GGGGACGGGG end CAG pomoter/enhancer→↓
CAGGGCGGGG TTCGGCTTCT GGCGTGTGAC CGGCGGCTCT AGCAGCCTCT GCTAaccatg ttcatgcctt cttcttttc ctacagctcc tgggcaacgt gctggttatt gtgctgtctc ↓←start ChR2
atcattttgg caaagaatta agcttgagct cgcgatccgc agcc *ATG GAT TAT GGA*

*GGC GCC CTG AGT GCC GTT GGG CGC GAG CTG CTA TTT GTA ACG AAC CCA*

*GTA GTC GTC AAT GGC TCT GTA CTT GTG CCT GAG GAC CAG TGT TAC TGC*

*GCG GGC TGG ATT GAG TCG CGT GGC ACA AAC GGT GCC CAA ACG GCG TCG*

*AAC GTG CTG CAA TGG CTT GCT GCT GGC TTC TCC ATC CTA CTG CTT ATG*

*TTT TAC GCC TAC CAA ACA TGG AAG TCA ACC TGC GGC TGG GAG GAG ATC*

*TAT GTG TGC GCT ATC GAG ATG GTC AAG GTG ATT CTT GAG TTC TTC TTC*

*GAG TTT AAG AAC CCG TCC ATG CTG TAT CTA GCC ACA GGC CAC CGC GTC*

*CAG TGG TTG CGT TAC GCC GAG TGG CTT CTC ACC TGC CCG GTC ATT CTC*

*ATT CAC CTG TCA AAC CTG ACG GGC TTG TCC AAC GAC TAC AGC AGG CGC*

*ACT ATG GGT CTG CTT GTG TCT GAT ATT GGC ACA ATT GTG TGG GGC GCC*

*ACT TCC GCT ATG GCC ACC GGA TAC GTC AAG GTC ATC TTC TTC TGC CTG*

*GGT CTG TGT TAT GGT GCT AAC ACG TTC TTT CAC GCT GCC AAG GCC TAC*

*ATC GAG GGT TAC CAT ACC GTG CCG AAG GGC CGG TGT CGC CAG GTG GTG*

*ACT GGC ATG GCT TGG CTC TTC TTC GTA TCA TGG GGT ATG TTC CCC ATC*

*CTG TTC ATC CTC GGC CCC GAG GGC TTC GGC GTC CTG AGC GTG TAC GGC*

*TCC ACC GTC GGC CAC ACC ATC ATT GAC CTG ATG TCG AAG AAC TGC TGG*

*GGT CTG CTC GGC CAC TAC CTG CGC GTG CTG ATC CAC GAG CAT ATC CTC*

*ATC CAC GGC GAC ATT CGC AAG ACC ACC AAA TTG AAC ATT GGT GGC ACT*

*GAG ATT GAG GTC GAG ACG CTG GTG GAG GAC GAG GCC GAG GCT GGC GCG*

*GTC AAC AAG GGC ACC GGC AAG* gaattcggag gcggaggtgg agctagc
               end ChR2→↑

↓←start GFP
AAA GGA GAA GAA CTC TTC ACT GGA GTT GTC CCA ATT CTT GTT GAA TTA

GAT GGT GAT GTT AAC GGC CAC AAG TTC TCT GTC AGT GGA GAG GGT GAA

GGT GAT GCA ACA TAC GGA AAA CTT ACC CTG AAG TTC ATC TGC ACT ACT

GGC AAA CTG CCT GTT CCA TGG CCA ACA CTA GTC ACT ACT CTG TGC TAT

GGT GTT CAA TGC TTT TCA AGA TAC CCG GAT CAT ATG AAA CGG CAT GAC

TTT TTC AAG AGT GCC ATG CCC GAA GGT TAT GTA CAG GAA AGG ACC ATC

TTC TTC AAA GAT GAC GGC AAC TAC AAG ACA CGT GCT GAA GTC AAG TTT

```
GAA GGT GAT ACC CTT GTT AAT AGA ATC GAG TTA AAA GGT ATT GAC TTC

AAG GAA GAT GGC AAC ATT CTG GGA CAC AAA TTG GAA TAC AAC TAT AAC

TCA CAC AAT GTA TAC ATC ATG GCA GAC AAA CAA AAG AAT GGA ATC AAA

GTG AAC TTC AAG ACC CGC CAC AAC ATT GAA GAT GGA AGC GTT CAA CTA

GCA GAC CAT TAT CAA CAA AAT ACT CCA ATT GGC GAT GGC CCT GTC CTT

TTA CCA GAC AAC CAT TAC CTG TCC ACA CAA TCT GCC CTT TCG AAA GAT

CCC AAC GAA AAG AGA GAC CAC ATG GTC CTT CTT GAG TTT GTA ACA GCT end GFP→↓
GCT GGG ATT ACA CAT GGC ATG GAT GAA CTG TAC AAC CAG TCT CAG
                                                  ↑←Start Kv2.1 Motif

CCC ATC CTG AAC ACT AAG GAG ATG GCC CCT CAG AGT AAA CCC CCT GAG

GAA CTG GAA ATG AGC TCC ATG CCA TCT CCA GTG GCT CCT CTG CCA GCT

AGG ACC GAG GGC GTG ATT GAC ATG AGA AGC ATG TCT AGT ATC GAT AGC

TTC ATT TCC TGC GCC ACC GAC TTC CCC GAA GCT ACA AGG TTT taactcgagt
                          end Kv2.1 Motif→↑ ctagacgtgg taccGATAAT CAACCTCTGG ATTACAAAAT TGTGAAAGA TTGACTGGTA
                ↑←start WPRE

TTCTTAACTA TGTTGCTCCT TTTACGCTAT GTGGATACGC TGCTTTAATG CCTTTGTATC

ATGCTATTGC TTCCCGTATG GCTTTCATTT TCTCCTCCTT GTATAAATCC TGGTTGCTGT

CTCTTTATGA GGAGTTGTGG CCCGTTGTCA GGCAACGTGG CGTGGTGTGC ACTGTGTTTG

CTGACGCAAC CCCCACTGGT TGGGGCATTG CCACCACCTG TCAGCTCCTT TCCGGGACTT

TCGCTTTCCC CCTCCCTATT GCCACGGCGG AACTCATCGC CGCCTGCCTT GCCCGCTGCT

GGACAGGGGC TCGGCTGTTG GCACTGACA ATTCCGTGGT GTTGTCGGGG AAGCTGACGT

CCTTTCCATG GCTGCTCGCC TGTGTTGCCA CCTGGATTCT GCGCGGGACG TCCTTCTGCT

ACGTCCCTTC GGCCCTCAAT CCAGCGGACC TTCCTTCCCG CGGCCTGCTG CCGGCTCTGC

GGCCTCTTCC GCGTCTTCGC CTTCGCCCTC AGACGAGTCG GATCTCCCTT TGGGCCGCCT

CCCCGCCTGA Tgcggggatc ctctagagtc gagagatctA CGGGTGGCAT CCCTGTGACC
 end WPRE→↑                                      ↑←start bGH-polyA

CCTCCCCAGT GCCTCTCCTG GCCCTGGAAG TTGCCACTCC AGTGCCCACC AGCCTTGTCC

TAATAAAATT AAGTTGCATC ATTTTGTCTG ACTAGGTGTC CTTCTATAAT ATTATGGGGT

GGAGGGGGGT GGTATGGAGC AAGGGGCAAG TTGGGAAGAC AACCTGTAGG GCCTGCGGGG

TCTATTGGGA ACCAAGCTGG AGTGCAGTGG CACAATCTTG GCTCACTGCA ATCTCCGCCT

CCTGGGTTCA AGCGATTCTC CTGCCTCAGC CTCCCGAGTT GTTGGGATTC CAGGCATGCA

TGACCAGGCT CAGCTAATTT TGTTTTTTTT GGTAGAGACG GGGTTTCACC ATATTGGCCA

GGCTGGTCTC CAACTCCTAA TCTCAGGTGA TCTACCCACC TTGGCCTCCC AAATTGCTGG

GATTACAGGC GTGAACCACT GCTCCCTTCC CTGTCCTTct gattttgtag gtaaccacgt
                          end bGH-polyA→↑ gcggaccgag cggccgcagg aaccctagt gatggagttg ccactccct ctctgcgcgc
                ↑←start AAV2 ITR
```

-continued

*tcgctcgctc actgaggccg ggcgaccaaa ggtcgcccga cgcccgggct tgcccgggc*

*ggcctcagtg agcgagcgag cgcgcagctg cctgcagg*
                            end AAV2 ITR→↑

(D) —[ITR]—[CAG]—[Chop2]—[Motif]—[WPRE]—[bGH polyA]—[ITR]

SEQ ID NO: 33: (same as above but without GFP)
5'-ITR-CAG-ChR2-(Kv2.1 Motif)-WPRE-bGHpolyA-ITR-3'

←start AAV2 ITR
*cctgcaggca gctgcgcgct cgctcgctca ctgaggccgc ccgggcaaag cccgggcgtc*

*gggcgacctt tggtcgcccg gcctcagtga gcgagcgagc gcgcagagag ggagtggcca*

*actccatcac tagggggttcc t*gcggccgca cgcgtgatat cCTAGTTATT AATAGTAATC
        end AAV2 ITR→↑                          ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GGCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGGA GCGGCTCGGG GCTGTCCGCG GGGGGACGGC TGCCTTCGGG GGGGACGGGG
                                        end CAG pomoter/enhancer→↓
CAGGGCGGGG TTCGGCTTCT GGCGTGTGAC CGGCGGCTCT AGCAGCCTCT GCTAaccatg ttcatgcctt cttctttttc ctacagctcc tgggcaacgt gctggttatt gtgctgtctc
                                                  ↓←start ChR2
atcattttgg caaagaatta agcttgagct cgcgatccgc agcc *ATG GAT TAT GGA*

*GGC GCC CTG AGT GCC GTT GGG CGC GAG CTG CTA TTT GTA ACG AAC CCA*

*GTA GTC GTC AAT GGC TCT GTA CTT GTG CCT GAG GAC CAG TGT TAC TGC*

*GCG GGC TGG ATT GAG TCG CGT GGC ACA AAC GGT GCC CAA ACG GCG TCG*

*AAC GTG CTG CAA TGG CTT GCT GCT GGC TTC TCC ATC CTA CTG CTT ATG*

*TTT TAC GCC TAC CAA ACA TGG AAG TCA ACC TGC GGC TGG GAG GAG ATC*

*TAT GTG TGC GCT ATC GAG ATG GTC AAG GTG ATT CTT GAG TTC TTC TTC*

*GAG TTT AAG AAC CCG TCC ATG CTG TAT CTA GCC ACA GGC CAC CGC GTC*

*CAG TGG TTG CGT TAC GCC GAG TGG CTT CTC ACC TGC CCG GTC ATT CTC*

ATT CAC CTG TCA AAC CTG ACG GGC TTG TCC AAC GAC TAC AGC AGG CGC

ACT ATG GGT CTG CTT GTG TCT GAT ATT GGC ACA ATT GTG TGG GGC GCC

ACT TCC GCT ATG GCC ACC GGA TAC GTC AAG GTC ATC TTC TTC TGC CTG

GGT CTG TGT TAT GGT GCT AAC ACG TTC TTT CAC GCT GCC AAG GCC TAC

ATC GAG GGT TAC CAT ACC GTG CCG AAG GGC CGG TGT CGC CAG GTG GTG

ACT GGC ATG GCT TGG CTC TTC TTC GTA TCA TGG GGT ATG TTC CCC ATC

CTG TTC ATC CTC GGC CCC GAG GGC TTC GGC GTC CTG AGC GTG TAC GGC

TCC ACC GTC GGC CAC ACC ATC ATT GAC CTG ATG TCG AAG AAC TGC TGG

GGT CTG CTC GGC CAC TAC CTG CGC GTG CTG ATC CAC GAG CAT ATC CTC

ATC CAC GGC GAC ATT CGC AAG ACC ACC AAA TTG AAC ATT GGT GGC ACT

GAG ATT GAG GTC GAG ACG CTG GTG GAG GAC GAG GCC GAG GCT GGC GCG

GTC AAC AAG GGC ACC GGC AAG gaattcggag gcggaggtgg agctagc
            end ChR2→↑

↓←Start Kv2.1 Motif
<u>CAG TCT CAG CCC ATC CTG AAC ACT AAG GAG ATG GCC CCT CAG AGT AAA</u>

<u>CCC CCT GAG GAA CTG GAA ATG AGC TCC ATG CCA TCT CCA GTG GCT CCT</u>

<u>CTG CCA GCT AGG ACC GAG GGC GTG ATT GAC ATG AGA AGC ATG TCT AGT</u>

<u>ATC GAT AGC TTC ATT TCC TGC GCC ACC GAC TTC CCC GAA GCT ACA AGG</u>

<u>TTT</u> taactcgagt ctagacgtgg tacc<u>GATAAT CAACCTCTGG ATTACAAAAT</u>
↑←end Kv2.1 Motif   ↑←start WPRE <u>TTGTGAAAGA TTGACTGGTA TTCTTAACTA TGTTGCTCCT TTTACGCTAT GTGGATACGC</u>

<u>TGCTTTAATG CCTTTGTATC ATGCTATTGC TTCCCGTATG GCTTTCATTT TCTCCTCCTT</u>

<u>GTATAAATCC TGGTTGCTGT CTCTTTATGA GGAGTTGTGG CCCGTTGTCA GGCAACGTGG</u>

<u>CGTGGTGTGC ACTGTGTTTG CTGACGCAAC CCCCACTGGT TGGGGCATTG CCACCACCTG</u>

<u>TCAGCTCCTT TCCGGGACTT TCGCTTTCCC CCTCCCTATT GCCACGGCGG AACTCATCGC</u>

<u>CGCCTGCCTT GCCCGCTGCT GGACAGGGGC TCGGCTGTTG GGCACTGACA ATTCCGTGGT</u>

<u>GTTGTCGGGG AAGCTGACGT CCTTTCCATG GCTGCTCGCC TGTGTTGCCA CCTGGATTCT</u>

<u>GCGCGGGACG TCCTTCTGCT ACGTCCCTTC GGCCCTCAAT CCAGCGGACC TTCCTTCCCG</u>

<u>CGGCCTGCTG CCGGCTCTGC GGCCTCTTCC GCGTCTTCGC CTTCGCCCTC AGACGAGTCG</u>

<u>GATCTCCCTT TGGGCCGCCT CCCCGCCTGA T</u>gcggggatc tctagagtc gagagatctA
        end WPRE→↑    start bGH-polyA→↑

CGGGTGGCAT CCCTGTGACC CCTCCCCAGT GCCTCTCCTG GCCCTGGAAG TTGCCACTCC

AGTGCCCACC AGCCTTGTCC TAATAAAATT AAGTTGCATC ATTTTGTCTG ACTAGGTGTC

CTTCTATAAT ATTATGGGGT GGAGGGGGGT GGTATGGAGC AAGGGGCAAG TTGGGAAGAC

AACCTGTAGG GCCTGCGGGG TCTATTGGGA ACCAAGCTGG AGTGCAGTGG CACAATCTTG

GCTCACTGCA ATCTCCGCCT CCTGGGTTCA AGCGATTCTC CTGCCTCAGC CTCCCGAGTT

GTTGGGATTC CAGGCATGCA TGACCAGGCT CAGCTAATTT TTGTTTTTTT GGTAGAGACG

-continued

```
GGGTTTCACC ATATTGGCCA GGCTGGTCTC CAACTCCTAA TCTCAGGTGA TCTACCCACC

TTGGCCTCCC AAATTGCTGG GATTACAGGC GTGAACCACT GCTCCCTTCC CTGTCCTTct
                                                  end bGH-polyA→↑ gattttgtag gtaaccacgt gcggaccgag cggccgcagg aaccctagt gatagagttg
                                             ↑←start AAV2 ITR gccactccct ctctgcgcgc tcgctcgctc actgaggccg ggcgaccaaa agtcgcccga cgcccgggct tgcccgggc ggcctcagtg agcgagcgag cgcgcagctg cctgcagg
                                                  end AAV2 ITR→↑
```

(E) SEQ ID NO: 34:
5'-ITR-CAG-ChR2-GFP-{Nav1.6 Motif}-WPRE-bGHpolyA-ITR-3'

←start AAV2 ITR
```
cctgcaggca gctgcgcgct cgctcgctca ctgaggccgc ccgggcaaag cccgggcgtc gggcgacctt tggtcgcccg gcctcagtga gcgagcgagc gcgcagagag ggagtggcca actccatcac taggggttcc tgcggccgca cgcgtgatat cCTAGTTATT AATAGTAATC
             end AAV2 ITR→↑                   ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GGCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGA GCGGCTCGGG GCTGTCCGCG GGGGGACGGC TGCCTTCGGG GGGGACGGGG
                                                  end CAG pomoter/enhancer→↓
CAGGGCGGGG TTCGGCTTCT GGCGTGTGAC CGGCGGCTCT AGCAGCCTCT GCTAaccatg ttcatgcctt cttcttttc ctacagctcc tgggcaacgt gctggttatt gtgctgtctc
                                                       ↓←start ChR2
atcattttgg caaagaatta agcttgagct cgcgatccga agcc ATG GAT TAT GGA

GGC GCC CTG AGT GCC GTT GGG CGC GAG CTG CTA TTT GTA ACG AAC CCA

GTA GTC GTC AAT GGC TCT GTA CTT GTG CCT GAG GAC CAG TGT TAC TGC

GCG GGC TGG ATT GAG TCG CGT GGC ACA AAC GGT GCC CAA ACG GCG TCG

AAC GTG CTG CAA TGG CTT GCT GCT GGC TTC TCC ATC CTA CTG CTT ATG

TTT TAC GCC TAC CAA ACA TGG AAG TCA ACC TGC GGC TGG GAG GAG ATC

TAT GTG TGC GCT ATC GAG ATG GTC AAG GTG ATT CTT GAG TTC TTC TTC

GAG TTT AAG AAC CCG TCC ATG CTG TAT CTA GCC ACA GGC CAC CGC GTC
```

```
CAG TGG TTG CGT TAC GCC GAG TGG CTT CTC ACC TGC CCG GTC ATT CTC
ATT CAC CTG TCA AAC CTG ACG GGC TTG TCC AAC GAC TAC AGC AGG CGC
ACT ATG GGT CTG CTT GTG TCT GAT ATT GGC ACA ATT GTG TGG GGC GCC
ACT TCC GCT ATG GCC ACC GGA TAC GTC AAG GTC ATC TTC TTC TGC CTG
GGT CTG TGT TAT GGT GCT AAC ACG TTC TTT CAC GCT GCC AAG GCC TAC
ATC GAG GGT TAC CAT ACC GTG CCG AAG GGC CGG TGT CGC CAG GTG GTG
ACT GGC ATG GCT TGG CTC TTC TTC GTA TCA TGG GGT ATG TTC CCC ATC
CTG TTC ATC CTC GGC CCC GAG GGC TTC GGC GTC CTG AGC GTG TAC GGC
TCC ACC GTC GGC CAC ACC ATC ATT GAC CTG ATG TCG AAG AAC TGC TGG
GGT CTG CTC GGC CAC TAC CTG CGC GTG CTG ATC CAC GAG CAT ATC CTC
ATC CAC GGC GAC ATT CGC AAG ACC ACC AAA TTG AAC ATT GGT GGC ACT
GAG ATT GAG GTC GAG ACG CTG GTG GAG GAC GAG GCC GAG GCT GGC GCG
GTC AAC AAG GGC ACC GGC AAG gaattcggag gcggaggtgg agctagc
                        end ChR2→↑

↓←start GFP
AAA GGA GAA GAA CTC TTC ACT GGA GTT GTC CCA ATT CTT GTT GAA TTA
GAT GGT GAT GTT AAC GGC CAC AAG TTC TCT GTC AGT GGA GAG GGT GAA
GGT GAT GCA ACA TAC GGA AAA CTT ACC CTG AAG TTC ATC TGC ACT ACT
GGC AAA CTG CCT GTT CCA TGG CCA ACA CTA GTC ACT ACT CTG TGC TAT
GGT GTT CAA TGC TTT TCA AGA TAC CCG GAT CAT ATG AAA CGG CAT GAC
TTT TTC AAG AGT GCC ATG CCC GAA GGT TAT GTA CAG GAA AGG ACC ATC
TTC TTC AAA GAT GAC GGC AAC TAC AAG ACA CGT GCT GAA GTC AAG TTT
GAA GGT GAT ACC CTT GTT AAT AGA ATC GAG TTA AAA GGT ATT GAC TTC
AAG GAA GAT GGC AAC ATT CTG GGA CAC AAA TTG GAA TAC AAC TAT AAC
TCA CAC AAT GTA TAC ATC ATG GCA GAC AAA CAA AAG AAT GGA ATC AAA
GTG AAC TTC AAG ACC CGC CAC AAC ATT GAA GAT GGA AGC GTT CAA CTA
GCA GAC CAT TAT CAA CAA AAT ACT CCA ATT GGC GAT GGC CCT GTC CTT
TTA CCA GAC AAC CAT TAC CTG TCC ACA CAA TCT GCC CTT TCG AAA GAT
CCC AAC GAA AAG AGA GAC CAC ATG GTC CTT CTT GAG TTT GTA ACA GCT
                                    end GFP→↓
GCT GGG ATT ACA CAT GGC ATG GAT GAA CTG TAC AAC ACC GTG AGG GTG
                                             ↑←Start Nav1.6 Motif
CCC ATC GCC GTG GGC GAG AGC GAC TTC GAG AAC CTG AAC ACC GAG GAC
GTG AGC AGC GAG AGC GAC CCC taactcgagt ctagacgtgg taccGATAAT
         end Nav1.6 Motif→↑                          ↑←start WPRE
CAACCTCTGG ATTACAAAAT TGTGAAAGA TTGACTGGTA TTCTTAACTA TGTTGCTCCT
TTTACGCTAT GTGGATACGC TGCTTTAATG CCTTTGTATC ATGCTATTGC TTCCCGTATG
GCTTTCATTT TCTCCTCCTT GTATAAATCC TGGTTGCTGT CTCTTTATGA GGAGTTGTGG
CCCGTTGTCA GGCAACGTGG CGTGGTGTGC ACTGTGTTTG CTGACGCAAC CCCCACTGGT
```

TGGGGCATTG CCACCACCTG TCAGCTCCTT TCCGGGACTT TCGCTTTCCC CCTCCCTATT

GCCACGGCGG AACTCATCGC CGCCTGCCTT GCCCGCTGCT GGACAGGGGC TCGGCTGTTG

GGCACTGACA ATTCCGTGGT GTTGTCGGGG AAGCTGACGT CCTTTCCATG GCTGCTCGCC

TGTGTTGCCA CCTGGATTCT GCGCGGGACG TCCTTCTGCT ACGTCCCTTC GGCCCTCAAT

CCAGCGGACC TTCCTTCCCG CGGCCTGCTG CCGGCTCTGC GGCCTCTTCC GCGTCTTCGC

CTTCGCCCTC AGACGAGTCG GATCTCCCTT TGGGCCGCCT CCCCGCCTGA Tgcggggatc
                                                                       end WPRE→↑ ctctagagtc gagagatctA *CGGGTGGCAT CCCTGTGACC CCTCCCCAGT GCCTCTCCTG*
           ↑←start bGH-polyA

*GCCCTGGAAG TTGCCACTCC AGTGCCCACC AGCCTTGTCC TAATAAAATT AAGTTGCATC*

*ATTTTGTCTG ACTAGGTGTC CTTCTATAAT ATTATGGGGT GGAGGGGGGT GGTATGGAGC*

*AAGGGGCAAG TTGGGAAGAC AACCTGTAGG GCCTGCGGGG TCTATTGGGA ACCAAGCTGG*

*AGTGCAGTGG CACAATCTTG GCTCACTGCA ATCTCCGCCT CCTGGGTTCA AGCGATTCTC*

*CTGCCTCAGC CTCCCGAGTT GTTGGGATTC CAGGCATGCA TGACCAGGCT CAGCTAATTT*

*TTGTTTTTTT GGTAGAGACG GGGTTTCACC ATATTGGCCA GGCTGGTCTC AACTCCTAA*

*TCTCAGGTGA TCTACCCACC TTGGCCTCCC AAATTGCTGG GATTACAGGC GTGAACCACT*

*GCTCCCTTCC CTGTCCTT*ct gattttgtag gtaaccacgt gcggaccgag
    end bGH-polyA→↑ cggccgcagg aaccctagt gatggagttg gccactccct ctctgcgcgc tcgctcgctc
        ↑←start AAV2 ITR actgaggccg ggcgaccaaa ggtcgcccga cgcccgggct tgccgggc ggcctcagtg agcgagcgag cgcgcagctg cctgcagg
            end AAV2 ITR→↑

(F) SEQ ID NO: 35 (same as above without GFP)
5'-ITR-CAG-ChR2-{Nav1.6Motif}-WPRE-bGHpolyA-ITR-3'

←start AAV2 ITR
cctgcaggca gctgcgcgct cgctcgctca ctgaggccgc ccgggcaaag cccgggcgtc gggcgacctt tggtcgcccg gcctcagtga gcgagcgagc gcgcagagag ggagtggcca actccatcac taggggttcc tgcggccgca cgcgtgatat cCTAGTTATT AATAGTAATC
         end AAV2 ITR→↑                       ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GGCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGGA GCGGCTCGGG GCTGTCCGCG GGGGACGGC TGCCTTCGGG GGGGACGGGG end CAG pomoter/enhancer→↓
CAGGGCGGGG TTCGGCTTCT GGCGTGTGAC CGGCGGCTCT AGCAGCCTCT GCTAaccatg ttcatgcctt cttcttttc ctacagctcc tgggcaacgt gctggttatt gtgctgtctc ↓←start ChR2
atcattttgg caaagaatta agcttgagct cgcgatccgc agcc ATG GAT TAT GGA

GGC GCC CTG AGT GCC GTT GGG CGC GAG CTG CTA TTT GTA ACG AAC CCA

GTA GTC GTC AAT GGC TCT GTA CTT GTG CCT GAG GAC CAG TGT TAC TGC

GCG GGC TGG ATT GAG TCG CGT GGC ACA AAC GGT GCC CAA ACG GCG TCG

AAC GTG CTG CAA TGG CTT GCT GCT GGC TTC TCC ATC CTA CTG CTT ATG

TTT TAC GCC TAC CAA ACA TGG AAG TCA ACC TGC GGC TGG GAG GAG ATC

TAT GTG TGC GCT ATC GAG ATG GTC AAG GTG ATT CTT GAG TTC TTC TTC

GAG TTT AAG AAC CCG TCC ATG CTG TAT CTA GCC ACA GGC CAC CGC GTC

CAG TGG TTG CGT TAC GCC GAG TGG CTT CTC ACC TGC CCG GTC ATT CTC

ATT CAC CTG TCA AAC CTG ACG GGC TTG TCC AAC GAC TAC AGC AGG CGC

ACT ATG GGT CTG CTT GTG TCT GAT ATT GGC ACA ATT GTG TGG GGC GCC

ACT TCC GCT ATG GCC ACC GGA TAC GTC AAG GTC ATC TTC TTC TGC CTG

GGT CTG TGT TAT GGT GCT AAC ACG TTC TTT CAC GCT GCC AAG GCC TAC

ATC GAG GGT TAC CAT ACC GTG CCG AAG GGC CGG TGT CGC CAG GTG GTG

ACT GGC ATG GCT TGG CTC TTC TTC GTA TCA TGG GGT ATG TTC CCC ATC

CTG TTC ATC CTC GGC CCC GAG GGC TTC GGC GTC CTG AGC GTG TAC GGC

TCC ACC GTC GGC CAC ACC ATC ATT GAC CTG ATG TCG AAG AAC TGC TGG

GGT CTG CTC GGC CAC TAC CTG CGC GTG CTG ATC CAC GAG CAT ATC CTC

ATC CAC GGC GAC ATT CGC AAG ACC ACC AAA TTG AAC ATT GGT GGC ACT

GAG ATT GAG GTC GAG ACG CTG GTG GAG GAC GAG GCC GAG GCT GGC GCG

GTC AAC AAG GGC ACC GGC AAG gaattcggag gcggaggtgg agctagc
      end ChR2→↑

ACC GTG AGG GTG CCC ATC GCC GTG GGC GAG AGC GAC TTC GAG AAC CTG
↑←Start Nav1.6 Motif AAC ACC GAG GAC GTG AGC AGC GAG AGC GAC CCC taactcgagt ctagacgtgg
       end Nav1.6 Motif→↑

```
taccGATAAT CAACCTCTGG ATTACAAAAT TTGTGAAAGA TTGACTGGTA TTCTTAACTA
    ↑←start WPRE

TGTTGCTCCT TTTACGCTAT GTGGATACGC TGCTTTAATG CCTTTGTATC ATGCTATTGC

TTCCCGTATG GCTTTCATTT TCTCCTCCTT GTATAAATCC TGGTTGCTGT CTCTTTATGA

GGAGTTGTGG CCCGTTGTCA GGCAACGTGG CGTGGTGTGC ACTGTGTTTG CTGACGCAAC

CCCCACTGGT TGGGGCATTG CCACCACCTG TCAGCTCCTT TCCGGGACTT TCGCTTTCCC

CCTCCCTATT GCCACGGCGG AACTCATCGC CGCCTGCCTT GCCCGCTGCT GGACAGGGGC

TCGGCTGTTG GGCACTGACA ATTCCGTGGT GTTGTCGGGG AAGCTGACGT CCTTTCCATG

GCTGCTCGCC TGTGTTGCCA CCTGGATTCT GCGCGGGACG TCCTTCTGCT ACGTCCCTTC

GGCCCTCAAT CCAGCGGACC TTCCTTCCCG CGGCCTGCTG CCGGCTCTGC GGCCTCTTCC

GCGTCTTCGC CTTCGCCCTC AGACGAGTCG GATCTCCCTT TGGGCCGCCT CCCCGCCTGA

Tgcggggatc ctctagagtc gagagatctA CGGGTGGCAT CCCTGTGACC CCTCCCCAGT
↑end WPRE→↑              ↑←start bGH-polyA

GCCTCTCCTG GCCCTGGAAG TTGCCACTCC AGTGCCCACC AGCCTTGTCC TAATAAAATT

AAGTTGCATC ATTTTGTCTG ACTAGGTGTC CTTCTATAAT ATTATGGGGT GGAGGGGGGT

GGTATGGAGC AAGGGGCAAG TTGGGAAGAC AACCTGTAGG GCCTGCGGGG TCTATTGGGA

ACCAAGCTGG AGTGCAGTGG CACAATCTTG GCTCACTGCA ATCTCCGCCT CCTGGGTTCA

AGCGATTCTC CTGCCTCAGC CTCCCGAGTT GTTGGGATTC CAGGCATGCA TGACCAGGCT

CAGCTAATTT TTGTTTTTTT GGTAGAGACG GGGTTTCACC ATATTGGCCA GGCTGGTCTC

CAACTCCTAA TCTCAGGTGA TCTACCCACC TTGGCCTCCC AAATTGCTGG GATTACAGGC

GTGAACCACT GCTCCCTTCC CTGTCCTTct gattttgtag gtaaccacgt gcggaccgag
                                end bGH-polyA→↑

↓←start AAV2 ITR
cggccgcagg aacccctagt gatgagttg gccactccct ctctgcgcgc tcgctcgctc actgaggccg ggcgaccaaa ggtcgcccga cgcccgggct ttgcccgggc ggcctcagtg agcgagcgag cgcgcagctg cctgcagg
                end AAV2 ITR→↑

(G) SEQ ID NO: 36:
5'-ITR-CAG-ChR2-GFP-{NLG1 Motif}-WPRE-bGHpolyA-ITR-3'

←start AAV2 ITR
cctgcaggca gctgcgcgct cgctcgctca ctgaggccgc ccgggcaaag cccgggcgtc gggcgacctt tggtcgcccg gcctcagtga gcgagcgagc gcgcagagag ggagtggcca actccatcac taggggttcc tgcggccgca cgcgtgatat cCTAGTTATT AATAGTAATC
            end AAV2 ITR→↑                  ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA
```

```
CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGGA GCGGCTCGGG GCTGTCCGCG GGGGACGGC TGCCTTCGGG GGGGACGGGG
``` end CAG pomoter/enhancer→↓

```
CAGGGCGGGG TTCGGCTTCT GGCGTGTGAC CGGCGGCTCT AGCAGCCTCT GCTAaccatg ttcatgcctt cttcttttc ctacagctcc tgggcaacgt gctggttatt gtgctgtctc
```

↓←start ChR2

```
atcattttgg caaagaatta agcttgagct cgcgatccgc agcc ATG GAT TAT GGA

GGC GCC CTG AGT GCC GTT GGG CGC GAG CTG CTA TTT GTA ACG AAC CCA

GTA GTC GTC AAT GGC TCT GTA CTT GTG CCT GAG GAC CAG TGT TAC TGC

GCG GGC TGG ATT GAG TCG CGT GGC ACA AAC GGT GCC CAA ACG GCG TCG

AAC GTG CTG CAA TGG CTT GCT GCT GGC TTC TCC ATC CTA CTG CTT ATG

TTT TAC GCC TAC CAA ACA TGG AAG TCA ACC TGC GGC TGG GAG GAG ATC

TAT GTG TGC GCT ATC GAG ATG GTC AAG GTG ATT CTT GAG TTC TTC TTC

GAG TTT AAG AAC CCG TCC ATG CTG TAT CTA GCC ACA GGC CAC CGC GTC

CAG TGG TTG CGT TAC GCC GAG TGG CTT CTC ACC TGC CCG GTC ATT CTC

ATT CAC CTG TCA AAC CTG ACG GGC TTG TCC AAC GAC TAC AGC AGG CGC

ACT ATG GGT CTG CTT GTG TCT GAT ATT GGC ACA ATT GTG TGG GGC GCC

ACT TCC GCT ATG GCC ACC GGA TAC GTC AAG GTC ATC TTC TTC TGC CTG

GGT CTG TGT TAT GGT GCT AAC ACG TTC TTT CAC GCT GCC AAG GCC TAC

ATC GAG GGT TAC CAT ACC GTG CCG AAG GGC CGG TGT CGC CAG GTG GTG

ACT GGC ATG GCT TGG CTC TTC TTC GTA TCA TGG GGT ATG TTC CCC ATC

CTG TTC ATC CTC GGC CCC GAG GGC TTC GGC GTC CTG AGC GTG TAC GGC

TCC ACC GTC GGC CAC ACC ATC ATT GAC CTG ATG TCG AAG AAC TGC TGG

GGT CTG CTC GGC CAC TAC CTG CGC GTG CTG ATC CAC GAG CAT ATC CTC

ATC CAC GGC GAC ATT CGC AAG ACC ACC AAA TTG AAC ATT GGT GGC ACT

GAG ATT GAG GTC GAG ACG CTG GTG GAG GAC GAG GCC GAG GCT GGC GCG

GTC AAC AAG GGC ACC GGC AAG gaattcggag gcggaggtgg agctagc
```
               end ChR2→↑

↓←start GFP
```
AAA GGA GAA GAA CTC TTC ACT GGA GTT GTC CCA ATT CTT GTT GAA TTA

GAT GGT GAT GTT AAC GGC CAC AAG TTC TCT GTC AGT GGA GAG GGT GAA

GGT GAT GCA ACA TAC GGA AAA CTT ACC CTG AAG TTC ATC TGC ACT ACT
```

```
GGC AAA CTG CCT GTT CCA TGG CCA ACA CTA GTC ACT ACT CTG TGC TAT

GGT GTT CAA TGC TTT TCA AGA TAC CCG GAT CAT ATG AAA CGG CAT GAC

TTT TTC AAG AGT GCC ATG CCC GAA GGT TAT GTA CAG GAA AGG ACC ATC

TTC TTC AAA GAT GAC GGC AAC TAC AAG ACA CGT GCT GAA GTC AAG TTT

GAA GGT GAT ACC CTT GTT AAT AGA ATC GAG TTA AAA GGT ATT GAC TTC

AAG GAA GAT GGC AAC ATT CTG GGA CAC AAA TTG GAA TAC AAC TAT AAC

TCA CAC AAT GTA TAC ATC ATG GCA GAC AAA CAA AAG AAT GGA ATC AAA

GTG AAC TTC AAG ACC CGC CAC AAC ATT GAA GAT GGA AGC GTT CAA CTA

GCA GAC CAT TAT CAA CAA AAT ACT CCA ATT GGC GAT GGC CCT GTC CTT

TTA CCA GAC AAC CAT TAC CTG TCC ACA CAA TCT GCC CTT TCG AAA GAT

CCC AAC GAA AAG AGA GAC CAC ATG GTC CTT CTT GAG TTT GTA ACA GCT
```

```
                                          end GFP→↓
GCT GGG ATT ACA CAT GGC ATG GAT GAA CTG TAC AAC GTG GTT CTT CGG
                                                ↑←Start NLG-1 Motif

ACC GCC TGT CCC CCA GAT TAC ACA CTA GCT ATG AGG AGG TCA CCT GAT

GAT GTT CCC TTA ATG ACA CCC AAC ACC ATT ACA ATG taactcgagt
                               end NLG-1 Motif→↑ ctagacgtgg taccGATAAT CAACCTCTGG ATTACAAAAT TGTGAAAGA TTGACTGGTA
                ↑←start WPRE

TTCTTAACTA TGTTGCTCCT TTTACGCTAT GTGGATACGC TGCTTTAATG CCTTTGTATC

ATGCTATTGC TTCCCGTATG GCTTTCATTT TCTCCTCCTT GTATAAATCC TGGTTGCTGT

CTCTTTATGA GGAGTTGTGG CCCGTTGTCA GGCAACGTGG CGTGGTGTGC ACTGTGTTTG

CTGACGCAAC CCCCACTGGT TGGGGCATTG CCACCACCTG TCAGCTCCTT TCCGGGACTT

TCGCTTTCCC CCTCCCTATT GCCACGGCGG AACTCATCGC CGCCTGCCTT GCCCGCTGCT

GGACAGGGGC TCGGCTGTTG GCACTGACA ATTCCGTGGT GTTGTCGGGG AAGCTGACGT

CCTTTCCATG GCTGCTCGCC TGTGTTGCCA CCTGGATTCT GCGCGGGACG TCCTTCTGCT

ACGTCCCTTC GGCCCTCAAT CCAGCGGACC TTCCTTCCCG CGGCCTGCTG CCGGCTCTGC

GGCCTCTTCC GCGTCTTCGC CTTCGCCCTC AGACGAGTCG GATCTCCCTT TGGGCCGCCT

CCCCGCCTGA Tgcggggatc tctagagtc gagagatctA CGGGTGGCAT CCCTGTGACC
   end WPRE→↑                             ↑←start bGH-polyA

CCTCCCCAGT GCCTCTCCTG GCCCTGGAAG TTGCCACTCC AGTGCCCACC AGCCTTGTCC

TAATAAAATT AAGTTGCATC ATTTTGTCTG ACTAGGTGTC CTTCTATAAT ATTATGGGGT

GGAGGGGGGT GGTATGGAGC AAGGGGCAAG TTGGGAAGAC AACCTGTAGG GCCTGCGGGG

TCTATTGGGA ACCAAGCTGG AGTGCAGTGG CACAATCTTG GCTCACTGCA ATCTCCGCCT

CCTGGGTTCA AGCGATTCTC CTGCCTCAGC CTCCCGAGTT GTTGGGATTC CAGGCATGCA

TGACCAGGCT CAGCTAATTT TTGTTTTTTT GGTAGAGACG GGGTTTCACC ATATTGGCCA

GGCTGGTCTC CAACTCCTAA TCTCAGGTGA TCTACCCACC TTGGCCTCCC AAATTGCTGG

GATTACAGGC GTGAACCACT GCTCCCTTCC CTGTCCTTct gattttgtag gtaaccacgt
                                 end bGH-polyA→↑
```

-continued gcggaccgag cggccgcagg aaccctagt gatagagttg gccactccct ctctgcgcgc
                ↑←start AAV2 ITR tcgctcgctc actgaggccg ggcgaccaaa ggtcgcccga cgcccgggct tgcccgggc ggcctcagtg agcgagcgag cgcgcagctg cctgcagg
                        end AAV2 ITR→↑

(H) SEQ ID NO: 37 (same as above but without GFP)
5'-ITR-CAG-ChR2-(NLG-1Motif)-WPRE-bGHpolyA-ITR-3'

←start AAV2 ITR
cctgcaggca gctgcgcgct cgctcgctca ctgaggccgc cgggcaaag cccgggcgtc gggcgaccct tggtcgcccg gcctcagtga gcgagcgagc gcgcagagag ggagtggcca actccatcac tagggttcc tgcggccgca cgcgtgatat cCTAGTTATT AATAGTAATC
        end AAV2 ITR→↑                       ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGA GCGGCTCGGG GCTGTCCGCG GGGGACGGC TGCCTTCGGG GGGACGGGG end CAG pomoter/enhancer→↓
CAGGGCGGGG TTCGGCTTCT GGCGTGTGAC CGGCGGCTCT AGCAGCCTCT GCTAaccatg ttcatgcctt cttctttttc ctacagctcc tgggcaacgt gctggttatt gtgctgtctc
                                                      ↓←start ChR2
atcattttgg caaagaatta agcttgagct cgcgatccgc agcc *ATG GAT TAT GGA*

*GGC GCC CTG AGT GCC GTT GGG CGC GAG CTG CTA TTT GTA ACG AAC CCA*

*GTA GTC GTC AAT GGC TCT GTA CTT GTG CCT GAG GAC CAG TGT TAC TGC*

*GCG GGC TGG ATT GAG TCG CGT GGC ACA AAC GGT GCC CAA ACG GCG TCG*

*AAC GTG CTG CAA TGG CTT GCT GCT GGC TTC TCC ATC CTA CTG CTT ATG*

*TTT TAC GCC TAC CAA ACA TGG AAG TCA ACC TGC GGC TGG GAG GAG ATC*

*TAT GTG TGC GCT ATC GAG ATG GTC AAG GTG ATT CTT GAG TTC TTC TTC*

*GAG TTT AAG AAC CCG TCC ATG CTG TAT CTA GCC ACA GGC CAC CGC GTC*

*CAG TGG TTG CGT TAC GCC GAG TGG CTT CTC ACC TGC CCG GTC ATT CTC*

*ATT CAC CTG TCA AAC CTG ACG GGC TTG TCC AAC GAC TAC AGC AGG CGC*

```
ACT ATG GGT CTG CTT GTG TCT GAT ATT GGC ACA ATT GTG TGG GGC GCC

ACT TCC GCT ATG GCC ACC GGA TAC GTC AAG GTC ATC TTC TTC TGC CTG

GGT CTG TGT TAT GGT GCT AAC ACG TTC TTT CAC GCT GCC AAG GCC TAC

ATC GAG GGT TAC CAT ACC GTG CCG AAG GGC CGG TGT CGC CAG GTG GTG

ACT GGC ATG GCT TGG CTC TTC TTC GTA TCA TGG GGT ATG TTC CCC ATC

CTG TTC ATC CTC GGC CCC GAG GGC TTC GGC GTC CTG AGC GTG TAC GGC

TCC ACC GTC GGC CAC ACC ATC ATT GAC CTG ATG TCG AAG AAC TGC TGG

GGT CTG CTC GGC CAC TAC CTG CGC GTG CTG ATC CAC GAG CAT ATC CTC

ATC CAC GGC GAC ATT CGC AAG ACC ACC AAA TTG AAC ATT GGT GGC ACT

GAG ATT GAG GTC GAG ACG CTG GTG GAG GAC GAG GCC GAG GCT GGC GCG

GTC AAC AAG GGC ACC GGC AAG gaattcggag gcggaggtgg agctagc
                            end ChR2→↑

GTG GTT CTT CGG ACC GCC TGT CCC CCA GAT TAC ACA CTA GCT ATG AGG
↑←Start NLG-1 Motif AGG TCA CCT GAT GAT GTT CCC TTA ATG ACA CCC AAC ACC ATT ACA ATG
                                                  end NLG1 Motif→↑ taactcgagt ctagacgtgg taccGATAAT CAACCTCTGG ATTACAAAAT TTGTGAAAGA
                         ↑←start WPRE

TTGACTGGTA TTCTTAACTA TGTTGCTCCT TTTACGCTAT GTGGATACGC TGCTTTAATG

CCTTTGTATC ATGCTATTGC TTCCCGTATG GCTTTCATTT TCTCCTCCTT GTATAAATCC

TGGTTGCTGT CTCTTTATGA GGAGTTGTGG CCCGTTGTCA GGCAACGTGG CGTGGTGTGC

ACTGTGTTTG CTGACGCAAC CCCCACTGGT TGGGGCATTG CCACCACCTG TCAGCTCCTT

TCCGGGACTT TCGCTTTCCC CCTCCCTATT GCCACGGCGG AACTCATCGC CGCCTGCCTT

GCCCGCTGCT GGACAGGGGC TCGGCTGTTG GGCACTGACA ATTCCGTGGT GTTGTCGGGG

AAGCTGACGT CCTTTCCATG GCTGCTCGCC TGTGTTGCCA CCTGGATTCT GCGCGGGACG

TCCTTCTGCT ACGTCCCTTC GGCCCTCAAT CCAGCGGACC TTCCTTCCCG CGGCCTGCTG

CCGGCTCTGC GGCCTCTTCC GCGTCTTCGC CTTCGCCCTC AGACGAGTCG ATCTCCCTT

TGGGCCGCCT CCCCGCCTGA Tgcggggatc tctagagtc gagagatctA CGGGTGGCAT
                      end WPRE→↑                     ↑←start bGH-polyA

CCCTGTGACC CCTCCCCAGT GCCTCTCCTG GCCCTGGAAG TTGCCACTCC AGTGCCCACC

AGCCTTGTCC TAATAAAATT AAGTTGCATC ATTTTGTCTG ACTAGGTGTC CTTCTATAAT

ATTATGGGGT GGAGGGGGGT GGTATGGAGC AAGGGGCAAG TTGGGAAGAC AACCTGTAGG

GCCTGCGGGG TCTATTGGGA ACCAAGCTGG AGTGCAGTGG CACAATCTTG GCTCACTGCA

ATCTCCGCCT CCTGGGTTCA AGCGATTCTC CTGCCTCAGC CTCCCGAGTT GTTGGGATTC

CAGGCATGCA TGACCAGGCT CAGCTAATTT TTGTTTTTTT GGTAGAGACG GGGTTTCACC

ATATTGGCCA GGCTGGTCTC CAACTCCTAA TCTCAGGTGA TCTACCCACC TTGGCCTCCC

AAATTGCTGG GATTACAGGC GTGAACCACT GCTCCCTTCC CTGTCCTTct gattttgtag
                                                        end bGH-polyA→↑ gtaaccacgt gcggaccgag cggccgcagg aaccctagt gatggagttg gccactccct
                                ↑←start AAV2 ITR
```
ctctgcgcgc tgctcgctc actgaggccg ggcgaccaaa ggtcgcccga cgcccgggct ttgcccgggc ggcctcagtg agcgagcgag cgcgcagctg cctgcagg
                                                                          end AAV2 ITR→↑

(I) SEQ ID NO: 38:
5'-ITR-CAG-ChR2-GFP-{MLPH Motif}-WPRE-bGHpolyA-ITR-3'

←start AAV2 ITR
cctgcaggca gctgcgcgct cgctcgctca ctgaggccgc ccgggcaaag cccgggcgtc gggcgaccit tggtcgcccg gcctcagtga gcgagcgagc gcgcagagag ggagtggcca actccatcac taggggttcc tgcggccgca cgcgtgatat cCTAGTTATT AATAGTAATC
        end AAV2 ITR→↑                             ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGA GCGGCTCGGG GCTGTCCGCG GGGGACGGC TGCCTTCGGG GGGGACGGGG
                                                             end CAG pomoter/enhancer→↓
CAGGGCGGGG TTCGGCTTCT GGCGTGTGAC CGGCGGCTCT AGCAGCCTCT GCTAaccatg ttcatgcctt cttcttttc ctacagctcc tgggcaacgt gctggttatt gtgctgtctc
                                                                    ↓←start ChR2
atcattttgg caaagaatta agcttgagct cgcgatccgc agcc ATG GAT TAT GGA

GGC GCC CTG AGT GCC GTT GGG CGC GAG CTG CTA TTT GTA ACG AAC CCA

GTA GTC GTC AAT GGC TCT GTA CTT GTG CCT GAG GAC CAG TGT TAC TGC

GCG GGC TGG ATT GAG TCG CGT GGC ACA AAC GGT GCC CAA ACG GCG TCG

AAC GTG CTG CAA TGG CTT GCT GCT GGC TTC TCC ATC CTA CTG CTT ATG

TTT TAC GCC TAC CAA ACA TGG AAG TCA ACC TGC GGC TGG GAG GAG ATC

TAT GTG TGC GCT ATC GAG ATG GTC AAG GTG ATT CTT GAG TTC TTC TTC

GAG TTT AAG AAC CCG TCC ATG CTG TAT CTA GCC ACA GGC CAC CGC GTC

CAG TGG TTG CGT TAC GCC GAG TGG CTT CTC ACC TGC CCG GTC ATT CTC

ATT CAC CTG TCA AAC CTG ACG GGC TTG TCC AAC GAC TAC AGC AGG CGC

ACT ATG GGT CTG CTT GTG TCT GAT ATT GGC ACA ATT GTG TGG GGC GCC

ACT TCC GCT ATG GCC ACC GGA TAC GTC AAG GTC ATC TTC TTC TGC CTG

*GGT CTG TGT TAT GGT GCT AAC ACG TTC TTT CAC GCT GCC AAG GCC TAC*

*ATC GAG GGT TAC CAT ACC GTG CCG AAG GGC CGG TGT CGC CAG GTG GTG*

*ACT GGC ATG GCT TGG CTC TTC TTC GTA TCA TGG GGT ATG TTC CCC ATC*

*CTG TTC ATC CTC GGC CCC GAG GGC TTC GGC GTC CTG AGC GTG TAC GGC*

*TCC ACC GTC GGC CAC ACC ATC ATT GAC CTG ATG TCG AAG AAC TGC TGG*

*GGT CTG CTC GGC CAC TAC CTG CGC GTG CTG ATC CAC GAG CAT ATC CTC*

*ATC CAC GGC GAC ATT CGC AAG ACC ACC AAA TTG AAC ATT GGT GGC ACT*

*GAG ATT GAG GTC GAG ACG CTG GTG GAG GAC GAG GCC GAG GCT GGC GCG*

*GTC AAC AAG GGC ACC GGC AAG* gaattcggag gcggaggtgg agctagc
      end ChR2→↑

↓←start GFP
AAA GGA GAA GAA CTC TTC ACT GGA GTT GTC CCA ATT CTT GTT GAA TTA

GAT GGT GAT GTT AAC GGC CAC AAG TTC TCT GTC AGT GGA GAG GGT GAA

GGT GAT GCA ACA TAC GGA AAA CTT ACC CTG AAG TTC ATC TGC ACT ACT

GGC AAA CTG CCT GTT CCA TGG CCA ACA CTA GTC ACT ACT CTG TGC TAT

GGT GTT CAA TGC TTT TCA AGA TAC CCG GAT CAT ATG AAA CGG CAT GAC

TTT TTC AAG AGT GCC ATG CCC GAA GGT TAT GTA CAG GAA AGG ACC ATC

TTC TTC AAA GAT GAC GGC AAC TAC AAG ACA CGT GCT GAA GTC AAG TTT

GAA GGT GAT ACC CTT GTT AAT AGA ATC GAG TTA AAA GGT ATT GAC TTC

AAG GAA GAT GGC AAC ATT CTG GGA CAC AAA TTG GAA TAC AAC TAT AAC

TCA CAC AAT GTA TAC ATC ATG GCA GAC AAA CAA AAG AAT GGA ATC AAA

GTG AAC TTC AAG ACC CGC CAC AAC ATT GAA GAT GGA AGC GTT CAA CTA

GCA GAC CAT TAT CAA CAA AAT ACT CCA ATT GGC GAT GGC CCT GTC CTT

TTA CCA GAC AAC CAT TAC CTG TCC ACA CAA TCT GCC CTT TCG AAA GAT

CCC AAC GAA AAG AGA GAC CAC ATG GTC CTT CTT GAG TTT GTA ACA GCT end GFP→↓
GCT GGG ATT ACA CAT GGC ATG GAT GAA CTG TAC AAC <u>AGG GAC CAG CCT</u>
                 ↑←Start MLPH Motif <u>CTG AAC AGC AAA AAG AAA AAG AGG CTC CTG AGC TTC AGG GAC GTG GAC</u>

<u>TTC GAG GAG GAC AGC GAC</u> taactcgagt ctagacgtgg tacc<u>GATAAT CAACCTCTGG</u>
end MLPH Motif→↑        ↑←start WPRE <u>ATTACAAAAT TGTGAAAGA TTGACTGGTA TTCTTAACTA TGTTGCTCCT TTTACGCTAT</u>

<u>GTGGATACGC TGCTTTAATG CCTTTGTATC ATGCTATTGC TTCCCGTATG GCTTTCATTT</u>

<u>TCTCCTCCTT GTATAAATCC TGGTTGCTGT CTCTTTATGA GGAGTTGTGG CCCGTTGTCA</u>

<u>GGCAACGTGG CGTGGTGTGC ACTGTGTTTG CTGACGCAAC CCCCACTGGT TGGGGCATTG</u>

<u>CCACCACCTG TCAGCTCCTT TCCGGGACTT TCGCTTTCCC CCTCCCTATT GCCACGGCGG</u>

<u>AACTCATCGC CGCCTGCCTT GCCCGCTGCT GGACAGGGGC TCGGCTGTTG GCACTGACA</u>

<u>ATTCCGTGGT GTTGTCGGGG AAGCTGACGT CCTTTCCATG GCTGCTCGCC TGTGTTGCCA</u>

<u>CCTGGATTCT GCGCGGGACG TCCTTCTGCT ACGTCCCTTC GGCCCTCAAT CCAGCGGACC</u>

TTCCTTCCCG CGGCCTGCTG CCGGCTCTGC GGCCTCTTCC GCGTCTTCGC CTTCGCCCTC

AGACGAGTCG GATCTCCCTT TGGGCCGCCT CCCCGCCTGA Tgcggggatc ctctagagtc
                    end WPRE→↑ gagagatctA CGGGTGGCAT CCCTGTGACC CCTCCCCAGT GCCTCTCCTG GCCCTGGAAG
  ↑←start bGH-polyA

TTGCCACTCC AGTGCCCACC AGCCTTGTCC TAATAAAATT AAGTTGCATC ATTTTGTCTG

ACTAGGTGTC CTTCTATAAT ATTATGGGGT GGAGGGGGGT GGTATGGAGC AAGGGGCAAG

TTGGGAAGAC AACCTGTAGG GCCTGCGGGG TCTATTGGGA ACCAAGCTGG AGTGCAGTGG

CACAATCTTG GCTCACTGCA ATCTCCGCCT CCTGGGTTCA AGCGATTCTC CTGCCTCAGC

CTCCCGAGTT GTTGGGATTC CAGGCATGCA TGACCAGGCT CAGCTAATTT TTGTTTTTTT

GGTAGAGACG GGGTTTCACC ATATTGGCCA GGCTGGTCTC CAACTCCTAA TCTCAGGTGA

TCTACCCACC TTGGCCTCCC AAATTGCTGG GATTACAGGC GTGAACCACT GCTCCCTTCC

CTGTCCTTCt gattttgtag gtaaccacgt gcggaccgag cggccgcagg aacccctagt
  ↑←end bGH-polyA               ↑←start AAV2 ITR gatggagttg gccactccct ctctgcgcgc tcgctcgctc actgaggccg ggcgaccaaa ggtcgcccga cgcccgggct tgccgggc ggcctcagtg agcgagcgag cgcgcagctg cctgcagg
  ↑←end AAV2 ITR (J) SEQ ID NO: 39 (same as above without GFP)
5'-ITR—CAG—ChR2—{MLPH-Motif}—WPRE—bGHpolyA—ITR-3'

←start AAV2 ITR
cctgcaggca gctgcgcgct cgctcgctca ctgaggccgc ccgggcaaag cccgggcgtc gggcgacctt tggtcgcccg gccgcagtga gcgagcgagc gcgcagagag ggagtggcca actccatcac taggggttcc tgcggccgca cgcgtgatat cCTAGTTATT AATAGTAATC
    end AAV2 ITR→↑          ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GGCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGGA GCGGCTCGGG GCTGTCCGCG GGGGACGGC TGCCTTCGGG GGGGACGGGG end CAG pomoter/enhancer→↓
CAGGGCGGGG TTCGGCTTCT GGCGTGTGAC CGGCGGCTCT AGCAGCCTCT GCTAaccatg ttcatgcctt cttctttttc ctacagctcc tgggcaacgt gctggttatt gtgctgtctc ↓←start ChR2
atcatttgg caaagaatta agcttgagct cgcgatccgc agcc *ATG GAT TAT GGA*

*GGC GCC CTG AGT GCC GTT GGG CGC GAG CTG CTA TTT GTA ACG AAC CCA*

*GTA GTC GTC AAT GGC TCT GTA CTT GTG CCT GAG GAC CAG TGT TAC TGC*

*GCG GGC TGG ATT GAG TCG CGT GGC ACA AAC GGT GCC CAA ACG GCG TCG*

*AAC GTG CTG CAA TGG CTT GCT GCT GGC TTC TCC ATC CTA CTG CTT ATG*

*TTT TAC GCC TAC CAA ACA TGG AAG TCA ACC TGC GGC TGG GAG GAG ATC*

*TAT GTG TGC GCT ATC GAG ATG GTC AAG GTG ATT CTT GAG TTC TTC TTC*

*GAG TTT AAG AAC CCG TCC ATG CTG TAT CTA GCC ACA GGC CAC CGC GTC*

*CAG TGG TTG CGT TAC GCC GAG TGG CTT CTC ACC TGC CCG GTC ATT CTC*

*ATT CAC CTG TCA AAC CTG ACG GGC TTG TCC AAC GAC TAC AGC AGG CGC*

*ACT ATG GGT CTG CTT GTG TCT GAT ATT GGC ACA ATT GTG TGG GGC GCC*

*ACT TCC GCT ATG GCC ACC GGA TAC GTC AAG GTC ATC TTC TTC TGC CTG*

*GGT CTG TGT TAT GGT GCT AAC ACG TTC TTT CAC GCT GCC AAG GCC TAC*

*ATC GAG GGT TAC CAT ACC GTG CCG AAG GGC CGG TGT CGC CAG GTG GTG*

*ACT GGC ATG GCT TGG CTC TTC TTC GTA TCA TGG GGT ATG TTC CCC ATC*

*CTG TTC ATC CTC GGC CCC GAG GGC TTC GGC GTC CTG AGC GTG TAC GGC*

*TCC ACC GTC GGC CAC ACC ATC ATT GAC CTG ATG TCG AAG AAC TGC TGG*

*GGT CTG CTC GGC CAC TAC CTG CGC GTG CTG ATC CAC GAG CAT ATC CTC*

*ATC CAC GGC GAC ATT CGC AAG ACC ACC AAA TTG AAC ATT GGT GGC ACT*

*GAG ATT GAG GTC GAG ACG CTG GTG GAG GAC GAG GCC GAG GCT GGC GCG*

*GTC AAC AAG GGC ACC GGC AAG* gaattcggag gcggaggtgg agctagc
                end ChR2→↑

<u>AGG GAC CAG CCT CTG AAC AGC AAA AAG AAA AAG AGG CTC CTG AGC TTC</u>
↑←Start MLPH Motif <u>AGG GAC GTG GAC TTC GAG GAG GAC AGC GAC</u> taactcgagt ctagacgtgg
                       end MLPH Motif→↑ tacc<u>GATAAT CAACCTCTGG ATTACAAAAT TTGTGAAAGA TTGACTGGTA TTCTTAACTA</u>
    ↑←start WPRE <u>TGTTGCTCCT TTTACGCTAT GTGGATACGC TGCTTTAATG CCTTTGTATC ATGCTATTGC</u>

<u>TTCCCGTATG GCTTTCATTT TCTCCTCCTT GTATAAATCC TGGTTGCTGT CTCTTTATGA</u>

<u>GGAGTTGTGG CCCGTTGTCA GGCAACGTGG CGTGGTGTGC ACTGTGTTTG CTGACGCAAC</u>

<u>CCCCACTGGT TGGGGCATTG CCACCACCTG TCAGCTCCTT TCCGGGACTT TCGCTTTCCC</u>

```
CCTCCCTATT GCCACGGCGG AACTCATCGC CGCCTGCCTT GCCCGCTGCT GGACAGGGGC

TCGGCTGTTG GGCACTGACA ATTCCGTGGT GTTGTCGGGG AAGCTGACGT CCTTTCCATG

GCTGCTCGCC TGTGTTGCCA CCTGGATTCT GCGCGGGACG TCCTTCTGCT ACGTCCCTTC

GGCCCTCAAT CCAGCGGACC TTCCTTCCCG CGGCCTGCTG CCGGCTCTGC GGCCTCTTCC

GCGTCTTCGC CTTCGCCCTC AGACGAGTCG GATCTCCCTT TGGGCCGCCT CCCCGCCTGA
```

Tgcggggatc ctctagagtc gagagatctA *CGGGTGGCAT CCCTGTGACC CCTCCCCAGT*
↑←end WPRE                      ↑←start bGH-polyA

*GCCTCTCCTG GCCCTGGAAG TTGCCACTCC AGTGCCCACC AGCCTTGTCC TAATAAAATT*

*AAGTTGCATC ATTTTGTCTG ACTAGGTGTC CTTCTATAAT ATTATGGGGT GGAGGGGGGT*

*GGTATGGAGC AAGGGGCAAG TTGGGAAGAC AACCTGTAGG GCCTGCGGGG TCTATTGGGA*

*ACCAAGCTGG AGTGCAGTGG CACAATCTTG GCTCACTGCA ATCTCCGCCT CCTGGGTTCA*

*AGCGATTCTC CTGCCTCAGC CTCCCGAGTT GTTGGGATTC CAGGCATGCA TGACCAGGCT*

*CAGCTAATTT TTGTTTTTTT GGTAGAGACG GGGTTTCACC ATATTGGCCA GGCTGGTCTC*

*CAACTCCTAA TCTCAGGTGA TCTACCCACC TTGGCCTCCC AAAATTGCTGG GATTACAGGC*

*GTGAACCACT GCTCCCTTCC CTGTCCTT*ct gattttgtag gtaaccacgt gcggaccgag
          end bGH-polyA→↑ cggccgcagg aaccectagt gatggagttg gccactccct ctctgcgcgc tcgctcgctc
       ↑←start AAV2 ITR actgaggccg ggcgaccaaa ggtcgcccga cgcccgggct ttgcccgggc ggcctcagtg agcgagcgag cgcgcagctg cctgcagg
                end AAV2 ITR→↑

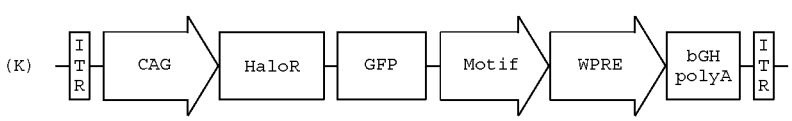

SEQ ID NO: 40:
5'-ITR-CAG-HaloR-GFP-(Kv2.1Motif)-WPRE-bGHpolyA-ITR-3

←start AAV2 ITR
cctgcaggca gctgcgcgct cgctcgctca ctgaggccgc ccgggcaaag cccgggcgtc gggcgacctt tggtcgcccg gcctcagtga gcgagcgagc gcgcagagag ggagtggcca actccatcac taggggttcc tgcggccgca cgcgtgatat cCTAGTTATT AATAGTAATC
              end AAV2 ITR→↑                    ↑←start CAG pomoter/enhancer

```
AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC
```

-continued

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GGCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGGA GCGGCTCGGG GCTGTCCGCG GGGGACGGC TGCCTTCGGG GGGGACGGGG end CAG pomoter/enhancer→↓
CAGGGCGGGG TTCGGCTTCT GGCGTGTGAC CGGCGGCTCT AGCAGCCTCT GCTAaccatg ttcatgcctt cttcttttc ctacagctcc tgggcaacgt gctggttatt gtgctgtctc ↓←start HaloR
atcattttgg caaagaatta agcttgagct cgcgatccgc agcc ATG ACT GAG ACA

TTG CCA CCG GTA ACG GAA TCG GCT GTT GCG CTA CAG GCG GAG GTG ACC

CAG AGG GAG CTG TTC GAG TTC GTT CTC AAC GAC CCC CTC CTC GCC AGT

TCG CTG TAT ATT AAT ATC GCA CTG GCA GGG CTG TCG ATA CTG CTT TTC

GTG TTC ATG ACG CGC GGA CTC GAC GAC CCA CGG GCG AAA CTC ATC GCC

GTT TCG ACG ATT TTG GTG CCG GTG GTC TCT ATC GCG AGC TAC ACC GGC

CTT GCA TCG GGG CTC ACC ATC AGC GTC CTC GAG ATG CCA GCC GGC CAC

TTC GCC GAG GGG TCC TCG GTG ATG CTC GGC GGC GAA GAG GTA GAC GGC

GTC GTG ACG ATG TGG GGC CGC TAT CTG ACG TGG GCC CTT TCG ACA CCG

ATG ATA CTG CTG GCG CTT GGG CTG CTT GCT GGC TCT AAC GCC ACG AAG

CTC TTT ACC GCC ATC ACC TTC GAC ATC GCG ATG TGT GTC ACC GGC CTC

GCA GCC GCG CTG ACG ACC TCT TCG CAC CTG ATG CGG TGG TTC TGG TAC

GCC ATC AGT TGT GCG TGT TTC CTC GTC GTC CTC TAC ATC CTG CTC GTC

GAG TGG GCA CAG GAC GCC AAG GCT GCC GGT ACT GCG GAT ATG TTC AAT

ACG CTG AAG CTG CTG ACC GTT GTC ATG TGG CTC GGC TAC CCC ATC GTG

TGG GCA CTC GGC GTT GAG GGC ATC GCC GTT CTT CCG GTC GGA GTC ACG

TCG TGG GGA TAC AGC TTC CTC GAC ATC GTC GCG AAG TAC ATC TTC GCG

TTC CTG CTG CTC AAC TAC CTC ACG TCG AAC GAG AGC GTC GTC TCC GGC

TCG ATA CTC GAC GTG CCG TCC GCG TCG GGC ACT CCC GCT GAC GAC
                    end HaloR→↑ gaattcggag gcggaggtgg agctagc AAA GGA GAA GAA CTC TTC ACT GGA GTT
              ↑←start GFP

GGA GTT GTC CCA ATT CTT GTT GAA TTA GAT GGT GAT GTT AAC GGC CAC

AAG TTC TCT GTC AGT GGA GAG GGT GAA GGT GAT GCA ACA TAC GGA AAA

CTT ACC CTG AAG TTC ATC TGC ACT ACT GGC AAA CTG CCT GTT CCA TGG

CCA ACA CTA GTC ACT ACT CTG TGC TAT GGT GTT CAA TGC TTT TCA AGA

TAC CCG GAT CAT ATG AAA CGG CAT GAC TTT TTC AAG AGT GCC ATG CCC

GAA GGT TAT GTA CAG GAA AGG ACC ATC TTC TTC AAA GAT GAC GGC AAC

TAC AAG ACA CGT GCT GAA GTC AAG TTT GAA GGT GAT ACC CTT GTT AAT

AGA ATC GAG TTA AAA GGT ATT GAC TTC AAG GAA GAT GGC AAC ATT CTG

```
GGA CAC AAA TTG GAA TAC AAC TAT AAC TCA CAC AAT GTA TAC ATC ATG

GCA GAC AAA CAA AAG AAT GGA ATC AAA GTG AAC TTC AAG ACC CGC CAC

AAC ATT GAA GAT GGA AGC GTT CAA CTA GCA GAC CAT TAT CAA CAA AAT

ACT CCA ATT GGC GAT GGC CCT GTC CTT TTA CCA GAC AAC CAT TAC CTG

TCC ACA CAA TCT GCC CTT TCG AAA GAT CCC AAC GAA AAG AGA GAC CAC

ATG GTC CTT CTT GAG TTT GTA ACA GCT GCT GGG ATT ACA CAT GGC ATG
                                end GFP→↓
GAT GAA CTG TAC AAC CAG TCT CAG CCC ATC CTG AAC ACT AAG GAG ATG
                     ↑←Start Kv2.1 Motif

GCC CCT CAG AGT AAA CCC CCT GAG GAA CTG GAA ATG AGC TCC ATG CCA

TCT CCA GTG GCT CCT CTG CCA GCT AGG ACC GAG GGC GTG ATT GAC ATG

AGA AGC ATG TCT AGT ATC GAT AGC TTC ATT TCC TGC GCC ACC GAC TTC

CCC GAA GCT ACA AGG TTT taactcgagt ctagacgtgg taccGATAAT CAACCTCTGG
       end Kv2.1 Motif→↑                              ↑←Start WPRE

ATTACAAAAT TGTGAAAGA TTGACTGGTA TTCTTAACTA TGTTGCTCCT TTTACGCTAT

GTGGATACGC TGCTTTAATG CCTTTGTATC ATGCTATTGC TTCCCGTATG GCTTTCATTT

TCTCCTCCTT GTATAAATCC TGGTTGCTGT CTCTTTATGA GGAGTTGTGG CCCGTTGTCA

GGCAACGTGG CGTGGTGTGC ACTGTGTTTG CTGACGCAAC CCCCACTGGT TGGGGCATTG

CCACCACCTG TCAGCTCCTT TCCGGGACTT TCGCTTTCCC CCTCCCTATT GCCACGGCGG

AACTCATCGC CGCCTGCCTT GCCCGCTGCT GGACAGGGGC TCGGCTGTTG GGCACTGACA

ATTCCGTGGT GTTGTCGGGG AAGCTGACGT CCTTTCCATG GCTGCTCGCC TGTGTTGCCA

CCTGGATTCT GCGCGGGACG TCCTTCTGCT ACGTCCCTTC GGCCCTCAAT CCAGCGGACC

TTCCTTCCCG CGGCCTGCTG CCGGCTCTGC GGCCTCTTCC GCGTCTTCGC CTTCGCCCTC

AGACGAGTCG GATCTCCCTT TGGGCCGCCT CCCCGCCTGA Tgcggggatc tctagagtc
                                                 end WPRE→↑ gagagatctA CGGGTGGCAT CCCTGTGACC CCTCCCCAGT GCCTCTCCTG GCCCTGGAAG
           ↑←start bGH-polyA

TTGCCACTCC AGTGCCCACC AGCCTTGTCC TAATAAAATT AAGTTGCATC ATTTTGTCTG

ACTAGGTGTC CTTCTATAAT ATTATGGGGT GGAGGGGGGT GGTATGGAGC AAGGGGCAAG

TTGGGAAGAC AACCTGTAGG GCCTGCGGGG TCTATTGGGA ACCAAGCTGG AGTGCAGTGG

CACAATCTTG GCTCACTGCA ATCTCCGCCT CCTGGGTTCA AGCGATTCTC CTGCCTCAGC

CTCCCGAGTT GTTGGGATTC CAGGCATGCA TGACCAGGCT CAGCTAATTT TTGTTTTTTT

GGTAGAGACG GGGTTTCACC ATATTGGCCA GGCTGGTCTC CAACTCCTAA TCTCAGGTGA

TCTACCCACC TTGGCCTCCC AAATTGCTGG GATTACAGGC GTGAACCACT GCTCCCTTCC

CTGTCCTTct gattttgtag gtaaccacgt gcggaccgag cggccgcagg aacccctagt
    ↑←end bGH-polyA                                  ↑←start AAV2 ITR gatggagttg gccactccct ctctgcgcgc tcgctcgctc actgaggccg ggcgaccaaa ggtcgcccga cgcccgggct tgccggggc ggcctcagtg agcgagcgag cgcgcagctg cctgcagg
    ↑←end AAV2 ITR
```

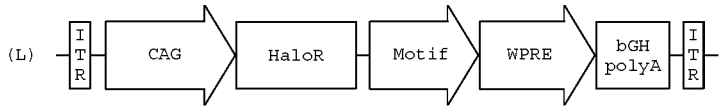

SEQ ID NO: 41 (same as above without the GFP)
5'-ITR-CAG-HaloR-(Kv2.1Motif)-WPRE-bGHpolyA-ITR-3'

←start AAV2 ITR
*cctgcaggca gctgcgcgct +cgctcgctca ctgaggccgc ccgggcaaag cccgggcgtc*

*gggcgacctt tggtcgcccg gcctcagtga gcgagcgagc gcgcagagag ggagtggcca*

*actccatcac taggggttcc t*gcggccgca cgcgtgatat cCTAGTTATT AATAGTAATC
        end AAV2 ITR→↑                  ↑←start CAG pomoter/enhancer <u>AATTACGGGG TCATTAGTTC ATAGCCCATA TATGGAGTTC CGCGTTACAT AACTTACGGT</u>

<u>AAATGGCCCG CCTGGCTGAC CGCCCAACGA CCCCCGCCCA TTGACGTCAA TAATGACGTA</u>

<u>TGTTCCCATA GTAACGCCAA TAGGGACTTT CCATTGACGT CAATGGGTGG AGTATTTACG</u>

<u>GTAAACTGCC CACTTGGCAG TACATCAAGT GTATCATATG CCAAGTACGC CCCCTATTGA</u>

<u>CGTCAATGAC GGTAAATGGC CCGCCTGGCA TTATGCCCAG TACATGACCT TATGGGACTT</u>

<u>TCCTACTTGG CAGTACATCT ACGTATTAGT CATCGCTATT ACCATGCATG GTCGAGGTGA</u>

<u>GCCCCACGTT CTGCTTCACT CTCCCCATCT CCCCCCCCTC CCCACCCCCA ATTTTGTATT</u>

<u>TATTTATTTT TTAATTATTT TGTGCAGCGA TGGGGGCGGG GGGGGGGGGG GGGCGCGCGC</u>

<u>CAGGCGGGGC GGGGCGGGGC GAGGGGCGGG GCGGGGCGAG GCGGAGAGGT GCGGCGGCAG</u>

<u>CCAATCAGAG CGGCGCGCTC CGAAAGTTTC CTTTTATGGC GAGGCGGCGG CGGCGGCGGC</u>

<u>CCTATAAAAA GCGAAGCGCG CGGCGGGCGG GAGTCGCTGC GACGCTGCCT TCGCCCCGTG</u>

<u>CCCCGCTCCG CCGCCGCCTC GCGCCGCCCG CCCCGGCTCT GACTGACCGC GTTACTCCCA</u>

<u>CAGGTGAGCG GGCGGGACGG CCCTTCTCCT CCGGGCTGTA ATTAGCGCTT GGTTTAATGA</u>

<u>CGGCTTGTTT CTTTTCTGTG GCTGCGTGAA AGCCTTGAGG GGCTCCGGGA GGGCCCTTTG</u>

<u>TGCGGGGGGA GCGGCTCGGG GCTGTCCGCG GGGGGACGGC TGCCTTCGGG GGGGACGGGG</u> end CAG pomoter/enhancer→↓
<u>CAGGGCGGGG TTCGGCTTCT GGCGTGTGAC CGGCGGCTCT AGCAGCCTCT GCTA</u>accatg ttcatgcctt cttcttttc ctacagctcc tgggcaacgt gctggttatt gtgctgtctc ↓←start HaloR
atcattttgg caaagaatta agcttgagct cgcgatccgc agcc *ATG ACT GAG ACA*

*TTG CCA CCG GTA ACG GAA TCG GCT GTT GCG CTA CAG GCG GAG GTG ACC*

*CAG AGG GAG CTG TTC GAG TTC GTT CTC AAC GAC CCC CTC CTC GCC AGT*

*TCG CTG TAT ATT AAT ATC GCA CTG GCA GGG CTG TCG ATA CTG CTT TTC*

*GTG TTC ATG ACG CGC GGA CTC GAC GAC CCA CGG GCG AAA CTC ATC GCC*

*GTT TCG ACG ATT TTG GTG CCG GTG GTC TCT ATC GCG AGC TAC ACC GGC*

*CTT GCA TCG GGG CTC ACC ATC AGC GTC CTC GAG ATG CCA GCC GGC CAC*

*TTC GCC GAG GGG TCC TCG GTG ATG CTC GGC GGC GAA GAG GTA GAC GGC*

*GTC GTG ACG ATG TGG GGC GCG TAT CTG ACG TGG GCC CTT CGC ACA CCG*

*ATG ATA CTG CTG GCG CTT GGG CTG CTT GCT GGC TCT AAC GCC ACG AAG*

*CTC TTT ACC GCC ATC ACC TTC GAC ATC GCG ATG TGT GTC ACC GGC CTC*

*GCA GCC GCG CTG ACG ACC TCT TCG CAC CTG ATG CGG TGG TTC TGG TAC*

*GCC ATC AGT TGT GCG TGT TTC CTC GTC GTC CTC TAC ATC CTG CTC GTC*

*GAG TGG GCA CAG GAC GCC AAG GCT GCC GGT ACT GCG GAT ATG TTC AAT*

*ACG CTG AAG CTG CTG ACC GTT GTC ATG TGG CTC GGC TAC CCC ATC GTG*

*TGG GCA CTC GGC GTT GAG GGC ATC GCC GTT CTT CCG GTC GGA GTC ACG*

*TCG TGG GGA TAC AGC TTC CTC GAC ATC GTC GCG AAG TAC ATC TTC GCG*

*TTC CTG CTC AAC TAC CTC ACG TCG AAC GAG AGC GTC GTC TCC GGC*

*TCG ATA CTC GAC GTG CCG TCC GCG TCG GGC ACT CCC GCT GAC GAC*
                  end HaloR→↑ gaattcggag gcggaggtgg agctagc <u>CAG TCT CAG CCC ATC CTG AAC ACT AAG</u>
           ↑←Start Kv2.1 Motif <u>GAG ATG GCC CCT CAG AGT AAA CCC CCT GAG GAA CTG GAA ATG AGC TCC</u>

<u>ATG CCA TCT CCA GTG GCT CCT CTG CCA GCT AGG ACC GAG GGC GTG ATT</u>

<u>GAC ATG AGA AGC ATG TCT AGT ATC GAT AGC TTC ATT TCC TGC GCC ACC</u>

<u>GAC TTC CCC GAA GCT ACA AGG TTT</u> taactcgagt ctagacgtgg tacc<u>GATAAT</u>
     end Kv2.1 Motif→↑            ↑←Start WPRE <u>CAACCTCTGG ATTACAAAAT TGTGAAAGA TTGACTGGTA TTCTTAACTA TGTTGCTCCT</u>

<u>TTTACGCTAT GTGGATACGC TGCTTTAATG CCTTTGTATC ATGCTATTGC TTCCCGTATG</u>

<u>GCTTTCATTT TCTCCTCCTT GTATAAATCC TGGTTGCTGT CTCTTTATGA GGAGTTGTGG</u>

<u>CCCGTTGTCA GGCAACGTGG CGTGGTGTGC ACTGTGTTTG CTGACGCAAC CCCCACTGGT</u>

<u>TGGGGCATTG CCACCACCTG TCAGCTCCTT TCCGGGACTT TCGCTTTCCC CCTCCCTATT</u>

<u>GCCACGGCGG AACTCATCGC CGCCTGCCTT GCCCGCTGCT GGACAGGGGC TCGGCTGTTG</u>

<u>GGCACTGACA ATTCCGTGGT GTTGTCGGGG AAGCTGACGT CCTTTCCATG GCTGCTCGCC</u>

<u>TGTGTTGCCA CCTGGATTCT GCGCGGGACG TCCTTCTGCT ACGTCCCTTC GGCCCTCAAT</u>

<u>CCAGCGGACC TTCCTTCCCG CGGCCTGCTG CCGGCTCTGC GGCCTCTTCC GCGTCTTCGC</u>

<u>CTTCGCCCTC AGACGAGTCG GATCTCCCTT TGGGCCGCCT CCCCGCCTGA T</u>gcggggatc
                      end WPRE→↑ ctctagagtc gagagatctA *CGGGTGGCAT CCCTGTGACC CCTCCCCAGT GCCTCTCCTG*
     ↑←start bGH-polyA

*GCCCTGGAAG TTGCCACTCC AGTGCCCACC AGCCTTGTCC TAATAAAATT AAGTTGCATC*

*ATTTTGTCTG ACTAGGTGTC CTTCTATAAT ATTATGGGGT GGAGGGGGGT GGTATGGAGC*

*AAGGGGCAAG TTGGGAAGAC AACCTGTAGG GCCTGCGGGG TCTATTGGGA ACCAAGCTGG*

*AGTGCAGTGG CACAATCTTG GCTCACTGCA ATCTCCGCCT CCTGGGTTCA AGCGATTCTC*

*CTGCCTCAGC CTCCCGAGTT GTTGGGATTC CAGGCATGCA TGACCAGGCT CAGCTAATTT*

*TTGTTTTTTT GGTAGAGACG GGGTTTCACC ATATTGGCCA GGCTGGTCTC CAACTCCTAA*

*TCTCAGGTGA TCTACCCACC TTGGCCTCCC AAATTGCTGG GATTACAGGC GTGAACCACT*

*GCTCCCTTCC CTGTCCTT*ct gattttgtag gtaaccacgt gcggaccgag
  end bGH-polyA→↑ cggccgcagg aaccctagt gatggagttg gccactccct ctctgcgcgc tcgctcgctc
   ↑←start AAV2 ITR -continued actgaggccg ggcgaccaaa ggtcgcccga cgcccgggct tgcccgggc ggcctcagtg agcgagcgag cgcgcagctg cctgcagg
                end AAV2 ITR→↑

(M) SEQ ID NO: 42
5′-ITR-CAG-HaloR-GFP-(Nav1.6 Motif)-WPRE-bGHpolyA-ITR-3′

←start AAV2 ITR
cctgcaggca gctgcgcgct cgctcgctca ctgaggccgc ccgggcaaag cccgggcgtc gggcgacctt tggtcgcccg gcctcagtga gcgagcgagc gcgcagagag ggagtggcca actccatcac taggggttcc tgcggccgca cgcgtgatat cCTAGTTATT AATAGTAATC
        end AAV2 ITR→↑                            ↑←start CAG pomoter/enhancer <u>AATTACGGGG TCATTAGTTC ATAGCCCATA TATGGAGTTC CGCGTTACAT AACTTACGGT</u>

<u>AAATGGCCCG CCTGGCTGAC CGCCCAACGA CCCCCGCCCA TTGACGTCAA TAATGACGTA</u>

<u>TGTTCCCATA GTAACGCCAA TAGGGACTTT CCATTGACGT CAATGGGTGG AGTATTTACG</u>

<u>GTAAACTGCC CACTTGGCAG TACATCAAGT GTATCATATG CCAAGTACGC CCCCTATTGA</u>

<u>CGTCAATGAC GGTAAATGGC CCGCCTGGCA TTATGCCCAG TACATGACCT TATGGGACTT</u>

<u>TCCTACTTGG CAGTACATCT ACGTATTAGT CATCGCTATT ACCATGCATG GTCGAGGTGA</u>

<u>GCCCCACGTT CTGCTTCACT CTCCCCATCT CCCCCCCCTC CCCACCCCCA ATTTTGTATT</u>

<u>TATTTATTTT TTAATTATTT TGTGCAGCGA TGGGGGCGGG GGGGGGGGG GGGCGCGCGC</u>

<u>CAGGCGGGGC GGGGCGGGGC GAGGGGCGGG GCGGGGCGAG GCGGAGAGGT GCGGCGGCAG</u>

<u>CCAATCAGAG CGGCGCGCTC CGAAAGTTTC CTTTTATGGC GAGGCGGCGG CGGCGGCGGC</u>

<u>CCTATAAAAA GCGAAGCGCG CGGCGGGCGG GAGTCGCTGC GACGCTGCCT TCGCCCCGTG</u>

<u>CCCCGCTCCG CCGCCGCCTC GCGCCGCCCG CCCCGGCTCT GACTGACCGC GTTACTCCCA</u>

<u>CAGGTGAGCG GCGGGACGG CCCTTCTCCT CCGGGCTGTA ATTAGCGCTT GGTTTAATGA</u>

<u>CGGCTTGTTT CTTTTCTGTG GCTGCGTGAA AGCCTTGAGG GGCTCCGGGA GGGCCCTTTG</u>

<u>TGCGGGGGGA GCGGCTCGGG GCTGTCCGCG GGGGACGGC TGCCTTCGGG GGGGACGGGG</u> end CAG pomoter/enhancer→↓
<u>CAGGGCGGGG TTCGGCTTCT GGCGTGTGAC CGGCGGCTCT AGCAGCCTCT GCTAaccatg</u> ttcatgcctt cttctttttc ctacagctcc tgggcaacgt gctggttatt gtgctgtctc

↓←start HaloR
atcattttgg caaagaatta agcttgagct cgcgatccgc agcc *ATG ACT GAG ACA*

*TTG CCA CCG GTA ACG GAA TCG GCT GTT GCG CTA CAG GCG GAG GTG ACC*

*CAG AGG GAG CTG TTC GAG TTC GTT CTC AAC GAC CCC CTC CTC GCC AGT*

*TCG CTG TAT ATT AAT ATC GCA CTG GCA GGG CTG TCG ATA CTG CTT TTC*

*GTG TTC ATG ACG CGC GGA CTC GAC GAC CCA CGG GCG AAA CTC ATC GCC*

*GTT TCG ACG ATT TTG GTG CCG GTG GTC TCT ATC GCG AGC TAC ACC GGC*

*CTT GCA TCG GGG CTC ACC ATC AGC GTC CTC GAG ATG CCA GCC GGC CAC*

*TTC GCC GAG GGG TCC TCG GTG ATG CTC GGC GGC GAA GAG GTA GAC GGC*

*GTC GTG ACG ATG TGG GGC CGC TAT CTG ACG TGG GCC CTT TCG ACA CCG*

*ATG ATA CTG CTG GCG CTT GGG CTG CTT GCT GGC TCT AAC GCC ACG AAG*

*CTC TTT ACC GCC ATC ACC TTC GAC ATC GCG ATG TGT GTC ACC GGC CTC*

*GCA GCC GCG CTG ACG ACC TCT TCG CAC CTG ATG CGG TGG TTC TGG TAC*

*GCC ATC AGT TGT GCG TGT TTC CTC GTC GTC CTC TAC ATC CTG CTC GTC*

*GAG TGG GCA CAG GAC GCC AAG GCT GCC GGT ACT GCG GAT ATG TTC AAT*

*ACG CTG AAG CTG CTG ACC GTT GTC ATG TGG CTC GGC TAC CCC ATC GTG*

*TGG GCA CTC GGC GTT GAG GGC ATC GCC GTT CTT CCG GTC GGA GTC ACG*

*TCG TGG GGA TAC AGC TTC CTC GAC ATC GTC GCG AAG TAC ATC TTC GCG*

*TTC CTG CTC AAC TAC CTC ACG TCG AAC GAG AGC GTC GTC TCC GGC*

*TCG ATA CTC GAC GTG CCG TCC GCG TCG GGC ACT CCC GCT GAC GAC* end HaloR→↑ gaattcggag gcggaggtgg agctagc AAA GGA GAA GAA CTC TTC ACT GGA GTT
                                 ↑←start GFP

GGA GTT GTC CCA ATT CTT GTT GAA TTA GAT GGT GAT GTT AAC GGC CAC

AAG TTC TCT GTC AGT GGA GAG GGT GAA GGT GAT GCA ACA TAC GGA AAA

CTT ACC CTG AAG TTC ATC TGC ACT ACT GGC AAA CTG CCT GTT CCA TGG

CCA ACA CTA GTC ACT ACT CTG TGC TAT GGT GTT CAA TGC TTT TCA AGA

TAC CCG GAT CAT ATG AAA CGG CAT GAC TTT TTC AAG AGT GCC ATG CCC

GAA GGT TAT GTA CAG GAA AGG ACC ATC TTC TTC AAA GAT GAC GGC AAC

TAC AAG ACA CGT GCT GAA GTC AAG TTT GAA GGT GAT ACC CTT GTT AAT

AGA ATC GAG TTA AAA GGT ATT GAC TTC AAG GAA GAT GGC AAC ATT CTG

GGA CAC AAA TTG GAA TAC AAC TAT AAC TCA CAC AAT GTA TAC ATC ATG

GCA GAC AAA CAA AAG AAT GGA ATC AAA GTG AAC TTC AAG ACC CGC CAC

AAC ATT GAA GAT GGA AGC GTT CAA CTA GCA GAC CAT TAT CAA CAA AAT

ACT CCA ATT GGC GAT GGC CCT GTC CTT TTA CCA GAC AAC CAT TAC CTG

TCC ACA CAA TCT GCC CTT TCG AAA GAT CCC AAC GAA AAG AGA GAC CAC

ATG GTC CTT CTT GAG TTT GTA ACA GCT GCT GGG ATT ACA CAT GGC ATG end GFP→↓
GAT GAA CTG TAC AAC <u>ACC GTG AGG GTG CCC ATC GCC GTG GGC GAG AGC</u>
                         ↑←Start Nav1.6 Motif <u>GAC TTC GAG AAC CTG AAC ACC GAG GAC GTG AGC AGC GAG AGC GAC CCC</u>
                                            end Nav1.6 Motif→↑ taactcgagt ctagacgtgg tacc<u>GATAAT CAACCTCTGG ATTACAAAAT TGTGAAAGA</u>
                                ↑←start WPRE <u>TTGACTGGTA TTCTTAACTA TGTTGCTCCT TTTACGCTAT GTGGATACGC TGCTTTAATG</u>

<u>CCTTTGTATC ATGCTATTGC TTCCCGTATG GCTTTCATTT TCTCCTCCTT GTATAAATCC</u>

<u>TGGTTGCTGT CTCTTTATGA GGAGTTGTGG CCCGTTGTCA GGCAACGTGG CGTGGTGTGC</u>

<u>ACTGTGTTTG CTGACGCAAC CCCCACTGGT TGGGGCATTG CCACCACCTG TCAGCTCCTT</u>

<u>TCCGGGACTT TCGCTTTCCC CCTCCCTATT GCCACGGCGG AACTCATCGC CGCCTGCCTT</u>

<u>GCCCGCTGCT GGACAGGGGC TCGGCTGTTG GCACTGACA ATTCCGTGGT GTTGTCGGGG</u>

<u>AAGCTGACGT CCTTTCCATG GCTGCTCGCC TGTGTTGCCA CCTGGATTCT GCGCGGGACG</u>

<u>TCCTTCTGCT ACGTCCCTTC GGCCCTCAAT CCAGCGGACC TTCCTTCCCG CGGCCTGCTG</u>

```
CCGGCTCTGC GGCCTCTTCC GCGTCTTCGC CTTCGCCCTC AGACGAGTCG GATCTCCCTT

TGGGCCGCCT CCCCGCCTGA Tgcggggatc ctctagagtc gagagatctA CGGGTGGCAT
            end WPRE→↑                              ↑←start bGH-polyA

CCCTGTGACC CCTCCCCAGT GCCTCTCCTG GCCCTGGAAG TTGCCACTCC AGTGCCCACC

AGCCTTGTCC TAATAAAATT AAGTTGCATC ATTTTGTCTG ACTAGGTGTC CTTCTATAAT

ATTATGGGGT GGAGGGGGGT GGTATGGAGC AAGGGGCAAG TTGGGAAGAC AACCTGTAGG

GCCTGCGGGG TCTATTGGGA ACCAAGCTGG AGTGCAGTGG CACAATCTTG GCTCACTGCA

ATCTCCGCCT CCTGGGTTCA AGCGATTCTC CTGCCTCAGC CTCCCGAGTT GTTGGGATTC

CAGGCATGCA TGACCAGGCT CAGCTAATTT TTGTTTTTTT GGTAGAGACG GGGTTTCACC

ATATTGGCCA GGCTGGTCTC CAACTCCTAA TCTCAGGTGA TCTACCCACC TTGGCCTCCC

AAATTGCTGG GATTACAGGC GTGAACCACT GCTCCCTTCC CTGTCCTTct gattttgtag
                                             end bGH-polyA→↑ gtaaccacgt gcggaccgag cggccgcagg aaccctagt gatggagttg gccactccct
                              ↑←start AAV2 ITR ctctgcgcgc tcgctcgctc actgaggccg gcgaccaaa ggtcgcccga cgcccgggct ttgcccgggc ggccgcagtg agcgagcgag cgcgcagctg cctgcagg
                                      end AAV2 ITR→↑
```

(N) SEQ ID NO: 43 (same as above without GFP)
5'-ITR–CAG–HaloR–(Nav1.6 Motif)–WPRE–bGHpolyA–ITR-3'

```
←start AAV2 ITR
cctgcaggca gctgcgcgct cgctcgctca ctgaggccgc ccgggcaaag cccgggcgtc gggcgacctt tggtcgcccg gcctcagtga gcgagcgagc gcgcagagag ggagtggcca actccatcac tagggggttcc tgcggccgca cgcgtgatat cCTAGTTATT AATAGTAATC
            end AAV2 ITR→↑                  ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GGCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGGA GCGGCTCGGG GCTGTCCGCG GGGGACGGC TGCCTTCGGG GGGGACGGGG
                                        end CAG pomoter/enhancer→↓
CAGGGCGGGG TTCGGCTTCT GGCGTGTGAC CGGCGGCTCT AGCAGCCTCT GCTAaccatg
```

-continued ttcatgcctt cttcttttc ctacagctcc tgggcaacgt gctggttatt gtgctgtctc

↓←start HaloR
atcattttgg caaagaatta agcttgagct cgcgatccgc agcc *ATG ACT GAG ACA*

*TTG CCA CCG GTA ACG GAA TCG GCT GTT GCG CTA CAG GCG GAG GTG ACC*

*CAG AGG GAG CTG TTC GAG TTC GTT CTC AAC GAC CCC CTC CTC GCC AGT*

*TCG CTG TAT ATT AAT ATC GCA CTG GCA GGG CTG TCG ATA CTG CTT TTC*

*GTG TTC ATG ACG CGC GGA CTC GAC GAC CCA CGG GCG AAA CTC ATC GCC*

*GTT TCG ACG ATT TTG GTG CCG GTG GTC TCT ATC GCG AGC TAC ACC GGC*

*CTT GCA TCG GGG CTC ACC ATC AGC GTC CTC GAG ATG CCA GCC GGC CAC*

*TTC GCC GAG GGG TCC TCG GTG ATG CTC GGC GGC GAA GAG GTA GAC GGC*

*GTC GTG ACG ATG TGG GGC CGC TAT CTG ACG TGG GCC CTT TCG ACA CCG*

*ATG ATA CTG CTG GCG CTT GGG CTG CTT GCT GGC TCT AAC GCC ACG AAG*

*CTC TTT ACC GCC ATC ACC TTC GAC ATC GCG ATG TGT GTC ACC GGC CTC*

*GCA GCC GCG CTG ACG ACC TCT TCG CAC CTG ATG CGG TGG TTC TGG TAC*

*GCC ATC AGT TGT GCG TGT TTC CTC GTC GTC CTC TAC ATC CTG CTC GTC*

*GAG TGG GCA CAG GAC GCC AAG GCT GCC GGT ACT GCG GAT ATG TTC AAT*

*ACG CTG AAG CTG CTG ACC GTT GTC ATG TGG CTC GGC TAC CCC ATC GTG*

*TGG GCA CTC GGC GTT GAG GGC ATC GCC GTT CTT CCG GTC GGA GTC ACG*

*TCG TGG GGA TAC AGC TTC CTC GAC ATC GTC GCG AAG TAC ATC TTC GCG*

*TTC CTG CTG CTC AAC TAC CTC ACG TCG AAC GAG AGC GTC GTC TCC GGC*

*TCG ATA CTC GAC GTG CCG TCC GCG TCG GGC ACT CCC GCT GAC GAC*
                                                                 end HaloR→↑
gaattcggag gcggaggtgg agctagc <u>ACC GTG AGG GTG CCC ATC GCC GTG GGC</u>
                           ↑←Start Nav1.6 Motif <u>GAG AGC GAC TTC GAG AAC CTG AAC ACC GAG GAC GTG AGC AGC GAG AGC</u>

<u>GAC CCC</u> taactcgagt ctagacgtgg tacc<u>GATAAT CAACCTCTGG ATTACAAAAT</u>
     ↑←end Nav1.6 Motif              ↑←Start WPRE <u>TTGTGAAAGA TTGACTGGTA TTCTTAACTA TGTTGCTCCT TTTACGCTAT GTGGATACGC</u>

<u>TGCTTTAATG CCTTTGTATC ATGCTATTGC TTCCCGTATG GCTTTCATTT TCTCCTCCTT</u>

<u>GTATAAATCC TGGTTGCTGT CTCTTTATGA GGAGTTGTGG CCCGTTGTCA GGCAACGTGG</u>

<u>CGTGGTGTGC ACTGTGTTTG CTGACGCAAC CCCCACTGGT TGGGGCATTG CCACCACCTG</u>

<u>TCAGCTCCTT TCCGGGACTT TCGCTTTCCC CCTCCCTATT GCCACGGCGG AACTCATCGC</u>

<u>CGCCTGCCTT GCCCGCTGCT GGACAGGGGC TCGGCTGTTG GGCACTGACA ATTCCGTGGT</u>

<u>GTTGTCGGGG AAGCTGACGT CCTTTCCATG GCTGCTCGCC TGTGTTGCCA CCTGGATTCT</u>

<u>GCGCGGGACG TCCTTCTGCT ACGTCCCTTC GGCCCTCAAT CCAGCGGACC TTCCTTCCCG</u>

<u>CGGCCTGCTG CCGGCTCTGC GGCCTCTTCC GCGTCTTCGC CTTCGCCCTC AGACGAGTCG</u>

<u>GATCTCCCTT TGGGCCGCCT CCCCGCCTGA T</u>gcggggatc tctagagtc
                                    end WPRE→↑ gagagatct*A CGGGTGGCAT CCCTGTGACC CCTCCCCAGT GCCTCTCCTG GCCCTGGAAG*
          ↑←start bGH-polyA

*TTGCCACTCC AGTGCCCACC AGCCTTGTCC TAATAAAATT AAGTTGCATC ATTTTGTCTG*

*ACTAGGTGTC CTTCTATAAT ATTATGGGGT GGAGGGGGGT GGTATGGAGC AAGGGGCAAG*

```
TTGGGAAGAC AACCTGTAGG GCCTGCGGGG TCTATTGGGA ACCAAGCTGG AGTGCAGTGG

CACAATCTTG GCTCACTGCA ATCTCCGCCT CCTGGGTTCA AGCGATTCTC CTGCCTCAGC

CTCCCGAGTT GTTGGGATTC CAGGCATGCA TGACCAGGCT CAGCTAATTT TTGTTTTTTT

GGTAGAGACG GGGTTTCACC ATATTGGCCA GGCTGGTCTC CAACTCCTAA TCTCAGGTGA

TCTACCCACC TTGGCCTCCC AAATTGCTGG GATTACAGGC GTGAACCACT GCTCCCTTCC
                 ↓←end bGH-polyA
CTGTCCTTCt gattttgtag gtaaccacgt gcggaccgag cggccgcagg aacccctagt
                                                      ↑←start AAV2 ITR gatggagttg gccactccct ctctgcgcgc tcgctcgctc actgaggccg ggcgaccaaa ggtcgcccga cgcccgggct tgcccgggc ggcctcagtg agcgagcgag cgcgcagctg cctgcagg
        ↑←end AAV2 ITR
```

(O) SEQ ID NO: 44
5'-ITR-CAG-HaloR-GFP-(NLG-1 Motif)-WPRE-bGHpolyA-ITR-3'

```
←start AAV2 ITR
cctgcaggca gctgcgcgct cgctcgctca ctgaggccgc ccgggcaaag cccgggcgtc gggcgacctt tggtcgcccg gcctcagtga gcgagcgagc gcgcagagag ggagtggcca actccatcac tagggggttcc tgcggccgca cgcgtgatat cCTAGTTATT AATAGTAATC
            end AAV2 ITR→↑                          ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGG GGGCGCGCGC

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GGCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGGA GCGGCTCGGG GCTGTCCGCG GGGGGACGGC TGCCTTCGGG GGGGACGGGG
                                end CAG pomoter/enhancer→↓
CAGGGCGGGG TTCGGCTTCT GGCGTGTGAC CGGCGGCTCT AGCAGCCTCT GCTAaccatg ttcatgcctt cttcttttc ctacagctcc tgggcaacgt gctggttatt gtgctgtctc
                                                        ↓←start HaloR
atcattttgg caaagaatta agcttgagct cgcgatccgc agcc ATG ACT GAG ACA

TTG CCA CCG GTA ACG GAA TCG GCT GTT GCG CTA CAG CGC GAG GTG ACC

CAG AGG GAG CTG TTC GAG TTC GTT CTC AAC GAC CCC CTC CTC GCC AGT
```

```
TCG CTG TAT ATT AAT ATC GCA CTG GCA GGG CTG TCG ATA CTG CTT TTC

GTG TTC ATG ACG CGC GGA CTC GAC GAC CCA CGG GCG AAA CTC ATC GCC

GTT TCG ACG ATT TTG GTG CCG GTG GTC TCT ATC GCG AGC TAC ACC GGC

CTT GCA TCG GGG CTC ACC ATC AGC GTC CTC GAG ATG CCA GCC GGC CAC

TTC GCC GAG GGG TCC TCG GTG ATG CTC GGC GGC GAA GAG GTA GAC GGC

GTC GTG ACG ATG TGG GGC CGC TAT CTG ACG TGG GCC CTT TCG ACA CCG

ATG ATA CTG CTG GCG CTT GGG CTG CTT GCT GGC TCT AAC GCC ACG AAG

CTC TTT ACC GCC ATC ACC TTC GAC ATC GCG ATG TGT GTC ACC GGC CTC

GCA GCC GCG CTG ACG ACC TCT TCG CAC CTG ATG CGG TGG TTC TGG TAC

GCC ATC AGT TGT GCG TGT TTC CTC GTC GTC CTC TAC ATC TGC TGC GTC

GAG TGG GCA CAG GAC GCC AAG GCT GCC GGT ACT GCG GAT ATG TTC AAT

ACG CTG AAG CTG CTG ACC GTT GTC ATG TGG CTC GGC TAC CCC ATC GTG

TGG GCA CTC GGC GTT GAG GGC ATC GCC GTT CTT CCG GTC GGA GTC ACG

TCG TGG GGA TAC AGC TTC CTC GAC ATC GTC GCG AAG TAC ATC TTC GCG

TTC CTG CTC AAC TAC CTC ACG TCG AAC GAG AGC GTC GTC TCC GGC

TCG ATA CTC GAC GTG CCG TCC GCG TCG GGC ACT CCC GCT GAC GAC
                                              end HaloR→↑
gaattcggag gcggaggtgg agctagc AAA GGA GAA GAA CTC TTC ACT GGA GTT
                              ↑←start GFP

GGA GTT GTC CCA ATT CTT GTT GAA TTA GAT GGT GAT GTT AAC GGC CAC

AAG TTC TCT GTC AGT GGA GAG GGT GAA GGT GAT GCA ACA TAC GGA AAA

CTT ACC CTG AAG TTC ATC TGC ACT ACT GGC AAA CTG CCT GTT CCA TGG

CCA ACA CTA GTC ACT ACT CTG TGC TAT GGT GTT CAA TGC TTT TCA AGA

TAC CCG GAT CAT ATG AAA CGG CAT GAC TTT TTC AAG AGT GCC ATG CCC

GAA GGT TAT GTA CAG GAA AGG ACC ATC TTC TTC AAA GAT GAC GGC AAC

TAC AAG ACA CGT GCT GAA GTC AAG TTT GAA GGT GAT ACC CTT GTT AAT

AGA ATC GAG TTA AAA GGT ATT GAC TTC AAG GAA GAT GGC AAC ATT CTG

GGA CAC AAA TTG GAA TAC AAC TAT AAC TCA CAC AAT GTA TAC ATC ATG

GCA GAC AAA CAA AAG AAT GGA ATC AAA GTG AAC TTC AAG ACC CGC CAC

AAC ATT GAA GAT GGA AGC GTT CAA CTA GCA GAC CAT TAT CAA CAA AAT

ACT CCA ATT GGC GAT GGC CCT GTC CTT TTA CCA GAC AAC CAT TAC CTG

TCC ACA CAA TCT GCC CTT TCG AAA GAT CCC AAC GAA AAG AGA GAC CAC

ATG GTC CTT CTT GAG TTT GTA ACA GCT GCT GGG ATT ACA CAT GGC ATG end GFP→↓
GAT GAA CTG TAC AAC GTG GTT CTT CGG ACC GCC TGT CCC CCA GAT TAC
                      ↑←Start NLG-1 Motif

ACA CTA GCT ATG AGG AGG TCA CCT GAT GAT GTT CCC TTA ATG ACA CCC

AAC ACC ATT ACA ATG taactcgagt ctagacgtgg tacc GATAAT CAACCTCTGG
end NLG-1 Motif→↑                                ↑←start WPRE
```

ATTACAAAAT TTGTGAAAGA TTGACTGGTA TTCTTAACTA TGTTGCTCCT TTTACGCTAT

GTGGATACGC TGCTTTAATG CCTTTGTATC ATGCTATTGC TTCCCGTATG GCTTTCATTT

TCTCCTCCTT GTATAAATCC TGGTTGCTGT CTCTTTATGA GGAGTTGTGG CCCGTTGTCA

GGCAACGTGG CGTGGTGTGC ACTGTGTTTG CTGACGCAAC CCCCACTGGT TGGGGCATTG

CCACCACCTG TCAGCTCCTT TCCGGGACTT TCGCTTTCCC CCTCCCTATT GCCACGGCGG

AACTCATCGC CGCCTGCCTT GCCCGCTGCT GGACAGGGGC TCGGCTGTTG GGCACTGACA

ATTCCGTGGT GTTGTCGGGG AAGCTGACGT CCTTTCCATG GCTGCTCGCC TGTGTTGCCA

CCTGGATTCT GCGCGGGACG TCCTTCTGCT ACGTCCCTTC GGCCCTCAAT CCAGCGGACC

TTCCTTCCCG CGGCCTGCTG CCGGCTCTGC GGCCTCTTCC GCGTCTTCGC CTTCGCCCTC

AGACGAGTCG GATCTCCCTT TGGGCCGCCT CCCCGCCTGA Tgcggggatc ctctagagtc
                                           end WPRE→↑ gagagatctA *CGGGTGGCAT CCCTGTGACC CCTCCCCAGT GCCTCTCCTG GCCCTGGAAG*
      ↑←start bGH-polyA

*TTGCCACTCC AGTGCCCACC AGCCTTGTCC TAATAAAATT AAGTTGCATC ATTTTGTCTG*

*ACTAGGTGTC CTTCTATAAT ATTATGGGGT GGAGGGGGGT GGTATGGAGC AAGGGGCAAG*

*TTGGGAAGAC AACCTGTAGG GCCTGCGGGG TCTATTGGGA ACCAAGCTGG AGTGCAGTGG*

*CACAATCTTG GCTCACTGCA ATCTCCGCCT CCTGGGTTCA AGCGATTCTC CTGCCTCAGC*

*CTCCCGAGTT GTTGGGATTC CAGGCATGCA TGACCAGGCT CAGCTAATTT TTGTTTTTTT*

*GGTAGAGACG GGGTTTCACC ATATTGGCCA GGCTGGTCTC CAACTCCTAA TCTCAGGTGA*

*TCTACCCACC TTGGCCTCCC AAATTGCTGG GATTACAGGC GTGAACCACT GCTCCCTTCC*

↓←end bGH-polyA
*CTGTCCTT*ct gattttgtag gtaaccacgt gcggaccgag *cggccgc*agg aacccctagt
                                               ↑←start AAV2 ITR gatggagttg gccactccct ctctgcgcgc tcgctcgctc actgaggccg ggcgaccaaa ggtcgcccga cgcccgggct ttgcccgggc ggcctcagtg agcgagcgag cgcgcagctg cctgcagg
       ↑←end AAV2 ITR

P. SEQ ID NO: 45 (same as above but without GFP)
5'-ITR—CAG—HaloR—(NLG-1 Motif)—WPRE—bGHpolyA—ITR-3'

←start AAV2 ITR
cctgcaggca gctgcgcgct cgctcgctca ctgaggccgc ccgggcaaag cccgggcgtc gggcgacctt tggtcgcccg gcctcagtga gcgagcgagc gcgcagagag ggagtggcca actccatcac taggggttcc tgcggccgca cgcgtgatat cCTAGTTATT AATAGTAATC
           end AAV2 ITR→↑                    ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

```
CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GGCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGGA GCGGCTCGGG GCTGTCCGCG GGGGACGGC TGCCTTCGGG GGGGACGGGG
``` end CAG pomoter/enhancer→↓

```
CAGGGCGGGG TTCGGCTTCT GGCGTGTGAC CGGCGGCTCT AGCAGCCTCT GCTAaccatg ttcatgcctt cttcttttc ctacagctcc tgggcaacgt gctggttatt gtgctgtctc
```
                                                             ↓←start HaloR
```
atcattttgg caaagaatta agcttgagct cgcgatccgc agcc ATG ACT GAG ACA

TTG CCA CCG GTA ACG GAA TCG GCT GTT GCG CTA CAG GCG GAG GTG ACC

CAG AGG GAG CTG TTC GAG TTC GTT CTC AAC GAC CCC CTC CTC GCC AGT

TCG CTG TAT ATT AAT ATC GCA CTG GCA GGG CTG TCG ATA CTG CTT TTC

GTG TTC ATG ACG CGC GGA CTC GAC GAC CCA CGG GCG AAA CTC ATC GCC

GTT TCG ACG ATT TTG GTG CCG GTG GTC TCT ATC GCG AGC TAC ACC GGC

CTT GCA TCG GGG CTC ACC ATC AGC GTC CTC GAG ATG CCA GCC GGC CAC

TTC GCC GAG GGG TCC TCG GTG ATG CTC GGC GGC GAA GAG GTA GAC GGC

GTC GTG ACG ATG TGG GGC CGC TAT CTG ACG TGG GCC CTT TCG ACA CCG

ATG ATA CTG CTG GCG CTT GGG CTG CTT GCT GGC TCT AAC GCC ACG AAG

CTC TTT ACC GCC ATC ACC TTC GAC ATC GCG ATG TGT GTC ACC GGC CTC

GCA GCC GCG CTG ACG ACC TCT TCG CAC CTG ATG CGG TGG TTC TGG TAC

GCC ATC AGT TGT GCG TGT TTC CTC GTC GTC CTC TAC ATC CTG CTC GTC

GAG TGG GCA CAG GAC GCC AAG GCT GCC GGT ACT GCG GAT ATG TTC AAT

ACG CTG AAG CTG CTG ACC GTT GTC ATG TGG CTC GGC TAC CCC ATC GTG

TGG GCA CTC GGC GTT GAG GGC ATC GCC GTT CTT CCG GTC GGA GTC ACG

TCG TGG GGA TAC AGC TTC CTC GAC ATC GTC GCG AAG TAC ATC TTC GCG

TTC CTG CTC CTC AAC TAC CTC ACG TCG AAC GAG AGC GTC GTC TCC GGC

TCG ATA CTC GAC GTG CCG TCC GCG TCG GGC ACT CCC GCT GAC GAC
```
                                                                                            end HaloR→↑
```
gaattcggag gcggaggtgg agctagc GTG GTT CTT CGG ACC GCC TGT CCC CCA
```
                       ↑←Start NLG-1 Motif
```
AAA AAG AGG CTC CTG AGC TTC AGG GAC GTG GAC TTC GAG GAG GAC AGC

GAT TAC ACA CTA GCT ATG AGG AGG TCA CCT GAT GAT GTT CCC TTA ATG

ACA CCC AAC ACC ATT ACA ATG taactcgagt ctagacgtgg taccGATAAT
```
        end NLG-1 Motif→↑                                      ↑←Start WPRE

CAACCTCTGG ATTACAAAAT TTGTGAAAGA TTGACTGGTA TTCTTAACTA TGTTGCTCCT

TTTACGCTAT GTGGATACGC TGCTTTAATG CCTTTGTATC ATGCTATTGC TTCCCGTATG

GCTTTCATTT TCTCCTCCTT GTATAAATCC TGGTTGCTGT CTCTTTATGA GGAGTTGTGG

CCCGTTGTCA GGCAACGTGG CGTGGTGTGC ACTGTGTTTG CTGACGCAAC CCCCACTGGT

TGGGGCATTG CCACCACCTG TCAGCTCCTT TCCGGGACTT TCGCTTTCCC CCTCCCTATT

GCCACGGCGG AACTCATCGC CGCCTGCCTT GCCCGCTGCT GGACAGGGGC TCGGCTGTTG

GGCACTGACA ATTCCGTGGT GTTGTCGGGG AAGCTGACGT CCTTTCCATG GCTGCTCGCC

TGTGTTGCCA CCTGGATTCT GCGCGGGACG TCCTTCTGCT ACGTCCCTTC GGCCCTCAAT

CCAGCGGACC TTCCTTCCCG CGGCCTGCTG CCGGCTCTGC GGCCTCTTCC GCGTCTTCGC

CTTCGCCCTC AGACGAGTCG GATCTCCCTT TGGGCCGCCT CCCCGCCTGA Tgcggggatc
                                                                        end WPRE→↑ ctctagagtc gagagatctA *CGGGTGGCAT CCCTGTGACC CCTCCCCAGT GCCTCTCCTG*
              ↑←start bGH-poly

*GCCCTGGAAG TTGCCACTCC AGTGCCCACC AGCCTTGTCC TAATAAAATT AAGTTGCATC*

*ATTTTGTCTG ACTAGGTGTC CTTCTATAAT ATTATGGGGT GGAGGGGGGT GGTATGGAGC*

*AAGGGGCAAG TTGGGAAGAC AACCTGTAGG GCCTGCGGGG TCTATTGGGA ACCAAGCTGG*

*AGTGCAGTGG CACAATCTTG GCTCACTGCA ATCTCCGCCT CCTGGGTTCA AGCGATTCTC*

*CTGCCTCAGC CTCCCGAGTT GTTGGGATTC CAGGCATGCA TGACCAGGCT CAGCTAATTT*

*TTGTTTTTTT GGTAGAGACG GGGTTTCACC ATATTGGCCA GGCTGGTCTC CAACTCCTAA*

*TCTCAGGTGA TCTACCCACC TTGGCCTCCC AAATTGCTGG GATTACAGGC GTGAACCACT*

*GCTCCCTTCC CTGTCCTT*ct gattttgtag gtaaccacgt gcggaccgag *cggccgc*agg
    end bGH-polyA→↑                                            start AAV2 ITR→↑ gtaaccacgt gcggaccgag *cggccgc*agg aaccctagt gatggagttg gccactccct
                             ↑←start AAV2 ITR ctctgcgcgc tcgctcgctc actgaggccg gcgaccaaa ggtcgcccga cgcccgggct ttgcccgggc ggcctcagtg agcgagcgag cgcgcagctg cctgcagg
                                      end AAV2 ITR→↑

(Q) SEQ ID NO: 46
5'-ITR—CAG—HaloR—GFP—(MLPH Motif)—WPRE—bGHpolyA—ITR-3'

←start AAV2 ITR
*cctgcaggca gctgcgcgct cgctcgctca ctgaggccgc ccgggcaaag cccgggcgtc*

*gggcgacctt tggtcgcccg gcctcagtga gcgagcgagc gcgcagagag ggagtggcca*

*actccatcac taggggttcc t*gcggccgca cgcgtgatat cCTAGTTATT AATAGTAATC
           end AAV2 ITR→↑                          ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

-continued

CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC

CAGGCGGGGC GGGGCGGGGC GAGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGA GCGGCTCGGG GCTGTCCGCG GGGGACGGC TGCCTTCGGG GGGGACGGGG end CAG pomoter/enhancer→↓
CAGGGCGGGG TTCGGCTTCT GGCGTGTGAC CGGCGGCTCT AGCAGCCTCT GCTAaccatg ttcatgcctt cttcttttc ctacagctcc tgggcaacgt gctggttatt gtgctgtctc ↓←start HaloR
atcattttgg caaagaatta agcttgagct cgcgatccgc agcc *ATG ACT GAG ACA*

*TTG CCA CCG GTA ACG GAA TCG GCT GTT GCG CTA CAG GCG GAG GTG ACC*

*CAG AGG GAG CTG TTC GAG TTC GTT CTC AAC GAC CCC CTC CTC GCC AGT*

*TCG CTG TAT ATT AAT ATC GCA CTG GCA GGG CTG TCG ATA CTG CTT TTC*

*GTG TTC ATG ACG CGC GGA CTC GAC GAC CCA CGG GCG AAA CTC ATC GCC*

*GTT TCG ACG ATT TTG GTG CCG GTG GTC TCT ATC GCG AGC TAC ACC GGC*

*CTT GCA TCG GGG CTC ACC ATC AGC GTC CTC GAG ATG CCA GCC GGC CAC*

*TTC GCC GAG GGG TCC TCG GTG ATG CTC GGC GGC GAA GAG GTA GAC GGC*

*GTC GTG ACG ATG TGG GGC CGC TAT CTG ACG TGG GCC CTT TCG ACA CCG*

*ATG ATA CTG CTG GCG CTT GGG CTG CTT GCT GGC TCT AAC GCC ACG AAG*

*CTC TTT ACC GCC ATC ACC TTC GAC ATC GCG ATG TGT GTC ACC GGC CTC*

*GCA GCC GCG CTG ACG ACC TCT TCG CAC CTG ATG CGG TGG TTC TGG TAC*

*GCC ATC AGT TGT GCG TGT TTC CTC GTC GTC CTC TAC ATC CTG CTC GTC*

*GAG TGG GCA CAG GAC GCC AAG GCT GCC GGT ACT GCG GAT ATG TTC AAT*

*ACG CTG AAG CTG CTG ACC GTT GTC ATG TGG CTC GGC TAC CCC ATC GTG*

*TGG GCA CTC GGC GTT GAG GGC ATC GCC GTT CTT CCG GTC GGA GTC ACG*

*TCG TGG GGA TAC AGC TTC CTC GAC ATC GTC GCG AAG TAC ATC TTC GCG*

*TTC CTG CTC CTC AAC TAC CTC ACG TCG AAC GAG AGC GTC GTC TCC GGC*

*TCG ATA CTC GAC GTG CCG TCC GCG TCG GGC ACT CCC GCT GAC GAC*
                                                                        end HaloR→↑ gaattcggag gcggaggtgg agctagc AAA GGA GAA GAA CTC TTC ACT GGA GTT
                              ↑←start GFP

GGA GTT GTC CCA ATT CTT GTT GAA TTA GAT GGT GAT GTT AAC GGC CAC

AAG TTC TCT GTC AGT GGA GAG GGT GAA GGT GAT GCA ACA TAC GGA AAA

CTT ACC CTG AAG TTC ATC TGC ACT ACT GGC AAA CTG CCT GTT CCA TGG

CCA ACA CTA GTC ACT ACT CTG TGC TAT GGT GTT CAA TGC TTT TCA AGA

TAC CCG GAT CAT ATG AAA CGG CAT GAC TTT TTC AAG AGT GCC ATG CCC

GAA GGT TAT GTA CAG GAA AGG ACC ATC TTC TTC AAA GAT GAC GGC AAC

TAC AAG ACA CGT GCT GAA GTC AAG TTT GAA GGT GAT ACC CTT GTT AAT

AGA ATC GAG TTA AAA GGT ATT GAC TTC AAG GAA GAT GGC AAC ATT CTG

GGA CAC AAA TTG GAA TAC AAC TAT AAC TCA CAC AAT GTA TAC ATC ATG

GCA GAC AAA CAA AAG AAT GGA ATC AAA GTG AAC TTC AAG ACC CGC CAC

AAC ATT GAA GAT GGA AGC GTT CAA CTA GCA GAC CAT TAT CAA CAA AAT

ACT CCA ATT GGC GAT GGC CCT GTC CTT TTA CCA GAC AAC CAT TAC CTG

TCC ACA CAA TCT GCC CTT TCG AAA GAT CCC AAC GAA AAG AGA GAC CAC

ATG GTC CTT CTT GAG TTT GTA ACA GCT GCT GGG ATT ACA CAT GGC ATG end GFP→↓
GAT GAA CTG TAC AAC <u>AGG GAC CAG CCT CTG AAC AGC AAA AAG AAA AAG</u>
        ↑←Start MLPH Motif <u>AGG CTC CTG AGC TTC AGG GAC GTG GAC TTC GAG GAG GAC AGC GAC</u>
                                       end MLPH Motif→↑ taactcgagt ctagacgtgg tacc<u>GATAAT CAACCTCTGG ATTACAAAAT TGTGAAAGA</u>
                       ↑←start WPRE <u>TTGACTGGTA TTCTTAACTA TGTTGCTCCT TTTACGCTAT GTGGATACGC TGCTTTAATG</u>

<u>CCTTTGTATC ATGCTATTGC TTCCCGTATG GCTTTCATTT TCTCCTCCTT GTATAAATCC</u>

<u>TGGTTGCTGT CTCTTTATGA GGAGTTGTGG CCCGTTGTCA GGCAACGTGG CGTGGTGTGC</u>

<u>ACTGTGTTTG CTGACGCAAC CCCCACTGGT TGGGGCATTG CCACCACCTG TCAGCTCCTT</u>

<u>TCCGGGACTT TCGCTTTCCC CCTCCCTATT GCCACGGCGG AACTCATCGC CGCCTGCCTT</u>

<u>GCCCGCTGCT GGACAGGGGC TCGGCTGTTG GGCACTGACA ATTCCGTGGT GTTGTCGGGG</u>

<u>AAGCTGACGT CCTTTCCATG GCTGCTCGCC TGTGTTGCCA CCTGGATTCT GCGCGGGACG</u>

<u>TCCTTCTGCT ACGTCCCTTC GGCCCTCAAT CCAGCGGACC TTCCTTCCCG CGGCCTGCTG</u>

<u>CCGGCTCTGC GGCCTCTTCC GCGTCTTCGC CTTCGCCCTC AGACGAGTCG GATCCCCTT</u>

<u>TGGGCCGCCT CCCCGCCTGA T</u>gcggggatc ctctagagtc gagagatct*A CGGGTGGCAT*
            end WPRE→↑                              ↑←start bGH-polyA

*CCCTGTGACC CCTCCCCAGT GCCTCTCCTG GCCCTGGAAG TTGCCACTCC AGTGCCCACC*

*AGCCTTGTCC TAATAAAATT AAGTTGCATC ATTTTGTCTG ACTAGGTGTC CTTCTATAAT*

*ATTATGGGGT GGAGGGGGGT GGTATGGAGC AAGGGGCAAG TTGGGAAGAC AACCTGTAGG*

*GCCTGCGGGG TCTATTGGGA ACCAAGCTGG AGTGCAGTGG CACAATCTTG GCTCACTGCA*

*ATCTCCGCCT CCTGGGTTCA AGCGATTCTC CTGCCTCAGC CTCCCGAGTT GTTGGGATTC*

*CAGGCATGCA TGACCAGGCT CAGCTAATTT TTGTTTTTTT GGTAGAGACG GGGTTTCACC*

*ATATTGGCCA GGCTGGTCTC CAACTCCTAA TCTCAGGTGA TCTACCCACC TTGGCCTCCC*

*AAATTGCTGG GATTACAGGC GTGAACCACT GCTCCCTTCC CTGTCCTT*ct gattttgtag
                                       end bGH-polyA→↑ gtaaccacgt gcggaccgag *cggccgc*agg aaccccctagt gatggagttg gccactccct
                                        ↑←start AAV2 ITR

```
ctctgcgcgc tcgctcgctc actgaggccg ggcgaccaaa ggtcgcccga cgcccgggct ttgcccgggc ggcctcagtg agcgagcgag cgcgcagctg cctgcagg
                                            end AAV2 ITR→↑
```

(R) SEQ ID NO: 47 (same as above without GFP)
5'-ITR-CAG-HaloR-(MLPH Motif)-WPRE-bGHpolyA-ITR-3'

←start AAV2 ITR
```
cctgcaggca gctgcgcgct cgctcgctca ctgaggccgc cgggcaaag cccgggcgtc gggcgacctt tggtcgcccg gcctcagtga gcgagcgagc gcgcagagag ggagtggcca actccatcac taggggttcc tgcggccgca cgcgtgatat cCTAGTTATT AATAGTAATC
            end AAV2 ITR→↑                   ↑←start CAG pomoter/enhancer

AATTACGGGG TCATTAGTTC ATAGCCCATA TATGGAGTTC CGCGTTACAT AACTTACGGT

AAATGGCCCG CCTGGCTGAC CGCCCAACGA CCCCCGCCCA TTGACGTCAA TAATGACGTA

TGTTCCCATA GTAACGCCAA TAGGGACTTT CCATTGACGT CAATGGGTGG AGTATTTACG

GTAAACTGCC CACTTGGCAG TACATCAAGT GTATCATATG CCAAGTACGC CCCCTATTGA

CGTCAATGAC GGTAAATGGC CCGCCTGGCA TTATGCCCAG TACATGACCT TATGGGACTT

TCCTACTTGG CAGTACATCT ACGTATTAGT CATCGCTATT ACCATGCATG GTCGAGGTGA

GCCCCACGTT CTGCTTCACT CTCCCCATCT CCCCCCCCTC CCCACCCCCA ATTTTGTATT

TATTTATTTT TTAATTATTT TGTGCAGCGA TGGGGGCGGG GGGGGGGGGG GGGCGCGCGC

CAGGCGGGGC GGGGCGGGGC GAGGGGCGGG GCGGGGCGAG GCGGAGAGGT GCGGCGGCAG

CCAATCAGAG CGGCGCGCTC CGAAAGTTTC CTTTTATGGC GAGGCGGCGG CGGCGGCGGC

CCTATAAAAA GCGAAGCGCG CGGCGGGCGG GAGTCGCTGC GACGCTGCCT TCGCCCCGTG

CCCCGCTCCG CCGCCGCCTC GCGCCGCCCG CCCCGGCTCT GACTGACCGC GTTACTCCCA

CAGGTGAGCG GCGGGACGG CCCTTCTCCT CCGGGCTGTA ATTAGCGCTT GGTTTAATGA

CGGCTTGTTT CTTTTCTGTG GCTGCGTGAA AGCCTTGAGG GGCTCCGGGA GGGCCCTTTG

TGCGGGGGGA GCGGCTCGGG GCTGTCCGCG GGGGGACGGC TGCCTTCGGG GGGGACGGGG
                                              end CAG pomoter/enhancer→↓
CAGGGCGGGG TTCGGCTTCT GGCGTGTGAC CGGCGGCTCT AGCAGCCTCT GCTAaccatg ttcatgcctt cttctttttc ctacagctcc tgggcaacgt gctggttatt gtgctgtctc ↓←start HaloR
atcattttgg caaagaatta agcttgagct cgcgatccgc agcc ATG ACT GAG ACA

TTG CCA CCG GTA ACG GAA TCG GCT GTT GCG CTA CAG GCG GAG GTG ACC

CAG AGG GAG CTG TTC GAG TTC GTT CTC AAC GAC CCC CTC CTC GCC AGT

TCG CTG TAT ATT AAT ATC GCA CTG GCA GGG CTG TCG ATA CTG CTT TTC

GTG TTC ATG ACG CGC GGA CTC GAC GAC CCA CGG GCG AAA CTC ATC GCC

GTT TCG ACG ATT TTG GTG CCG GTG GTC TCT ATC GCG AGC TAC ACC GGC

CTT GCA TCG GGG CTC ACC ATC AGC GTC CTC GAG ATG CCA GCC GGC CAC

TTC GCC GAG GGG TCC TCG GTG ATG CTC GGC GGC GAA GAG GTA GAC GGC

GTC GTG ACG ATG TGG GGC GCC TAT CTG ACG TGG GCC CTT TCG ACA CCG

ATG ATA CTG CTG GCG CTT GGG CTG CTT GCT GGC TCT AAC GCC ACG AAG

CTC TTT ACC GCC ATC ACC TTC GAC ATC GCG ATG TGT GTC ACC GGC CTC

GCA GCC GCG CTG ACG ACC TCT TCG CAC CTG ATG CGG TGG TTC TGG TAC
```

```
GCC ATC AGT TGT GCG TGT TTC CTC GTC GTC CTC TAC ATC CTG CTC GTC

GAG TGG GCA CAG GAC GCC AAG GCT GCC GGT ACT GCG GAT ATG TTC AAT

ACG CTG AAG CTG CTG ACC GTT GTC ATG TGG CTC GGC TAC CCC ATC GTG

TGG GCA CTC GGC GTT GAG GGC ATC GCC GTT CTT CCG GTC GGA GTC ACG

TCG TGG GGA TAC AGC TTC CTC GAC ATC GTC GCG AAG TAC ATC TTC GCG

TTC CTG CTC AAC TAC CTC ACG TCG AAC GAG AGC GTC GTC TCC GGC

TCG ATA CTC GAC GTG CCG TCC GCG TCG GCA CTC CCG GCT GAC GAC
                                              end HaloR→↑
gaattcggag gcggaggtgg agctagc AGG GAC CAG CCT CTG AAC AGC AAA AAG
                             ↑←Start MLPH Motif

AAA AAG AGG CTC CTG AGC TTC AGG GAC GTG GAC TTC GAG GAG GAC AGC

GAC taactcgagt ctagacgtgg taccGATAAT CAACCTCTGG ATTACAAAAT
    ↑←end NLPH Motif        ↑←Start WPRE

TTGTGAAAGA TTGACTGGTA TTCTTAACTA TGTTGCTCCT TTTACGCTAT GTGGATACGC

TGCTTTAATG CCTTTGTATC ATGCTATTGC TTCCCGTATG GCTTTCATTT TCTCCTCCTT

GTATAAATCC TGGTTGCTGT CTCTTTATGA GGAGTTGTGG CCCGTTGTCA GGCAACGTGG

CGTGGTGTGC ACTGTGTTTG CTGACGCAAC CCCCACTGGT TGGGGCATTG CCACCACCTG

TCAGCTCCTT TCCGGGACTT TCGCTTTCCC CCTCCCTATT GCCACGGCGG AACTCATCGC

CGCCTGCCTT GCCCGCTGCT GGACAGGGGC TCGGCTGTTG GGCACTGACA ATTCCGTGGT

GTTGTCGGGG AAGCTGACGT CCTTTCCATG GCTGCTCGCC TGTGTTGCCA CCTGGATTCT

GCGCGGGACG TCCTTCTGCT ACGTCCCTTC GGCCCTCAAT CCAGCGGACC TTCCTTCCCG

CGGCCTGCTG CCGGCTCTGC GGCCTCTTCC GCGTCTTCGC CTTCGCCCTC AGACGAGTCG

GATCTCCCTT TGGGCCGCCT CCCCGCCTGA Tgcggggatc tctagagtc
                                          end WPRE→↑ gagagatctA CGGGTGGCAT CCCTGTGACC CCTCCCCAGT GCCTCTCCTG GCCCTGGAAG
          ↑←start bGH-polyA

TTGCCACTCC AGTGCCCACC AGCCTTGTCC TAATAAAATT AAGTTGCATC ATTTTGTCTG

ACTAGGTGTC CTTCTATAAT ATTATGGGGT GGAGGGGGGT GGTATGGAGC AAGGGGCAAG

TTGGGAAGAC AACCTGTAGG GCCTGCGGGG TCTATTGGGA ACCAAGCTGG AGTGCAGTGG

CACAATCTTG GCTCACTGCA ATCTCCGCCT CCTGGGTTCA AGCGATTCTC CTGCCTCAGC

CTCCCGAGTT GTTGGGATTC AGGCATGCA TGACCAGGCT CAGCTAATTT TTGTTTTTTT

GGTAGAGACG GGGTTTCACC ATATTGGCCA GGCTGGTCTC CAACTCCTAA TCTCAGGTGA

TCTACCCACC TTGGCCTCCC AAATTGCTGG GATTACAGGC GTGAACCACT GCTCCCTTCC

↓←end bGH-polyA
CTGTCCTTct gattttgtag gtaaccacgt gcggaccgag cggccgcagg aacccctagt
                                                     ↑←start AAV2 ITR gatggagttg gccactccct ctctgcgcgc tcgctcgctc actgaggccg ggcgaccaaa ggtcgcccga cgcccgggct tgccgggc ggcctcagtg agcgagcgag cgcgcagctg cctgcagg
        ↑←end AAV2 ITR
```

Pharmaceutical Compositions and Methods of the Invention

The vectors that comprises the ChR2 or HaloR transgene and the targeting motifs disclosed herein for use to target retinal neurons as described above should be assessed for contamination using conventional methods and formulated into a sterile or aseptic pharmaceutical composition for administration by, for example, subretinal injection.

Such formulations comprise a pharmaceutically and/or physiologically acceptable vehicle, diluent, carrier or excipient, such as buffered saline or other buffers, e.g., HEPES, to maintain physiologic pH. For a discussion of such components and their formulation, see, generally, Gennaro, A E., *Remington: The Science and Practice of Pharmacy*, Lippincott Williams & Wilkins Publishers; 2003 or latest edition). See also, WO00/15822. For prolonged storage, the preparation may be frozen, for example, in glycerol.

The pharmaceutical composition described above is administered to a subject having a visual or blinding disease by any appropriate route, preferably by intravitreal or subretinal injection, depending on the retinal layer being targeted.

Disclosures from Bennett and colleagues (cited herein) concern targeting of retinal pigment epithelium—the most distal layer from the vitreal space. According to the present invention, the DNA construct is targeted to either retinal ganglion cells or bipolar cells. The ganglion cells are reasonably well-accessible to intravitreal injection. Intravitreal and/or subretinal injection can provide the necessary access to the bipolar cells, especially in circumstances in which the photoreceptor cell layer is absent due to degeneration—which is the case in certain forms of degeneration that the present invention is intended to overcome.

To test for the vector's ability to express the transgene, specifically in mammalian retinal neurons, preferably RGC, by AAV-mediated delivery, a combination of a preferred promoter sequence linked to a reporter gene such as GFP or LacZ can be packaged into rAAV virus particles, concentrated, tested for contaminating adenovirus and titered for rAAV. The right eyes of a number of test subjects, preferably inbred mice, are injected sub-retinally with about 1 μl of the rAAV preparation (e.g., greater than about $10^{10}$ infectious units ml). Two weeks later, the right (test) and left (control) eyes of half the animals are removed, fixed and stained with an appropriate substrate or antibody or other substance to reveal the presence of the reporter gene. A majority of the test retinas in injected eyes will exhibited a focal stained region, e.g., blue for LacZ/Xgal, or green for GFP consistent with a subretinal bleb of the injected virus creating a localized retinal detachment. All control eyes are negative for the reporter gene product. Reporter gene expression examined in mice sacrificed at later periods is detected for at least 10 weeks post-injection, which suggests persistent expression of the reporter transgene.

An effective amount of rAAV virions carrying a nucleic acid sequence according to this invention encoding the ChR2 or HaloR and targeting motif under the control of the promoter of choice, preferably CAG or a cell-specific promoter such as mGluR6, is preferably in the range of between about $10^{10}$ to about $10^{13}$ rAAV infectious units in a volume of between about 150 and about 800 μl per injection. The rAAV infectious units can be measured according to McLaughlin, S K et al., 1988, *J Virol* 62:1963. More preferably, the effective amount is between about $10^{10}$ and about $10^{12}$ rAAV infectious units and the injection volume is preferably between about 250 and about 500 μl. Other dosages and volumes, preferably within these ranges but possibly outside them, may be selected by the treating professional, taking into account the physical state of the subject (preferably a human), who is being treated, including, age, weight, general health, and the nature and severity of the particular ocular disorder.

It may also be desirable to administer additional doses ("boosters") of the present nucleic acid or rAAV compositions. For example, depending upon the duration of the transgene expression within the ocular target cell, a second treatment may be administered after 6 months or yearly, and may be similarly repeated. Neutralizing antibodies to AAV are not expected to be generated in view of the routes and doses used, thereby permitting repeat treatment rounds.

The need for such additional doses can be monitored by the treating professional using, for example, well-known electrophysiological and other retinal and visual function tests and visual behavior tests. The treating professional will be able to select the appropriate tests applying routine skill in the art. It may be desirable to inject larger volumes of the composition in either single or multiple doses to further improve the relevant outcome parameters.

Ocular Disorders

The ocular disorders for which the present methods are intended and may be used to improve one or more parameters of vision include, but are not limited to, developmental abnormalities that affect both anterior and posterior segments of the eye. Anterior segment disorders include glaucoma, cataracts, corneal dystrophy, keratoconus. Posterior segment disorders include blinding disorders caused by photoreceptor malfunction and/or death caused by retinal dystrophies and degenerations. Retinal disorders include congenital stationary night blindness, age-related macular degeneration, congenital cone dystrophies, and a large group of retinitis-pigmentosa (RP)-related disorders. These disorders include genetically pre-disposed death of photoreceptor cells, rods and cones in the retina, occurring at various ages. Among those are severe retinopathies, such as subtypes of RP itself that progresses with age and causes blindness in childhood and early adulthood and RP-associated diseases, such as genetic subtypes of LCA, which frequently results in loss of vision during childhood, as early as the first year of life. The latter disorders are generally characterized by severe reduction, and often complete loss of photoreceptor cells, rods and cones. (Trabulsi, E I, ed., *Genetic Diseases of the Eye*, Oxford University Press, NY, 1998).

In particular, this method is useful for the treatment and/or restoration of at least partial vision to subjects that have lost vision due to ocular disorders, such as RPE-associated retinopathies, which are characterized by a long-term preservation of ocular tissue structure despite loss of function and by the association between function loss and the defect or absence of a normal gene in the ocular cells of the subject. A variety of such ocular disorders are known, such as childhood onset blinding diseases, retinitis pigmentosa, macular degeneration, and diabetic retinopathy, as well as ocular blinding diseases known in the art. It is anticipated that these other disorders, as well as blinding disorders of presently unknown causation which later are characterized by the same description as above, may also be successfully treated by this method. Thus, the particular ocular disorder treated by this method may include the above-mentioned disorders and a number of diseases which have yet to be so characterized.

Visual information is processed through the retina through two pathways: an ON pathway which signals the light ON, and an OFF pathway which signals the light OFF (Wässle, supra). It is generally believed that the existence of the ON and OFF pathway is important for the enhancement of contrast sensitivity. The visual signal in the ON pathway is relay from ON-cone bipolar cells to ON ganglion cells. Both ON-cone bipolar cells and ON-ganglion cells are depolarized in response to light. On the other hand, the visual signal in the OFF pathway is carried from OFF-cone bipolar cells to OFF ganglion cells. Both OFF-cone bipolar cells and OFF-ganglion cells are hypopolarized in response to light. Rod bipolar cells, which are responsible for the ability to see in dim light (scotopic vision), are ON bipolar cells (depolarized in response to light). Rod bipolar cells relay the vision signal through AII amacrine cells (an ON type retinal cell) to ON an OFF cone bipolar cell.

Electrical/Visual Activity Recording and Measurement

Patch-Clamp Recordings

Dissociated retinal cells and retinal slice are prepared, e.g., as described by Pan, Z.-H. *J. Neurophysiol.* 83 513-527 (2000); J. Cui, Y P et al., *J. Physiol.* 553:895-909 (2003). Recordings with patch electrodes in the whole-cell configuration can be made by an EPC-9 amplifier and PULSE software (Heka Electronik, Lambrecht, Germany). Recordings are preferably made in Hanks' solution containing (in mM): NaCl, 138; $NaHCO_3$, 1; $Na_2HPO_4$, 0.3; KCl, 5; $KH_2PO_4$, 0.3; $CaCl_2$, 1.25; $MgSO_4$, 0.5; $MgCl_2$, 0.5; HEPES-NaOH, 5; glucose, 22.2; with phenol red, 0.001% v/v; adjusted to pH 7.2 with 0.3 N NaOH. The electrode solution contains (in mM): K-gluconate, 133; KCl, 7; $MgCl_2$, 4; EGTA, 0.1; HEPES, 10; Na-GTP, 0.5; and Na-ATP, 2; pH adjusted with KOH to 7.4. The resistance of the electrode is about 13 to 15 MΩ. The recordings are performed at room temperature.

Multielectrode Array Recordings

The multielectrode array recordings are on the procedures reported by Tian, N. et al., *Neuron* 39:85-96 (2003). Briefly, retinas are dissected and placed photoreceptor side down on a nitrocellulose filter paper strip. The mounted retina is placed in the MEA-60 multielectrode array recording chamber of 30 µm diameter electrodes spaced 200 µm apart (Multi Channel System MCS GmbH, Reutlingen, Germany), with the ganglion cell layer facing the recording electrodes. The retina is continuously perfused in oxygenated extracellular solution at 34° C. The extracellular solution preferably contains (in mM): NaCl, 124; KCl, 2.5; $CaCl_2$, 2; $MgCl_2$, 2; $NaH_2PO_4$, 1.25; $NaHCO_3$, 26; and glucose, 22 (pH 7.35 with 95% $O_2$ and 5% $CO_2$). Recordings are usually started 60 min after the retina is positioned in the recording chamber. The interval between onsets of each light stimulus is generally 10-15 s. The signals are filtered between 200 Hz (low cut off) and 20 kHz (high cut off). The responses from individual neurons are analyzed using, e.g., Offline Sorter software (Plexon, Inc., Dallas, Tex.).

Visual-Evoked Potential Recordings

Visual-evoked potential recordings are carried out, for example, in wild-type mice of the C57BL/6 and 129/Sy strains aged 4-6 months and in rd1/rd1 mice aged 6-11 months. Recordings are performed 2-6 months after viral vector injection. After general anesthesia, animals are mounted in a stereotaxic apparatus. Body temperature may be unregulated or maintained at 34° C. with a heating pad and a rectal probe. Pupils are dilated with 1% atropine and 2.5% accu-phenylephrine. A small portion of the skull (~1.5×1.5 mm) centered about 2.5 mm from the midline and 1 mm rostral to the lambdoid suture is drilled and removed. Recordings are made from visual cortex (area V1) by a glass micropipette (resistance ~0.5 M after filling with 4 M NaCl) advanced 0.4 mm beneath the surface of the cortex at the contralateral side of the stimulated eye. The stimuli are 20 ms pluses at 0.5 Hz. Responses are amplified (1,000 to 10,000), band-pass filtered (0.3-100 Hz), digitized (1 kHz), and averaged over 30-250 trials.

Light Stimulation

For dissociated cell and retinal slice recordings, light stimuli are generated by a 150 W xenon lamp-based scanning monochromator with bandwidth of 10 nm (TILL Photonics, Germany) and coupled to the microscope with an optical fiber. For multielectrode array recordings, light responses are evoked by the monochromator or a 175 W xenon lamp-based illuminator (Lambda LS, Sutter Instrument) with a band-pass filter of 400-580 nm and projected to the bottom of the recording chamber through a liquid light guider. For visual evoked potential, light stimuli are generated by the monochromator and projected to the eyes through the optical fiber. The light intensity is attenuated by neutral density filters. The light energy is measured by a thin-type sensor (TQ82017) and an optical power meter (e.g., Model: TQ8210, Advantest, Tokyo, Japan).

Restoration or Improvement of Light Sensitivity and Vision

Both in vitro and in vivo studies to assess the various parameters of the present invention may be used, along with any recognized animal model of a blinding human ocular disorder. Large animal models of human retinopathy, e.g., childhood blindness, are useful. The examples provided herein allow one of skill in the art to readily appreciate that this method may be used similarly to treat a range of retinal diseases.

While earlier studies by others have demonstrated that retinal degeneration can be retarded by gene therapy techniques, the present invention demonstrates a definite physiological recovery of function, which is expected to generate or improve various parameters of vision, including behavioral parameters. Behavioral measures can be obtained using known animal models and tests, for example performance in a water maze, wherein a subject in whom vision has been preserved or restored to varying extents will swim toward light (Hayes, J M et al., 1993, *Behav Genet* 23:395-403).

In models in which blindness is induced during adult life or in congenital blindness that develops slowly enough for the individual to experience vision before its loss, training in various tests may be done. When these tests are re-administered after visual loss to test the efficacy of the present compositions and methods for their vision-restorative effects, animals do not have to learn the tasks de novo while in a blind state. Other behavioral tests do not require learning and rely on instinctiveness of certain behaviors. An example is the optokinetic nystagmus test (Balkema G W et al., 1984, *Invest Ophthal Vis Sci.* 25:795-800; Mitchiner J C et al., 1976, *Vision Res.* 16:1169-71).

As is exemplified herein, the transfection of retinal neurons with DNA encoding Chop2 provides residual retinal neurons, principally bipolar cells and ganglion cells, with photosensitive membrane channels. Thus, it was possible to measure, with a strong light stimulus, the transmission of a visual stimulus to the animal's visual cortex, the area of the brain responsible for processing visual signals; this therefore constitutes a form of vision, as intended herein. Such vision may differ from forms of normal human vision and may be referred to as a sensation of light, also termed "light detection" or "light perception."

Thus, the term "vision" as used herein is defined as the ability of an organism to usefully detect light as a stimulus for differentiation or action. Vision is intended to encompass:

1. Light detection or perception—the ability to discern whether or not light is present
2. Light projection—the ability to discern the direction from which a light stimulus is coming;
3. Resolution—the ability to detect differing brightness levels (i.e., contrast) in a grating or letter target;
4. Recognition—the ability to recognize the shape of a visual target by reference to the differing contrast levels within the target.

Thus, "vision" includes the ability to simply detect the presence of light. This opens the possibility to train an affected subject who has been treated according to this invention to detect light, enabling the individual to respond remotely to his environment however crude that interaction might be. In one example, a signal array is produced to which a low vision person can respond to that would enhance the person's ability to communicate by electronic means remotely or to perform everyday tasks. In addition such a person's mobility would be dramatically enhanced if trained to use such a renewed sense of light resulting from "light detection." The complete absence of light perception leaves a person with no means (aside from hearing and smell) to discern anything about objects remote to himself.

The methods of the present invention that result in light perception, even without full normal vision, also improve or support normally regulated circadian rhythms which control many physiological processes including sleep-wake cycles and associated hormones. Although some blind individuals with residual RGCs can mediate their rhythms using RGC melanopsin, it is rare for them to do so. Thus, most blind persons have free-running circadian rhythms. Even when they do utilize the melanopsin pathway, the effect is very weak. The methods of the present invention are thus expected to improve health status of blind individuals by enabling absent light entrainment or improving weakened (melanopsin-mediated) light entrainment of circadian rhythms which leads to better overall health and well-being.

In addition to rhythms, the present invention provides a basis to improve deficits in other light-induced physiological phenomena. Photoreceptor degeneration may result in varying degrees of negative masking, or suppression, of locomotor activity during the intervals in the circadian cycle in which the individual should be sleeping. Suppression of pineal melatonin may occur. Both contribute to the entrainment process. Thus, improvement in these responses/activities in a subject in whom photoreceptors are or have degenerated contributes, independently of vision per se, to appropriate sleep/wake cycles that correspond with the subject's environment in the real world.

Yet another benefit of the present invention is normalization of pupillary light reflexes because regulation of pupil size helps modulate the effectivenees of light stimuli in a natural feed back loop. Thus, the present invention promotes re-establishment of this natural feedback loop, making vision more effective in subject treated as described herein.

In certain embodiments, the present methods include the measurement of vision before, and preferably after, administering the present vector. Vision is measured using any of a number of methods well-known in the art or ones not yet established. Most preferred are:

(1) A light detection response by the subject after exposure to a light stimulus—in which evidence is sought for a reliable response of an indication or movement in the general direction of the light by the subject individual when the light is turned on.
(2) a light projection response by the subject after exposure to a light stimulus in which evidence is sought for a reliable response of indication or movement in the specific direction of the light by the individual when the light is turned on.
(3) light resolution by the subject of a light vs. dark patterned visual stimulus, which measures the subject's capability of resolving light vs dark patterned visual stimuli as evidenced by:
   (a) the presence of demonstrable reliable optokinetically produced nystagmoid eye movements and/or related head or body movements that demonstrate tracking of the target (see above) and/or
   (b) the presence of a reliable ability to discriminate a pattern visual stimulus and to indicate such discrimination by verbal or non-verbal means, including, for example pointing, or pressing a bar or a button; or
(4) electrical recording of a visual cortex response to a light flash stimulus or a pattern visual stimulus, which is an endpoint of electrical transmission from a restored retina to the visual cortex. Measurement may be by electrical recording on the scalp surface at the region of the visual cortex, on the cortical surface, and/or recording within cells of the visual cortex.

It is known in the art that it is often difficult to make children who have only light perception appreciate that they have this vision. Training is required to get such children to react to their visual sensations. Such a situation is mimicked in the animal studies exemplified below. Promoting or enhancing light perception, which the compositions and methods of the present invention will accomplish, is valuable because patients with light perception not only are trainable to see light, but they can usually be trained to detect the visual direction of the light, thus enabling them to be trained in mobility in their environment. In addition, even basic light perception can be used by visually impaired individuals, including those whose vision is improved using the present compositions and methods, along with specially engineered electronic and mechanical devices to enable these individuals to accomplish specific daily tasks. Beyond this and depending on their condition, they may even be able to be trained in resolution tasks such as character recognition and even reading if their impairment permits. Thus it is expected that the present invention enhances the vision of impaired subjects to such a level that by applying additional training methods, these individuals will achieve the above objectives.

Low sensitivity vision may emulate the condition of a person with a night blinding disorder, an example of which is Retinitis Pigmentosa (RP), who has difficulty adapting to light levels in his environment and who might use light amplification devices such as supplemental lighting and/or night vision devices.

Thus, the visual recovery that has been described in the animal studies described below would, in human terms, place the person on the low end of vision function. Nevertheless, placement at such a level would be a significant benefit because these individuals could be trained in mobility and potentially in low order resolution tasks which would provide them with a greatly improved level of visual independence compared to total blindness.

The mice studied in the present Examples were rendered completely devoid of photoreceptors; this is quite rare, even in the worst human diseases. The most similar human state is RP. In most cases of RP, central vision is retained till the very end. In contrast, in the studied mouse model, the mouse becomes completely blind shortly after birth.

Common disorders encountered in low vision are described by J. Tasca and E. A. Deglin in Chap. 6 of

*Essentials of Low Vision Practice*, R. L. Brilliant, ed., Butterworth Heinemann Publ., 1999, which is incorporated by reference in its entirety. There is reference to similar degenerative conditions, but these references show form vision that is measurable as visual acuity. Ganglion cell layers are not retained in all forms of RP, so the present approach will not work for such a disorder.

When applying the present methods to humans with severe cases of RP, it is expected that central vision would be maintained for a time at some low level while the peripheral retina degenerated first. It is this degenerating retina that is the target for re-activation using the present invention. In essence, these individuals would be able to retain mobility vision as they approached blindness gradually.

Subjects with macular degeneration, characterized by photoreceptor loss within the central "sweet spot" of vision (Macula Lutea), are expected to benefit by treatment in accordance with the present invention, in which case the resolution capability of the recovered vision would be expected to be higher due to the much higher neuronal density within the human macula.

While it is expected that bright illumination of daylight and artificial lighting that may be used by a visually impaired individual will suffice for many visual activities that are performed with vision that has recovered as a result of the present treatments. It is also possible that light amplification devices may be used, as needed, to further enhance the affected person's visual sensitivity. The human vision system can operate over a 10 log unit range of luminance. On the other hand, microbial type rhodopsins, such as ChR2, operate over up to a 3 log unit range of luminance. In addition, the light conditions the patient encounters could fall outside of the operating range of the light sensor. To compensate for the various light conditions, a light pre-amplification or attenuation device could be used to expand the operation range of the light conditions. Such device would contain a camera, imaging processing system, and microdisplays, which can be assembled from currently available technologies, such as night vision goggles and/or 3D adventure and entertainment system. (See, for example the following URL on the Worldwide web—emagin.com/.)

The present invention may be used in combination with other forms of vision therapy known in the art. Chief among these is the use of visual prostheses, which include retinal implants, cortical implants, lateral *geniculate* nucleus implants, or optic nerve implants. Thus, in addition to genetic modification of surviving retinal neurons using the present methods, the subject being treated may be provided with a visual prosthesis before, at the same time as, or after the molecular method is employed.

The effectiveness of visual prosthetics can be improved with training of the individual, thus enhancing the potential impact of the ChR2 or HaloR transformation of patient cells as discussed herein. An example of an approach to training is found in US 2004/0236389 (Fink et al.), incorporated by reference. The training method may include providing a non-visual reference stimulus to a patient having a visual prosthesis based on a reference image. The non-visual reference stimulus is intended to provide the patient with an expectation of the visual image that the prosthesis will induce. Examples of non-visual reference stimuli are a pinboard, Braille text, or a verbal communication. The visual prosthesis stimulates the patient's nerve cells, including those cells whose responsiveness has been improved by expressing ChR2 and/or HaloR as disclosed herein, with a series of stimulus patterns attempting to induce a visual perception that matches the patient's expected perception derived from the non-visual reference stimulus. The patient provides feedback to indicate which of the series of stimulus patterns induces a perception that most closely resembles the expected perception. The patient feedback is used as a "fitness function" (also referred to as a cost function or an energy function). Subsequent stimuli provided to the patient through the visual prosthesis are based, at least in part, on the previous feedback of the patient as to which stimulus pattern(s) induce the perception that best matches the expected perception. The subsequent stimulus patterns may also be based, at least in part, on a fitness function optimization algorithm, such as a simulated annealing algorithm or a genetic algorithm.

Thus, in certain embodiments of this invention, the method of improving or restoring vision in a subject further comprises training of that subject, as discussed above. Preferred examples of training methods are:
  (a) habituation training characterized by training the subject to recognize (i) varying levels of light and/or pattern stimulation, and/or (ii) environmental stimulation from a common light source or object as would be understood by one skilled in the art; and
  (b) orientation and mobility training characterized by training the subject to detect visually local objects and move among said objects more effectively than without the training.

In fact, any visual stimulation techniques that are typically used in the field of low vision rehabilitation are applicable here.

The remodeling of inner retinal neurons triggered by photoreceptor degeneration has raised a concerns about retinal-based rescue strategies after the death of photoreceptors (Strettoi and Pignatelli 2000, *Proc Natl Acad Sci USA.* 97:11020-5; Jones, B W et al., 2003, *J Comp Neurol* 464:1-16; Jones, B W and Marc, R E, 2005, *Exp Eye Res.* 81:123-37; Jones, B W et al., 2005, *Clin Exp Optom.* 88:282-91). Retinal remodeling is believed to result from deafferentation, the loss of afferent inputs from photoreceptors—in other words, the loss of light induced activities. So after death of rods and cones, there is no light evoked input to retinal bipolar cells and ganglion cells, and through them to higher visual centers. In response to the loss of such input, the retina and higher visual network are triggered to undergo remodeling, in a way seeking other forms of inputs. Said otherwise, the retina needs to be used to sense light in order to maintain its normal network, and with the loss of light sensing, the network will deteriorate via a remodeling process. This process is not an immediate consequence of photoreceptor death; rather it is a slow process, providing a reasonably long window for intervention.

Thus, an additional utility of restoring light sensitivity to inner retinal neurons in accordance with the present invention is the prevention or delay in the remodeling processes in the retina, and, possibly, in the higher centers. Such retinal remodeling may have undesired consequences such as corruption of inner retinal network, primarily the connection between bipolar and RGCs. By introducing the light-evoked activities in bipolar cells or RGCs, the present methods would prevent or diminish the remodeling due to the lack of input; the present methods introduce this missing input (either starting from bipolar cells or ganglion cells), and thereby stabilize the retinal and higher visual center network. Thus, independently of its direct effects on vision, the present invention would benefit other therapeutic approaches such as photoreceptor transplantation or device implants.

Having now generally described the invention, the same will be more readily understood through reference to the following examples which are provided by way of illustration, and are not intended to be limiting of the present invention, unless specified.

Example I

Transgene Expression in Different Cellular Sites or Compartments

A. Materials and Methods
Viral Vectors:

Adeno-associated virus serotype 2 (rAAV2) cassette carrying a channelopsin-2 and GFP (Chop2-GFP) fusion construct (Bi, A. et al. *Neuron* 50:23-33 (2006); WO2007/131180) were modified by inserting subcellular sorting motifs at the 3' end of GFP (or, if no reporter is present, at the 3' end of ChR2 or HaloR. As described above, viral vectors carrying the transgene of ChR2-GFP-(motif) with a hybrid CMV early enhancer/chicken (β-actin) promoter (CAG) were packaged and affinity purified at the Gene Transfer Vector Core of the University of Iowa.
Design of the vectors was is described above.

Animal and Viral Vector Injection:

3-4 adult C57BL/6J mice aged 1-2 months per construct were used for the study. The mice were anesthetized by intraperitoneal injection of ketamine (120 mg/kg) and xylazine (15 mg/kg). Under a dissecting microscope, a small perforation was made with a needle in the sclera region posterior to the limbus, and 1.0 μl of viral vector suspension at a concentration of >1×10$^{12}$ gv/ml was injected into the intravitreal space of each eye. Four weeks after viral vector injection, animals were sacrificed by CO2 asphyxiation followed by decapitation and enucleation.

Histology:

Enucleated eyes were fixed in 4% paraformaldehyde in phosphate buffer (PB) for 20 minutes and the dissected retina flat mounted onto a microscope slide for histological studies. The flat mounts were examined under a Zeiss Apotome microscope and Zstack images were taken at ~562 ms exposure time at optical sections of 1 μm apart in order to capture the axon, soma, and entire depth of the dendritic tree of each RGC.

Image Analysis and Fluorescence Intensity Ratio Calculations:

Intensity profiles of axon, soma, and dendrites for each RGC were measured in ImageJ (obtained from NIH) by applying lines of width of 5 pixels. For each RGC, axon intensity profile was obtained by averaging 3 measurements, somatic intensity profile was obtained by averaging 3 measurements, and dendritic intensity profile was obtained by averaging 9 measurements (3 proximal, 3 intermediate, and 3 distal). Dendrite/axon (D/A) and soma/axon (S/A) intensity ratios were then calculated from the average values for each RGC.

Statistical Analysis of Fluorescence Intensity Ratios:

A one-way analysis of variance (ANOVA) was conducted with Bonferroni correction. $P<0.05$ is considered significantly different for somatic fluorescence intensity (Soma F.I.) measurements, dendrite to axon (D/A) ratios and soma to axon (S/A) ratios between groups.

B. Results

Results are shown in FIG. 1 and in Table 2 below.

TABLE 2

Comparison of Transduced GFP Expression in Different Cellular Sites or Compartments Mediated by Different Motifs:

| Sorting Motif | n* | Fluorescence Intensity at subcellular site Mean ± SE | | | Conclusion: targeted site (receptivce field) |
| --- | --- | --- | --- | --- | --- |
| | | Soma | Dendrite | Axon | |
| Control | 29 | 146.0 ± 8.3 | 65.2 ± 4.2 | 36.6 ± 1.9 | |
| Kv2.1 | 24 | 117.7 ± 6.0 | 2.31 ± 0.88† | 18.8 ± 1.4† | Soma, proximal dendritic (center) |
| Nav1.6 | 24 | 74.7 ± 8.2† | 10.6 ± 3.3† | 25.3 ± 1.6† | Axon initial segment, soma (center) |
| MLPH | 25 | 128.7 ± 9.3 | 73.5 ± 4.6 | 20.8 ± 1.9† | Somatodendritic (surroung = off center) |
| NLG-1 | 25 | 133.2 ± 7.2 | 76.2 ± 3.1 | 23.2 ± 1.9† | Somatodendritic (surroung = off center) |
| AMPAR | 23 | 143.2 ± 8.8 | 81.5 ± 3.8 | 47.9 ± 3.0† | No selective targeting in this experiment |
| Kv4.2 | 26 | 142.0 ± 8.9 | 76.6 ± 4.8 | 41.1 ± 2.9 | |
| nAChR | 29 | 120.0 ± 4.8 | 67.3 ± 3.3 | 31.8 ± 1.8 | |
| TLCN | 19 | 157.3 ± 15.9 | 53.4 ± 5.5 | 31.2 ± 3.4 | |

*n = number of cells analyzed
†Difference from control significant at $p < 0.05$ Use of the Kv2.1 motif and targeted ChR2, and would similarly target HaloR, to soma and proximal dendritic regions (the center of receptive field) of RGCs. Use of Nav1.6 motif targets to soma and axon initial segments (the center of the receptive field). Kv2.1 appears to achieve such targeting more effectively than does Nav1.6.

Use of NLG-1 and MLPH sorting motifs targeted ChR2 (and would target HaloR) to distal dendritic regions (the surround of the receptive field) because, compared to control, they are more biased to distal dendritic regions. NLG appears to do this better.

Use of Kv2.1, Nav1.6, NLG-1 and MLPH reduces expression of the ChR2 or HaloR in the axons of retinal ganglion cells. Although not shown directly in FIG. 1 or Table 2, the ankyrin binding domain of Nav1.6 preferentially targeted Chop2-GFP to the axon initial segments as well as decreased expression in the dendrites of RGCs with D/A ratio 4.5 fold less than control. However the overall fluorescence intensity was lower for Nav1.6 compared to the control which contributed to the lack of significant difference in the S/A ratio compared to control. A previous (preliminary) study reported use of Anbthe ankyrin binding domain to target Chop2 to the somata of rabbit retinal ganglion cells via biolistic gene transfer (Greenberg, K. P. et al. Invest. Ophthal. Vis Sci 2009 (abstract) 2009).

Motifs from nAchR, KV4.2, TLCN, and AMPAR did not show statistically significant differences from the control group in somatic fluorescence, D/A ratio, and S/A ratio in this study. However, it is believed that with varying conditions, further modified vectors, etc., these too are useful as sorting motifs for targeting of, and spatially selective expression of transduced ChR2 or HaloR in RGC.

Example II

Physiological Responses of Cells Expressing ChR2

Studies were conducted (data not shown) in which the RGCs transduced by vectors comprising ChR2 and the Kv2.1 motif (center-targeting), which indeed showed enhanced expression in the center (Soma, proximal dendritic, were tested for electrical responses to light stimuli. A light slit was used to move a light along the cell, and recordings were made where the cell responded by depolarization. The responsiveness of such cells were enhanced compared to those of controls (transduced with vector not containing the sorting motif) indicating a close correlation between the histological evidence for site-specific expression of a transgene (GFP) and spatial organization of a transgene similarly introduced (ChR2). These results confirm the utility of this approach to evoking improved light responsiveness with organization reflective of normal retinal function (spatial specificity) in cells treated using the present methods.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A nucleic acid molecule encoding a rhodopsin for differential expression in subcellular regions of a retinal ganglion cell (RGC), which molecule comprises:
   (a) a first nucleotide sequence encoding a light-gated channel rhodopsin or a light-driven ion pump rhodopsin;
   (b) linked in frame to (a), a second nucleotide sequence encoding a polypeptide sorting motif, wherein the sorting motif targets the center of said neuron's receptive field and wherein the nucleotide sequence encoding the sorting motif is:
      (1) a nucleotide sequence encoding voltage-gated potassium channel 2.1 (Kv2.1), which is or comprises SEQ ID NO: 1; or
      (2) a nucleotide sequence encoding ankyrin binding domain of voltage-gated sodium channel 1.6 (Nav1.6), which is or comprises SEQ ID NO: 3;
   (c) operatively linked to (a) and (b), a transcriptional regulatory sequence; and
   (d) a polyadenylation sequence.

2. A nucleic acid molecule encoding a rhodopsin for differential expression in subcellular regions of a retinal ganglion cell (RGC), which molecule comprises:
   (a) a first nucleotide sequence encoding a light-gated channel rhodopsin or a light-driven ion pump rhodopsin;
   (b) linked in frame to (a), a second nucleotide sequence encoding a polypeptide sorting motif, wherein the sorting motif targets the center of said neuron's receptive field and wherein the amino acid sequence of the encoded sorting motif is:
      (1) the amino acid sequence of Kv2.1, which is or comprises SEQ ID NO: 2; or
      (2) the amino acid sequence of the ankyrin-binding domain of Nav1.6, which is or comprises SEQ ID NO: 4
   (c) operatively linked to (a) and (b), a transcriptional regulatory sequence; and
   (d) a polyadenylation sequence.

3. The nucleic acid molecule according to claim 1 or 2, wherein
   (e) comprises:
      (i) a cytomegalovirus enhancer/chicken 13-actin promoter (CAG), and
      (ii) woodchuck hepatitis virus posttranscriptional regulatory element (WPRE); and
   (f) comprises:
      (i) polyadenylation sequence is from bovine growth hormone (bGHpolyA) or
      (ii) SV 40-derived polyadenylation sequence.

4. The nucleic acid molecule according to claim 1 or 2, which further comprises, linked in frame with (a) and (b), a third nucleotide sequence encoding a reporter polypeptide.

5. The nucleic acid molecule according to claim 4, wherein the reporter polypeptide is green fluorescent protein (GFP) encoded by SEQ ID NO: 25.

6. The nucleic acid molecule according to claim 1 or 2, wherein the light-gated channel rhodopsin is channelrhodopsin-2 (ChR2), SEQ ID NO: 20 or 22, and the light driven ion pump rhodopsin is halorhodopsin (HaloR), SEQ ID NO: 24.

7. The nucleic acid molecule according to claim 3, wherein the CAG comprises SEQ ID NO: 26, the WPRE comprises SEQ ID NO: 27 and the polyadenylation sequence is from bovine growth hormone (bGHpolyA), SEQ ID NO: 28.

8. The nucleic acid molecule according to claim 1 or 2, wherein the sorting motif is one that targets one or more of the following subcellular regions: soma, proximal dendritic region, or axon initial segment.

9. The nucleic acid molecule according to claim 1 or 2, wherein the sorting motif is one that targets the surround or off-center of said neuron's receptive field.

10. The nucleic acid molecule according to claim 9, wherein the sorting motif is one that targets the somatodendritic region of said neurons.

11. The nucleic acid molecule according to claim 9 or 10, wherein the nucleotide sequence encoding the sorting motif is:
   (a) a nucleotide sequence encoding the cytoplasmic C-terminal segment of neuroligin-1 (NLG-1), which is or comprises SEQ ID NO:5; or
   (b) a nucleotide sequence encoding the myosin binding domain of melanophilin (MLPH), which is or comprises SEQ ID NO:7.

12. The nucleic acid molecule according to claim 9 or 10, wherein the amino acid sequence of the sorting motif is:
   (a) the amino acid sequence of the cytoplasmic C-terminal segment of NLG-1 which is or comprises, SEQ ID NO:6; or
   (b) the amino acid sequence of the myosin-binding domain of MLPH, which is or comprises SEQ ID NO:8.

13. A recombinant adeno-associated virus-2 (rAAV2) expression vector comprising the nucleic acid molecule according to claim 1 or 2, wherein the sequence of the nucleic acid molecule is flanked at its 5' end by a 5' inverted terminal repeat (ITR) and at its 3' end by a 3' ITR of AAV2, the sequence of which ITR is, respectively, SEQ ID NO: 17 and SEQ ID NO: 18.

14. The expression vector according to claim 13 having one of the following schematic structures:

(a) 5'-ITR-CAG-ChR2-GFP{Motif}-WPRE-bGHpolyA-ITR-3';

(b) 5'-ITR-CAG-ChR2-{Motif}-WPRE-bGHpolyA-ITR-3';

(c) 5'-ITR-CAG-HaloR-GFP-{Motif}-WPRE-bGHpolyA-ITR-3';
or (d) 5'-ITR-CAG-HaloR-{Motif}-WPRE-bGHpolyA-ITR-3';

wherein:
   (i) the 5' ITR comprises SEQ ID NO:17 and the 3' ITR comprises SEQ ID NO: 18;
   (ii) {Motif} is a nucleotide sequence encoding said sorting motif; and
   (iii) any two or more of ChR2, GFP and Motif or HaloR GFP and Motif, are linked in-frame.

15. The expression vector according to claim 14, wherein the schematic structure and nucleotide sequence is selected from the group consisting of:

SEQ ID NO: 32
(a) 5'-ITR-CAG-ChR2-GFP-(Kv2.1 Motif)-WPRE-
    bGHpolyA-ITR-3';

SEQ ID NO: 33
(b) 5'-ITR-CAG-ChR2-(Kv2.1 Motif)-WPRE-
    bGHpolyA-ITR-3';

-continued

```
                                       SEQ ID NO: 34
(c) 5'-ITR-CAG-ChR2-GFP-(Nav2.6 Motif)-WPRE-
bGHpolyA-ITR-3';
and SEQ ID NO: 35
(d) 5'-ITR-CAG-ChR2-(Nav2.6 Motif)-WPRE-
bGHpolyA-ITR-3'.
```

16. The expression vector according to claim 14, wherein the schematic structure and nucleotide sequence is selected from the group consisting of:

```
                                       SEQ ID NO: 36
(a) 5'-ITR-CAG-ChR2-GFP-(NLG-1 Motif)-WPRE-
bGHpolyA-ITR-3';

SEQ ID NO: 37
(b) 5'-ITR-CAG-ChR2-(NLG-1 Motif)-WPRE-bGHpolyA-
ITR-3';

SEQ ID NO: 38
(c) 5'-ITR-CAG-ChR2-GFP-(MLPH Motif)-WPRE-bGHpolyA-
ITR-3';
and

SEQ ID NO: 39
(d)5'-ITR-CAG-ChR2-(MLPH Motif)-WPRE-bGHpolyA-
ITR-3'.
```

17. The expression vector according to claim 14, wherein the schematic structure and nucleotide sequence is selected from the group consisting of:

```
                                       SEQ ID NO: 40
(a) 5'-ITR-CAG-HaloR-GFP-(Kv2.1 Motif)-WPRE-
bGHpolyA-ITR-3';

SEQ ID NO: 41
(b) 5'-ITR-CAG-HaloR-(Kv2.1 Motif)-WPRE-
bGHpolyA-ITR-3';

SEQ ID NO: 42
(c) 5'-ITR-CAG-HaloR-GFP-(Nav2.6 Motif)-WPRE-
bGHpolyA-ITR-3';
and SEQ ID NO: 43
(d) 5'-ITR-CAG-HaloR-(Nav2.6 Motif)-WPRE-
bGHpolyA-ITR-3'.
```

18. The expression vector according to claim 14, wherein the schematic structure and nucleotide sequence is selected from the group consisting of:

```
                                       SEQ ID NO: 44
(a) 5'-ITR-CAG-HaloR-GFP-(NLG-1 Motif)-WPRE-
bGHpolyA-ITR-3';

SEQ ID NO: 45
(b) 5'-ITR-CAG-HaloR-(NLG-1 Motif)-WPRE-
bGHpolyA-ITR-3';

SEQ ID NO: 46
(c) 5'-ITR-CAG-HaloR-GFP-(MLPH Motif)-WPRE-
bGHpolyA-ITR-3';
and

SEQ ID NO: 47
(d) 5'-ITR-CAG-HaloR-(MLPH Motif)-WPRE-
bGHpolyA-ITR-3'.
```

19. The expression vector according to claim 13, which further comprises AAV vector backbone nucleotide sequence SEQ ID NO:29 linked to the 3' end of said AAV 3' ITR sequence.

20. A method of restoring light sensitivity to a retina, comprising:
(a) delivering to a retinal neuron, preferably a retinal ganglion cell (RGC), a nucleic acid expression vector that comprises a nucleic acid according to claim 1 or 2;
(b) expressing said vector in said neurons,
wherein the expression of said sorting motif with said rhodopsin results in selected expression of said rhodopsin and, when present, said reporter polypeptide, in subcellular regions of the RGC for which said motifs are selective, thereby restoring said light sensitivity.

21. A method of selectively expressing a light-gated channel rhodopsin or a light-driven ion pump rhodopsin in a desired subcellular site or sites of a retinal ganglion cell (RGC), comprising
(a) delivering to said RGC a nucleic acid molecule according to claim 1 or 10 or expression vector according to claim 13;
(b) expressing said nucleic acid molecule or expression vector in said desired subcellular sites of said RGC.

22. The method of claim 21 wherein said desired subcellular site is soma, proximal dendritic region, or axon initial segment.

23. The method of claim 21, wherein the sorting motif is one that targets the rhodopsin to the center of said RGC's receptive field.

24. The method of claim 21 wherein said desired subcellular site is the somatodendritic region.

25. The method of claim 21, wherein the sorting motif is one that targets the surround or off-center of the RGC's receptive field.

* * * * *

UNITED STATES PATENT AND TRADEMARK OFFICE
CERTIFICATE OF CORRECTION

PATENT NO. : 9,453,241 B2
APPLICATION NO. : 13/696252
DATED : September 27, 2016
INVENTOR(S) : Zhuo-Hua Pan Page 1 of 1

It is certified that error appears in the above-identified patent and that said Letters Patent is hereby corrected as shown below:

In the Claims:

At Column 194, Claim number 14, Line number 40:
"(a)    5'–ITR–CAG–ChR2–GFP{Motif}–WPRE–bGHpolyA–"
should read
--(a)   5'–ITR–CAG–ChR2–GFP–{Motif}–WPRE–bGHpolyA– --

At Column 195, Claim number 17, Line number 37:
"(b)    5 '–ITR–CAG–HaloR–(NLG-1 Motif)–WPRE–"
should read
--(b)   5'–ITR–CAG–HaloR–(NLG-1 Motif)–WPRE– --

At Column 196, Claim number 20, Line number 23:
"that comprises a nucleic acid according to claim 1 or 2;"
should read
--that comprises a nucleic acid according to claim 1 or 2; and--

At Column 196, Claim number 21, Line number 36:
"ing to claim 13;"
should read
--ing to claim 13; and--

Signed and Sealed this
Tenth Day of January, 2017

Michelle K. Lee
*Director of the United States Patent and Trademark Office*